United States Patent
Nishitani et al.

(10) Patent No.: US 7,696,354 B2
(45) Date of Patent: Apr. 13, 2010

(54) CEPHEM COMPOUNDS HAVING BROAD ANTIBACTERIAL SPECTRUM

(75) Inventors: Yasuhiro Nishitani, Osaka (JP); Yoshinori Yamano, Toyonaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 12/100,307

(22) Filed: Apr. 9, 2008

(65) Prior Publication Data

US 2009/0131655 A1 May 21, 2009

Related U.S. Application Data

(62) Division of application No. 10/507,502, filed as application No. PCT/JP03/03249 on Mar. 18, 2003, now Pat. No. 7,384,928.

(30) Foreign Application Priority Data

Mar. 18, 2002 (JP) ............................. 2002-073526

(51) Int. Cl.
*C07D 277/38* (2006.01)
(52) U.S. Cl. .................................. 548/194
(58) Field of Classification Search .................. 548/194
See application file for complete search history.

(56) References Cited

U.S. PATENT DOCUMENTS

| 4,427,677 | A |   | 1/1984  | Takaya et al. |         |
|-----------|---|---|---------|---------------|---------|
| 4,525,473 | A |   | 6/1985  | Aburaki et al.|         |
| 4,550,102 | A |   | 10/1985 | Teraji et al. |         |
| 4,692,519 | A |   | 9/1987  | Naito et al.  |         |
| 4,788,185 | A |   | 11/1988 | Miyake et al. |         |
| 4,925,948 | A | * | 5/1990  | Takaya et al. | 548/195 |
| 5,585,485 | A |   | 12/1996 | Ascher et al. |         |
| 7,067,481 | B2|   | 6/2006  | Fatheree et al.|        |
| 7,067,482 | B2|   | 6/2006  | Fatheree et al.|        |

FOREIGN PATENT DOCUMENTS

| EP | 0 055 465 A2   | 7/1982  |
| JP | 59-130294 A    | 7/1984  |
| WO | WO 9741128 A1  | 11/1997 |

OTHER PUBLICATIONS

Nishimura et al.m "Studies on Condensed-Heterocyclic Azoliuym Cephalosporins," Journal of Antibiotics, vol. 45, No. 4, 1992, pp. 485-499.

* cited by examiner

*Primary Examiner*—Laura L. Stockton
(74) *Attorney, Agent, or Firm*—Finnegan, Henderson, Farabow, Garrett & Dunner, LLP

(57) ABSTRACT

A compound of the formula:

(I)

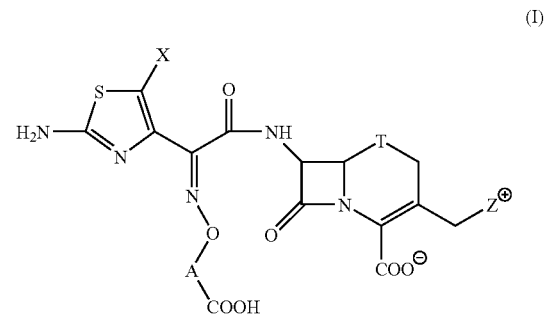

(wherein,
T is S, SO or O;
X is halogen, CN, carbamoyl optionally substituted with lower alkyl, lower alkyl, lower alkoxy, or lower alkylthio;
A is substituted lower alkylene (wherein the substituent is optionally substituted mono lower alkyl, optionally substituted lower alkylidene, or optionally substituted lower alkylene);
$Z^+$ is an optionally substituted, a cation and an N atom-containing heterocyclic group), ester, amino-protected compound wherein the amino bonds to a thiazole ring at the 7-position, or pharmaceutically acceptable salt or solvate thereof.

3 Claims, No Drawings

CEPHEM COMPOUNDS HAVING BROAD ANTIBACTERIAL SPECTRUM

This is a division of application Ser. No. 10/507,502, filed Sep. 13, 2004 now U.S. Pat. No. 7,384,928 which is a National Stage Application of PCT/JP03/03249 filed Mar. 18, 2003 which claims priority to Japanese Application JP2002-073526 filed Mar. 18, 2002, all of which are incorporated herein by reference.

TECHNICAL FIELD

The present invention relates to cephem compounds having a broad antibacterial spectrum over various pathogenic bacteria and pharmaceutical compositions containing the same, as well as a production method and intermediates therefor. The compounds of the present invention are stable against β-lactamase and efficacious against β-lactamase-producing cephem-resistant bacteria including *Pseudomonas aeruginosa*.

BACKGROUND

Study of so-called broad spectrum cephem compounds having potent antibacterial activities against various Gram-positive and Gram-negative bacteria has recently been focused on cephem compounds wherein the 7-side chain is substituted with aminothiazole or aminothiadiazole and the 3-position with a cyclic-type quarternary ammoniummethyl group. For example, the known 7-aminothiazole types include cefepime hydrochloride (U.S. Pat. No. 4,406,899), cefpirome sulfate (U.S. Pat. No. 4,609,653, JP(A) S57-192394), and cefoselis sulfate (JP(A) H07-196665, WO97/41128), and the 7-aminothiadiazole types include cefclidin (U.S. Pat. No. 4,748,171), and cefozopran hydrochloride (U.S. Pat. No. 4,864,022, JP(A) S62-149682, JP(A) H03-47189). Such types of cephem compounds are also reported in JP Patent publication (Kokai) S-58-4789 which discloses compounds having an "optionally substituted 2 or more of N atoms-containing heterocycle cation group" at the 3-position and in JP Patent publication (Kokai) S-60-155183 which discloses compounds having a "2 or more of N atoms-containing unsaturated condensed heterocyclic cation group" at the 3-position.

Documents such as JP Patent publication (Kokai) S-60-97982, JP Patent publication (Kokai) S-59-130294, JP Patent publication (Kokai) S-60-34973, JP Patent publication (Kokai) S-62-114990, JP Patent publication (Kokai) S-64-42491, and WO87/06232 etc. disclose cephem compounds which have a halogen on an aminothiazole ring at the 7-position or which are substituted with COOH at the end of the oxime part on the 7-side chain. These documents do not disclose a cephem compound having the both structural characteristics.

A cephem compound, which has a halogen on an aminothiazole ring at the 7-position and is substituted with COOH at the end of the oxime part on the 7-side chain, is known in JP Patent publication (Kokai) S-60-231684. However, a specifically disclosed compound is that wherein the methylene group bonding to the oxime part on the 7-side chain is non-substituted or dimethyl-substituted type. JP Patent publication (Kokai) S-57-131794 and JP Patent publication (Kokai) H-1-308286 discloses compounds wherein the methylene group bonding to the oxime part on the 7-side chain is substituted with monomethyl, however, the configuration is not specified and a quarternary ammonium group is not disclosed as a possible substituent on the methylene group at the 3-position. Further, any antibacterial activities against cephem-resistant *Pseudomonas aeruginosa* are not described therein.

A cephem compound having a quarternary ammonium group at the 3-position and a side chain of aminothiazole/oxime type at the 7-position, so-called broad spectrum antibacterial-type cephem, is known as being efficatious against G(−) bacteria including *Pseudomonas aeruginosa*. For example, ceftazidime has been reported as being stable against β-lactamase and possesing a relatively potent activity against β-lactamase-producing *Pseudomonas aeruginosa* (Acta Microbiologica Hungarica 35 (4), pp. 327-359 (1988)).

Under the above circumstances, among G(−) bacteria, the number of bacteria resistant to some broad spectrum antibacterial-type cephems has recently increased. The frequency of clinical isolation of cephem-resistant *Pseudomonas aeruginosa*, which highly produce β-lactamase, esp. Class C-type β-lactamase, has raised, which is recognized as a social problem worldwide ("Classification and Epidemiology of Recent β-lactamase". Clinic and Microorganism Vol. 26 No. 2 1999.3 P103-109). However, a cephem compound with a potent activity against such cephem-resistant *Pseudomonas aeruginosa* has not been reported.

Therefore, the development of a novel cephem compound with broad antibacterial spectrum, preferably a compound possessing a potent activity against cephem-resistant *Pseudomonas aeruginosa* which produce β-lactamase has been desired. In preference, such a compound is useful as an injection.

DISCLOSURE OF THE INVENTION

The present inventors have found that the stability of a cephem compound against β-lactamase produced by cephem-resistant *Pseudomonas aeruginosa* can be improved so as to enhanse the antibacterial activity against such *Pseudomonas aeruginosa*, by means of introducing a halogen atom or the like into an aminothiazole ring on the 7-side chain, a carboxyl group into the end of the oxime group bonding to the carbon atom at α-position, and an N-containing heterocyclic group, preferably a quarternary ammonium group into the 3-position, respectively.

As a more preferable embodiment, the inventors have found that the antibacterial activity can further be enhanced by introducing a lower alkyl preferably methyl as α-configuration into the methylene group, whereby to accomplish the present invention shown below.

1. A compound of the formula:

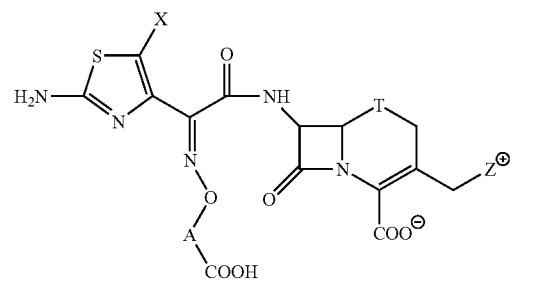

(wherein,

T is S, SO or O;

X is halogen, CN, carbamoyl optionally substituted with lower alkyl, lower alkyl, lower alkoxy, or lower alkylthio;

A is substituted lower alkylene (wherein the substituent is optionally substituted mono lower alkyl, optionally substituted lower alkylidene, or optionally substituted lower alkylene);

$Z^+$ is an optionally substituted, a cation and an N atom-containing heterocyclic group), ester, amino-protected compound wherein the amino bonds to a thiazole ring at the 7-position, or pharmaceutically acceptable salt or solvate thereof.

2. A compound according to the above 1 wherein T is S, ester, amino-protected compound wherein the amino bonds to a thiazole ring at the 7-position, or pharmaceutically acceptable salt or solvate thereof.

3. A compound according to the above 1 wherein T is O, ester, amino-protected compound wherein the amino bonds to a thiazole ring at the 7-position, or pharmaceutically acceptable salt or solvate thereof.

4. A compound according to the above 1 wherein X is halogen or lower alkyl, ester, amino-protected compound wherein the amino bonds to a thiazole ring at the 7-position, or pharmaceutically acceptable salt or solvate thereof.

5. A compound according to the above 1 wherein A is of the formula:

(wherein, $R^1$ and $R^2$ are different each other and independently hydrogen or optionally substituted lower alkyl, or taken together may form optionally substituted lower alkylidene or optionally substituted lower alkylene.), ester, amino-protected compound wherein the amino bonds to a thiazole ring at the 7-position, or pharmaceutically acceptable salt or solvate thereof.

6. A compound according to the above 5 wherein A is a divalent group of any of the following formulae, ester, amino-protected compound wherein the amino bonds to a thiazole ring at the 7-position, or pharmaceutically acceptable salt or solvate thereof.

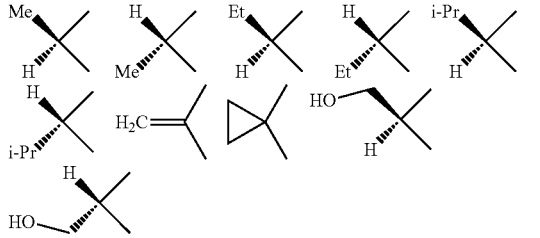

(wherein, Me is methyl; Et is ethyl; i-Pr is isopropyl)

7. A compound according to the above 5 wherein $R^1$ and $R^2$ are different each other and independently hydrogen or lower alkyl, ester, amino-protected compound wherein the amino bonds to a thiazole ring at the 7-position, or pharmaceutically acceptable salt or solvate thereof.

8. A compound according to the above 5 wherein $R^1$ and $R^2$ are different each other and independently hydrogen or methyl, ester, amino-protected compound wherein the amino bonds to a thiazole ring at the 7-position, or pharmaceutically acceptable salt or solvate thereof.

9. A compound according to the above 5 wherein "-A-COOH" is a group of the formula:

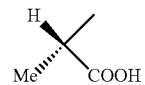

ester, amino-protected compound wherein the amino bonds to a thiazole ring at the 7-position, or pharmaceutically acceptable salt or solvate thereof.

10. A compound according to the above 1 wherein $Z^+$ is a saturated or unsaturated, monocyclic or condensed cyclic, and at least one or more of N atoms-containing quarternary ammonium group of the formula:

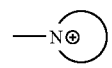

which may have 1 to 4 substituents, ester, amino-protected compound wherein the amino bonds to a thiazole ring at the 7-position, or pharmaceutically acceptable salt or solvate thereof.

11. A compound according to the above 1, ester, amino-protected compound wherein the amino bonds to a thiazole ring at the 7-position, or pharmaceutically acceptable salt or solvate thereof, wherein $Z^+$ is a heterocyclic group of any one of the formulae:

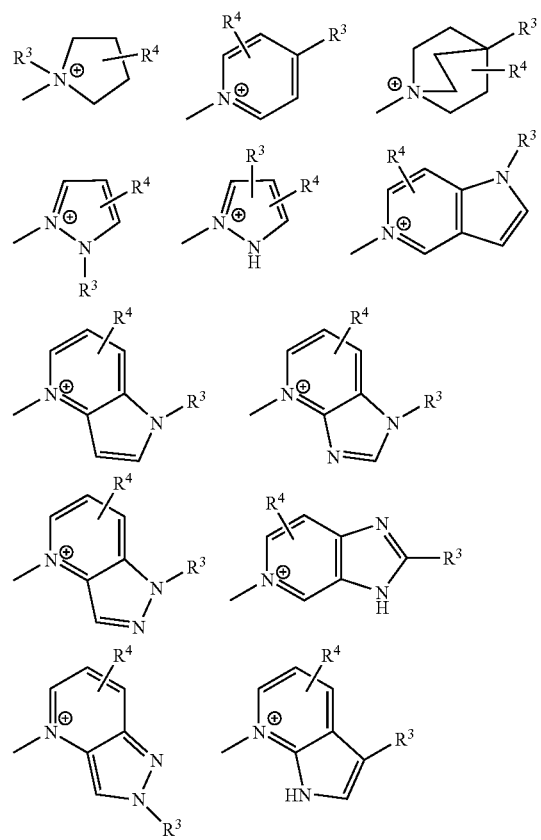

-continued

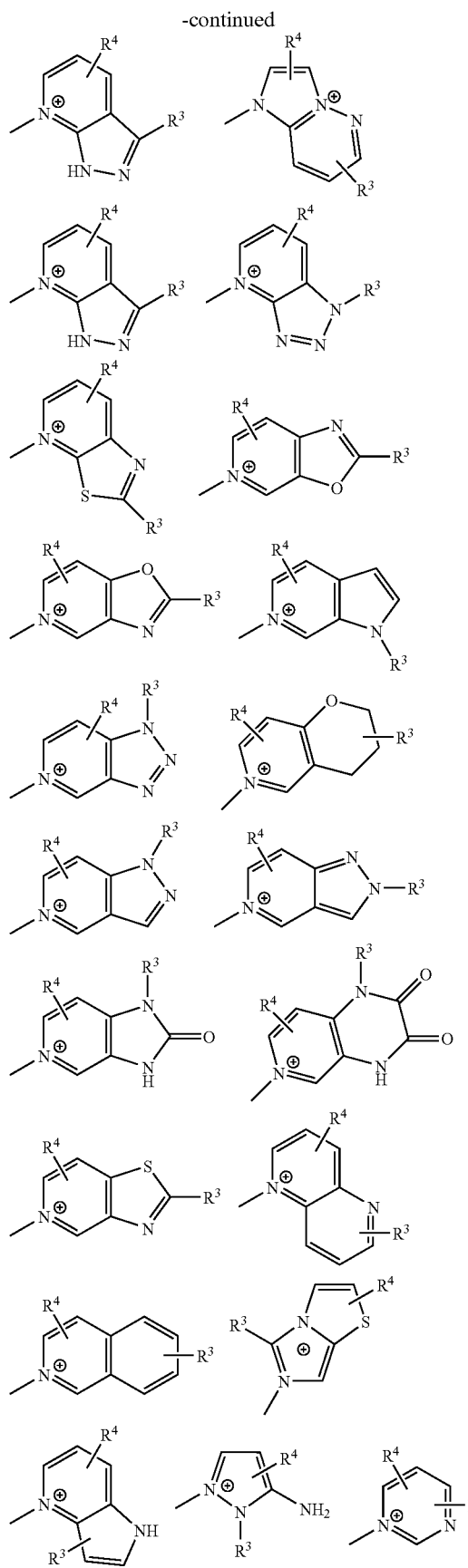
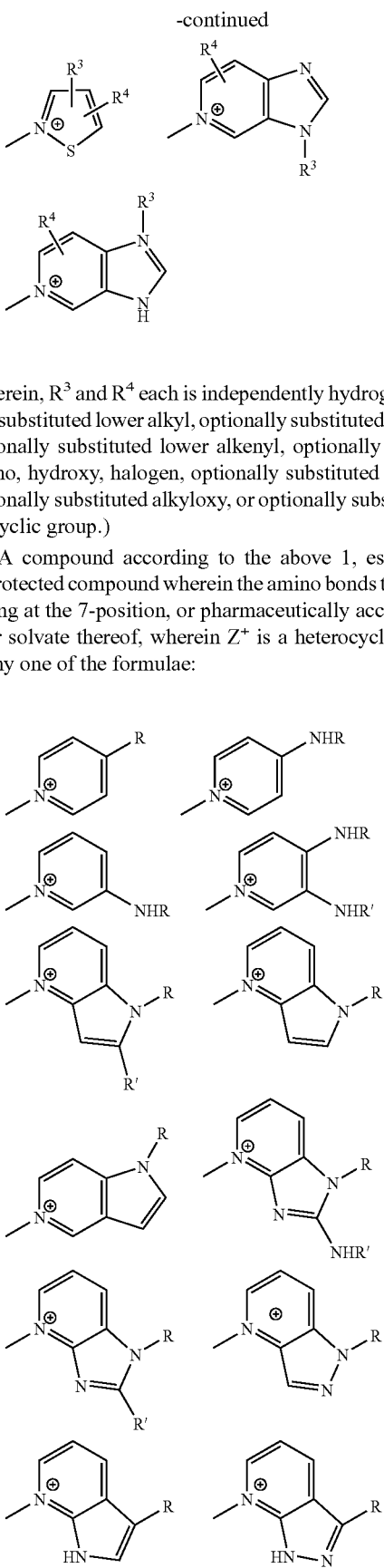

(wherein, $R^3$ and $R^4$ each is independently hydrogen, optionally substituted lower alkyl, optionally substituted cycloalkyl, optionally substituted lower alkenyl, optionally substituted amino, hydroxy, halogen, optionally substituted carbamoyl, optionally substituted alkyloxy, or optionally substituted heterocyclic group.)

12. A compound according to the above 1, ester, amino-protected compound wherein the amino bonds to a thiazole ring at the 7-position, or pharmaceutically acceptable salt or solvate thereof, wherein $Z^+$ is a heterocyclic group of any one of the formulae:

-continued

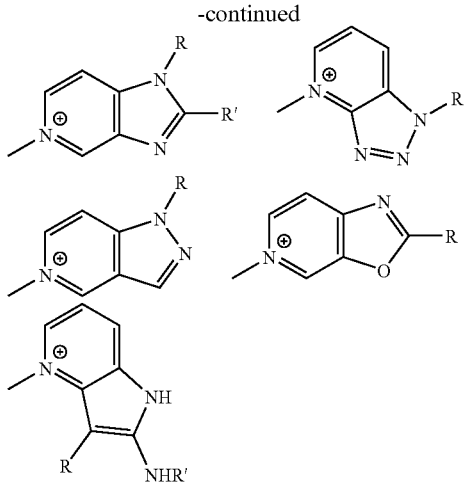

(wherein, R and R' each is independently hydrogen, lower alkyl, amino, mono- or di-lower alkylamino, lower alkenyl, amino lower alkyl, lower alkylamino lower alkyl, lower alkylamino lower alkylamino, amino lower alkyloxyamino, amino substitute with optionally substituted heterocyclic group, hydroxy lower alkyl, hydroxy lower alkylamino lower alkyl, lower alkoxy lower alkyl, carbamoyl lower alkyl, carboxy lower alkyl, lower alkylcarbonylamino lower alkyl, lower alkoxycarbonylamino lower alkyl, lower alkyloxy, the other various optionally substituted lower alkyl, lower alkyl having 2 kinds of substituents, or optionally substituted heterocyclic group.)

13. A compound according to the above 1, ester, amino-protected compound wherein the amino bonds to a thiazole ring at the 7-position, or pharmaceutically acceptable salt or solvate thereof, wherein $Z^+$ is a heterocyclic group of any one of the formulae:

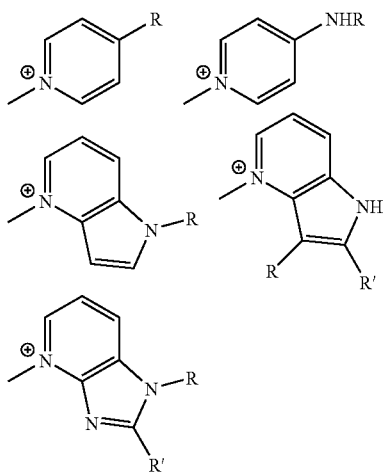

(wherein, R is independently hydrogen, lower alkyl, amino lower alkyl, lower alkylamino lower alkyl, amino substituted with optionally substituted heterocyclic group, or optionally substituted heterocyclic group; R' is amino.)

14. A compound according to the above 1, ester, amino-protected compound wherein the amino bonds to a thiazole ring at the 7-position, or pharmaceutically acceptable salt or solvate thereof, wherein $Z^+$ is a heterocyclic group of any one of the formulae:

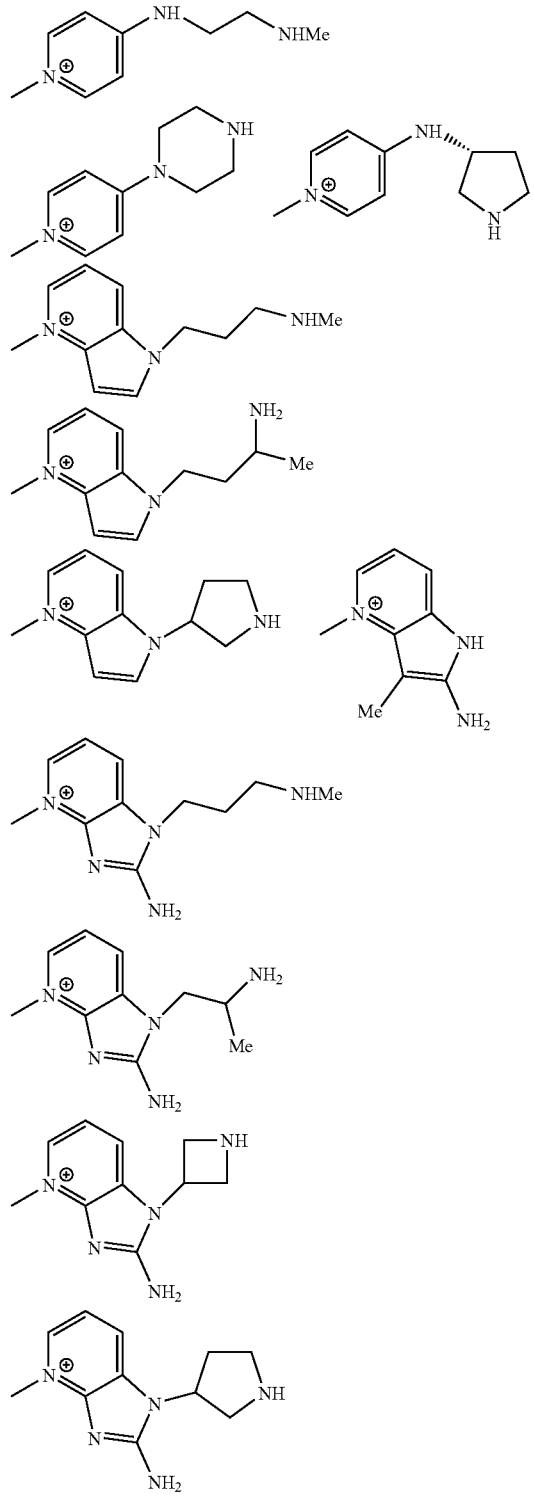

(wherein, Me is methyl.)

15. A compound according to the above 1, ester, amino-protected compound wherein the amino bonds to a thiazole ring at the 7-position, or pharmaceutically acceptable salt or solvate thereof, wherein T is S; X is halogen; A is a divalent group shown in any of the above 5 to 9; Z⁺ is a heterocyclic group shown in any of the above 10 to 14.

16. A compound according to the above 1, ester, amino-protected compound wherein the amino bonds to a thiazole ring at the 7-position, or pharmaceutically acceptable salt or solvate thereof, wherein T is S; X is halogen; A is a divalent group shown in the above 8; Z⁺ is a heterocyclic group shown in the above 12.

17. A compound according to the above 1, ester, amino-protected compound wherein the amino bonds to a thiazole ring at the 7-position, or pharmaceutically acceptable salt or solvate thereof, wherein T is S; X is halogen; A is a divalent group shown in the above 9; Z⁺ is a heterocyclic group shown in the above 13 or 14.

18. A compound according to the above 1 of the following formula, or pharmaceutically acceptable salt or solvate thereof.

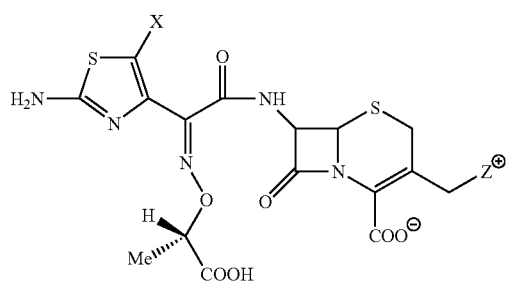

(I)

(wherein, X is halogen; Z⁺ is a heterocyclic group of any of the formulae)

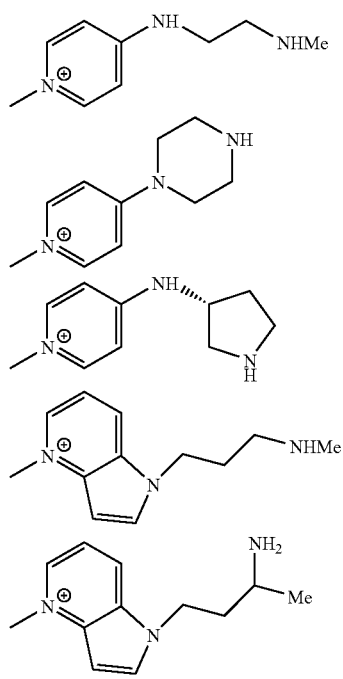

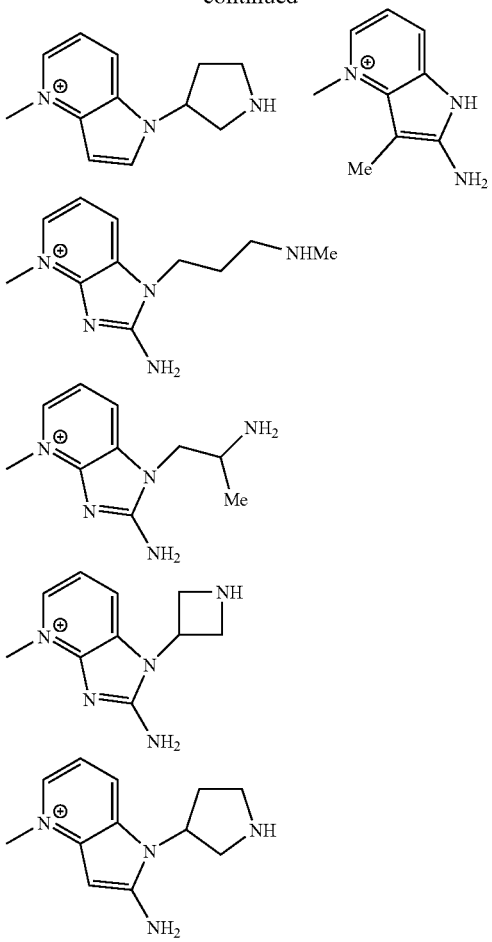

(wherein, Me is methyl)

19. A compound of the formula:

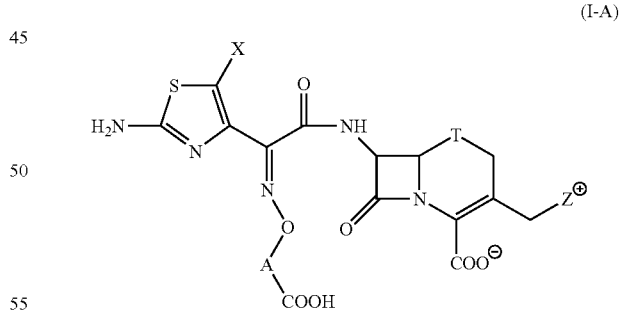

(I-A)

(wherein,
T is S SO or O;
X is halogen, CN, carbamoyl optionally substituted with lower alkyl, lower alkyl, lower alkoxy, or lower alkylthio:
A is optionally substituted lower alkylene (excluding that the substituent is optionally substituted mono lower alkyd optionally substituted lower alkylidene, or optionally substituted lower alkylene);
Z⁺ is optionally substituted, a cation- and an N atom-containing heterocyclic group), ester, amino-protected compound wherein the amino bonds to a thiazole ring at the 7-position, or pharmaceutically acceptable salt or solvate thereof excluding that T is S;

X is halogen and 1) A is methylene; $Z^+$ is pyridinium or 2) A is dimethylmethylene; $Z^+$ is imidazo[1,2-a]pyridinium).

20. A compound of the above 19, ester, amino-protected compound wherein the amino bonds to a thiazole ring at the 7-position, or pharmaceutically acceptable salt or solvate thereof, wherein T is S, X is halogen or lower alkyl; A is methylene optionally substituted with di-lower alkyl.

21. A compound of the above 20, ester, amino-protected compound wherein the amino bonds to a thiazole ring at the 7-position, or pharmaceutically acceptable salt or solvate thereof, of any of the formula:

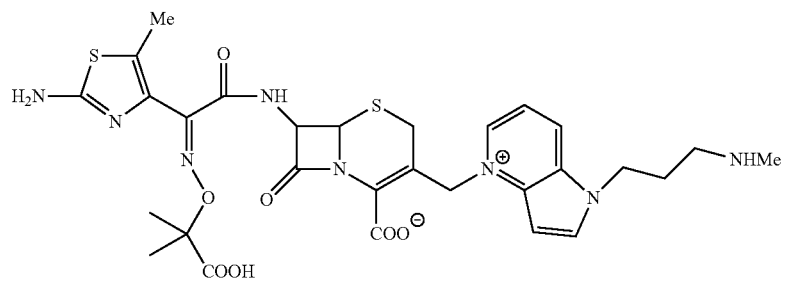

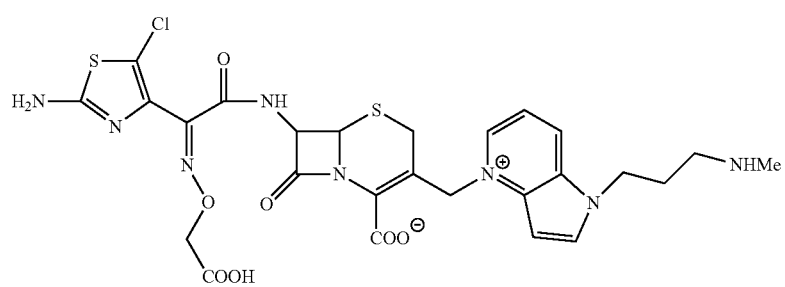

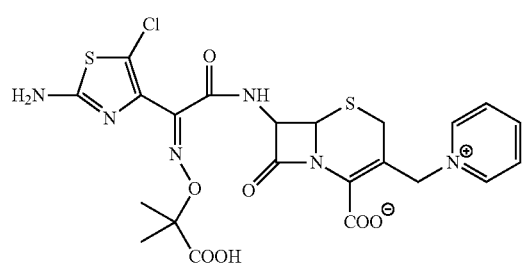

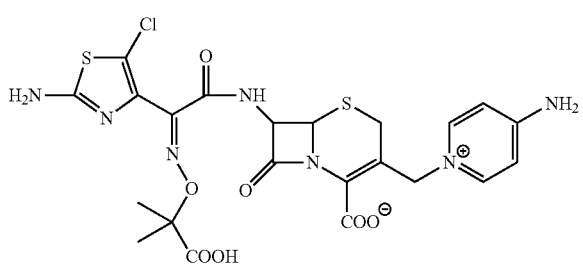

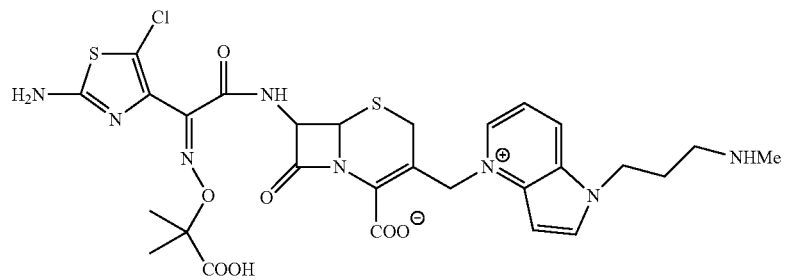

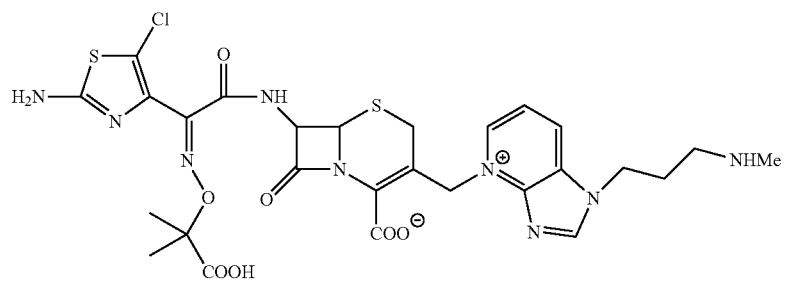

-continued

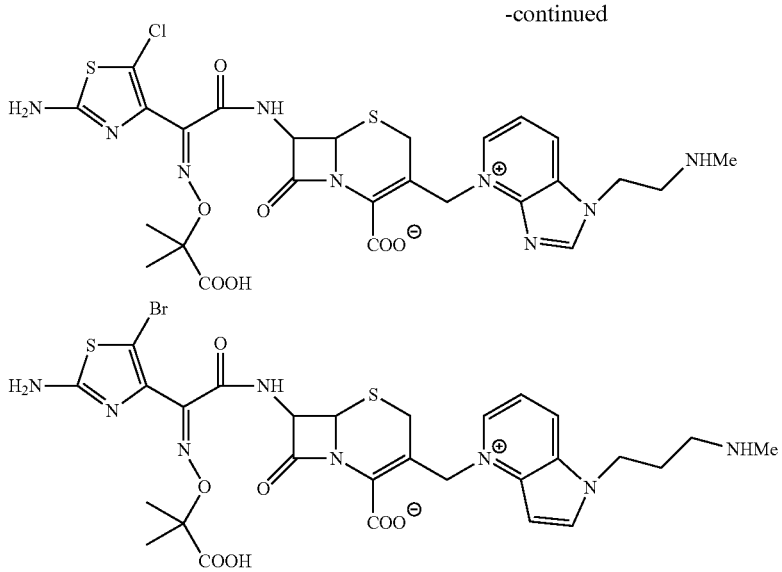

22. A pharmaceutical composition containing a compound of the above 1 to 21, ester, amino-protected compound wherein the amino bonds to a thiazole ring at the 7-position, or pharmaceutically acceptable salt or solvate thereof.
23. An antibacterial composition containing a compound of the above 1 to 21, ester, amino-protected compound wherein the amino bonds to a thiazole ring at the 7-position, or pharmaceutically acceptable salt or solvate.
24. A compound or pharmaceutically acceptable salt, of the formula:

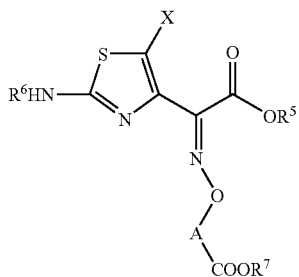

(IV)

(wherein, X is halogen, CN, carbamoyl optionally substituted with lower alkyl, lower alkyl, lower alkoxy, or lower alkylthio; A is of the formula:

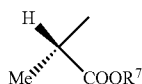

$R^5$ is hydrogen or carboxy-protecting group, $R^6$ is hydrogen or amino-protecting group; $R^7$ is hydrogen or carboxy-protecting group)
25. A compound or pharmaceutically acceptable salt according to the above 24, wherein X is halogen or lower alkyl.
26. A compound or pharmaceutically acceptable salt according to the above 24, wherein X is halogen.

Further, the present invention provides a method for preparing the invention compounds and intermediates thereof, as well as a method for prevention or treatment of bacterial infection by administering the invention compound, and use of the invention compound for preparing an antibacterial agent.

BEST MODE FOR CARRYING OUT THE INVENTION

Terms used herein are explained below. Unless otherwise mentioned, each term, by itself or as part of another, has the following meaning.

(Definition of T)
T is S, SO or O, preferably S or O, and more preferably S.

(Definition of X)
X is halogen, CN, carbamoyl optionally substituted with lower alkyl, lower alkyl, lower alkoxy, or lower alkylthio.
Halogen includes F, Cl, and Br, preferably Cl or Br, and more preferably Cl.
Examples of lower alkyl include a straight or branched C1 to C6 alkyl such as methyl, ethyl, n-propyl, i-propyl, t-butyl, n-pentyl, and n-hexyl, and preferably is C1 to C3 alkyl, and more preferably is methyl.
Examples of lower alkoxy include oxy bonding to lower alkyl, such as methoxy, ethoxy, n-propoxy, i-propoxy, t-butoxy, n-pentyloxy, and n-hexyloxy, preferably C1 to C3 alkoxy, and more preferably methoxy.
Examples of lower alkylthio include thio bonding to the lower alkyl, such as methylthio, ethylthio, n-propoxy, i-propylthio, t-butylthio, n-pentylthio, and n-hexylthio, preferably C1 to C3 alkylthio, and more preferably methylthio.
X is preferably halogen (e.g., Cl, Br) or lower alkyl (e.g., methyl), more preferably halogen.

(Definition of A)
A can be any of divalent groups which does not bring a negative effect into the antibacterial activity of compound (I) or compound (I-A), and preferably A is lower alkylene optionally substituted with $R^1$, $R^2$ or the like. In compound (I), A is substituted lower alkylene.

The lower alkylene is a divalent group derived from the above-mentioned lower alkyl, preferably C1 to C3 alkylene, more preferably methylene (—CH$_2$—).

A is more preferably methylene substituted with the following R$^1$ and R$^2$, and preferably A is of the following configuration.

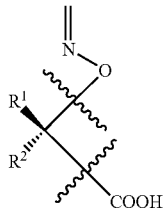

(Definition of R$^1$, R$^2$)

R$^1$ and R$^2$ are each independently hydrogen, optionally substituted lower alkyl or taken together may form optionally substituted lower alkylidene or optionally substituted lower alkylene, provided that in compound (I), R$^1$ and R$^2$ are different each other.

The lower alkyl includes the above-mentioned lower alkyl, preferably C1 to C4 alkyl, more preferably methyl, ethyl, or propyl (e.g., n-propyl, i-propyl, and most preferably methyl.

The lower alkylidene includes a divalent group which is derived from the above lower alkyl by deducting two hydrogens bonding to the same carbon atom, for example, =CH$_2$, =CHCH$_3$, =CHCH$_2$CH$_3$, =C(CH$_3$)$_2$, =CHC(CH$_3$)$_3$, preferably =CH$_2$, =CHCH$_3$, or =C(CH$_3$)$_2$, and more preferably =CH$_2$.

The lower alkylene includes —(CH$_2$)n-(n is an integer from 2 to 4, preferably 2). R$^1$ and R$^2$ taken together may form lower alkylene, which taken together with the neighboring carbon atom can form the following cycloalkyl, preferably cyclopropyl or cyclobutyl, and more preferably cyclopropyl.

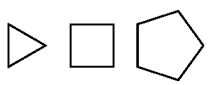

When the above lower alkyl, lower alkylidene, or lower alkylene is substituted, the substituents include halogen (e.g., F, Cl), hydroxy, lower alkoxy (e.g., methoxy, ethoxy), and preferably hydroxy.

The combination of (R$^1$, R$^2$) is preferably, (methyl, hydrogen), (hydrogen, methyl), or (methyl, methyl) or taken together may form =CH$_2$, —(CH$_2$)$_2$— etc. In compound (I), more preferred is hydrogen and lower alkyl, most preferred is (R$^1$, R$^2$)=(methyl, hydrogen), or (hydrogen, methyl). Particularly preferred is hydrogen, methyl).

In compound (I), preferred are the following divalent groups.

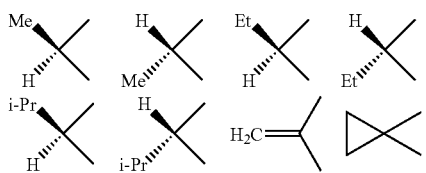

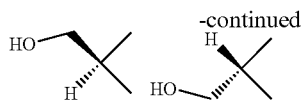

(wherein, Me is methyl; Et is ethyl; i-Pr is isopropyl.)

(Definition of Z$^+$)

Z$^+$ is an optionally substituted, a cation- and N-containing heterocyclic group. Unless the pharmacological activity is negatively influenced, the number and position of the substituent, the kind of cation, and the kind of heterocycle can be of variety. Z$^+$ includes various kinds of groups which are well known to or readily recognized by a skilled person in the invention field as a heterocyclic group at the 3-position of cephem compounds. The cation preferably locates around the N atom neighboring to the 3-methylene of compound (I).

Z$^+$ is preferably of the formula:

and a saturated or unsaturated, monocyclic or condensed quarternary ammonium group which contains 1 or more, preferably 1 to 4, and more preferably 1 to 3 of N atoms, and optionally substituted with 1 to 4, and preferably 1 to 2 substituents. The heterocycle may further contain 1 or more of O and/or S.

The heterocycle is preferably a 5- to 10-, preferably 5- to 6-membered cycle.

The saturated N-containing heterocycle includes pyrrolidine, pyrazolidine, thiazolidine, oxazolidine, imidazolidine, piperidine, piperazine, morpholine, thiomorpholine, and a condensed ring containing the same.

The unsaturated N-containing heterocycle includes a monocycle (e.g.,: pyrrole, pyrazole, indazole, oxazole, isooxazole, thiazole, isothiazole, pyridine, pyridazine, pyrimidine, pyrazine, triazine, triazole), and a condensed bicycle containing the monocycle (e.g., indole, indolizine, benzimidazole, benzpyrazole, indolizine, quinoline, isoquinoline, naphthylizine, phthalazine, quinazoline, quinuclidie, benzoisooxazole, benzpyrazole, benzoxazole, benzoxadiazole, benzisothiazole, benzothiazole, benzotriazole, purine, indoline, pyrazoloimidazole, pyridazineimidazole, thiazoloimidazole, tetrahydropyranopyridine, oxazalo[4,5-c]pyridine, oxazolo[5,4-c]pyridine, 1H-pyrrolo[3,2-b]pyridine, 1H-pyrrolo[2,3-b]pyridine, 1H-pyrrolo[3,2-c]pyridine, 1H-pyrrolo[2,3-c]pyridine, 1H-pyrazlo[4,3-b]pyridine, 1H-pyrazolo[3,4-b]pyridine, 1H-imidazo[4,5-c]pyridine, 1H-imidazo[4,5-b]pyridine, thiazolo[4,5-c]pyridine, thiazolo[5,4-b]pyridine, 1,4-dihydro-pyrido[3,4-b]pyrazine, 1,3-dihydro-imidazo[4,5-c]pyridine, triazolopyridine).

In detail, Z$^+$ includes optionally substituted heterocyclic groups shown below.

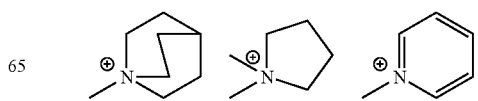

-continued
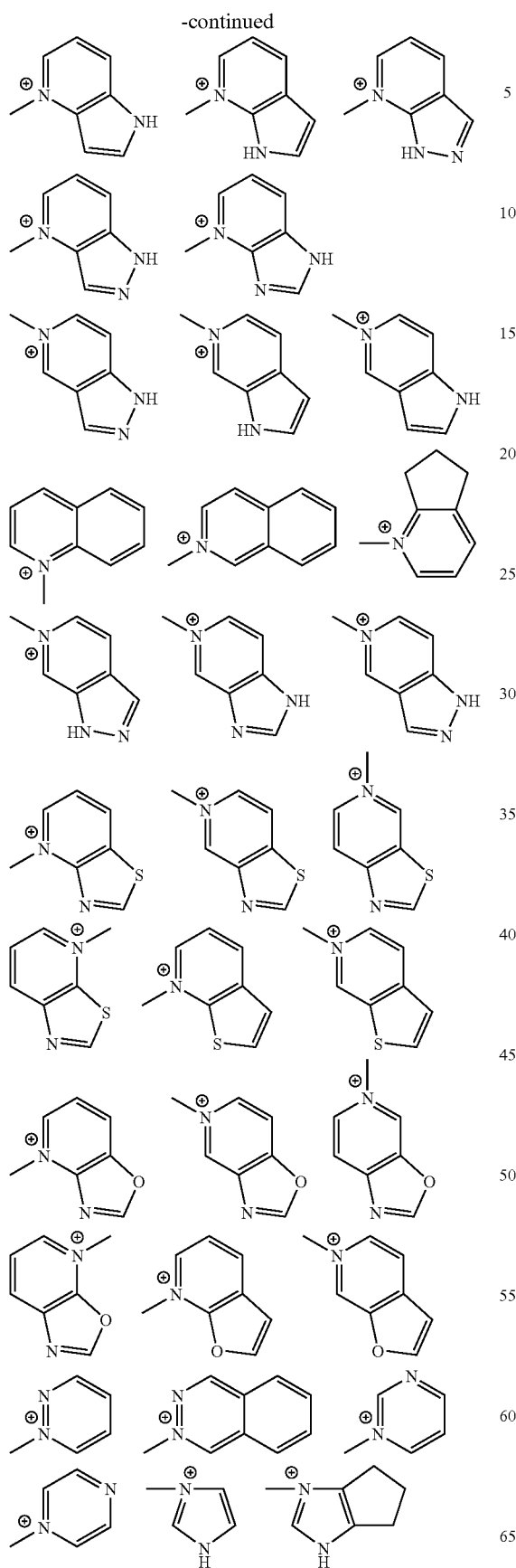
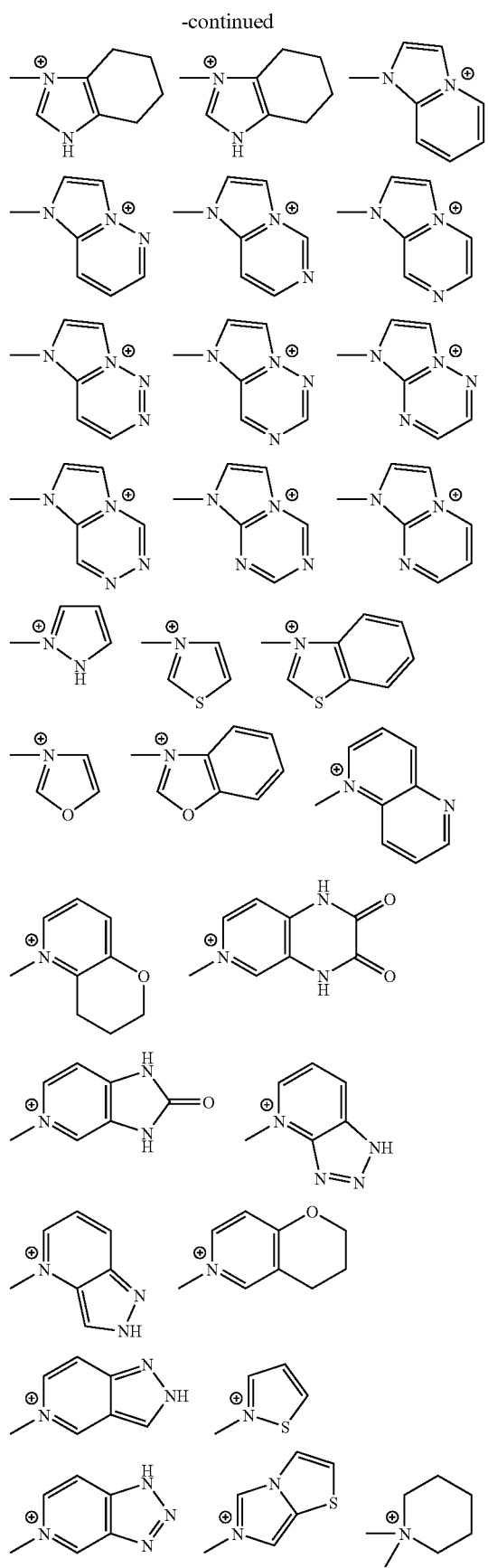

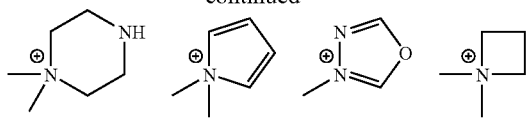

When the above heterocyclic group has a substituent(s), the substituents include 1 or more, preferably 1 to 4, more preferably 1 to 3, and most preferably 1 to 2, same or different substituent selected from the group consisting of lower alkyl (e.g., methyl, ethyl, n-butyl), optionally substituted lower alkyl (substituent: amino, lower alkylamino (e.g., —NHCH$_3$), optionally substituted lower alkylamino (e.g., —NHCH$_2$CH$_2$OH), optionally substituted heterocyclic group (e.g., 2-pyrrolidinyl, 3-pyrrolidinyl 5-(3-hydroxypyrrolidinyl)), hydroxy, cycloalkyl, carboxy, lower alkoxy (e.g., methoxy), —OCOCH$_3$, —OCONH$_2$, —OCONHOCH$_3$, —OCONHOH, —OCONHCH$_3$, —OCON(CH$_3$)$_2$, —OCONHN(CH$_3$)$_2$, —ONHCOOCH$_3$, —CONH$_2$, —CONHOCH$_3$, —CONHOH, lower alkoxycarbonylamino (e.g., —NHCOOCH$_3$), lower alkylcarbonylamino (e.g., —NHCOCH$_3$), —NHCONH$_2$, —NHSO$_2$NH$_2$, —NHCHO, —N(CH$_3$)C=NH(NH$_2$), halogen, oxo); optionally substituted amino (substituent: lower alkyl (e.g., methyl, ethyl, propyl), amino lower alkyl (e.g., —CH$_2$CH$_2$NH$_2$, —CH$_2$CH(NH$_2$)CH$_3$, —CH$_2$CH$_2$CH$_2$NH), lower alkylamino(lower)alkyl (e.g., —CH$_2$CH$_2$NHCH$_3$, —CH$_2$CH$_2$CH$_2$NHCH$_3$), optionally substituted heterocyclic group (e.g., 3-pyrrolidinyl, 4-piperidinyl, 2-thiazolyl, 5-(1-(2-hydroxyethyl)pyrazole), 5-(1-(2-aminoethyl)pyrazole)), lower alkyl substituted with an optionally substituted heterocyclic group (e.g., (2-pyrrolidinyl)methyl, 2-(5-amino-1-(pyrazolyl)ethyl)), guanidino lower alkyl (e.g., —CH$_2$CH$_2$NHC=NH(NH$_2$)), hydroxy(lower)alkyl (e.g., —CH$_2$CH$_2$OH, —CH$_2$CH$_2$CH$_2$OH), hydroxy(lower)alkylamino(lower)alkyl (e.g., —CH$_2$CH$_2$NHCH$_2$CH$_2$OH, amino(lower)alkyloxy (e.g., —OCH$_2$CH$_2$NH$_2$), lower alkylamino(lower)alkyloxy (e.g., —OCH$_2$CH$_2$NHCH$_3$, —OCH$_2$CH$_2$CH$_2$NHCH$_3$), —CHO, =CHN(CH$_3$)$_2$, —NHCHO, optionally substituted carbamoyl (e.g., —CONH$_2$, —CONHCH$_2$CH$_2$NHCH$_3$, CONHCH$_2$CH$_2$NHC=NH(NH$_2$)), —COOCH$_2$CH$_3$, —CH$_2$COOH, acyl (e.g., acetyl), aminoacyl (e.g., —COCH$_2$CH(CH$_3$NH$_2$)); optionally substituted carbamoyl (substituent:methyl, ethyl, —NHCHO); lower alkylene (e.g., —CH$_2$CH$_2$—, —CH$_2$CH$_2$CH$_2$—); optionally substituted lower alkenyl (e.g., —CH$_2$CH=CH$_2$); optionally substituted cycloalkyl (e.g., cyclopropyl); hydroxy; nitro; cyano; aldehyde; optionally substituted alkyloxy (e.g., —OCH$_3$, —OCH$_2$CH$_3$, —OCH$_2$CH$_2$NHCH$_3$, —OCH$_2$CH$_2$NHCH$_3$); lower alkylthio (e.g., —SCH$_3$); lower alkoxycarbonyl (e.g., —COOCH$_2$CH$_3$); halogen (e.g., F,Cl,Br), and optionally substituted heterocyclic group.

The optionally substituted heterocyclic group includes the above-mentioned Z and the bonding position is optional. Preferred is an N-containing saturated 4- to 6-membered ring, for example, azetidinyl (e.g., 3-azetidinyl), pyrrolidinyl(e.g., 3-pyrrolidinyl), piperidinyl (e.g., 4-piperidinyl, 1-(4-aminopiperidinyl), piperadinyl (e.g., 1-piperadinyl, 1-(3-methylpiperadinyl), pyrrolyl (e.g., 3-pyrrolyl, 4-(2-carbamoyl pyrrolyl)), pyrazolyl (e.g., 1-pyrazolyl, 4-pyrazolyl), oxadiazolyl (e.g., 2-oxadiazolyl), triazolyl (e.g., 1-triazolyl).

The above "lower" preferably means C1 to C6, and more preferably C1 to C3. The substituents on the heterocyclic group include preferably optionally substituted lower alkyl, optionally substituted lower alkenyl, optionally substituted amino and optionally substituted heterocyclic group, including the following R$^3$ and R$^4$, "—R", and "—NHR".

Z$^+$ is preferably the following heterocyclic group.

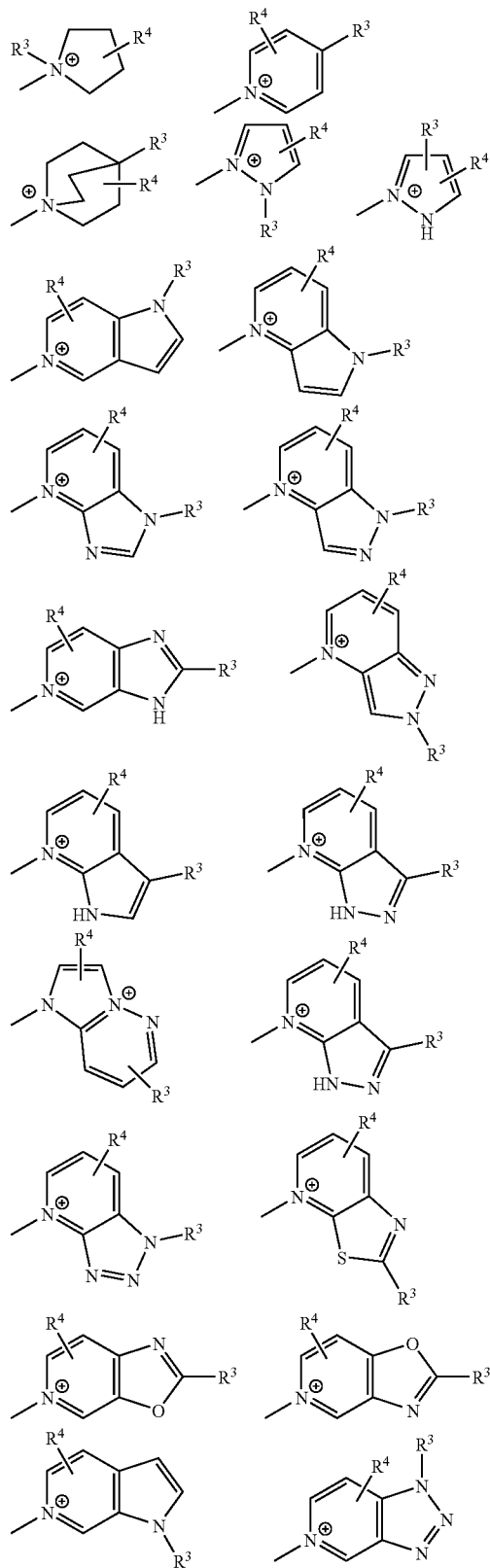

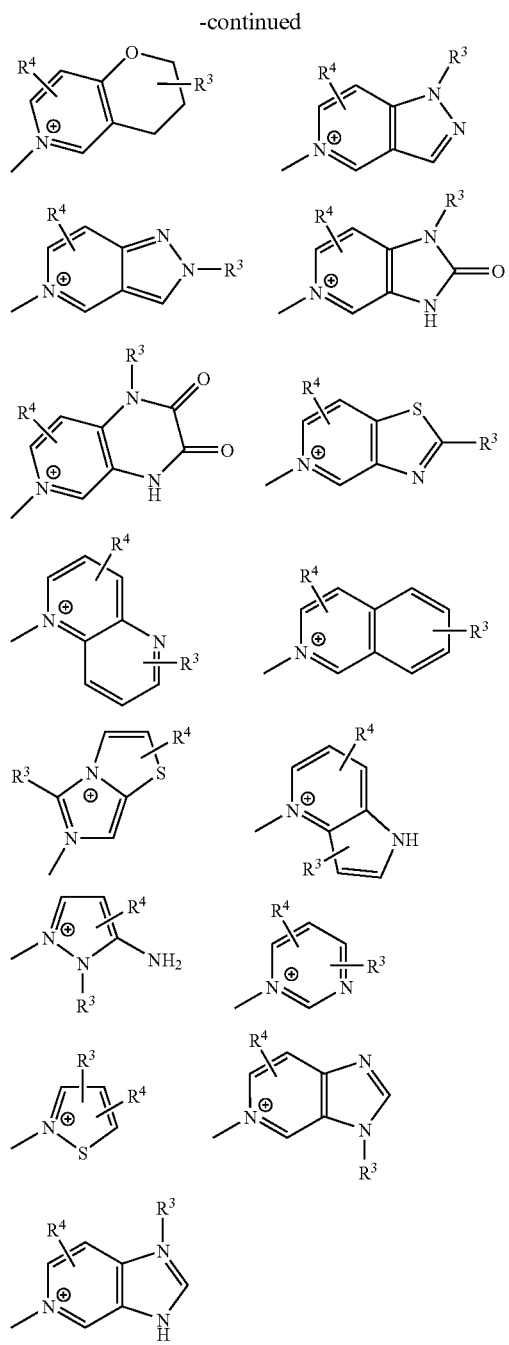
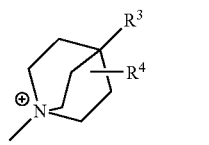  c
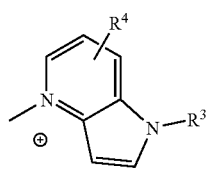  d
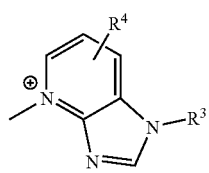  e
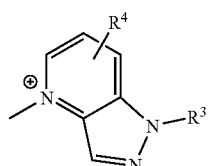  f
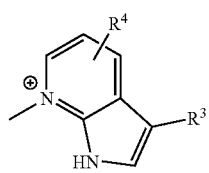  g
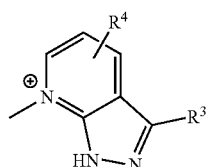  h
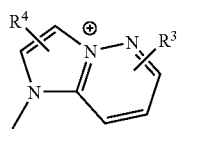  i
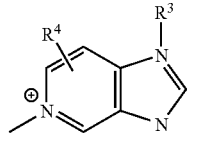  j
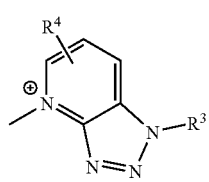  k
$Z^+$ is more preferably the following heterocyclic group, and more preferably a group shown by b, d, e or n.
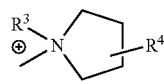  a
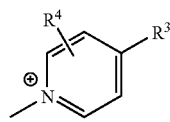  b

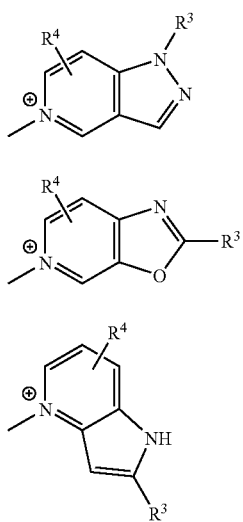

R³ and R⁴ are each selected from the substituents of the above-mentioned heterocycle, and preferred is hydrogen, the above-mentioned optionally substituted lower alkyl, optionally substituted lower alkenyl, optionally substituted amino or optionally substituted heterocyclic group, including the following "—R", "—R'", "—NHR", "—NHR'". R³ and R⁴ are each can locate at any substitutable position.

$Z^+$ is preferably the following heterocyclic group, and more preferably b-1, b-2, d-1, d-3, or e-1.

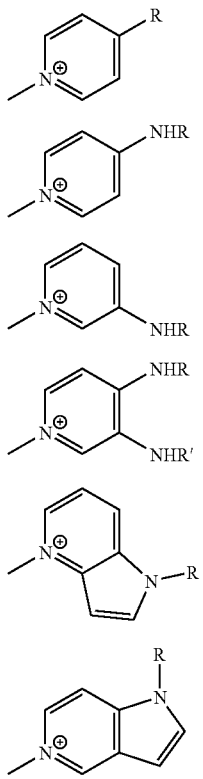

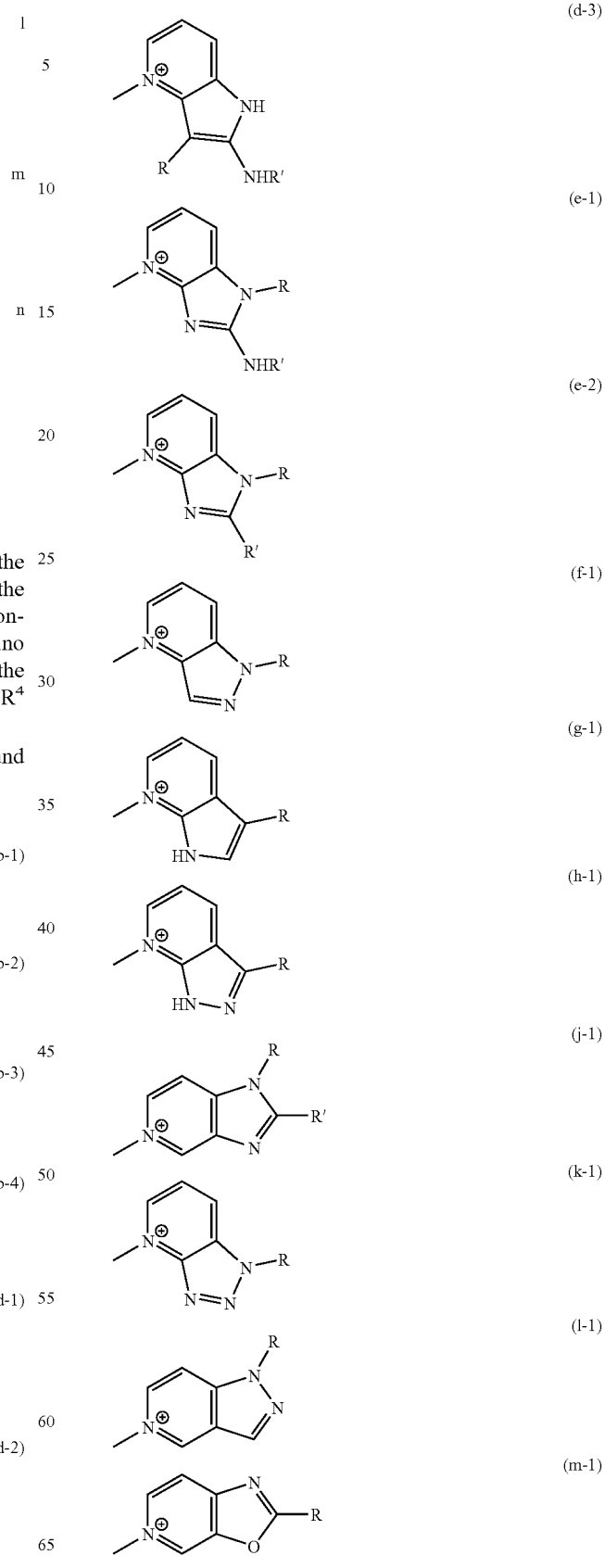

Each R and R' can be selected from the substituents of the above-mentioned heterocycle, and preferred is independently hydrogen, optionally substituted lower alkyl, optionally substituted amino, or optionally substituted heterocyclic group. More preferred is hydrogen, lower alkyl, lower alkenyl, amino lower alkyl, aminohydroxy (lower)alkyl, lower alkylamino(lower)alkyl, hydroxy(lower)alkyl, acyloxyamino (lower)alkyl, acylamino(lower)alkyl, sulfonylamino(lower) alkyl, carbamoyloxy lower)alkyl, lower alkylhydrazonoxy (lower)alkyl, carbamoylamino(lower)alkyl, alkoxycarbonylaminoxy(lower)alkyl, lower alkoxy(lower) alkyl, carbamoyl(lower)alkyl optionally substituted cycloalkyl, lower alkyl substituted with an optionally substituted heterocyclic group, carboxy(lower)alkyl, lower alkoxycarbonylamino(lower)alkyl, halogeno(lower)alkyl, lower alkylamino, amino (lower)alkylamino, lower alkylamino (lower)alkylamino, hydroxy(lower)alkylamino(lower)alkylamino, carbamoyloxy(lower)alkylamino, guanidino(lower) alkylamino, optionally substituted carbamoyl, optionally substituted alkyloxy, optionally substituted carbonylamino, amino substituted with an optionally substituted heterocyclic group, amino(lower)alkyloxy, or optionally substituted heterocyclic group.

R is preferably hydrogen, methyl, ethyl, cyclopropyl, —CH$_2$CH$_2$NH$_2$, —CH$_2$CH$_2$NHCH$_3$, —CH$_2$CH$_2$CH$_2$NHCH$_3$, —CH$_2$CH$_2$NHCH$_2$CH$_2$OH, —CH$_2$CH$_2$CH$_2$NHCH$_2$CH$_2$OH, —CH$_2$CH$_2$CH$_2$NH$_2$, —CH$_2$CH(NH$_2$)CH$_3$, —CH$_2$CH$_2$CH(NH$_2$)CH$_3$, —CH$_2$CH$_2$CH(NH$_2$)CH$_2$OH, —CH$_2$CH$_2$CH(NH$_2$)CH$_2$OCOCH$_3$, —CH$_2$CH(NHCH$_3$)CH$_3$, —CH$_2$CH$_2$OH, —CH$_2$CH$_2$OCONH$_2$, —CH$_2$CH$_2$OCONHOCH$_3$, —CH$_2$CH$_2$OCONHCH$_3$, —CH$_2$CH$_2$OCON(CH$_3$)$_2$, —CH$_2$CH$_2$OCONHN(CH$_3$)$_2$, —CH$_2$CH$_2$OCONHOH, —CH$_2$CH$_2$CH$_2$OCONH$_2$, —CH$_2$CH$_2$ONHCOOCH$_3$, —CH$_2$CH$_2$NHCOOH, —CH$_2$CONH$_2$, —CH$_2$CONHOCH$_3$, —CH$_2$CONHOH, —CH$_2$COOH, —CH$_2$CH$_2$NHCOCH$_3$, —CH$_2$CH$_2$NHCONH$_2$, —CH$_2$CH$_2$NHSO$_2$N$_2$, —CH$_2$CH$_2$NHCOOCH$_3$, —CH$_2$CH$_2$NHC(NH$_2$)=NH, —CH$_2$CH$_2$CH$_2$N(CH$_3$)C(NH$_2$)=NH, —NHCH$_2$CH$_2$N$_2$, —NHCH$_2$CH$_2$NHCH$_3$, —NH(CH$_3$CH$_2$CH$_2$NHCH$_3$, —N(CHO)CH$_2$CH$_2$NHCH$_3$, —NHCOCH$_2$CH(NH$_2$)CH$_3$, —CONHCH$_2$CH$_2$NHCH$_3$, —CONHCH$_2$CH$_2$NHC(NH$_2$) =NH, —OCH$_2$CH$_2$NHCH$_3$,3-azethidinyl, 3-pyrrolidinylamino, 3-pyrrolidinyl, 1-pyrazolyl, 5-(1-(2-hydroxyethyl) pyrazolyl), 5-(1-(2-aminoethyl)pyrazolyl), 2-(1-(5-aminopyrazolyl))ethyl, 4-pyrazolyl, 3-pyrazolyl, 4-(2-carbamoylpyrolyl), 2-pyrrolidinylmethyl, 3-pyrrolidinylmethyl, 5-(3-hydroxypyrrolidinyl)methyl, 2-thiazolyl, 2-oxadiazolyl, 1-triazolyl, 1-(3-methylpiperadinyl), 1-(4-aminopiperidinyl), or 4-piperidinyl.

R' is preferably hydrogen or optionally substituted amino. R' is preferably hydrogen, —NH$_2$, —NHCH$_3$, —N(CH$_3$)$_2$, —N=CHN(CH$_3$)$_2$, —N(CH$_3$)CH$_2$CH$_2$NH$_2$, —NHCH$_2$CH$_2$NHCH$_3$, —NHCOOCH$_2$CH$_3$, —NHOCH$_3$, or —NHCH$_2$COOH.

Z$^+$ is more preferably the following group.

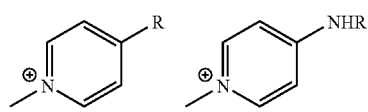

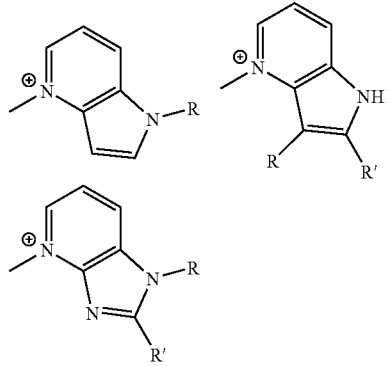

(wherein, each R is independently hydrogen, lower alkyl, amino lower alkyl, lower alkylamino(lower)alkyl, amino substituted with an optionally substituted heterocyclic group, or optionally substituted heterocyclic group; R' is amino)

Z$^+$ is most preferably the following group.

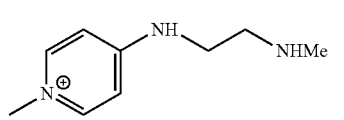

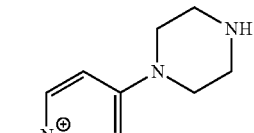

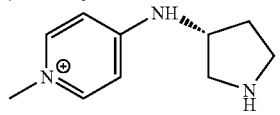

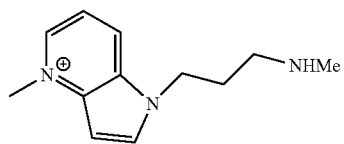

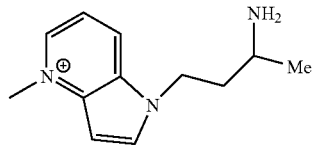

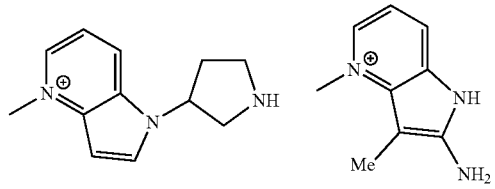

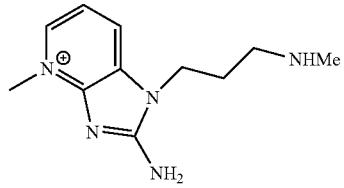

-continued

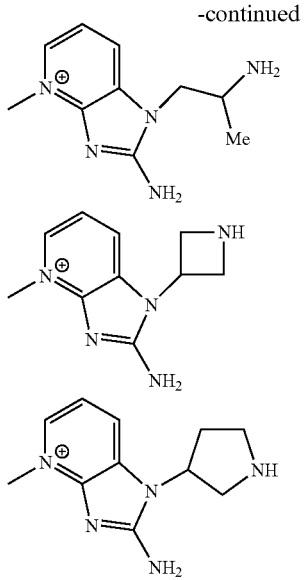

Compound (I) preferably includes the following compounds.

(a) a compound wherein T is S X is halogen or lower alkyl A is a divalent group shown in any of the above (5) to (9); $Z^+$ is a heterocyclic group shown in any of the above-mentioned (10) to (14).

(b) a compound wherein T is S; X is halogen or lower alkyl; A is a divalent group shown in any of the above (8); $Z^+$ is a heterocyclic group shown in the above-mentioned (12). Preferably, X is halogen and $Z^+$ is the above-mentioned (b-1), (b-2), (d-1), (d-3), (e-1), or (e-2).

(c) a compound wherein T is S; X is halogen; A is a divalent group shown in the above (9); $Z^+$ is a heterocyclic group shown in the above-mentioned (13) or (14).

Preferred embodiments include compounds of Examples 1, 3, 4, 5, 8, 9, 18, 19, 20, 79, 98, 111, 112, 124, 128, 132, 161, 164, and 185, and more preferred are compounds of Examples 8, 9, 18, 20, 79, 98, 124, 128, 132, 161, and 164.

The representative method for preparing compound (I) is explained below.

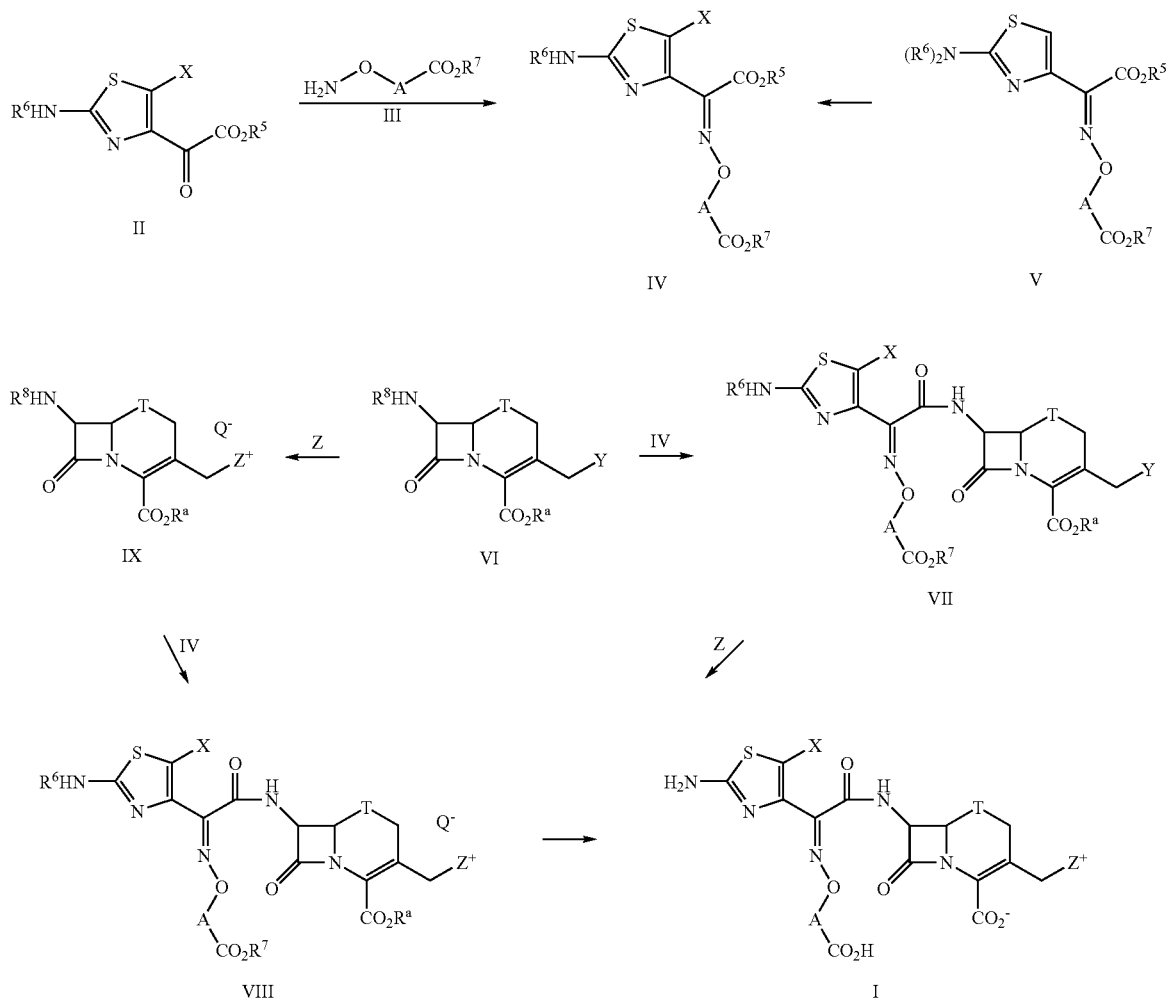

(wherein, T is the same as defined above; $R^5$ is hydrogen or carboxy-protecting group $R^6$ is hydrogen or amino-protecting group; $R^7$ is hydrogen or carboxy-protecting group $R^8$ is hydrogen or amino-protecting group; $R^a$ is hydrogen or carboxy-protecting group; Y is a leaving group (e.g., hydroxy, halogen (e.g., Cl, Br, I), carbamoyloxy, substituted carbamoyloxy, acyloxy, methanesulfonyloxy, toluenesulfonyloxy); $Q^-$ is a counter ion such as halogen)

(1) Production Method of Compound (Iv), Material of 7-side Chain (Method A)

Compound (II) and compound (III) are reacted to give compound (IV). In this case, preferably $R^5$ is hydrogen; $R^6$ is amino-protecting group; $R^7$ is carboxy-protecting group.

The amount of compound (III) is usually about 1 to 10 mol, preferably about 1 to 2 mol per compound (II) 1 mol.

Examples of reaction solvent include ether (e.g., dioxane, tetrahydrofran, diethylether, tert-butyl methyl ether, diisopropylether), ester (e.g., ethyl formate, ethyl acetate, n-butyl acetate), halogenated hydrocarbon (e.g., dichloromethane, chloroform, carbon tetrachloride), hydrocarbon (e.g., n-hexane, benzene, toluene), alcohol (e.g., methanol, ethanol, isopropanol), amide (e.g., formamide, N,N-dimethylformamide, N, N-dimethylacetamide, N-methylpyrrolidone), ketone (e.g., acetone, methyl ethyl ketone), nitrile (e.g., MeCN, propionitrile), dimethyl sulfoxide, water. These solvents can be used as single or a mixture.

The reaction temperature is usually about $-20$ to $100°$ C., preferably about 0 to $5°$ C.

(Method B)

Compound (V) is halogenated, optionally followed by deprotection, to give compound (IV). In this case, preferably $R^5$ is a carboxy-protecting group in compound (V) and hydrogen in compound (IV); $R^6$ is an amino-protecting group; $R^7$ is a carboxy-protecting group.

Examples of halogenating agent include N-chlorosuccinimide, N-chlorophthalimide, $Cl_2$, N-bromosuccinimide, N-bromophthalimide, $Br_2$, and $F_2$.

The amount of halogenating agent is usually about 1 to 20 mol, preferably about 1 to 2 mol per compound (V) 1 mol.

Examples of reaction solvent are the same as mentioned above.

The reaction temperature is usually about $-10$ to $100°$ C., preferably about 0 to $50°$ C.

(2) Acylation at 7-position and 3-side Chain Formation; Production of Compound (VII) and (VIII)

1) Acylation at 7-position

Compound (VI) and compound (IV) are reacted to give compound (VII). Preferably, $R^a$ is a carboxy-protecting group; $R^5$ is hydrogen; $R^6$ is an amino-protecting group: $R^7$ is a carboxy-protecting group; $R^8$ is hydrogen.

The amount of compound (M is usually about 1 to 5 mol, preferably about 1 to 2 mol per compound (VI) 1 mol.

Examples of solvents used in the reaction include ethers (e.g., dioxane, THF, diethylether, tert-butylmethylether, and diisopropylether), esters (e.g., ethyl formate, ethyl acetate, and n-butyl acetate), halogenated hydrocarbons (e.g., dichloromethane, chloroform, and carbon tetrachloride), hydrocarbons (e.g., n-hexane, benzene, and toluene), amides (e.g., formamide, N,N-dimethylformamide (DMF), N,N-dimethylacetoamide, and N-methylpyrrolidone), ketones (e.g., acetone and methylethylketone), nitrites (e.g., MeCN and propionitriles), dimethylsulfoxide, and water.

The reaction temperature is usually about $-40$ to $100°$ C., preferably about 0 to $30°$ C. Compound V, VII, VIII, T=SO) can be prepared by oxidating compound (VI VII, VIII, T=S). Preferably, compound (VII, T=SO) can be prepared by oxidating compound (VII, T=S).

Examples of oxidating agent include m-chloroperoxybenzoic acid (m-CPBA), hydrogen peroxid, and peracetic acid.

Compound (VI) can be prepared according to the method described in JP Patent publication (Kokai) S-60-231684, JP Patent publication (Kokai) S-62-149682 or the like.

The above amidation can be conducted after convertion of the carboxyl moiety into a reactive derivative. Examples of the reactive derivative include inorganic base salts, organic base salts, acid halides, acid azides, acid anhydrides, mixed acid anhydride, active amide, active ester, active thioester. The inorganic base includes alkaline metals (e.g., Na and K) and alkaline earth metals (e.g., Ca and Mg); The organic base includes trimethylamine, triethylamine, tert-butyldimethylamine, dibenzylmethylamine and benzyldimethylamine; the acid halide includes acid chloride and acid bromide; the mixed acid anhydride includes mixed monoalkylcarboxylic acid anhydride, mixed aliphatic carboxylic acid anhydride, aromatic carboxylic acid anhydride, organic sulfonic acid anhydride, the active amide includes amide formed with heterocyclic compound containing N atom, for example. Examples of the active ester include organic phosphate esters (e.g., diethoxy phosphate ester and diphenoxy phosphate ester), p-nitrophenyl ester, 2,4-dinitrophenyl ester, cyanomethyl ester, and the active thioester includes esters formed with aromatic heterocyclicthio compound (e.g., 2-pyridylthio ester).

The above reaction may be carried out using an appropriate condensing agent, if necessary. Examples of the condensing agent include e.g., 1-dimethylaminopropyl-3-ethylcarbodiimide-hydrochloride (WSCD.HCl), N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkoxyacetylene, 2-chloropyridiniummethyl iodine, and 2-fluoropyridiniummethyl iodine, trifluoroacetic acid anhydride.

2) 3-Side Chain Formation

Compound (VII) and Z (optionally substituted N-containing heterocycle) is reacted to give compound (VIII). Preferably, $R^6$ is an amino-protecting group $R^7$ is a carboxy-protecting group $R^a$ is a carboxy-protecting group Compound (VIII) may have a functional group as a substituent on Z, which can be protected.

The amount of Z is usually about 1 to 10 mol, preferably about 1 to 2 mol per compound (VII) 1 mol.

Examples of solvents include ethers (e.g., dioxane, THF, diethyl ether, tert-butyl methyl ether, and diisopropyl ether), esters (e.g., ethyl formate, ethyl acetate, and n-butyl acetate), halogenated hydrocarbons (e.g., dichloromethane, chloroform, and carbon tetrachloride), hydrocarbons (e.g., n-hexane, benzene, and toluene), amides (e.g., formamide, N,N-d- dimethylformamide (DMF), N,N-dimethylacetoamide, and N-methylpyrrolidone), ketones (e.g., acetone and methyl ethyl ketone), nitrites (e.g., MeCN and propionitrile), dimethyl sulfoxide, and water.

The reaction temperature is usually about 0 to 100° C., preferably about 0 to 50° C., and more preferably about 10 to 30° C.

Examples of reaction-accelerating agent include NaI.

Compound (VII, T=S) can be prepared by reducing compound (VIII,T=SO). The reducing agent includes metals (e.g., Zn, Sn) and iodide (e.g., KI).

(3) 3-side Chain Formation and Acylation at 7-position; Production of Compound (IX) and (VIII)

1) 3-side Chain Formation

Compound (VI) and Z (optionally substituted N-containing heterocycle) are reacted to give compound (IX). Preferably, $R^8$ is hydrogen; $R^a$ is a carboxy-protecting group. Compound (VIII) may have a functional group as a substituent on Z, which can be protected.

The amount of Z is usually about 1 to 10 mol, preferably about 1 to 2 mol per compound (VI) 1 mol.

Examples of solvents include ethers (e.g., dioxane, THF, diethyl ether, tert-butyl methyl ether, and diisopropyl ether), esters (e.g., ethyl formate, ethyl acetate, and n-butyl acetate), halogenated hydrocarbons (e.g., dichloromethane, chloroform, and carbon tetrachloride), hydrocarbons (e.g., n-hexane, benzene, and toluene), amides (e.g., formamide, N,N-dimethylformamide (DMF), N,N-dimethylacetoamide, and N-methylpyrrolidone), ketones (e.g., acetone and methyl ethyl ketone), nitrites (e.g., MeCN and propionitrile), dimethyl sulfoxide, and water.

The reaction temperature is usually about 0 to 100° C., preferably about 0 to 50° C., and more preferably about 10 to 30° C.

Examples of reaction-accelerating agent include NaI.

Compound (IX, T=SO) can be prepared by oxidating compound (IX, T=S).

Examples of oxidating agent include m-chloroperoxybenzoic acid (m-CPBA), hydrogen peroxide and peracetic acid.

2) Acylation at 7-position

Compound (IX) and compound (V) are reacted to give compound (VIII). Preferably, $R^a$ is a carboxy-protecting group; $R^5$ is hydrogen; $R^6$ is an amino-protecting group; $R^7$ is a carboxy-protecting group; $R^8$ is hydrogen.

The amount of compound (IV) is usually about 1 to 5 mol, preferably about 1 to 2 mol per compound (IX) 1 mol.

Examples of solvents include ethers (e.g., dioxane, THF, diethyl ether, tert-butylmethyl ether, and diisopropyl ether), esters (e.g., ethyl formate, ethyl acetate, and n-butyl acetate), halogenated hydrocarbons (e.g., dichloromethane, chloroform, and carbon tetrachloride), hydrocarbons (e.g., n-hexane, benzene, and toluene), amides (e.g., formamide, N,N-dimethylformamide (DMF), N,N-dimethylacetoamide, and N-methylpyrrolidone), ketones (e.g., acetone and methyl ethyl ketone), nitrites (e.g., MeCN and propionitrile), dimethyl sulfoxide, and water.

The reaction temperature is usually about −40 to 100° C., preferably about 0 to 30° C., and more preferably about 10 to 30° C.

The above amidation can be conducted after conversion of the carboxyl moiety into a reactive derivative or by using an appropriate condensing agent. Examples of the reactive derivative include inorganic base salts, organic base salts, acid halides, acid azides, acid anhydrides, mixed acid anhydride, active amide, active ester, active thioester.

(4) Deprotection

Compound (VIII) can be deprotected by a method well known to a person skilled in the art to give compound (I).

Examples of solvents include ethers (e.g., dioxane, THF, diethyl ether, tert-butylmethyl ether, and diisopropyl ether), esters (e.g., ethyl formate, ethyl acetate, and n-butyl acetate), halogenated hydrocarbons (e.g., dichloromethane, chloroform, and carbon tetrachloride), hydrocarbons (e.g., n-hexane, benzene, and toluene), amides (e.g., formamide, N,N-dimethylformamide (DMF), N,N-dimethylacetoamide, and N-methylpyrrolidone), ketones (e.g., acetone and methyl ethyl ketone), nitriles (e.g., MeCN and propionitrile), dimethyl sulfoxide, and water.

The reaction temperature is usually about −30 to 100° C., preferably about 0 to 50° C., and more preferably about 0 to 10° C.

Examples of catalyst include Lewis acid (e.g., $AlCl_3$, $SnCl_4$, $TiCl_4$) and protonic acid (e.g., HCl, $H_2SO_4$, $HClO_4$, HCOOH, phenol).

Thus obtained compound (I) can further be chemically modified to give the other compound (I), ester, amino-protected compound wherein the amino bonds to a thiazole ring at the 7-position, or pharmaceutically acceptable salt or solvate thereof.

Ester of compound (I) preferably includes esters which is formed at carboxyl moiety on the 7-side chain or at the 4-position. The ester compound formed at carboxyl moiety on the 7-side chain means a compound having an ester structure of the formula:

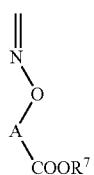

($R^7$ is an ester residue such as carboxy-protecting group)

The ester includes an ester which is readily metabolized in the body to carboxy.

The ester compound formed at the carboxyl moiety at the 4-position means a compound having an ester structure of the formula:

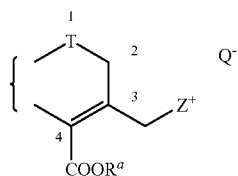

($R^a$ is an ester residue such as carboxy-protecting group; $Q^-$ is an counter ion such as halogen)

The ester includes an ester readily metabolized in the body to carboxy.

Examples of the above carboxy-protecting group include lower alkyl (e.g., methyl, ethyl, t-butyl), (substituted)aralkyl (e.g., benzyl, benzhydryl, p-methoxybenzyl, p-nitrobenzyl), silyl group (e.g., t-butydimethylsilyl, diphenyl t-butylsilyl).

The amino-protected compound (I) wherein the amino bonds to a thiazole ring at the 7-position means a compound wherein the thiazole ring is of the formula:

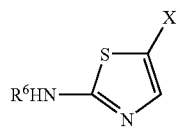

($R^6$ is an amino-protecting group) The amino-protecting group includes that which is readily metabolized in the body to amino. The above amino-protecting group includes lower alkoxycarbonyl (e.g., t-butoxycarbonyl, benzyloxycarbonyl, p-nitrobenzyloxy carbonyl), (substituted) aralkanoyl (e.g., p-nitrobenzoyl), acyl (e.g., formyl, chloro acetyl).

Examples of the pharmaceutically acceptable salt of compound (I) include salts formed with inorganic bases, ammonia organic bases, inorganic acids, organic acids, basic amino acids, halogen ions or the like, and inner salts. Examples of the inorganic base include alkali metal (e.g., Na and K) and alkaline earth metal (e.g., Mg).

Examples of the organic base include procaine, 2-phenylethylbenzylamine, dibenzylethylenediamine, ethanolamine, diethanolamine, tris(hydroxymethyl)aminomethane, polyhydroxyalkylamine, and N-methyl glucosamine. Examples of the inorganic acid include hydrochloric acid, hydrobromic acid, sulfuric acid, nitric acid, and phosphoric acid. Examples of the organic acid include p-toluene sulfonic acid, methanesulfonic acid, formic acid, trifluoroacetc acid and maleic acid. Examples of the basic amino acid include lysine, arginine, ornithine and histidine. Examples of solvate of compound (I) include water and alcohol.

The present invention further provides the above-mentioned compound (I-A). The definition of each group in compound (I-A) and production method thereof are in accordance with those for the above-mentioned compound (I).

Further, the present invention provides the above-mentioned compound (IV), (VII) and (IX). These compounds are useful as intermediates of compound (I). In particular, compound (IV) is an important intermediate for the exhibition of antibacterial activity of compound (I).

In compound (IV), X is preferably halogen or lower alkyl and more preferably halogen (e.g., Cl, Br).

The invention compounds with a broad antibacterial spectrum are useful for the prevention or treatment of various diseases caused by enteropathogenic bacteria of mammals, including respiratory tract infection, urinary tract infection, repiratory tract infection, septicemia, nephritis, cholecystitis, oral infection, endocarditis, pneumonia, bone meningitis, otitis media, enteritis, empyema, wound infection, and opportunistic infection.

The invention compound exhibits a potent antibacterial activity, preferably against gram-negative bacteria including *Pseudomonas*, *E. coli*, and *Haemophilus influenzae*. In particularly, the compound is extremely stable against β-lactamase, esp., C-class β-lactamase, produced by cephem-resistant *Pseudomonas*, thus being efficacious against the *Pseudomonas*. Accordingly, the invention compound can bring an excellent clinical effect even by single use without a β-lactamase inhibitor Further, the invention compound possesses an antibacterial activity against gram-positive bacteria including methicillin-resistant *Staphylococcus aureus* (MRSA) and penicillin-resistant *Staphylococcus aureus* (PRSE). Moreover, it has some excellent characteristics in the pharmacokinetics, such as blood concentration, continuous effect, and transition into tissues. In another embodiment, the invention compound has a high water solubility and particularly suitable for an injection agent.

Compound (I) or (I-A) can be administered parenterally or orally as an agent of injection, capsule, tablet or granule. Preferably, it can be administered as an injection agent. The daily dose for a patient or animal is usually about 0.1 to 100 mg/kg, preferably about 0.5 to 50 mg/kg, optionally in 2 to 4 divisions. The pharmaceutically acceptable carriers used for injections include e.g., distilled water, physiologic saline, and pH adjusting agents such as bases. For preparing capsules, granules, and tables, other pharmaceutically acceptable carriers can be used, such as excipients (e.g., starch, lactose, sucrose, calcium carbonate, calcium phosphate), binders (e.g., starch, Arabian gum, carboxymethyl cellulose, hydroxypropyl cellulose, crystalline cellulose), and lubricants (e.g., magnesium stearate, talc).

Reference Examples and Examples are shown below.

(Abbreviation)

Me: methyl; Et: ethyl; iPr: isopropyl; Bu: butyl; Ac: acetyl; DMF: dimethylformamide; THF: tetrahydrofran; DMA: dimethylacetoamide: WSCD: 1-dimethylaminopropyl-3-ethylcarbodiimide; m-CPBA: m-chloroperoxybenzoic acid; Boc: t-butoxycarbonyl; PMB: p-methoxybenzyl; BH: benzhydryl: TBS: t-butyldimethylsilyl; Ph: phenyl

REFERENCE EXAMPLE 1

Synthesis of 7-side Chain

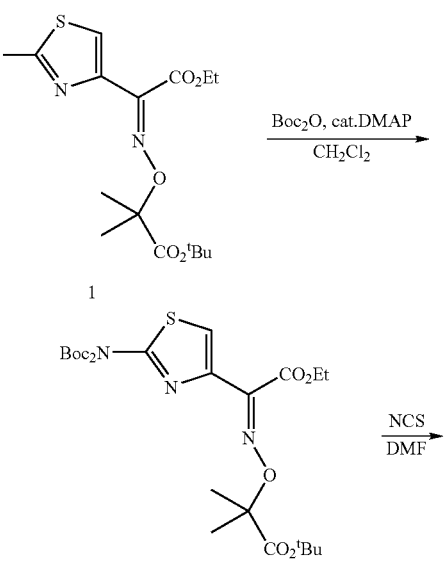

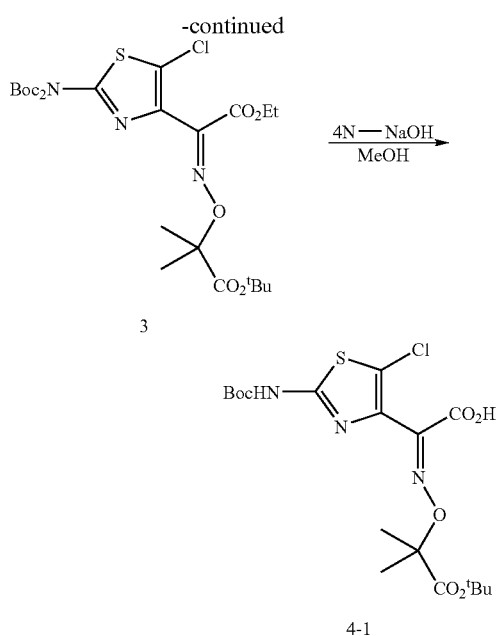

(1) To a solution of compound 1 (71.4 g, 200 mmol) in dry CH$_2$Cl$_2$ 714 nm, was added at room temperature 4-dimethylaminopyridine (DMAP) 2.44 g (0.1 eq) and Boc$_2$O 95.2 ml (2.1 eq) was added dropwise. The reaction mixture was stirred at room temperature for 21 hr, which was poured to a saturated NH$_4$Cl aq. solution containing 1N—HCl 19 ml, then the organic layer was separated, washed with brine, dried over anhydrous Na$_2$SO$_4$, and concentrated in vacuum to give compound 2 (112g).

$^1$H-NMR (CDCl$_1$) δ: 1.35 (3H, t, J=6.9 Hz), 1.43 (9H, s), 1.51 (6H, s), 1.53 (18H, s), 4.36 (2H, q, J=6.9 Hz), 7.38 (1H, s). IR (KBr) cm$^{-1}$: 2979, 2938, 1781, 1743, 1722, 1494, 1457, 1369, 1346, 1328, 1284, 1135. MS(ESI): 558$^+$(M+H$^+$) Elemental analysis C$_{25}$H$_{39}$N$_3$O$_9$S. Calc.: C, 53.84; H, 7.05; N, 7.54; S, 5.75(%). Found: C, 53.70; H, 6.91; N, 7.49 S, 5.81(%).

(2) To a solution of compound 2 101 g (181 mmol) in DMF 400 ml, was added at room temperature N-chlorosuccinimide (NCS) 9.65 g (0.4 eq) and the mixture was stirred at room temperature for 3 hr. NCS 9.65 g (0.4 eq) was added thereto and the mixture was stirred at room temperature for 2 hr, then NCS 9.65 g (0.4 eq) was further added followed by 4 hr stirring at room temperature. The mixture was allowed to stand at 4° C. overnight, which was poured to 1000 ml water containing Na$_2$SO$_4$ 30 g, followed by extraction with AcOEt (500 ml×2). The obtained organic layer was washed with brine, dried over anhydrous Na$_2$SO$_4$, and concentrated in vacuum. Purification with silica gel column chromatography, followed by concentration in vacuum, gave compound 3 (104 g).

$^1$H-NMR(CDCl$_3$) δ: 1.34 (3H, t, J=6.9 Hz), 1.44 (9H, s), 1.52 (6H, s), 1.53 (18H, s), 4.33 (2H, q, J=6.9 Hz). IR (KBr) cm$^{-1}$: 2979, 2938, 1781, 1743, 1722, 1494, 1457, 1369, 1346, 1328, 1284, 1135. MS(ESI): 614$^+$(M+Na$^+$). Elemental analysis C$_{25}$H$_{36}$ClN$_3$O$_9$S. Calc.: C, 50.71; H, 6.47; N, 7.10; S, 5.42; Cl, 5.99(%). Found: C, 50.57; H, 6.40; N, 7.01; S, 5.13; Cl, 5.93(%).

(3) To a solution of compound 383.2 g (140 mmol) in MeOH 1600 ml, 8N-NaOH 175 ml was added dropwise under ice-cooling. The mixture was stirred under ice-cooling for 0.5 hr and further stirred at room temperature for 5.5 hr. 5N—HCl 210 ml was added dropwise (the pH of the reaction solution is 5.3) thereto and the mixture was allowed to stand overnight at room temperature. The mixture was concentrated under reduced pressure to remove MeOH, resulting in precipitation of white precipitates, followed by adding water 1000 ml and filtration. The obtained white solid was washed with ice water and dried under reduced pressure to give compound 4-1 60.9 g.

$^1$H-NMR (CDCl$_3$) δ: 1.46 (9H, s), 1.52 (9H, s), 1.58 (6H, s), 5.20-6.20 (2H, brs). IR (KBr) cm$^{-1}$: 3426, 3220, 3081, 2981, 2937, 1720, 1556, 1455, 1394, 1369, 1249, 1155. MS(ESI): 464$^+$(M+H$^+$). Elemental analysis C$_{18}$H$_{26}$ClN$_3$O$_7$S, 0.6H$_2$O. Calc.: C, 45.54; H, 5.77; N, 8.85; S, 6.75; Cl, 7.47(%). Found: C, 45.38; H, 5.59; N, 8.82; S, 6.67; Cl, 7.75(%).

REFERENCE EXAMPLE 2

Synthesis of 7-side Chain

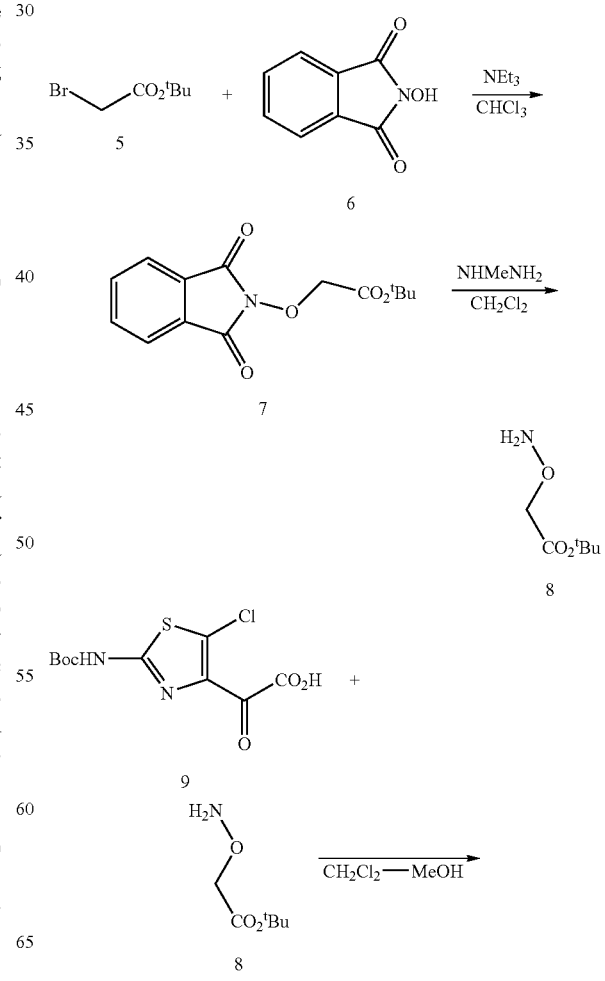

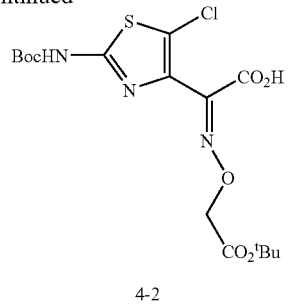

4-2

(1) To a solution of compound 5 (8.8 ml, 60 mmol) and compound 6 (6.52 g 40 mmol) in dry $CHCl_3$ 180 ml, was added dropwise triethylamine 6.12 ml under ice-cooling, and the mixture was stirred at room temperature for 3 days. After adding triethylamine 3.0 ml, the mixture was further stirred at room temperature for 1 day, which was poured to a saturated $NaHCO_3$ aq. solution, followed by extraction with $CHCl_3$. The obtained organic layer was washed with a saturated $NH_4CL$ aq. solution, dried over anhydrous $MgSO_4$, and concentrated under reduced pressure to give compound 7 (10.5 g).

$^1$H-NMR($CDCl_3$) δ: 1.49 (9H, s), 4.71 (2H, s), 7.70-7.90 (4H, m). IR (KBr) $cm^{-1}$: 2980, 2939, 1788, 1745, 1730, 1465, 1441, 1374, 1247, 1186, 1160, 1137, 1043. MS(ESI): 300$^+$ (M+Na$^+$). Elemental analysis $C_{14}H_{15}NO_5 \cdot 0.2H_2O$. Calc.: C, 59.87; H, 5.53; N, 4.99(%). Found: C, 60.04; H, 5.55; N, 5.13(%).

(2) To a solution of compound 7 (1.67 g 6 mmol) in dry $CH_2Cl_2$ 16 ml, was added methyl hydrazine 0.32 ml under ice-cooling and the mixture was stirred for 15 min. The obtained white precipitations were filtered off to give compound 8 in the filtrate. MeOH 6 ml was added thereto under ice-cooling, and compound 9 (1.53 g 5 mmol) was added thereto. After stirring under ice-cooling for 10 min, the mixture was further stirred at room temperature for 2.5 hr and under reflux for 1 hr, then allowed to stand at room temperature for 3 days. The obtained precipitation was filtered and washed with water to give compound 4-2 (1.36 g).

$^1$H-NMR ($d_6$-DMSO) δ: 1.42 (9H, s), 1.46 (9H, s), 4.36 (2H, s), 6.0-9.0 (1H, brs), 11.9 (1H, brs). IR (KBr) $cm^{-1}$: 3429, 3136, 2982, 2936, 1739, 1715, 1626, 1557, 1458, 1392, 1381, 1370, 1249, 1157. MS(FAB): 434$^-$(M–H$^-$). HR-MS (FAB): calcd for $C_{16}H_{21}Cl_1N_3O_7S$ 434.0789 found 434.0782.

The relation of substituent, compound No and structure of Example compounds are exemplified below.

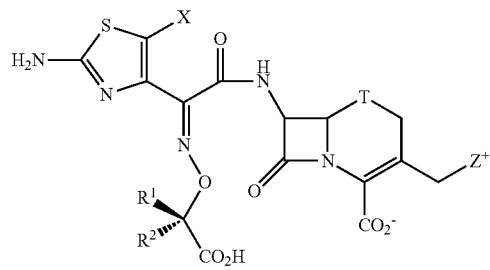

Example of compound No

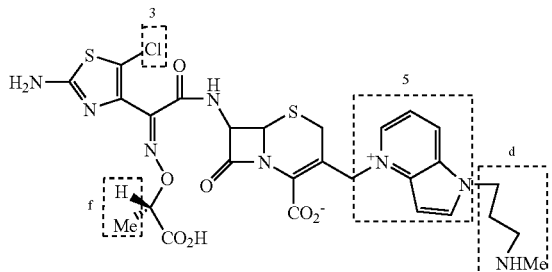

I-3f-5d
7-side chain ⟵ ⟶ 3-side chain

| | 7-side chain | |
|---|---|---|
| X | R1 | R2 |
| 1: H | a: H | H |
| 2: Me | b: =$CH_2$ | |
| 3: Cl | c: —$(CH_2)_2$— | |
| 4: Br | d: Me | Me |
| | e: Me | H |
| | f: H | Me |

-continued
| | | |
|---|---|---|
| g: Et | | H |
| h: H | | Et |
| i: iPr | | H |
| j: H | | iPr |
| k: CH$_2$OH | | H |
| l: H | | CH$_2$OH |
3-side chain
Z
1
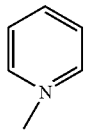
2
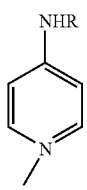
R =
a: H
b: Me
c: (CH$_2$)$_2$NHMe
d: (CH$_2$)$_3$NHMe
3
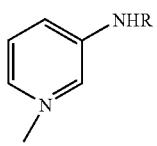
4
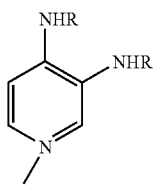
5
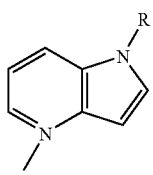
6
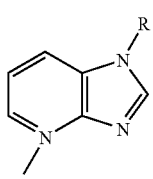
7
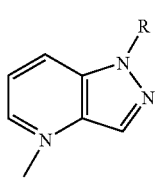

The structure of compound (I) of Examples 1 to 21 are shown below.

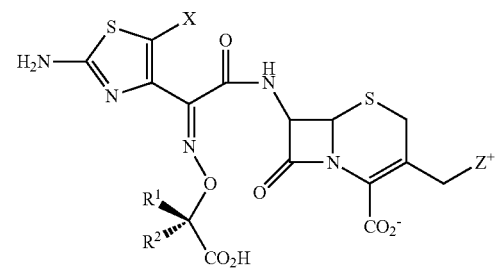

| Example | Compound No | X | R1 | R2 | Z |
|---|---|---|---|---|---|
| 1 | I-2d-5d | Me | Me | Me | 5d |
| 2 | I-3a-5d | Cl | H | H | 5d |
| 3 | I-3d-1 | Cl | Me | Me | 1 |
| 4 | I-3d-2a | Cl | Me | Me | 2a |
| 5 | I-3d-5d | Cl | Me | Me | 5d |
| 6 | I-3d-5d | Cl | Me | Me | 6d |
| 7 | I-3d-5c | Cl | Me | Me | 5c |
| 8 | I-3e-5d | Cl | Me | H | 5d |
| 9 | I-3f-5d | Cl | H | Me | 5d |
| 10 | I-3g-5d | Cl | Et | H | 5d |
| 11 | I-3h-5d | Cl | H | Et | 5d |
| 12 | I-3i-5d | Cl | iPr | H | 5d |
| 13 | I-3j-5d | Cl | H | iPr | 5d |

-continued

| Example | Compound No | X | R1 | R2 | Z |
|---|---|---|---|---|---|
| 14 | I-3k-5d | Cl | CH$_2$OH | H | 5d |
| 15 | I-3l-5d | Cl | H | CH$_2$OH | 5d |
| 16 | I-3f-2a | Cl | H | Me | 2a |
| 17 | I-3c-2a | Cl | —(CH$_2$)$_3$— | | 2a |
| 18 | I-3c-5d | Cl | —(CH$_2$)$_3$— | | 5d |
| 19 | I-3b-5d | Cl | =CH$_2$ | | 5d |
| 20 | I-44-5d | Br | Me | Me | 5d |
| 21 | I-4f-5d | Br | H | Me | 5d |

The synthesis method and physical data are shown below. The synthesis was conducted according to the method of Example 2, 5 etc.

EXAMPLE 1

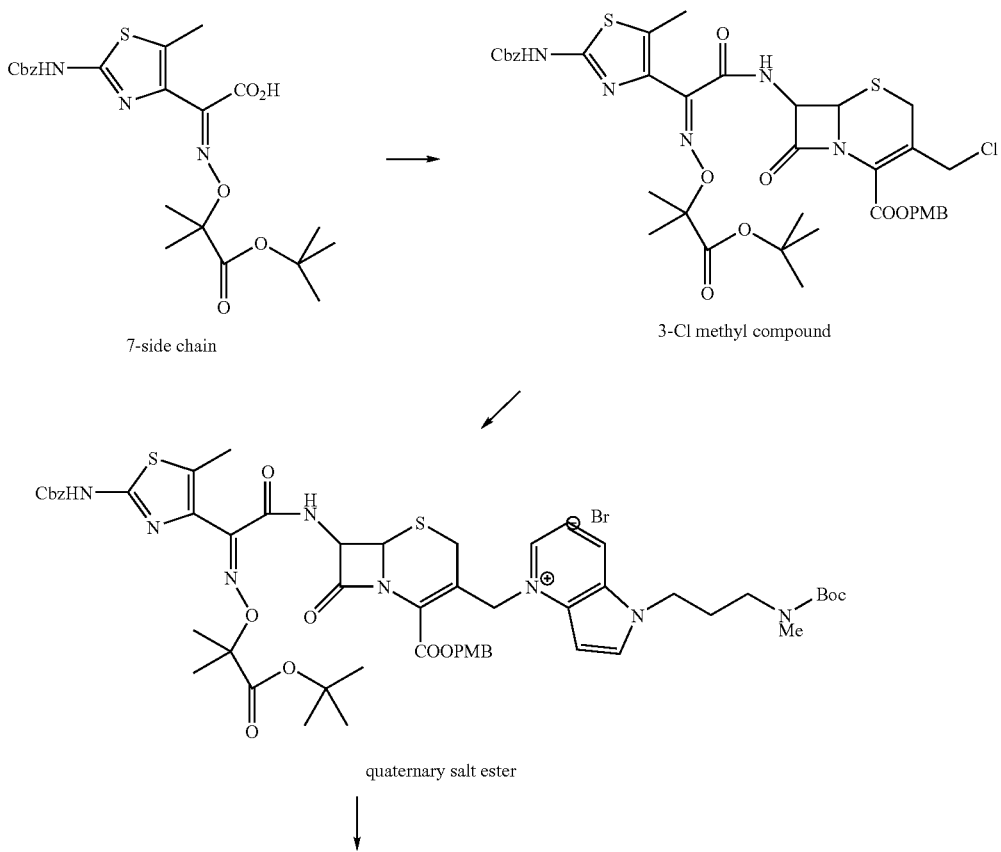

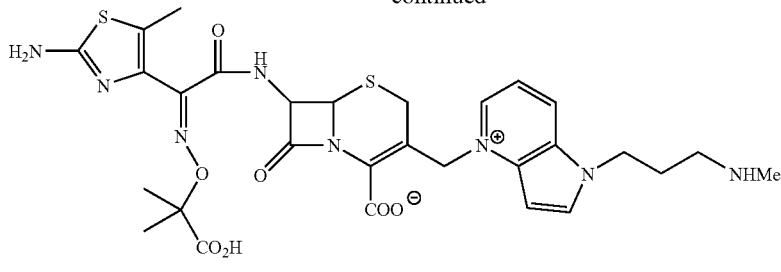

I-2d-5d

I-2d-5d:
$^1$H-NMR (D$_2$O) δ: 1.46 (6H, s), 2.27 (3H, s), 2.31 (2H, m), 2.69 (3H, s), 3.06 (2H, m), 3.18 and 3.39 (2H, ABq, J=17.7 Hz), 4.52 (2H, t, J=7.2 Hz), 5.18 (1H, d, J=4.8 Hz), 5.55 and 5.69 (2H, ABq, J=15.0 Hz), 5.82 (1H, d, J=4.8 Hz), 7.04 (1H, d, J=3.6 Hz), 7.69 (1H, dd, J=6.0 and 8.4 Hz), 8.12 (1H, d, J=3.6 Hz), 8.59 (1H, d, J=8.4 Hz), 8.65 (1H, d, J=6.0 Hz). IR (KBr) cm$^{-1}$: 3413, 2983, 2458, 1774, 1610, 1498, 1467, 1392, 1359, 1288, 1195, 1162, 1122. MS(ESI): 671$^+$(M+H$^-$). Elemental analysis C$_{29}$H$_{34}$N$_3$O$_7$S$_2$·5.6H$_2$O. Calc.: C, 45.14; H, 5.90; N, 14.52; S, 8.31(%). Found: C, 45.15; H, 5.32; N, 14.36; S, 8.49(%).

Quaternary Salt Ester:
$^1$H-NMR (d$_6$-DMSO) δ: 1.37 (9H, s), 1.38 (6H, s), 1.42 (9H, s), 2.03 (2H, m), 2.41 (3H, s), 2.78 (3H, brs), 3.18 (2H, m), 3.36 and 3.56 (2H, m), 3.75 (3H, s), 4.43 (2H, m), 5.17 (1H, d, J=5.1 Hz), 5.21 (2H, s), 5.22 and 5.29 (2H, ABq, J=11.4 Hz), 5.67 and 5.72 (2H, ABq, J=16.2 Hz), 5.96 (1H, dd, J=5.1 and 8.7 Hz), 6.90 (2H, d, J=8.7 Hz), 6.96 (1H, d, J=3.6 Hz), 7.33 (2H, d, J=8.7 Hz), 7.34-7.45 (5H, 7.78 (5H, m), 7.78 (1H, m), 8.43 (1H, d, J=3.3 Hz), 8.62 (1H, d, J=6.0 Hz), 8.88 (1H, d, J=8.4 Hz), 9.49 (1H, d, J=8.7 Hz), 12.1 (1H, brs). IR (KBr) cm$^{-1}$: 3423, 3089, 2973, 2933, 1791, 1724, 1685, 1556, 1515, 1496, 1454, 1390, 1365, 1299, 1247, 1222, 1174, 1145, 1062, 1027. MS(ESI): 1081$^+$(C$_{54}$H$_{65}$N$_8$O$_{12}$S$_2^+$).

3-chloromethyl Compound:
$^1$H-NMR (CDCl$_3$) δ: 1.42 (9H, s), 1.57 (3H, s), 1.58 (3H, s), 2.48 (3H, s), 3.47 and 3.64 (2H, ABq, J=18.3 Hz), 3.81 (3H, s), 4.44 and 4.55 (2H, ABq, J=11.7 Hz), 5.04 (1H, d, J=5.1 Hz), 5.20 and 5.26 (2H, ABq, J=12.0 Hz), 5.25 (2H, S), 6.04 (1H, dd, J=5.1 and 9.3 Hz), 6.90 (2H, d, J=9.0 Hz), 7.35 (2H, d, J=9.0 Hz), 7.30-7.40 (5H, m), 7.90 (1H, d, J=9.3 Hz), 8.38 (1H, brs). IR (KBr) cm$^{-1}$: 3386, 3283, 2979, 2937, 1789, 1726, 1692, 1613, 1557, 1515, 1455, 1383, 1367, 1300, 1247, 1224, 1142, 1094, 1061. MS(ESI): 828$^+$(M+H$^+$). Elemental analysis C$_{38}$H$_{42}$ClN$_5$O$_{10}$S$_2$·0.05 CHCl$_3$·0.7 H$_2$O. Calc.: C, 53.96; H, 5.17; N, 8.27; S, 7.57; Cl, 4.81(%). Found: C, 54.03; H, 5.14; N, 8.16; S, 7.29; Cl, 4.81(%).

7-side Chain
$^1$H-NMR (d$_6$-DMSO) δ: 1.39 (9H, s), 1.41 (6H, s), 2.43 (3H, s), 5.22 (2H, s), 7.30-7.40 (5H, m), 12.0 (1H, brs). IR (KBr) cm$^{-1}$: 3430, 3193, 2981, 2937, 1731, 1614, 1596, 1562, 1455, 1392, 1369, 1299, 1228, 1187, 1141, 1062. MS(ESI): 478$^+$(M+H$^+$).

EXAMPLE 2

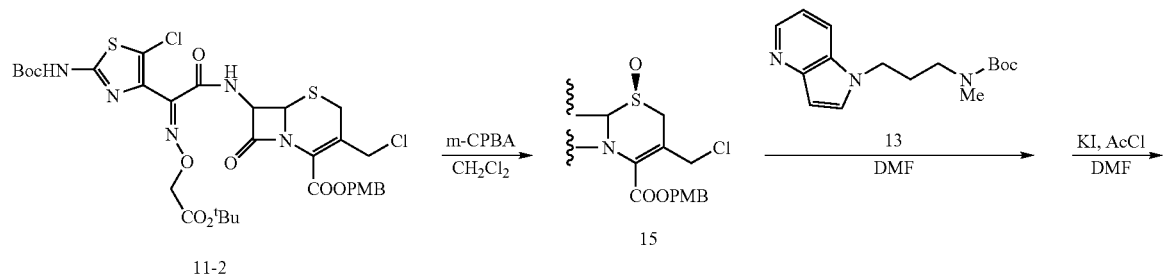

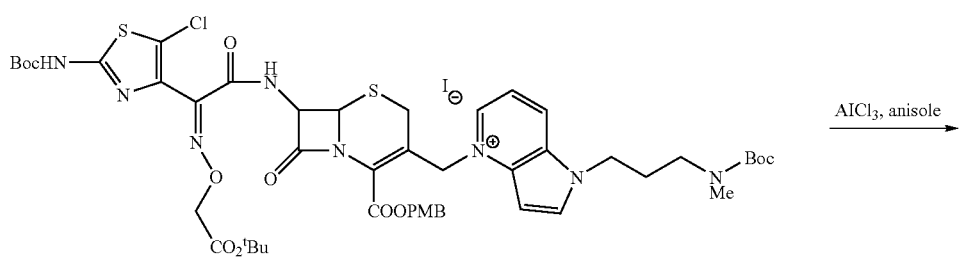

-continued

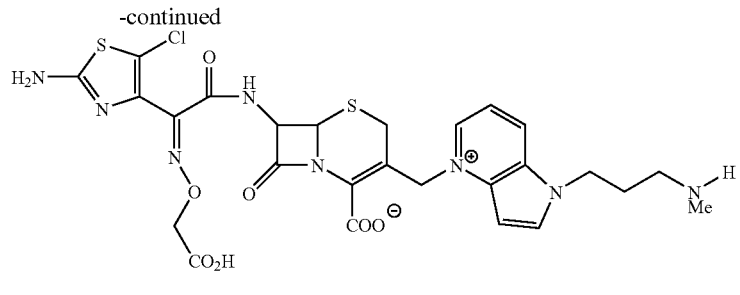

16-2(I-3a-5d)

(1) A solution of compound 11-2 (1.20 g 1.53 mmol) in CH$_2$Cl$_2$ 12 ml was cooled to −50° C. in nitrogen atmosphere, to which was added 2 ml solution of 65% m-CPBA (366 mg 0.9 eq) and the mixture was stirred at −50° C. to −40° C. for 15 min. The reaction mixture was poured to a saturated Na$_2$S$_2$O$_3$ solution and extracted with CHCl$_3$. The obtained organic layer was washed with a saturated NaHCO$_3$ aq. solution and brine, dried over anhydrous MgSO$_4$, and concentrated under reduced pressure. The obtained compound 15 (1.18 g 1.47 mmol) was dissolved to DMF 2 ml under nitrogen atmosphere, to which were added a solution of NaBr (303 mg 2 eq) and compound 13 (627 mg 1.55 eq) in DMF 2 ml. The mixture was stirred at room temperature for 5 hr and allowed to stand overnight at 4° C. DMF 20 ml and KI 1.7 g were added thereto under nitrogen atomosphere and the mixture was cooled to −50° C. AcCl 0.523 ml was added dropwise and the mixture was stirred at −50° C. for 1 hr and at −50° C. to −10° C. for 1.5 hr. The reaction solution was added dropwise to a 5% NaCl solution containing Na$_2$S$_2$O$_3$ 1 g under ice-cooling to give precipitates. The precipitates were collected by filtration and dried using P$_2$O$_5$ under reduced pressure to give compound 14-2 (1.59 g) as powder.

Compound 14-2

$^1$H-NMR (ds-DMSO) δ: 1.40 (9H, a), 1-46 (18H, s), 2.03 (2H, m), 2.78 (3H, brs), 3.18 (2H, t, J=7.2 Hz), 3.27 and 3.43 (2H, ABq, J=18.3 Hz), 3.75 (3H, s), 4.43 (2H, t, J=6.6 Hz), 4.55 (2H, s), 5.18 (1H, d, J=4.8 Hz), 5.21 and 5.28 (2H, ABq, J=120 Hz), 5.65 and 5.73 (2H, ABq, J=15.3 Hz), 5.95 (1H, dd, J=4.8 and 8.7 Hz), 6.89 (2H, d, J=8.7 Hz), 7.00 (1H, d, J=3.3 Hz), 7.35 (2H, d, J=8.7 Hz), 7.78 (1H, dd, J=6.3 and 8.1 Hz), 8.43 (1H, d, J=3.3 Hz), 8.60 (1H, d, J=6.3 Hz), 8.88 (1H, d, J=8.1 Hz), 9.65 (1H, d, J=8.7 Hz), 12.1 (1H, brs). IR (KBr) cm$^{-1}$: 3427, 3058, 2976, 2933, 1791, 1718, 1686, 1630, 1613, 1584, 1550, 1515, 1496, 1455, 1393, 1368, 1300, 1247, 1156, 1080, 1063, 1022. MS(ESI): 1039$^+$(C$_{48}$H$_{60}$ClN$_8$O$_{12}$S$_2$$^+$).

Compound 11-2

$^1$H-NMR(CDCl$_3$) δ: 1.44 (9H, s), 1.53 (9H, s), 3.47 and 3.63 (2H, ABq, J=18.0 Hz), 3.82 (3H, s), 4.45 (2H, s), 4.68 and 4.75 (2H, ABq, J=16.8 Hz), 5.05 (1H, d, J=4.8 Hz), 5.20 and 5.27 (2H, ABq, J=12.0 Hz), 5.98 (1H, dd, J=4.8 and 9.3 Hz), 6.91 (2H, d, J=8.7 Hz), 7.35 (2H, d, J=8.7 Hz), 8.11 (1H, brs), 8.49 (1H, d, J=9.3 Hz). IR (KBr) cm$^{-1}$: 3382, 3277, 2979, 2935, 2837, 1791, 1722, 1613, 1551, 1515, 1455, 1369, 1302, 1246, 1157, 1085, 1062, 1036, 1021. MS(FAB): 786$^+$ (M+H$^+$). HR-MS(FAB): calcd for C$_{32}$H$_{38}$Cl$_2$N$_5$O$_{10}$S$_2$ 786.1437 found 786.1434.

(2) Compound 14-2 (1.59 g, about 1.47 mmol) was deprotected according to Example 5 (3) to give compound 16-2 (I-3a-5d, 270 mg).

$^1$H-NMR (d$_6$-DMSO) δ: 1.40 (9H, s), 1.46 (18H, s), 2.03 (2H, m), 2.78 (3H, brs), 3.18 (2H, t, J=7.2 Hz), 3.27 and 3.43 (2H, ABq, J=18.3 Hz), 3.75 (3H, s), 4.43 (2H, t, J=6.6 Hz), 4.55 (2H, s), 5.18 (1H, d, J=4.8 Hz), 5.21 and 5.28 (2H, ABq, J=12.0 Hz), 5.65 and 5.73 (2H, ABq, J=15.3 Hz), 5.95 (1H, dd, J=4.8 and 8.7 Hz), 6.89 (2H, d, J=8.7 Hz), 7.00 (1H, d, J=3.3 Hz), 7.35 (2H, d, J=8.7 Hz), 7.78 (1H, dd, J=6.3 and 8.1 Hz), 8.43 (1H, d, J=3.3 Hz), 8.60 (1H, d, J=6.3 Hz), 8.88 (1H, d, J=8.1 Hz), 9.65 (1H, d, J=8.7 Hz), 12.1 (1H, brs). IR (KBr) cm$^{-1}$: 3427, 3058, 2976, 2933, 1791, 1718, 1686, 1630, 1613, 1584, 1550, 1515, 1496, 1455, 1393, 1368, 1300, 1247, 1156, 1080, 1063, 1022. MS(ESI): 1039$^+$(C$_{48}$H$_{60}$ClN$_8$O$_{12}$S$_2$$^+$).

EXAMPLE 3

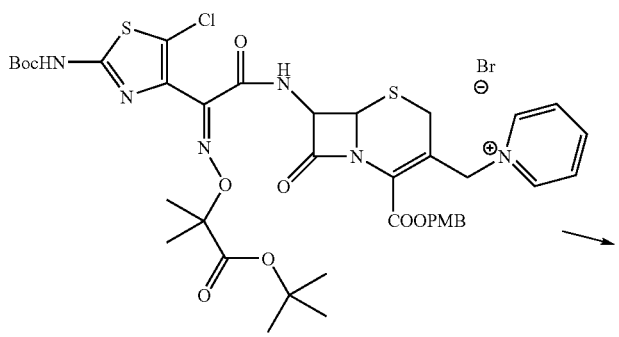

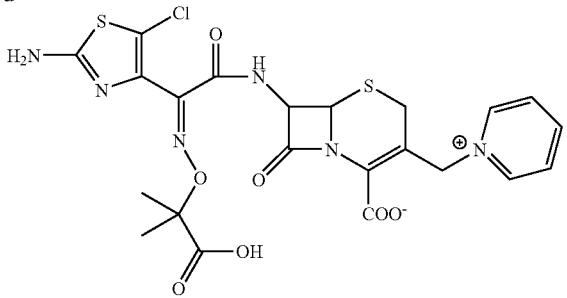

I-3d-1:

$^1$H-NMR (D$_2$O) δ: 1.54 (6H, s), 3.22 and 3.64 (2H, ABq, J=17.7 Hz), 5.28 (1H, d, J=4.8 Hz), 5.34 and 5.58 (2H, ABq, J=14.4 Hz), 5.88 (1H, d, J=4.8 Hz), 8.09 (2H, t like), 8.58 (1H, t like), 8.96 (2H, d, J=6.0 Hz). IR (KBr) cm$^{-1}$: 3417, 3058, 2989, 2938, 2524, 1778, 1673, 1625, 1536, 1486, 1386, 1340, 1157. MS(ESI): 581$^+$(M+H$^+$). Elemental analysis C$_{22}$H$_{21}$ClN$_6$O$_7$S$_2$·2.9H$_2$O. Calc.: C, 41.73; H, 4.27; N, 13.27 Cl, 5.60; S, 10.13(%). Found: C, 41.74; H, 3.99; N, 13.16; Cl, 5.53; S, 10.20(%).

Quaternary Salt Ester:

$^1$H-NMR (d$_6$-DMSO) δ: 1.37 (9H, s), 1.42 (3H, s), 1.44 (3H, s), 1.46 (9H, s), 3.51 (2H, brs), 3.77 (3H, s), 5.20 and 5.26 (2H, ABq, J=12.0 Hz), 5.22 (1H, d, J=5.1 Hz), 5.58 (2H, brs), 5.98 (1H, dd, J=5.1 and 9.0 Hz), 6.93 (2H, d, J=8.4 Hz), 7.35 (2H, d, J=8.4 Hz), 8.20 (2H, t like), 8.66 (1H, t like), 8.99 (2H, d, J=5.7 Hz), 9.57 (1H, d, J=9.0 Hz), 12.1 (1H, brs). IR(KBr) cm$^{-1}$: 3428, 3054, 2979, 2935, 1791, 1718, 1629, 1614, 1548, 1515, 1481, 1455, 1392, 1369, 1299, 1247, 1153, 1064, 1029. MS(ESI): 857$^+$(C$_{39}$H$_{46}$ClN$_6$O$_{10}$S$_2$$^+$).

EXAMPLE 4

I-3d-2a:

$^1$H-NMR (D2O) δ: 1.40 (6H, s), 3.18 and 3.55 (2H, ABq, J=17.7 Hz), 4.88 and 5.02 (2H, ABq, J=14.7 Hz), 5.23 (1H, d, J=4.8 Hz), 5.84 (1H, d, J=4.8 Hz), 6.83 and 8.05 (4H, A2B2q, J=7.5). IR (Br) cm$^{-1}$: 3400, 3189, 2993, 1770, 1654, 1604, 1537, 1398, 1361, 1165. Elemental analysis C$_{27}$H$_{21.2}$N$_7$O$_7$S$_2$ClNa$_{0.8}$·5H$_2$O Calc.: C, 37.55; H, 4.47; N, 13.93; S, 9.11; Cl, 5.04; Na, 2.61(%). Found: C, 37.34; H, 4.28; N, 13.73; S, 9.07; Cl, 4.97; Na, 2.70(%).

Quaternary Salt Ester:

$^1$H-NMR (CDCl$_3$) δ: 1.43 (9H, s), 1.51 (9H, s), 1.55 (9H, s), 1.58 (3H, s), 1.59 (3H, s), 3.35 and 3.92 (2H, ABq, J=19.2 Hz), 3.82 (3H, s), 5.24~5.30 (3H, m), 5.31 and 5.57 (2H, Abq, J=14.4 Hz), 6.01 (1H, dd, J=4.8, 8.7 Hz), 6.90 and 7.36 (4H, A2B2q, J=9 Hz), 8.04-8.12 (3H, m), 8.35 (1H, br s), 8.63 (2H, J=7.5 Hz), 8.98 (1H, s). IR (KBr) cm$^{-1}$: 3422, 3274, 2979, 2934, 1794, 1719, 1641, 1530, 1457, 1369, 1299, 1246, 1146, 842.

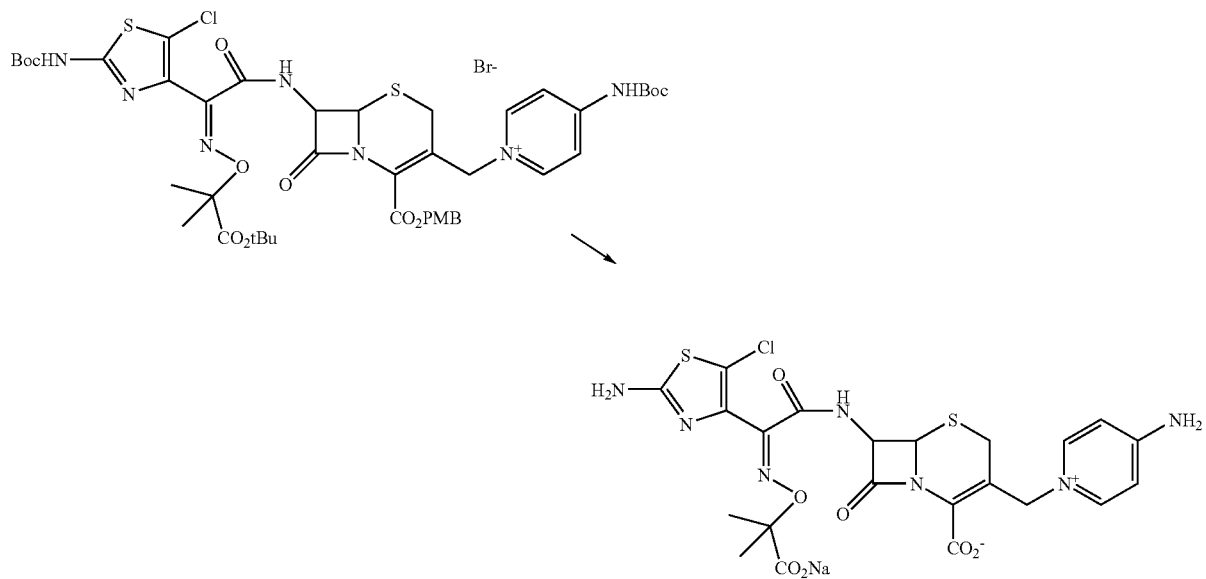

EXAMPLE 5
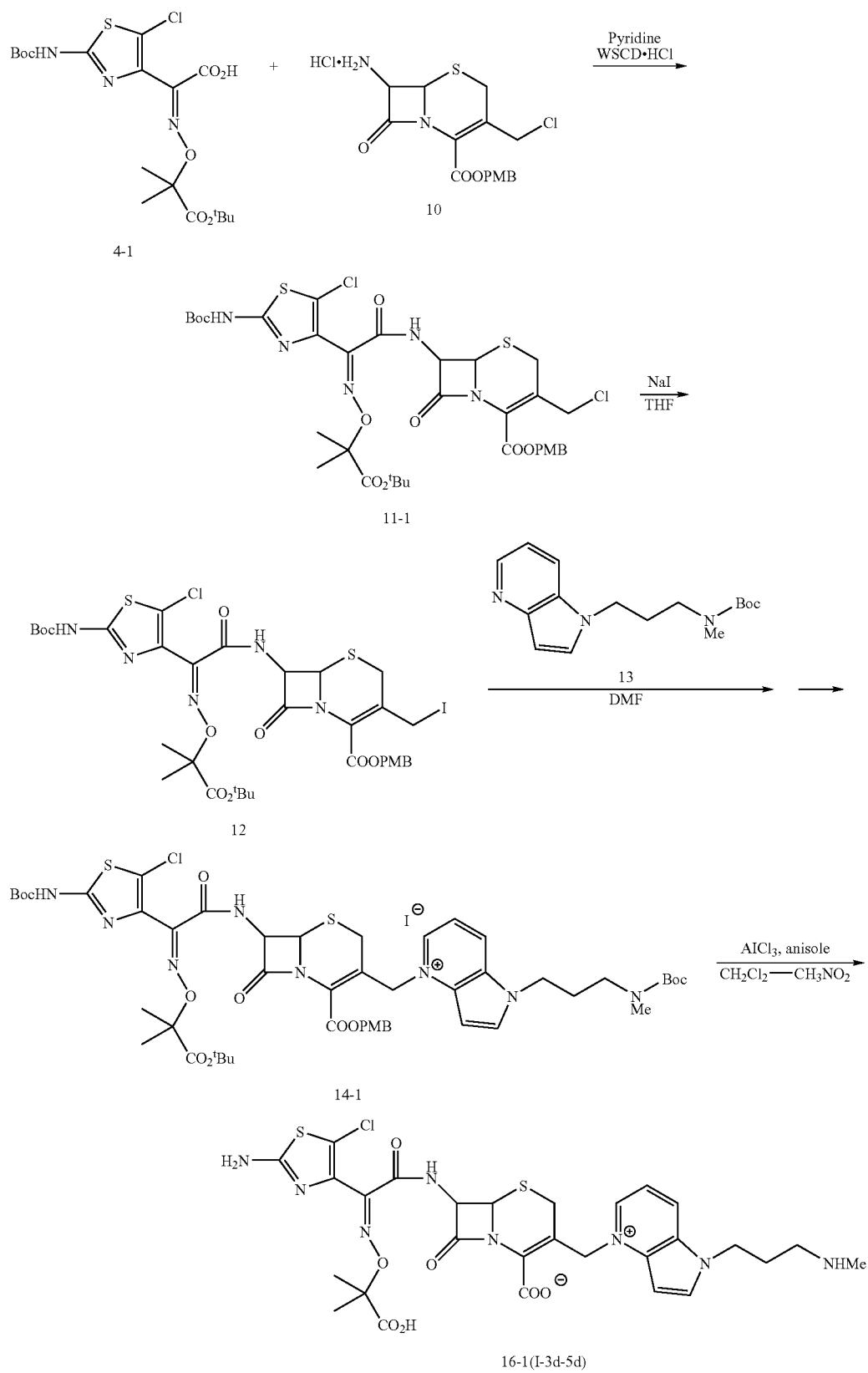

(1) To a solution of compound 4-1 (10.3, 22.2 mmol) obtained in Reference Example 1 and compound 10 (9.90 g 24.4 mmol) in dry DMA 100 ml, were added WSCD.HCl (5.11 g 1.2 eq) and pyridine (1-80 ml, 1.0 eq) under ice-cooling and the mixture was stirred at room temperature for 1 hr. The reaction mixture was poured to ice water 300 ml and extracted with AcOE (200 ml×2). The obtained organic layer washed with brine, dried over anhydrous $MgSO_4$, and concentrated in vacuum. Purification with silica gel column chromatography, followed by concentration in vacuum, gave compound 11-1 (13.7 g) as foam.

$^1$H-NMR (CDCl$_3$) δ: 1.42 (9H, s), 1.52 (9H, s), 1.60 (6H, s), 3.48 and 3.65 (2H, ABq, J=18.0 Hz), 3.82 (3H, s), 4.45 and 4.55 (2H, ABq, J=11.7 Hz), 5.04 (1H, d, J=5.1 Hz), 5.20 and 5.27 (2H, ABq, J=12.0 Hz), 6.03 (1H, dd, J=5.1 and 9.3 Hz), 6.91 (2H, d, J=8.7 Hz), 7.35 (2H, d, J=8.7 Hz), 8.03 (1H, d, J=9.3 Hz), 8.13 (1H, brs). IR (KBr) cm$^{-1}$: 3396, 3284, 2979, 2937, 2836, 1791, 1722, 1614, 1550, 1515, 1455, 1384, 1369, 1301, 1247, 1155, 1035. MS(ESI): 814$^+$(M+H$^+$). Elemental analysis $C_{34}H_{41}Cl_2N_5O_{10}S_2$.0.2 CHCl$_3$.0.4H$_2$O. Calc.: C, 48.56; H, 5.00; N, 8.28; S, 7.58; Cl, 10.90(%). Found: C, 48.51; H, 4.85; N, 8.11; S, 7.56; Cl, 11.00(%).

(2) To a solution of compound 11-1 (5.0 g 6.14 mmol) in THF 50 ml which was cooled to 15° C. under nitrogen atomosphere, was added NaI 2.76 g (3 eq) and the mixture was stirred at 15° C. for 30 min. The reaction solution was poured to ice water 150 ml and extracted with AcOE. The obtained organic layer was washed with a saturated $Na_2S_2O_3$ aq. solution and brine, dried over anhydrous $MgSO_4$, and concentrated under reduced pressure to give compound 12 (5.51 g) as a form. To a solution of compound 12 (2.72 g 3.0 mmol) in DMF 12 ml, was added a solution of compound 13 (868 mg 1 eq) in DMF 3 ml under nitrogen atomosphere. After stirring at room temperature for 1 hr, the reaction mixture was added dropwise to a 5% NaCl solution under ice-cooling to give pale yellow precipitates, which was collected by filtration. Drying with $P_2O_5$ under reduced pressure gave compound 14-1 (3.26 g) as powder.

$^1$H-NMR (d$_6$-DMSO) δ: 1.37 (9H, s), 1.43 (6H, s), 1.46 (18H, s), 2.03 (2H, m), 2.78 (3H, brs), 3.17 (2H, m), 3.28 and 3.39 (2H, ABq, J=16.2 Hz), 3.76 (3H, s), 4.43 (2H, m), 5.18 (1H, d, J=5.1 Hz), 5.22 and 5.30 (2H, ABq, J=11.7 Hz), 5.70 (2H, brs), 5.95 (1H, dd, J=5.1 and 8.7 Hz), 6.90 (2H, d, J=8.7 Hz), 6.95 (1H, d, J=3.3 Hz), 7.33 (2H, d, J=8.7 Hz), 7.78 (1H, dd, J=5.7 and 8.4 Hz), 8.43 (1H, d, J=3.3 Hz), 8.63 (1H, d, d=5.7 Hz), 8.88 (1H, d, J=8.4 Hz), 9.58 (1H, d, J=8.7 Hz), 12.1 (1H, brs). IR (KBr) cm$^{-1}$: 3423, 2977, 2935, 1789, 1718, 1685, 1629, 1612, 1550, 1515, 1496, 1455, 1392, 1367, 1299, 1249, 1153. MS(ESI): 1067$^+$(C$_{50}$H$_{64}$ClN$_8$O$_{12}$S$_2$$^+$).

(3) To a solution of compound 14-1 (3.20 g) in MeNO$_2$ 30 ml and anisole 30 ml, was added a AlCl$_3$-MeNO$_2$ solution (1.5M, 21 ml) in nitrogen atomosphere under ice-cooling and the mixture was stirred for 1 hr. Ice, 1N HCl, CH$_3$CN and Et$_2$O were added thereto, and the water layer was separated and concentrated in vacuum. Purification with HP-20 chromato, followed by lyophilization, gave compound 16-1 (I-3d-5d, colorless powder, 900 mg).

$^1$H-NMR (1) δ: 2.30 (2H, m), 2.68 (3H, s), 3.05 (2H, m), 3.15 and 3.38 (2H, ABq, J=17.7 Hz), 4.52 (2H, t, J=6.9 Hz), 4.54 (2H, s), 5.16 (1H, d, J=4.8 Hz), 5.56 and 5.67 (2H, ABq, J=15.0 Hz), 5.83 (1H, d, J=4.8 Hz), 7.04 (1H, d, J=3.6 Hz), 7.68 (1H, dd, J=6.0 and 8.1 Hz), 8.12 (H1, d, J=3.6 Hz), 8.59 (1H, d, J=8.1 Hz), 8.65 (1H, d, J=6.0 Hz). IR (KBr) cm$^{-1}$: 3394, 2817, 1773, 1604, 1539, 1498, 1466, 1391, 1361, 1317, 1163, 1121, 1055, 1033. MS(ESI): 663$^+$(M+H$^+$). Elemental analysis $C_{26}H_{27}ClN_8O_7S_2$.3.7 H$_2$O. Calc. C, 42.79; H, 4.75; N, 15.35; Cl, 4.86; S, 8.79(%). Found: C, 42.78; H, 4.66; N, 15.42; Cl, 4.81; S, 9.02(%).

EXAMPLE 6

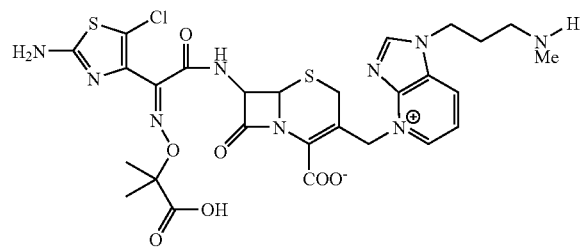

I-3d-6d:

$^1$H-NMR (Ds-DMSO-D$_2$O) δ: 1.38 (6H, brs), 2.23 (2H, brs), 2.48 (3H, s), 2.92 (2H, brs), 3.13 and 3.52 (2H, ABq, J=17.4 Hz), 4.55 (2H, brs), 5.06 (1H, d, J=4.8 Hz), 5.59 and 5.70 (2H, ABq, J=12.9 Hz), 5.79 (1H, d, J=4.8 Hz), 7.71 (1H, t like), 8.82 (1H, d, J=7.8), 9.04 (1H, s), 9.19 (1H, d, J=5.1 Hz). IR(KBr) cm$^{-1}$: 3421, 2460, 1772, 1610, 1538, 1488, 1465, 1394, 1359, 1315, 1234, 1159. MS(ESI): 692$^+$(M+H$^+$). Elemental analysis $C_{27}H_{30}ClN_9O_7S_2$.5.3H$_2$O). Calc.: C, 40.98; H, 5.18; N, 15.93; Cl, 4.93; S, 8.10(%). Found: C, 40.70; H, 4.88; N, 15.74; Cl, 4.94; S, 7.97(%).

EXAMPLE 7

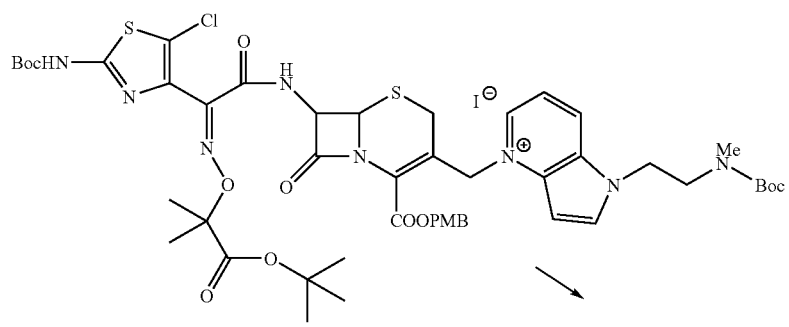

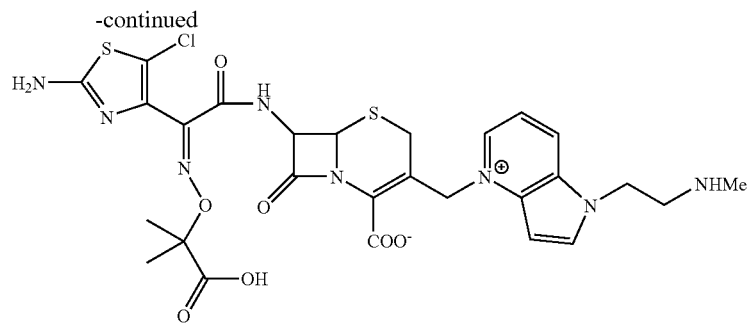

I-3d-5c:
$^1$H-NMR (D$_2$O) δ: 1.48 (6H, s), 2.73 (3H, s), 3.17 and 3.40 (2H, ABq, J=17.7 Hz), 3.61 (2H, t, J=6.0 Hz), 4.79 (2H, t, J=6.0 Hz), 5.17 (1H, d, J=5.1 Hz), 5.57 and 5.69 (2H, ABq, J=150 Hz), 5.81 (1H, d, J=5.1 Hz), 7.10 (1H, d, J=3.3 Hz), 7.70 (1H, dd, J=6.3 and 8.1 Hz), 8.14 (1H, d, J=3.3 Hz), 8.61 (1H, d, J=8.1 Hz), 8.69 (1H, d, J=6.3 Hz). IR (KBr) cm$^{-1}$: 3401, 2987, 2451, 1772, 1606; 1538, 1500, 1467, 1396, 1361, 1288, 1159, 1120. MS(ESI): 677$^+$(M+H$^+$). Elemental analysis C$_{27}$H$_{29}$ClN$_8$O$_7$S$_2$.6.5 H$_2$O. Calc.: C, 40.83; H, 5.33; N, 14.11; Cl, 4.46: S, 8.07(%). Found: C, 40.82; H, 5.14; N, 14.12; Cl, 4.57; S, 8.03(%).

Quaternary Salt Ester:
$^1$H-NMR (d$_6$-DMSO) δ: 1.37 (9H, s), 1.39 (3H, s), 1.43 (3H, s), 1.46 (18H, s), 2.80 (3H, brs), 3.27 and 3.39 (2H, m), 3.59 (2H, m), 3.76 (3H, s), 4.60 (2H, brs), 5.17 (1H, d, J=5.1 Hz), 5.23 and 5.31 (2H, ABq, J=12.0 Hz), 5.72 (2H, brs), 5.96 (1H, dd, J=5.1 and 8.7 Hz), 6.92 (2H, d, J=8.4 Hz), 7.02 (1H, d, J=3.6 Hz), 7.36 (2H, d, J=8.4 Hz), 7.82 (1H, m), 8.31 (1H, d, J=3.6 Hz), 8.67 (1H, m), 8.85 (1H, m), 9.58 (1H, d, J=8.7 Hz), 12.1 (1H, brs).

EXAMPLE 8

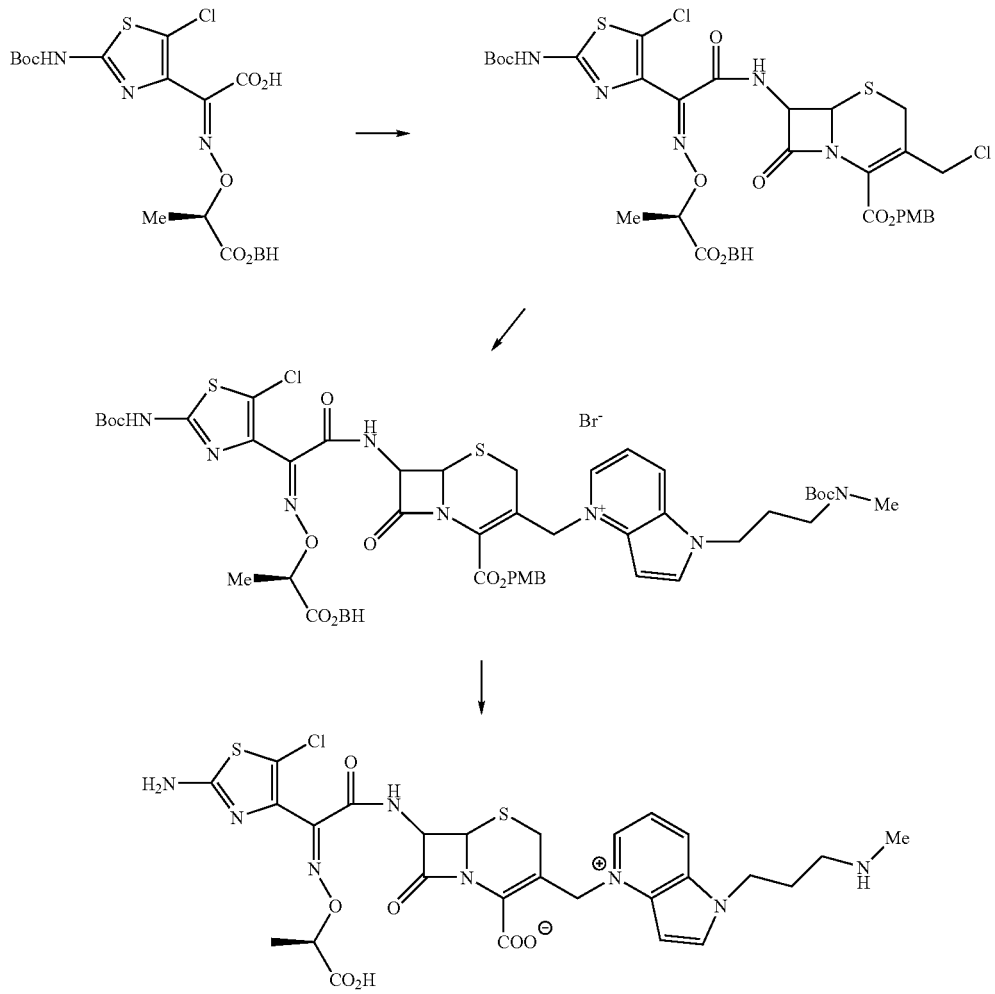

I-3e-5d:

¹H-NMR (D2O) δ: 1.40 (3H, d, J=6.9 Hz), 2.31 (2H, q like), 2.68 (3H, s), 3.05 (2H, t like), 3.14 and 3.39 (2H, ABq, J=17.7 Hz), 4.52 (2H, t like), 4.61 (1H, q, J=6.9 Hz), 5.19 (1H, d, J=4.8 Hz), 5.57 and 5.67 (2H, ABq, J=15 Hz), 5.80 (1H, d, J=4.5 Hz), 7.06 (1H, d, J=3.6), 7.69 (1H, dd, J=6.0, 8.1 Hz), 8.12 (1H, d, J=3.6 Hz), 8.59 (1H, d, J=8.1 Hz), 8.64 (1H, d, J=6.0 Hz). IR (KBr) cm⁻¹: 3411, 1774, 1606, 1539, 1498, 1392, 1363, 1034, 759. Positive ESIMS: m/z 677 [M+H]+. Negative ESIMS: m/z 675 [M−H]−. Elemental analysis as $C_{27}H_{29}N_8O_7S_2Cl$, 6.2H₂O Calc.: C, 41.11; H, 5.29; N, 14.20; S, 8.13; Cl, 4.49(%). Found: C, 40.99; H, 5.07; N, 14.15; S, 8.21; Cl, 4.76(%).

Quaternary Salt Ester:

¹H-NMR (CDCl₃) δ: 1.48 (9H, s), 1.51 (9H, s), 1.60 (3H, d, J=7.2 Hz), 2.22 (2H, t like), 2.91 (3H, s), 3.17 and 3.73 (2H, ABq, J=18.6 Hz), 3.37 (2H, t like), 3.81 (3H, s), 4.44 (2H, t like), 5.03 (1H, q, J=7.2 Hz), 5.17 (1H, d, J=5.1 Hz), 5.24 and 5.30 (2H, ABq, J=11.7 Hz), 5.63 and 5.75 (2H, ABq, J=15 Hz), 6.01 (1H, dd, J=5.1, 9 Hz), 6.87 (2H, d, J=8.7 Hz), 6.88 (1H, s), 7.24~7.35 (12H, m), 7.59 (1H, dd, J=6,8.1 Hz), 7.78 (1H, d, J=9 Hz), 8.24 (1H, m), 8.34 (1H, br s), 8.48 (1H, d, J=8.1 Hz), 8.53 (1H, d, d=6.0 Hz) IR (KBr) cm⁻¹: 3430, 3091, 3060, 1793, 1718, 1684, 1630, 1549, 1516, 1367, 1247, 1153, 1034, 754, 702.

3-chloromethyl Compound:

¹H-NMR (CDCl₃) δ: 1.53 (9H, s), 1.65 (3H, d, J=7.2 Hz), 3.23 and 3.47 (2H, ABq, J=18.3 Hz), 3.82 (3H, s), 4.39 and 4.55 (2H, ABq, J=12 Hz), 4.99 (1H, d, J=5.1 Hz), 5.10 (1H, q, J=7.2 Hz), 5.21 and 5.27 (2H, ABq, J=12 Hz), 5.99 (1H, dd, J=5.1, 9.9 Hz), 6.91 (3H, m), 7.16~7.37 (12H, m), 7.76 (1H, d, J=9.9 Hz), 8.20 (1H, br s). IR (r) cm⁻¹: 3373, 3286, 2979, 2937, 1791, 1720, 1612, 1550, 1515, 1248, 1155, 1035, 700.

7-side Chain (NEt₃ Salt):

¹H-NMR (CDCl3) δ: 1.50 (9H, s), 1.51 (3H, d, J=7.2 Hz), 4.94 (1H, q, J=7.2), 6.89 (1H, s), 7.23~7.35 (10H, m). IR (KBr) cm⁻¹: 3429, 2981, 2937, 1739; 1714, 1612, 1556, 1250, 1157, 1036, 964, 700, Positive ESIMS: m/z 560[M+H]+, m/z 582[M+Na]+. Negative ESIMS: m/z 558[M−H]−, m/z 580[M+Na−2H]−.

EXAMPLE 9

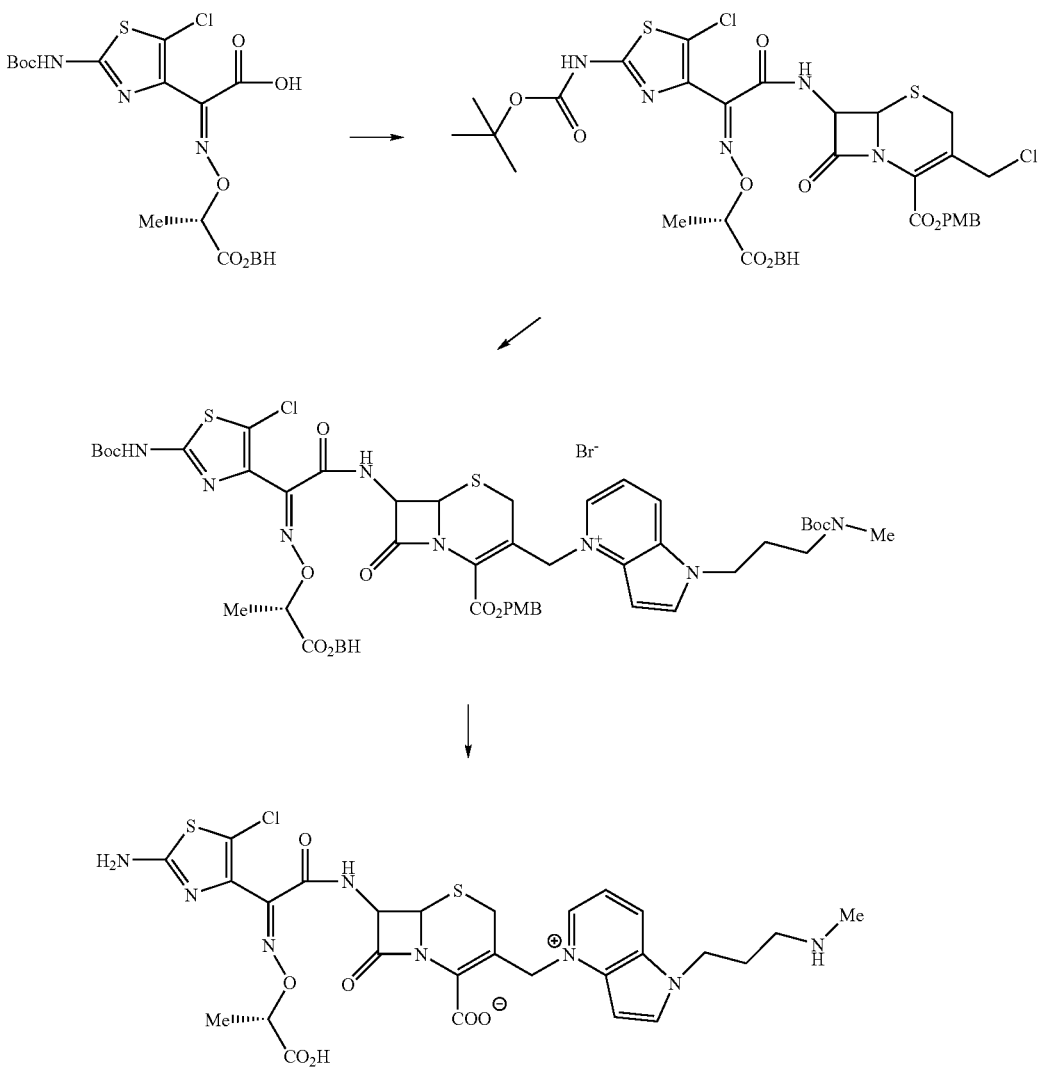

I-3f-5d $^1$H-NMR (D2O) δ: 1.43 (3H, d, J=7.2 Hz), 2.31 (2H, q like), 2.68 (3H, s), 3.05 (2H, t, J=8 Hz), 3.18 and 3.37 (2H, ABq, J=18 Hz), 4.53 (2H, t like), 4.65 (1H, q, J=7.2 Hz), 5.17 (1H, d, J=4.8 Hz), 5.54 and 5.70 (2H, ABq, J=15 Hz), 5.86 (1H, d, J=4.5 Hz), 7.03 (1H, d, J=3.6 Hz), 7.69 (1H, dd, J=6, 8.4 Hz), 8.13 (1H, d, J=3.6 Hz), 8.60 (1H, d, J=8.4 Hz), 8.64 (1H, d, J=6 Hz). IR (KBr) cm$^{-1}$: 3398, 1775, 1603, 1541, 1392, 1363, 1320, 1286, 1033, 762. Positive ESIMS: m/z 677 [M+H]+. Negative ESIMS: m/z 675 M−H−. Elemental analysis as $C_{27}H_{29}N_8O_7S_2Cl \cdot 6.2H_2O$. Calc.: C, 41.11; H, 5.29; N, 14.20; S, 8.13; Cl, 4.49(%). Found: C, 40.88; H, 4.88; N, 14.23; S, 8.05; Cl, 4.57(%).

Quaternary Salt Ester:

$^1$H-NMR (CDCl$_3$) δ: 1.48 (9H, s), 1.51 (9H, s), 1.62 (3H, d, J=7.2 Hz), 2.21 (2H, m), 2.91 (3H, s), 3.24 and 3.82 (2H, ABq, J=18.9 Hz), 3.36 (2H, m), 3.81 (3H, s), 4.43 (2H, t like), 5.09 (1H, q, J=7.2 Hz), 5.16 (1H, d, J=5.1 Hz), 5.24 and 5.31 (2H, ABq, J=11.7 Hz), 5.58 and 5.75 (2H, ABq, J=14.7 Hz), 5.99 (1H, dd, J=5.1, 8.7 Hz), 6.86 (1H, s), 6.87 (2H, d, J=8.7 Hz), 7.00 (1H, br s), 7.24-7.38 (12H, m), 7.55 (1H, t like), 7.78 (1, d, J=8.7 Hz), 8.25 (1H, br s), 8.47 (1H, d, J=10.2 Hz), 8.50 (1H, d, J=6 Hz).

3-chloromethyl Compound:

$^1$H-NMR (CDCl$_3$) δ: 1.53 (9H, s), 1.64 (6H, d, J=7.2 Hz), 3.39 and 3.58 (2H, ABq, J=18.3 Hz), 3.81 (3H, s), 4.42 and 4.59 (2H, ABq, J=12 Hz), 4.97 (1H, d, J=5.1 Hz), 5.08 (1H, q, J=7.2 Hz), 5.20 and 5.27 (2H, ABq, J=11.7 Hz), 6.01 (1H, dd, J=5.1, 9.3 Hz), 6.88-6.91 (3H, m), 7.06-7.35 (12H, m), 7.85 (1H, d, J=9.3 Hz), 8.15 (1H, br s). IR (KBr) cm$^{-1}$: 3281, 2980, 2935, 2836, 1790, 1719, 1612, 1552, 1515, 1454, 1369, 1247, 1155, 1035, 700.

7-Side Chain:

$^1$H-NMR (CDCl$_3$) δ: 1.47 (9H, s), 1.49 (3H, J=7.2 Hz), 4.99 (1H, q, J=7.2 Hz).

EXAMPLE 10

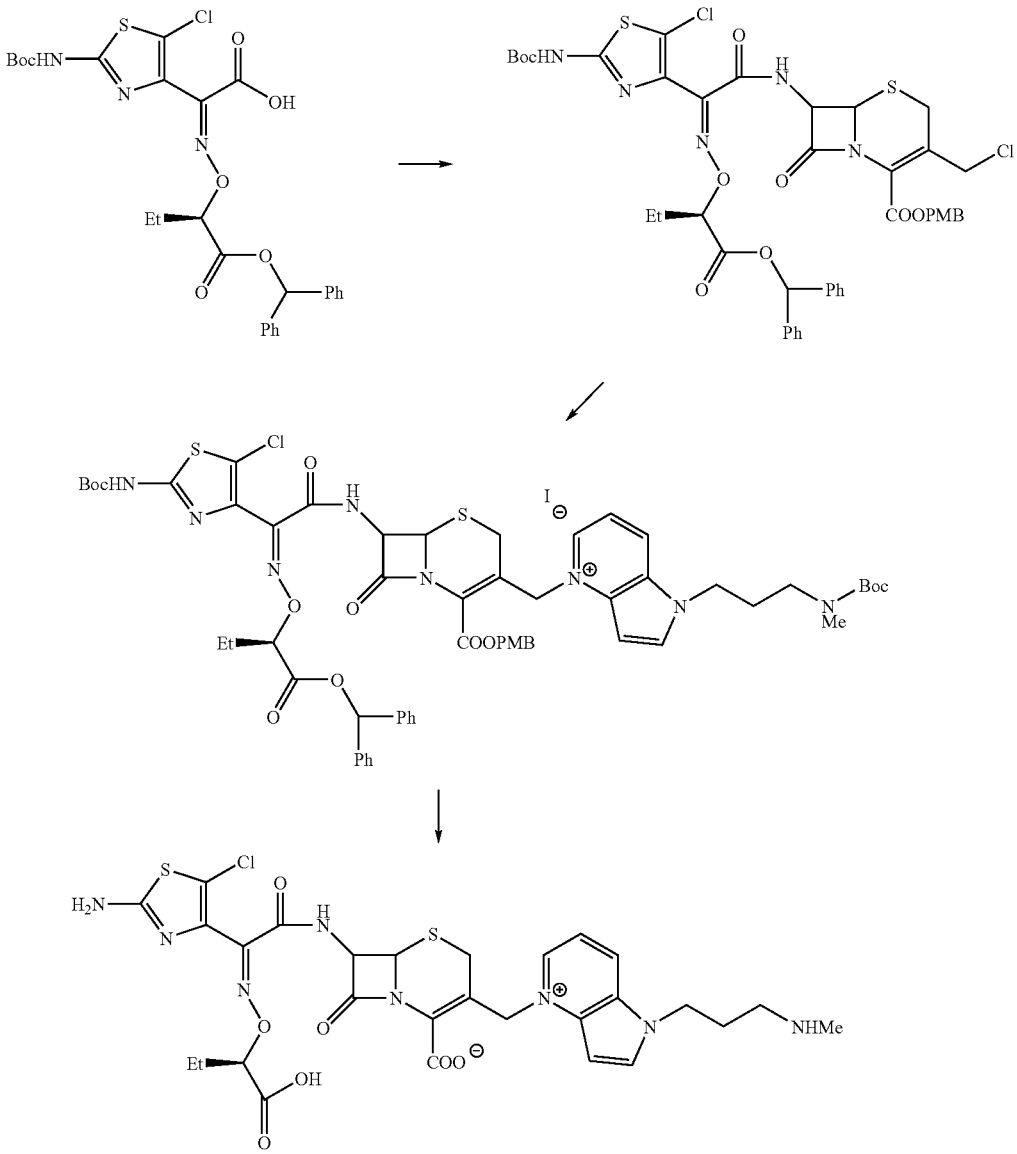

I-3g-5d:

¹H-NMR (D₂O): 0.90 (3H, t, J=7.5 Hz), 1.79 (2H, quintet-like), 2.31 (2H, quintet-like), 2.69 (3H, s), 3.05 (2H, t, J=8.1 Hz), 3.12 and 3.39 (2H, ABq, J=18.0 Hz), 4.45 (1H, t, J=6.6 Hz), 4.52 (2H, t, J=7.2 Hz), 5.19 (1H, d, J=4.8 Hz), 5.58 and 5.66 (2H, ABq, J=14.7 Hz), 5.78 (1H, d, J=4.8 Hz), 7.06 (1H, d, J=3.3 Hz), 7.69 (1H, dd, J=6.0 and 8.1 Hz), 8.12 (1H, d, J=3.3 Hz), 8.59 (1H, d, J=8.1 Hz), 8.65 (1H, d, J=6.0 Hz). IR (KBr) cm⁻¹: 3397, 2967, 1774, 1604, 1537, 1497, 1459, 1390, 1361, 1315, 1159, 1120, 1051, 1031. MS(ESI): 691⁺ (M+H⁺). Elemental analysis as C₂₈H₃₁ClN₈O₇S₂.4.9 H₂O. Calc.: C, 43.15; H, 5.28; N, 14.38; Cl, 4.55; S, 8.23(%). Found: C, 43.02; H, 5.01; N, 14.51; Cl, 4.54; S, 8.27(%).

Quaternary Salt Ester:

¹H-NMR (d₆-DMSO) δ: 0.90 (3H, t, J=7.2 Hz), 1.36 (9H, brs), 1.45 (9H, s), 1.85 (2H, quintet-like), 2.03 (2H, quintet-like), 2.78 (3H, brs), 3.18 (2H, t, J=6.9 Hz), 3.28 and 3.34 (2H, ABq, J=15.9 Hz), 3.75 (3H, s), 4.43 (2H, t, J=6.9 Hz), 4.71 (1H, t, J=6.6 Hz), 5.18 (1H, d, J=4.8 Hz), 5.21 and 5.30 (2H, ABq, J=11.7 Hz), 5.66 and 5.72 (2H, ABq, J=15.6 Hz), 5.99 (1H, dd, J=4.8 and 9.0 Hz), 6.84 (1H, s), 6.88 (2H, d, J=8.7 Hz), 6.97 (1H, d, J=3.6 Hz), 7.20-7.44 (12H, m), 7.76 (1H, dd, d=6.3 and 8.1 Hz), 8.42 (1H, d, J=3.6 Hz), 8.60 (1H, d, J=6.3 Hz), 8.88 (1H, d, J=8.1 Hz), 9.69 (1H, d, J=9.0 Hz), 12.1 (1H, brs). IR (KBr) cm⁻¹: 3414, 3062, 3032, 2975, 2935, 1791, 1717, 1686, 1630, 1613, 1585, 1550, 1515, 1495, 1455, 1393, 1367, 1248.1154, 1018. MS(ESI): 924⁺(M+H⁺).

3-chloromethyl Compound:

¹H-NMR (CDCl₃) δ: 1.08 (3H, t, J=7.2 Hz), 1.53 (9H, s), 1.90-2.10 (2H, m), 3.26 and 3.50 (2H, ABq, J=18.3 Hz), 3.82 (3H, s), 4.40 and 4.56 (2H, ABq, J=11.7 Hz), 4.91 (1H, dd, J=5.1 and 9.0 Hz), 4.99 (1H, d, J=5.1 Hz), 5.21 and 5.28 (2H, ABq, J=11.7 Hz), 5.98 (1H, dd, J=5.1 and 9.6 Hz), 6.91 (2H, d, J=8.7 Hz), 6.93 (1H, s), 7.25-7.32 (10H, m), 7.36 (21, d, d=8.7 Hz), 7.72 (1H, d, J=9.6 Hz), 8.01 (1H, brs). IR (KBr) cm⁻¹: 3378, 3291, 3063, 3032, 2975, 2935, 1791, 1721, 1613, 1550, 1515, 1455, 1384, 1368, 1301, 1246, 1155, 1109, 1058, 1032, 1003.

7-side Chain

¹H-NMR (d₆-DMSO) δ: 0.89 (3H, t, J=7.5 Hz), 1.46 (9H, s), 1.78 (2H, quintet like), 4.52 (1H, t, J=6.9 Hz), 6.84 (1H, s), 7.23-7.46 (10H, m), 12.0 (1H, brs). IR (KBr) cm⁻¹: 3428, 3164, 3063, 3032, 2978, 2936, 1717, 1623, 1557, 1496, 1455, 1392, 1370, 1292, 1251, 1210, 1157, 1105, 1056, 1036. MS(ESI): 574⁺(M+H⁺).

EXAMPLE 11

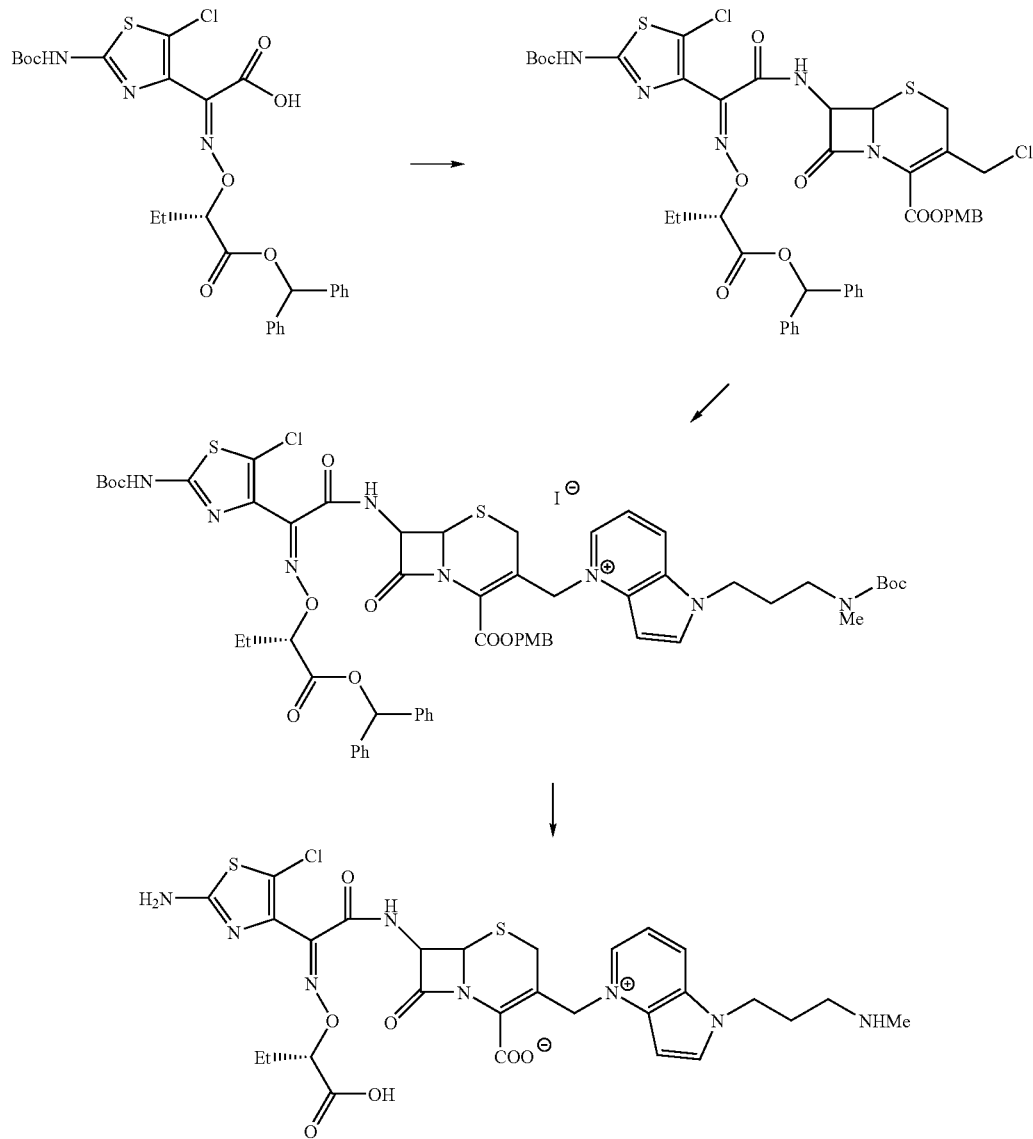

I-3h-5d:

¹H-NMR (D₂O) δ: 0.93 (3H, t, J=7.5 Hz), 1.83 (2H, quintet-like), 2.30 (2H, quintet-like), 2.69 (3H, s), 3.05 (2H, t, J=8.1 Hz), 3.16 and 3.37 (2H, ABq, J=17.7 Hz), 4.52 (1H, t, J=6.0 Hz), 4.52 (2H, t, J=6.3 Hz), 5.17 (1H, d, J=4.8 Hz), 5.55 and 5.68 (2H, ABq, J=15.0 Hz), 5.85 (1H, d, J=4.8 Hz), 7.03 (1H, d, J=3.6 Hz), 7.69 (1H, dd, J=6.0 and 8.4 Hz), 8.12 (1H, d, J=3.6 Hz), 8.58 (1H, d, J=8.4 Hz), 8.64 (1H, d, J=6.0 Hz). IR (KBr) cm⁻¹: 3388, 2970, 1775, 1602, 1539, 1498, 1463, 1392, 1362, 1316, 1160, 1121, 1061, 1032. MS(ESI): 691⁺ (M+H⁺). Elemental analysis as $C_{28}H_{31}ClN_8O_7S_2 \cdot 5.6\ H_2O$. Calc.: C, 42.46; H, 5.37; N, 14.15; Cl, 4.48; S, 8.10(%). Found: C, 42.38; H, 5.02; N, 14.25; Cl, 4.41; S, 8.02(%).

Quaternary Salt Ester:

¹H-NMR (d₆-DMSO) δ: 0.86 (3H, t, J=7.2 Hz), 1.36 (9H, brs), 1.46 (9H, s), 1.83 (2H, quintet-like), 2.03 (2H, quintet-like), 2.77 (3H, brs), 3.18 (2H, t, J=6.9 Hz), 3.29 and 3.39 (2H, ABq, J=18.9 Hz), 3.76 (3H, s), 4.43 (2H, t, J=6.6 Hz), 4.73 (1H, t, J=6.6 Hz), 5.19 (1H, d, J=4.8 Hz), 5.21 and 5.30 (2H, ABq, J=11.7 Hz), 5.70 (2H, brs), 5.98 (1H, dd, J=4.8 and 8.7 Hz), 6.84 (1H, s), 6.89 (2H, d, J=9.0 Hz), 6.96 (1H, d, J=3.0 Hz), 7.20-7.44 (1H, m), 7.78 (1H, dd, J=6.3 and 8.4 Hz), 8.42 (1H, d, J=3.0 Hz), 8.60 (1H, d, J=6.3 Hz), 8.88 (1H, d, J=8.4 Hz), 9.74 (1H, d, J=8.7 Hz), 12.1 (1H, brs). IR (KBr) cm⁻¹: 3423, 3061, 3032, 2974, 2934, 1791, 1718, 1686, 1630, 1613, 1585, 1549, 1515, 1495, 1455, 1392, 1367, 1247, 1154, 1123, 1060, 1029. MS(ESI): 1177⁺($C_{59}H_{66}ClN_8O_{12}S_2^+$).

3-chloromethyl Compound:

¹H-NMR (CDCl₃) δ: 1.02 (3H, t, J=7.2 Hz), 1.53 (9H, s), 1.96-2.08 (2H, m), 3.40 and 3.59 (2H, ABq, J=18.0 Hz), 3.81 (3H, s), 4.43 and 4.58 (1H, ABq, J=11.7 Hz), 4.93 (1H, t, J=6.3 Hz), 4.99 (1H, d, J=5.1 Hz), 5.20 and 5.28 (2H, ABq, J=11.7 Hz), 6.01 (1H, dd, J=5.1 and 9.0 Hz), 6.90 (2H, d, J=9.0 Hz), 6.95 (1H, s), 7.25-7.31 (10H, m), 7.35 (2H, d, J=9.0 Hz), 7.91 (1H, d, J=9.0 Hz), 7.93 (1H, brs). IR (KBr) cm⁻¹: 3283, 3063, 3031, 2976, 2936, 2836, 1791, 1721, 1613, 1550, 1515, 1455, 1384, 1369, 1301, 1246, 1155, 1058, 1033, 1004. MS(ESI): 924⁺(M+H⁺). Elemental analysis as $C_{43}H_{43}Cl_2N_5O_{10}S_2 \cdot 0.3\ CHCl_3 \cdot 0.8H_2O$. Calc.: C, 53.33; H, 4.64; N, 7.18; S, 6.58; Cl, 10.54(%).

7-side Chain

¹H-NMR (d₆-DMSO) δ: 0.89 (3H, t, J=7.5 Hz), 1.46 (9H, s), 1.78 (2H, quintet like), 4.52 (1H, t, J=6.9 Hz), 6.84 (1H, s), 7.23-7.46 (10H, m), 12.0 (1H, brs). IR (KBr) cm⁻¹: 3431, 3180, 3064, 3033, 2978, 2934, 1736, 1715, 1621, 1557, 1496, 1455, 1391, 1370, 1295, 1250, 1211, 1158, 1118, 1064, 1034. MS(ESI): 574⁺(M+H⁺).

EXAMPLE 12

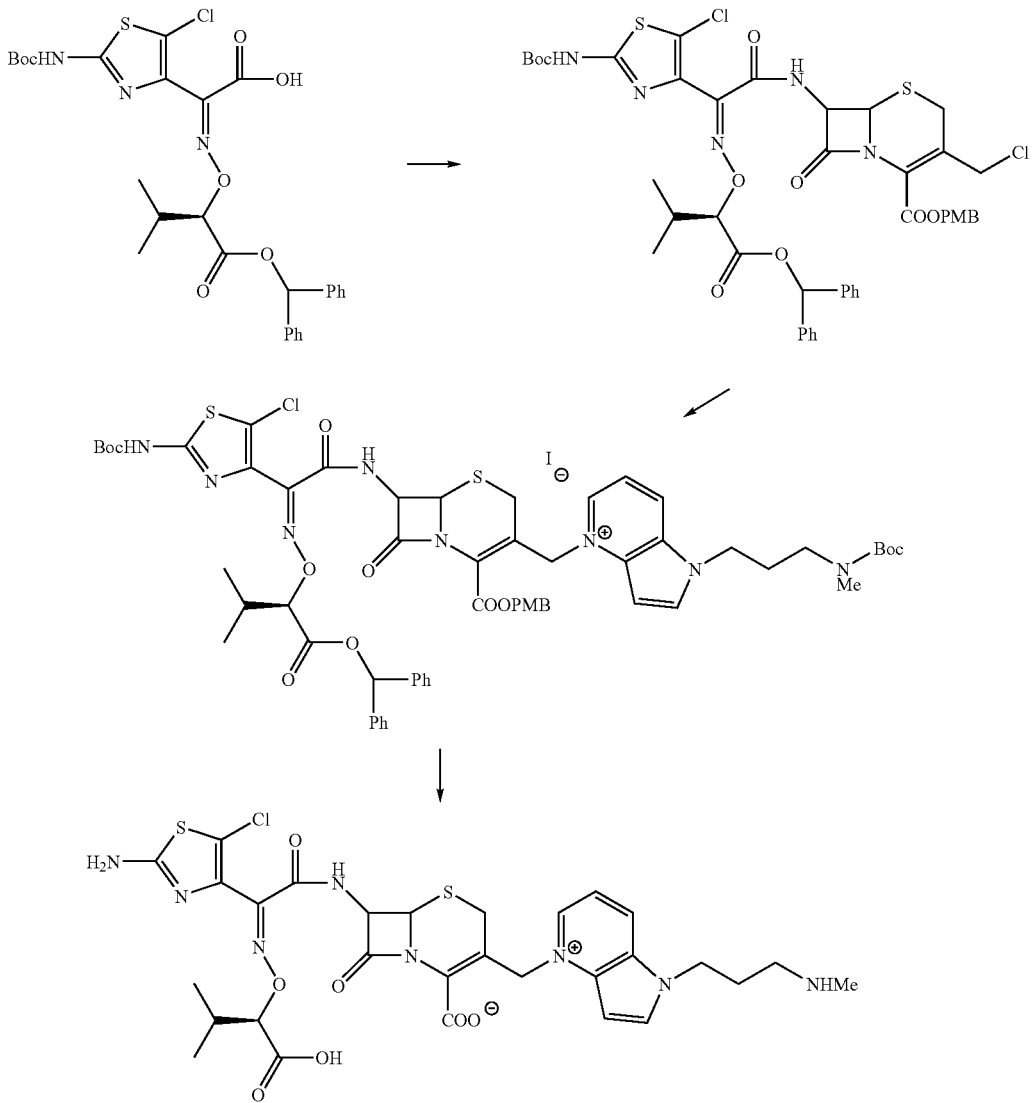

I-3i-5d:

¹H-NMR (D₂O) δ: 0.93 (6H, d, J=6.9 Hz), 2.09 (1H, sextet-like), 2.31 (2H, quintet-like), 2.68 (3H, s), 3.04 (2H, t, J=8.1 Hz), 3.13 and 3.39 (2H, ABq, J=17.7 Hz), 4.27 (1H, d, J=6.0 Hz), 4.53 (2H, t, J=6.9 Hz), 5.19 (1H, d, J=4.8 Hz), 5.58 and 5.66 (2H, ABq, J=15.0 Hz), 5.80 (1H, d, J=4.8 Hz), 7.07 (1H, d, J=3.3 Hz), 7.69 (1H, dd, J=6.3 and 8.7 Hz), 8.12 (1H, d, J=3.3 Hz), 8.60 (1H, d, J=8.7 Hz), 8.65 (1H, d, J=6.3 Hz). IR (KBr) cm⁻¹: 3396, 2965, 1775, 1604, 1538, 1498, 1466, 1391, 1364, 1223, 1121, 1062, 1027. MS(ESI): 705⁺(M+H⁺). Elemental analysis as $C_{29}H_{33}ClN_8O_7S_2 \cdot 4.28 H_2O$. Calc.: C, 44.52; H, 5.35; N, 14.32 Cl, 4.53; S, 8.20(%). Found: C, 44.14; H, 4.96 N, 14.38; Cl, 4.53; S, 8.14(%).

Quarternary Ammonium Salt Ester:

¹H-NMR (d₆-DMSO) δ: 0.88 (3H, d, J=6.9 Hz), 0.90 (3H, d, J=6.6 Hz), 1.36 (9H, brs), 1.45 (9H, s), 2.02 (2H, quintet-like), 2.15 (1H, sextet-like), 2.77 (3H, brs), 3.17 (2H, t, J=6.9 Hz), 3.26 and 3.40 (2H, ABq, J=18.3 Hz), 3.75 (3H, s), 4.42 (2H, t-like), 4.50 (1H, t, J=6.3 Hz), 5.18 (1H, d, J=5.1 Hz), 5.20 and 5.30 (2H, ABq, J=11.7 Hz), 5.65 and 5.71 (2H, ABq, J=15.6 Hz), 6.00 (1H, dd, J=5.1 and 8.4 Hz), 6.86 (1H, s), 6.87 (2H, d, J=8.4 Hz), 6.97 (1H, d, J=3.3 Hz), 7.20-7.45 (12H, m), 7.75 (1H, dd, J=6.0 and 7.8 Hz), 8.41 (1H, d, J=3.3 Hz), 8.58 (1H, d, J=6.0 Hz), 8.87 (1H, d, J=7.8 Hz), 9.72 (1H, d, J=8.4 Hz), 12.1 (1H, brs). IR (KBr) cm⁻¹: 3393, 3061, 3031, 2972, 2933, 1791, 1719, 1686, 1630, 1613, 1550, 1515, 1495, 1455, 1392, 1367, 1248, 1175, 1155, 1125, 1029.

3-chloromethyl Compound:

¹H-NMR (CDCl₃) δ: 0.99 (3H, d, J=7.2 Hz), 1.02 (3H, d, J=7.2 Hz), 1.53 (9H, s), 2.37 (1H, sextet-like), 3.35 and 3.55 (2H, ABq, J=18.3 Hz), 3.82 (3H, s), 4.42 and 4.54 (2H, ABq, J=12.0 Hz), 4.76 (1H, d, J=6.0 Hz), 4.99 (1H, d, J=5.1 Hz), 5.21 and 5.28 (2H, ABq, J=11.7 Hz), 5.95 (1H, dd, J=5.1 and 9.3 Hz), 6.91 (2H, d, J=8.7 Hz), 6.94 (1H, s), 7.25-7.32 (10H, m), 7.36 (2H, d, J=8.7 Hz), 7.51 (1H, d, J=9.3 Hz), 8.03 (1H, brs). IR (KBr) cm⁻¹: 3292, 3063, 3031, 2970, 2935, 2876, 2836, 1792, 1722, 1613, 1550, 1515, 1454, 1387, 1369, 1333, 1302, 1247, 1155, 1096, 1031. MS(ESI): 938⁺(M+H⁺).

7-side Chain

¹H-NMR (D₆-DMSO) δ: 0.83 (3H, d, J=6.9 Hz), 0.93 (3H, d, J=6.6 Hz), 1.46 (9H, s), 2.05 (1H, sex., J=ca 6.9 Hz), 4.28 (1H, d, J=7.2 Hz), 6.86 (1H, s), 7.24-7.31 (6H, m), 7.43-7.45 (4H, m). IR(KBr) cm⁻¹: 3431, 2971, 2934, 1740, 1715, 1619, 1555, 1371, 1251, 1157, 1034, 699.

EXAMPLE 13

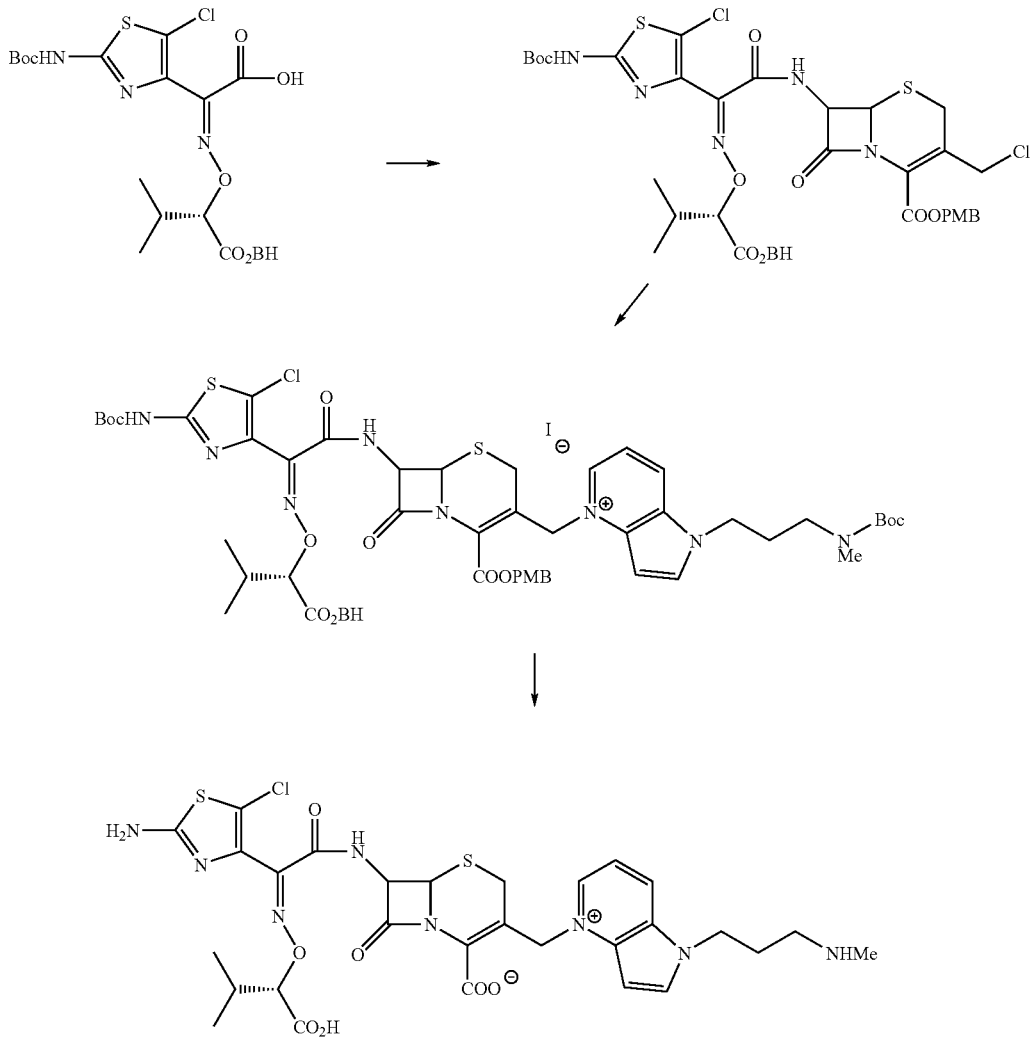

I-3j-5d:

$^1$H-NMR (2) δ: 0.94 (3H, d, J=7.2 Hz), 0.98 (3H, d, J=6.9 Hz), 2.13 (1H, sextet-like), 2.31 (2H, quintet-like), 2.68 (3H, s), 2.91 (2H, t, J=7.8 Hz), 3.15 and 3.37 (2H, ABq, J=17.7 Hz), 4.35 (1H, d, J=5.4 Hz), 4.52 (2H, t, J=6.9 Hz), 5.17 (1H, d, J=4.8 Hz), 5.55 and 5.67 (2H, ABq, J=15.3 Hz), 5.87 (1H, d, J=4.8 Hz), 7.04 (1H, d, J=3.3 Hz), 7.69 (1H, dd, J=6.0 and 8.1 Hz), 8.12 (1H, d, J=3.3 Hz), 8.59 (1H, d, J=8.1 Hz), 8.64 (1H, d, J=6.0 Hz). IR (KBr) cm$^{-1}$: 3389, 2965, 1777, 101, 1539, 1498, 1466, 1391, 1364, 1223, 1120, 1062, 1019. MS(ESI): 705$^+$(M+H$^+$). Elemental analysis as $C_{29}H_{33}ClN_8O_7S_2 \cdot 6.5\ H_2O$. Calc.: C, 42.36; H, 5.64; N, 13.63; Cl, 4.31; S, 7.80(%). Found: C, 42.01; H, 4.82; N, 13.51; Cl, 4.26; S, 7.89(%).

7-side Chain $^1$H-NMR (d$_6$-DMSO) δ: 0.85 (3H, d, J=6.6 Hz), 0.93 (3H, d, J=6.6 Hz), 1.46 (9H, s), 2.07 (1H, sextet-like), 4.35 (1H, d, J=7.2 Hz), 6.87 (1H, s), 7.1-7.5 (11H, m), 12.0 (1H, brs). IR (KBr) cm$^{-1}$: 3422, 3207, 3064, 3032, 2976, 2933, 2876, 1717, 1629, 1555, 1495, 1455, 1393, 1370, 1295, 1248, 1156, 1055, 1032. MS(ESI): 588$^+$(1+H$^+$). Elemental analysis as $C_{28}H_{30}ClN_8O_7S_1 \cdot 1.04H_2O \cdot 0.12\ AcOEt$. Calc.: C, 55.41; H, 5.39; N, 6.81; Cl, 5.74; S, 5.19(%). Found: C, 55.44; H, 5.11; N, 7.20; Cl, 5.67; S, 4.80(%).

3-chloromethyl Compound:

$^1$H-NMR (CDCl$_3$) δ: 0.95 (3H, d, J=7.2 Hz), 1.04 (3H, d, J=6.9 Hz), 1.53 (9H, S), 2.35 (1H, m), 3.43 and 3.59 (2H, ABq, J=18.3 Hz), 3.81 (3H, s), 4.45 and 4.57 (2H, ABq, J=11.7 Hz), 4.84 (1H, d, J=4.5 Hz), 4.99 (1H, d, J=4.8 Hz), 5.21 and 5.28 (2H, ABq, J=12.0 Hz), 5.99 (1H, dd, J=4.8 and 9.0 Hz), 6.91 (2H, d, J=8.7 Hz), 6.98 (1H, s), 7.25-7.32 (10H, m), 7.35 (2H, d, J=8.7 Hz), 7.92 (1H, s), 7.99 (1H, d, J=9.0 Hz). IR (KBr) cm$^{-1}$: 3392, 3283, 3062, 3032, 2969, 2934, 2835, 1791, 1721, 1613, 1585, 1551, 1514, 1455, 1387, 1368, 1302, 1246, 1155, 1096, 1061, 1030. MS(ESI): 938$^+$(M+H$^+$). Elemental analysis as $C_{44}H_{45}Cl_2N_5O_{10}S_2 \cdot 0.1\ CHCl_3 \cdot 0.4H_2O \cdot 0.4AcOEt$. Calc.: C, 55.26; H, 4.98 N, 7.05; S, 6.46; Cl, 8.21(%). Found: C, 55.22; H, 4.64; N, 6.90; S, 6.20; Cl, 8.37(%).

Quarternary Ammonium Salt Ester:

$^1$H-NMR (d$_6$-DMSO) δ: 0.87 (3H, d, J=6.9 Hz), 0.89 (3H, d, J=7.2 Hz), 1.36 (9H, brs), 1.46 (9H, s), 2.03 (2H, quintet-like), 2.15 (1H, sextet-like), 2.78 (3H, brs), 3.18 (2H, t-like), 3.27 and 3.43 (2H, ABq, J=13.2 Hz), 3.76 (3H, s), 4.43 (2H, t-like), 4.56 (1H, d, J=6.0 Hz), 5.20 (1H, d, J=5.4 Hz), 5.21 and 5.30 (2H, ABq, J=11.7 Hz), 5.70 (2H, brs), 6.00 (1H, dd, J=5.4 and 8.4 Hz), 6.86 (1H, s), 6.89 (2H, d, J=8.7 Hz), 6.95 (1H, d, J=3.3 Hz), 7.21-7.44 (1H, m), 7.78 (1H, dd, J=6.3 and 8.4 Hz), 8.41 (1H, d, J=3.3 Hz), 8.60 (1H, d, J=6.3 Hz), 8.87 (1H, d, J=8.4 Hz), 9.74 (1H, d, J=8.4 Hz), 12.1 (1H, brs). IR (KBr) cm$^{-1}$: 3423, 3061, 3032, 2972, 2933, 1792, 1718, 1685, 1630, 1613, 1584, 1550, 1515, 1495, 1455, 1392, 1367, 1247, 1154, 1061, 1028. MS(ESI): 1191$^+$(M−I$^+$).

EXAMPLE 14

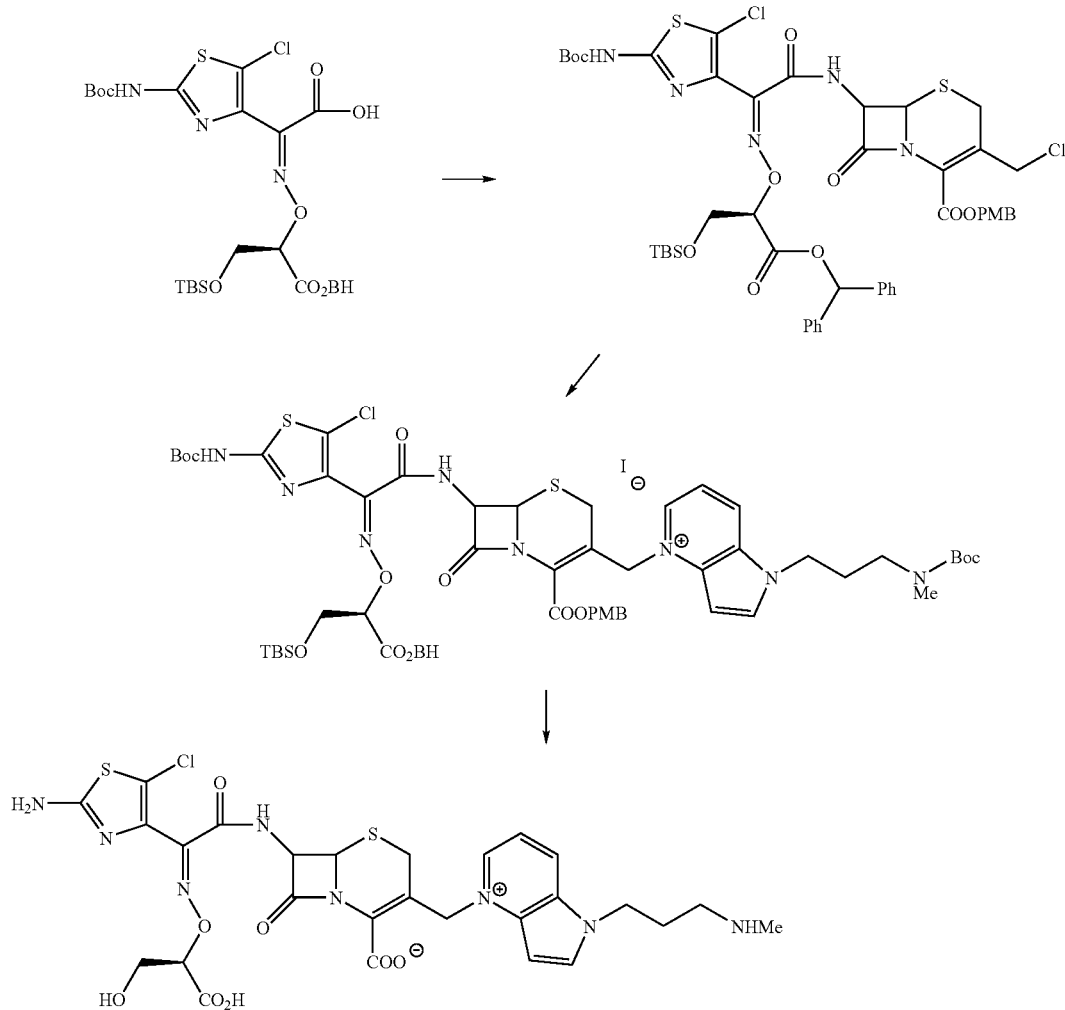

I-3k-5d:

¹H-NMR (D₂O) δ: 2.31 (2H, quintet-like), 2.68 (3H, s), 3.05 (2H, t, J=8.1 Hz), 3.14 and 3.40 (2H, ABq, J=18.0 Hz), 3.91 (2H, m), 4.53 (2H, t, J=6.9 Hz), 4.69 (1H, m), 5.20 (1H, d, J=4.8 Hz), 5.58 and 5.67 (2H, ABq, J=14.7 Hz), 5.84 (1H, d, J=4.8 Hz), 7.06 (1H, d, d=3.6 Hz), 7.69 (1H, dd, J=6.3 and 8.4 Hz), 8.12 (1H, d, J=3.6 Hz), 8.60 (1H, d, J=8.4 Hz), 8.65 (1H, d, J=6.3 Hz). IR (KBr) cm⁻¹: 3388, 1772, 1605, 1539, 1498, 1466, 1391, 1362, 1321, 1223, 1152, 1120, 1064, 1034. MS(ESI): 693⁺(M+H⁺). Elemental analysis as $C_{27}H_{29}ClN_8O_8S_2 \cdot 5.62H_2O$. Calc.: C, 40.82; H, 5.11; N, 14.11, Cl, 4.46; S, 8.07(%). Found: C, 40.41; H, 4.70; N, 14.05; Cl, 4.27; S, 8.03 (96).

7-side Chain

¹H-NMR (d₆-DMSO) δ: −0.03 (3H, s), −0.01 (3H, s), 0.77 (9H, s), 1.46 (9H, s), 3.86-3.99 (2H, m), 4.62 (1H, t-like), 6.83 (1H, s), 7.20-7.50 (11H, m), 11.1 (1H, brs). IR (KBr) cm⁻¹: 3450, 3159, 3078, 2956, 2795, 1772, 1698, 1428, 1418, 1373, 1294, 1240, 1190, 1002. MS(ESI): 690⁺(M+H⁺).

3-chloromethyl Compound:

¹H-NMR (CDCl₃) δ: 0.00 (6H, s), 0.82 (9H, s), 1.49 (9H, s), 3.21 and 3.46 (2H, ABq, J=18.0 Hz), 3.77 (3H, s), 4.12 (2H, t-like), 4.36 and 4.52 (2H, ABq, J=12.0 Hz), 4.93 (1H, d, J=4.8 Hz), 5.04 (1H, m), 5.16 and 5.24 (2H, ABq, J=11.7 Hz), 5.93 (1H, dd, J=4.8 and 9.3 Hz), 6.85 (2H, d, J=8.7 Hz), 6.89 (1H, s), 7.22-7.29 (10H, m), 7.32 (2H, d, J=8.7 Hz), 7.61 (1H, d, J=9.3 Hz), 8.22 (1H, s). IR (KBr) cm⁻¹: 3470, 3283, 2954, 2932, 1788, 1720, 1612, 1585, 1556, 1514, 1455, 1388, 1368, 1301, 1248, 1173, 1157, 1102, 1064, 1034.

Quanternary Ammonium Salt Ester:

IR (KBr) cm⁻¹: 3421, 3062, 3032, 2930, 2855, 1791, 1718, 1686, 1630, 1612, 1585, 1550, 1515, 1495, 1455, 1392, 1367, 1248, 1175, 1154, 1102, 1064, 1029. MS(ESI): 1293⁺(M-I⁺).

EXAMPLE 15

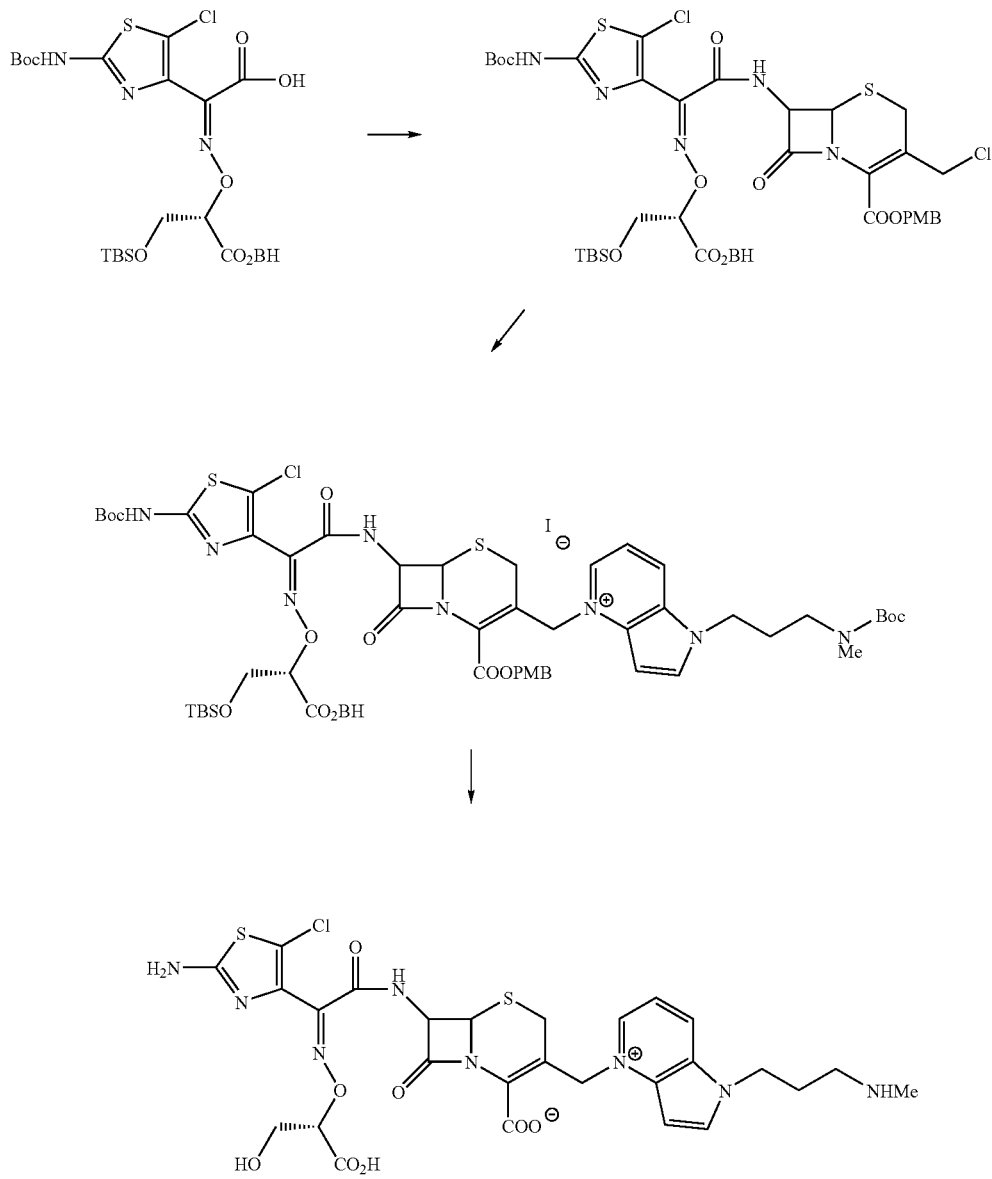

I-3i-5d:

¹H-NMR (D₂O) δ: 2.31 (2H, quintet-like), 2.68 (3H, s), 3.05 (2H, t, J=8.1 Hz), 3.17 and 3.38 (2H, ABq, J=17.7 Hz), 3.94 (2H, m), 4.53 (2H, t, J=7.2 Hz), 4.70 (1H, m), 5.18 (1H, d, J=4.8 Hz), 5.55 and 5.68 (2H, ABq, J=15.0 Hz), 5.88 (1H, d, J=4.8 Hz), 7.04 (1H, d, J=3.3 Hz), 7.69 (1H, dd, J=6.3 and 8.4 Hz), 8.12 (1H, d, J=3.3 Hz), 8.60 (1H d, J=8.4 Hz), 8.64 (1H, d, J=6.3 Hz). IR (KBr) cm⁻¹: 3398, 1774, 1603, 1538, 1498, 1466, 1392, 1362, 1320, 1064. MS(ESI): 693⁺(M+H⁺). Elemental analysis as $C_{21}H_{29}ClN_8O_8S_2 \cdot 9.0 H_2O$. Calc.: C, 37-92; H, 5.54; N, 13.10, C, 4.15; S, 7.50(%). Found: C, 37-77; H, 4.42; N, 13.09; Cl, 4.24; S, 7.49(%).

7-side Chain

¹H-NMR (d₆-DMSO) δ: −0.03 (3H, s), −0.01 (3H, s), 0.77 (9H, s), 1.46 (9H, s), 3.87-3.99 (2H, m), 4.63 (1H, t-like), 6.83 (1H, s), 7.22-7.48 (11H, m), 11.1 (1H, brs). IR (KBr) cm⁻¹: 3450, 3159, 3078, 2955, 2794, 1772, 1697, 1428, 1417, 1373, 1294, 1240, 1191, 1002. MS(ESI): 690⁺(M+H⁺).

Quarternary Ammonium Salt Ester:

IR (KBr) cm⁻¹: 3423, 3062, 3032, 2930, 2855, 1792, 1718, 1687, 1630, 1613, 1585, 1550, 1515, 1495, 1455, 1392, 1367, 1248, 1174, 1154, 1102, 1064, 1030. MS(ESI): 1293⁺(M−I⁺).

EXAMPLE 16

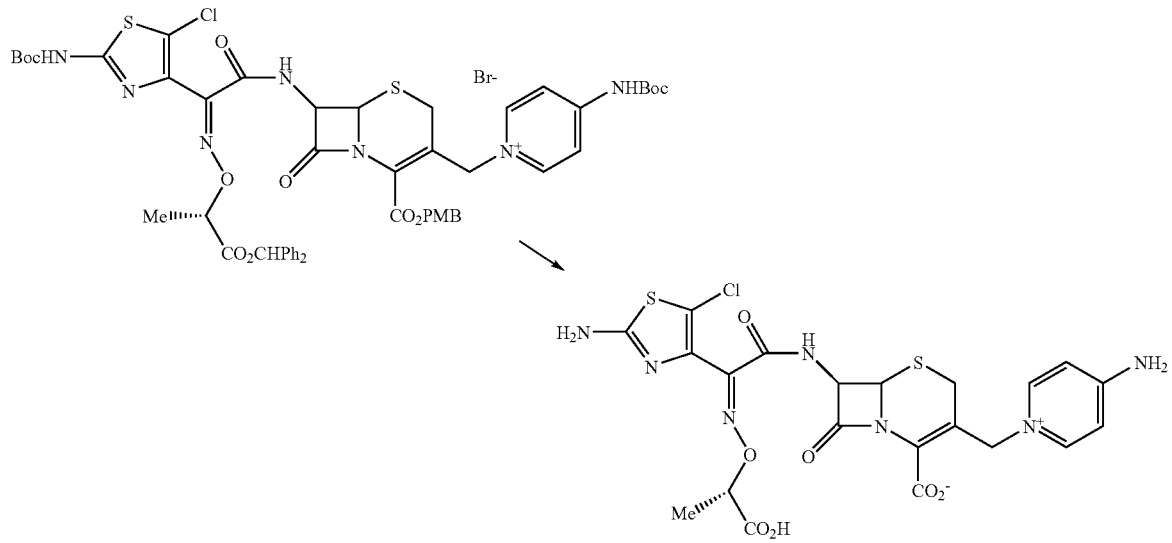

I-3f-2a:

¹H-NMR (D6-dmso) δ: 1.39 (3H, J=7.2 Hz), 2.99 and 3.44 (2H, ABq, J=17.4 Hz), 4.56 (1H, q, J=7.2 Hz), 4.68 and 5.16 (2H, ABq, J=13.2 Hz), 5.05 (1H, d, J=4.8 Hz), 5.71 (1H, dd, J=4.8, 8.4 Hz), 6.83 and 8.46 (4H, A2B2q, J=6.6 Hz), 7.42 (2H, s), 8.19 (2H, s), 9.71 (1H, d, J=8.4 Hz). IR (KBr) cm⁻¹: 3409, 3205, 1776, 1656, 1539, 1375, 1168, 1035, 842. Positive ESIMS: m/z 582 [M+H]+. Negative ESIMS: m/z 580 [M−H]−.

Quaternary Salt Ester:

¹H-NMR(CDCl3-CD3OD) δ: 1.53 (9H, s), 1.56 (9H, s), 1.61 (3H, d, J=7.2 Hz), 3.18 and 3.75 (2H, ABq, J=18.6 Hz), 3.83 (3H, s), 4.99 (1H, q, J=7.2 Hz), 5.09 (1H, d, J=5.1 Hz), 5.21 and 5.31 (2H, ABq, J=11.7 Hz), 5.27 and 5.47 (2H, ABq, J=13.8 Hz), 5.94 (1H, d, J=5.1 Hz), 6.90 (2H, J=9 Hz), 6.91 (1H, s), 7.31-7.36 (12H, m), 7.96 (2H, m), 8.73 (1H, d, J=6.6 Hz). IR (KBr) cm⁻¹: 3401, 2978, 2935, 1793, 1741, 1719, 1642, 1587, 1532, 1247, 1148, 1063, 701.

EXAMPLE 17

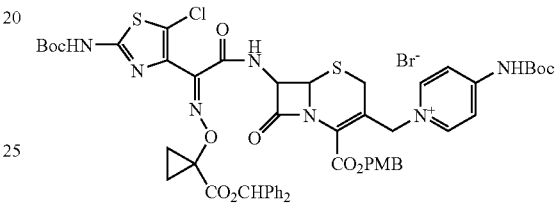

-continued

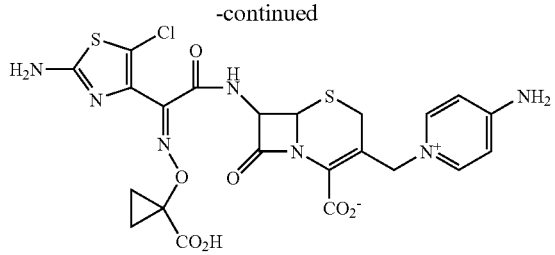

I-3c-2a:

$^1$H-NMR (D6-dmso) δ: 1.28-1.36 (4H, m), 3.03 and 3.44 (2H, ABq, J=17.7 Hz), 4.72 and 5.12 (2H, ABq, J=13.8 Hz), 5.05 (1H, d, J=4.8 Hz), 5.71 (1H, dd, J=4.8, 8.7 Hz), 6.85 and 8.40 (4H, A2Bq, J=6.6 Hz), 7.45 (2H, s), 8.27 (2H, s), 9.71 (1H, m). IR (KBr) cm$^{-1}$: 3349, 3199, 1776, 1656, 1538, 1376, 1170, 1035, 972. Positive ESIMS: m/z 594[M+H]+. Negative ESIMS: m/z 592 [M−H]−.

Quaternary Salt Ester:

$^1$H-NMR (CDCl3) δ: 1.35 (9H, s), 1.41-1.54 (22H, m), 3.22 and 3.89 (2H, A-Bq, J=18.3 Hz), 3.83 (3H, s), 6.12 (1H, d, J=5.1 Hz), 5.22 and 5.30 (2H, ABq, J=11.7 Hz), 5.48 and 5.64 (2H, Aq, J=8.4 Hz), 6.02 (1H, dd, J=5.1, 9 Hz), 6.91 and 7.34 (4H, A2B2q, J=8.4 Hz), 8.17 (1H, br s), 8.38 and 8.93 (4H, A2B2q, J=7.5 Hz), 8.61 (1H, d, J=9 Hz), 10.2 (1H, s). IR (KBr) cm$^{-1}$: 3425, 3249, 2979, 2935, 1794, 1718, 1642, 1586, 1532, 1458, 1370, 1247, 1149, 1031, 838.

EXAMPLE 18

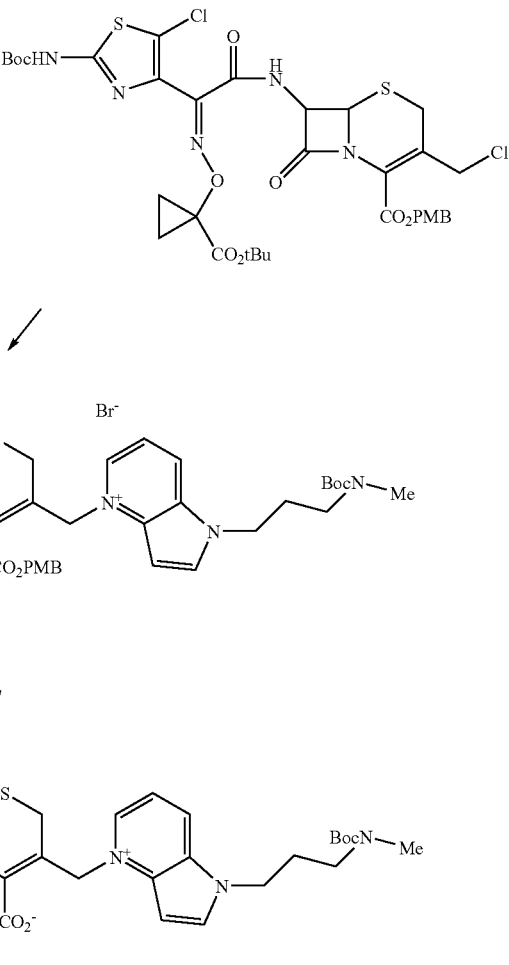

I-3c-5d:

$^1$H—N NMR 20) δ: 1.26-1.32 (4H, m), 2-31 (2H, q like), 2.68 (3H, s), 3.06 (2H, t, J=8.1 Hz), 3.15 and 3.39 (2H, ABq, J=17.7 Hz), 4.54 (2H, t like), 5.17 (1H, d, J=4.5 Hz), 5.57 and 5.68 (2H, ABq, J=15 Hz), 5.80 (1H, d, J=4.5 Hz), 7.05 (1H, d, J=3.3 Hz), 7.70 (1H, t, J=ca7 Hz), 8.13 (1H, d, J=2.4 Hz), 8.60 (1H, d, J=8.4 Hz), 8.65 (1H, d, J=6 Hz). IR (KBr) cm$^{-1}$: 3398, 2820, 1773, 1608, 1540, 1395, 1225, 1033, 968, 761. Positive ESIMS: m/z 689 [M+H]+. Negative ESIMS: m/z 687 [M−H]−.

Quaternary Salt Ester:

$^1$H-NMR (CDCl$_3$) δ: 1.41 (9H, s), 1.46-1.52 (22H, m), 2.23 (2H, m), 2.92 (3H, s), 3.35 and 3.78 (2H, ABq, J=18 Hz), 3.38 (2H, m), 3.81 (3H, s), 4.45 (2H, t like), 5.20 (1H, d, J=5.1 Hz), 5.24 and 5.30 (2H, ABq, J=11.4 Hz), 5.76 and 5.90 (2H, ABq, J=14.1 Hz), 6.02 (1H, dd, J=5.1, 8.7 Hz), 6.87 and 7.33 (4H, A2B2q, J=8.4 Hz), 7.01 (1H, br s), 7.64 (1H, t-like), 802 (1H, br s), 8.30 (2H, m), 8.51 (2H, d like), 8.61 (1H, d, J=9 Hz). IR (KBr) cm$^{-1}$: 3424, 3253, 2976, 2932, 1793, 1716, 1685, 1632, 1613, 1549, 1516, 1455, 1392, 1367, 1248, 1152, 1031, 754.

3-Cl methyl Compound:

$^1$H-NMR (CDCl$_3$) δ: 1.41 (9H, s), 1.47-1.53 (13H, m), 3.48 and 3.63 (2H, ABq, J=18.3 Hz), 3.82 (3H, s), 4.49 (2H, s), 5.06 (1H, d, J=5.1 Hz), 5.08 (1H, q, J=7.2 Hz), 5.21 and 5.28 (2H, ABq, J=11.7 Hz), 5.99 (1H, dd, J=5.1, 9.3 Hz), 6.91 and 7.36 (4H, A2B2q, J=8.7 Hz), 8.13 (1H, br s), 8.59 (1H, d, J=9.3 Hz). IR (KBr) cm$^{-1}$: 3378, 3268, 2979, 2935, 2838, 1793, 1719, 1613, 1550, 1517, 1457, 1369, 1248, 1154, 1032.

7-side Chain $^1$H-NMR (CDCl$_3$) δ: 1.40 (9H, s), 1.43-1.55 (13H, m). IR(CHCl3) cm$^{-1}$: 3405, 2983, 2935, 1719, 1626, 1550, 1153.

EXAMPLE 19

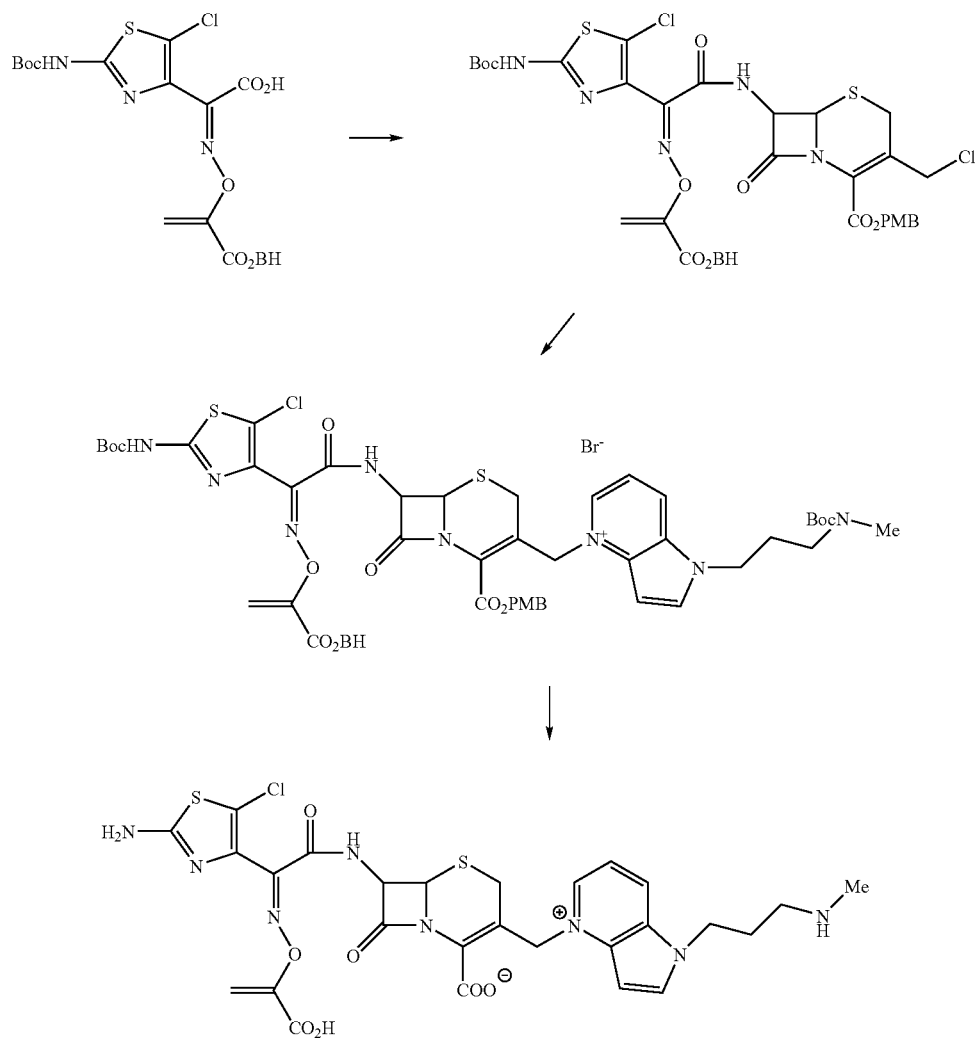

I-3b-5d:

¹H-NMR (D2O) δ: 2.31 (2H, q like, J=7.5 Hz), 2.68 (3H, s), 3.04 (2H, t-like), 3.17 and 3.31 (2H, ABq, J=17.7 Hz), 4.53 (2H, t like), 5.10 (1H, d, J=2.1 Hz), 5.12 (1H, d, J=4.5 Hz), 5.27 (1H, d, J=2.1 Hz), 5.51 and 5.76 (2H, ABq, J=15 Hz), 5.88 (1H, d, J=4.5 Hz), 6.99 (1H, d, J=3.6), 7.67 (1H, dd, J=6.4, 8.1 Hz), 8.12 (1H, d, J=3.6 Hz), 8.59 (1H, d, J=8.1 Hz), 8.63 (1H, d, J=6.4 Hz). IR (KBr) cm⁻¹: 3398, 1774, 1606, 1539.1498, 1468, 1392, 1203, 759. Positive ESIMS: m/z 675 [M+H]+. Elemental analysis as $C_{27}H_{27}N_8O_7S_2Cl$, 5.5$H_2O$. Calc.: C, 41.89; H, 4.95; N, 14.47; S, 8.28; Cl, 4.58(%). Found: C, 4.92; H, 4.72; N, 14.49; S, 8.38; Cl, 4.66(%).

Quaternary Salt Ester:

¹H-NMR (CDCl₃) δ: 1.48 (9H, s), 1.53 (9H, s), 2.20 (2H, m), 2.90 (3H, s), 3.19 and 3.64 (2H, ABq, J=18 Hz), 3.36 (2H, t Like), 3.78 (3H, s), 4.42 (2H, t like), 4.95 (1H, d, J=4.8 Hz), 5.20 and 5.28 (2H, ABq, J=11.7 Hz), 5.59 (1H, d, J=1.5 Hz), 5.75 (1H, d, J=1-5 Hz), 5.84 (1H, dd, J=4.8, 8.6 Hz), 6.83 (2H, d, J=8.7 Hz), 6.89 (1H, s), 7.04 (1H, br s), 7.23-7.36 (12H, m), 7.62 (1H, m), 8.20 (1H, m), 8.46 (1H, d, J=9.3 Hz), 8.56 (1H, d, J=6.0 Hz), 8.65 (1H, m). IR(CHCl3) cm⁻¹: 3403, 1793, 1720, 1685, 1632, 1613, 1551, 1517, 1154.

3-chloromethyl Compound:

¹H-NMR (CDCl₃) δ: 1.53 (9H, s), 3.23 and 3.43 (2H, ABq, J=18 Hz), 3.80 (3H, s), 4.36 and 4.55 (2H, ABq, J=12 Hz), 4.75 (1H, d, J=51 Hz), 5.16 and 5.25 (2H, Aq, J=11.4 Hz), 5.61 (1H, d, J=1.8), 5.81 (1H, d, J=1.8), 5.88 (1H, dd, J=5.1, 9.0 Hz), 6.87-6.92 (3H, m), 7.16-7.39 (12H, m), 8.56 (1H, br s), IR (CHCl₃) cm⁻¹: 3403, 1793, 1725, 1613, 1550, 1517, 1248, 1215, 1155.

7-side Chain:

¹H-NMR (CDCl₃) δ: 1.48 (9H, s), 5.65 (1H, d, J=2.4), 5.75 (1H, d, J=2.4), 6.93 (1H, s), 7.27-7.34 (10H, m). Positive FABMS(Matrix:m-NBA): m/z 558[M+H]+, 580[M+Na]+, 1115[2M+H]+. Negative FABMS (Matrix:m-NBA): m/z 556 [M−H]−1113[2M H]−. IR(CHCl3) cm⁻¹: 3602, 3404, 1723, 1603, 1550, 1285, 1253, 1227, 1155.

EXAMPLE 20

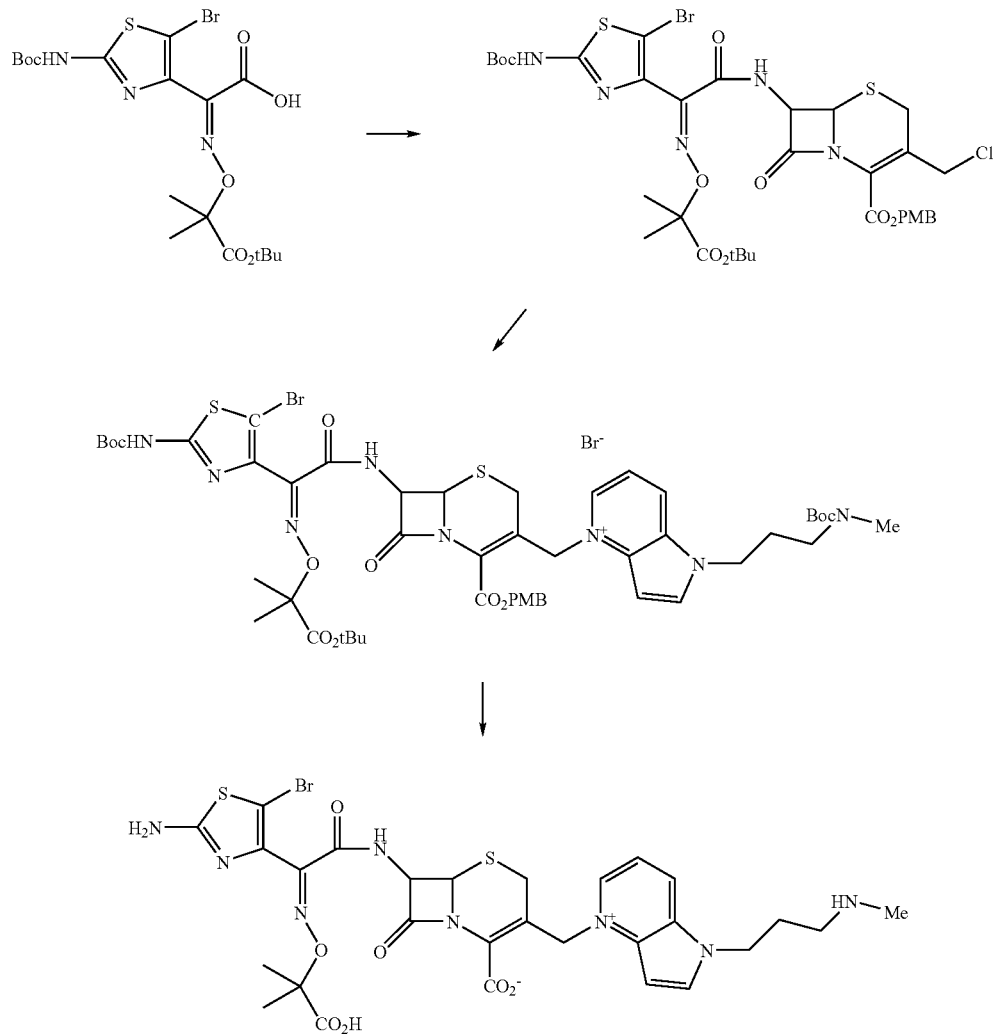

I-4-d-5d:

$^1$H-NMR (D2O) δ: 1.47 (6H, s), 2.30 (2H, q like), 2.68 (3H, s), 3.06 (2H, t, J=8 Hz), 3.18 and 3.39 (2H, ABq, J=17.7 Hz), 4.52 (2H, t like), 5.18 (1H, d, J=4.8 Hz), 5.56 and 5.68 (2H, ABq, J=15 Hz), 5.82 (1H, d, d=4.8 Hz), 7.04 (1H, d$_7$ J=3.3 Hz), 7.68 (1H, t like), 8.12 (1H, d, J=3.6 Hz), 8.58 (1H, d, J=8.1 Hz), 8.64 (1H, d, J=6 Hz). IR (KBr) cm$^{-1}$: 3405, 1772, 1608, 1535, 1394, 1362, 1160, 790, 760. Positive ESIMS: m/z 735 [M+H]+. Negative ESIMS: m/z 733 [M−H]−. Elemental analysis $C_{28}H_{31}N_8O_7S_2Br.5H_2O$. Calc.: C, 40.73; H, 5.00; N, 13.57; S, 7.77; Br, 9.68(%). Found: C, 40.67; H, 4.91; N, 13.39; S, 7.50; Br, 9.64(%).

Quaternary Salt Ester:

$^1$H-NMR (CDCl$_3$) δ: 1.43 (9H, s), 1.48 (9H, s), 1.51 (3H, s), 1.59 (3H, s), 2.22 (2H, m), 2.91 (3H, s), 3.37 (2H, t like), 3.31 and 3.80 (2H, ABq, J=18.6 Hz), 3.82 (3H, s), 4.45 (2H, t like), 5.19 (1H, d, J=5.4 Hz), 5.23 and 5.30 (2H, ABq, J=11.4 Hz), 5.64 and 5.79 (2H, ABq, J=15 Hz), 6.07 (1H, dd, J=5.4, 9 Hz), 6.87 and 7.33 (4H, A2B2q, J=8.7 Hz), 7.04 (1H, br s), 7.67 (1H, t like), 8.06 (1H, d, J=9 Hz), 8.26 (1H, br s), 8.39 (1H, br s), 8.52 (1H, d, J=9 Hz), 8.58 (1H, d, J=6 Hz).

3-chloromethyl Compound:

$^1$H-NMR (CDCl$_3$) δ 1.43 (9H, s), 1.52 (9H, s), 1.62 (6H, s), 3.48 and 3.65 (2H, ABq, J=18.3 Hz), 3.82 (3H, s), 4.44 and 4.55 (2H, ABq, J=12 Hz), 5.04 (1H, d, J=4.8 Hz), 5.19 and 5.27 (2H, ABq, J=12 Hz), 6.03 (1H, dd, J=5.1, 9 Hz), 6.91 and 7.35 (4H, A2B2q, J=8.7 Hz), 8.02 (1H, d, J=9 Hz), 8.17 (1H, br s). IR (KBr) cm$^{-1}$: 3280, 2980, 2935, 2837, 1789, 1720, 1614, 1549, 1516, 1369, 1248, 1155.

7-side Chain:

$^1$H-NMR (CDCl$_3$) δ: 1.48 (9H, s), 1.49 (9H, s), 1.53 (3H, s), 1.56 (3H, s). IR(CHCl3) cm$^{-1}$: 3406, 3019, 2983, 2937, 1724, 1544, 1369, 1226, 1151. Positive ESIMS: m/z 508[M+H]+, m/z 530[M+Na]+. Negative ESIMS: m/z 506M−H]−, m/z 528[M+Na−2H].

The other example compounds are shown below.

EXAMPLE 22

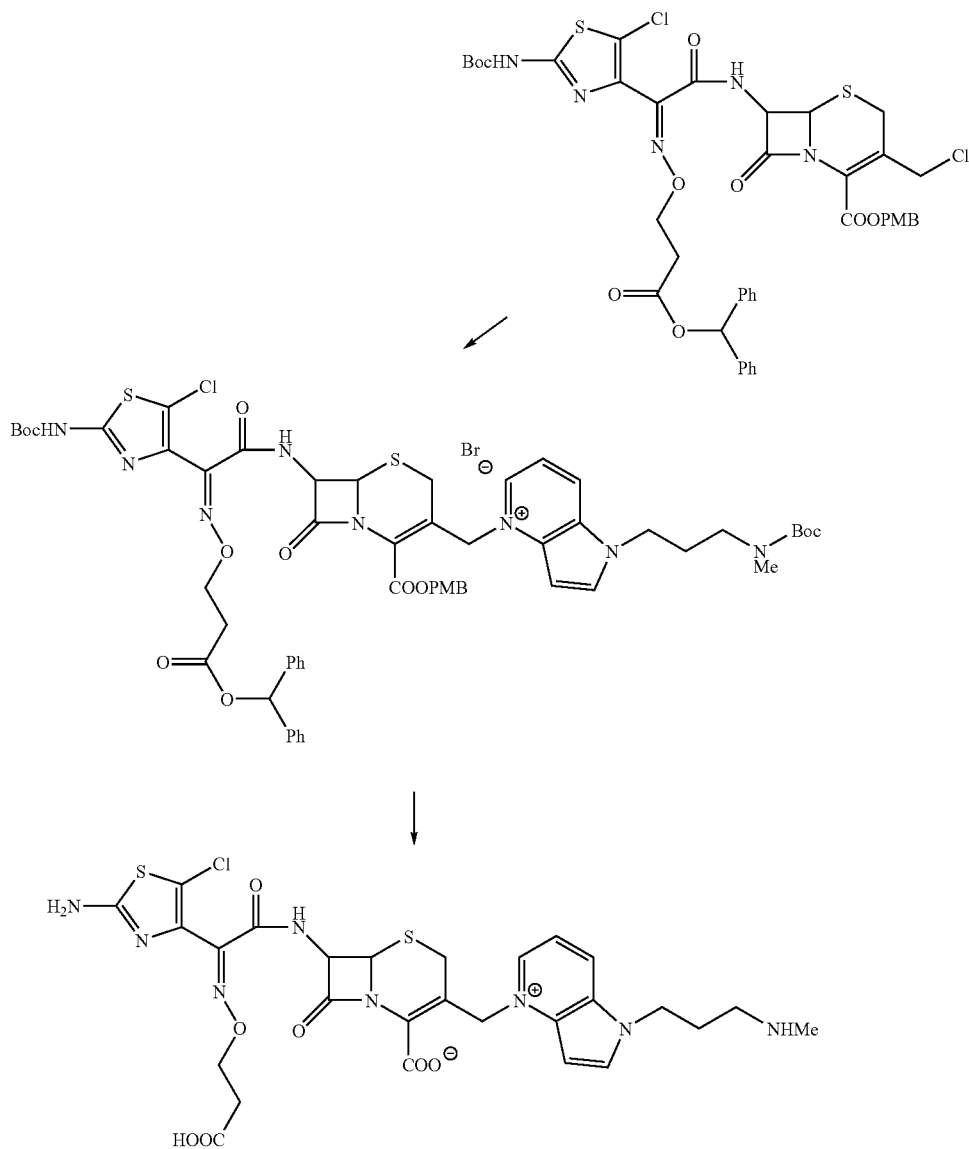

$^1$H-NMR (D$_2$O) δ: 2.31 (2H, m), 2.59 (2H, t, J=6.9 Hz), 2.69 (3H, s), 3.06 (2H, m), 3.21 and 3.35 (2H, ABq, J=17.7 Hz), 4.39 (2H, m), 4.53 (2H, t, J=6.9 Hz), 5.14 (1H, d, J=5.1 Hz), 5.54 and 5.71 (2H, ABq, J=15.0 Hz), 5.76 (1H, d, J=5.1 Hz), 7.03 (1H, d, J=3.3 Hz), 7.69 (1H, dd, J=6.3 and 8.4 Hz), 8.13 (1H, d, J=3.3 Hz), 8.60 (1H, d, J=8.4 Hz), 8.66 (1H, d, J=6.3 Hz). IR (KBr) cm$^{-1}$: 3397, 3132, 2458, 1775, 1615, 1540, 1499, 1466, 1389, 1223, 1164, 1122, 1063, 1027. MS(ESI): 677$^+$(M+H$^+$). Elemental analysis as C$_{27}$H$_{29}$ClN$_8$O$_7$S$_2$.2.8H$_2$O. Calc.: C, 44.57; H, 4.79; N, 15.40; Cl, 4.87; S, 8.81(%). Found: C, 44.51; H, 4.57; N, 15.37; Cl, 4.81; S, 8.66(%).

3-chloromethyl Compound:

$^1$H-NMR (CDCl$_3$) δ: 1.52 (9H, s), 2.89 (2H, m), 3.28 and 3.53 (2H, ABq, J=18.3 Hz), 3.81 (3H, s), 4.22 and 4.54 (2H, ABq, J=12.0 Hz), 4.59 (3H, t, J=6.6 Hz), 4.95 (1H, s, J=4.8 Hz), 5.17 and 5.26 (2H, ABq, J=11.7 Hz), 5.90 (1H, dd, J=4.8 and 8.7 Hz), 6.84 (1H, s), 6.90 (2H, d, J=9.0 Hz), 7.24-7.38 (12H, m), 7.48 (1H, d, J=8.7 Hz), 8.50 (1H, brs). IR (KBr) cm$^{-1}$: 3283, 3062, 3031, 2978, 2836, 1789, 1721, 1613, 1549, 1515, 1454, 1386, 1369, 1302, 1246, 1158, 1096, 1063, 1031. MS(ESI): 910$^+$(M+H$^+$). Elemental analysis as C$_{42}$H$_{41}$Cl$_2$N$_5$O$_{10}$S$_2$.0.3 CHCl$_3$.0.7 H$_2$O. Calc.: C, 52.96; H, 4.49; N, 7.30; S, 6.69; Cl, 10.72(%). Found: C, 52.91; H, 4.34; N, 7.33; S, 6.64; Cl, 10.74(%).

Quaternary Salt Ester:

$^1$H-NMR (d$_6$-DMSO) δ: 1.37 (9H, s), 1.46 (9H, s), 2.03 (2H, m), 2.77 (3H, brs), 2.87 (2H, t, J=6.6 Hz), 3.18 (2H, t, J=6.6 Hz), 3.28 and 3.35 (2H, m), 3.75 (3H, a), 4.36 (2H, t, J=6.3 Hz), 4.43 (2H, t, J=6.6 Hz), 5.15 (1H, d, J=4.8 Hz), 5.21 and 5.29 (2H, ABq, J=11.7 Hz), 5.66 and 5.72 (2H, ABq, J=15.0 Hz), 5.94 (1H, dd, J=4.8 and 9.0 Hz), 6.75 (1H, s), 6.88 (2H, d, J=8.7 Hz), 6.99 (1H, d, J=3.3 Hz), 7.20-7.40 (12H, m), 7.78 (1H, dd, J=6.0 and 8.1 Hz), 8.43 (1H, d, J=3.3 Hz), 8.59 (1H, d, J=6.0 Hz), 8.88 (1H, d, J=8.1 Hz), 9.72 (1H, d, J=9.0

Hz), 12.1 (1H, brs). IR (KBr) cm$^{-1}$: 3424, 3061, 3031, 2975, 2934, 1791, 1719, 1685, 1630, 1613, 1548, 1515, 1495, 1455, 1392, 1367, 1247, 1156, 1029. MS(ESI): 1163$^+$ ($C_{58}H_{64}ClN_8O_{12}S_2^+$).

EXAMPLE 23

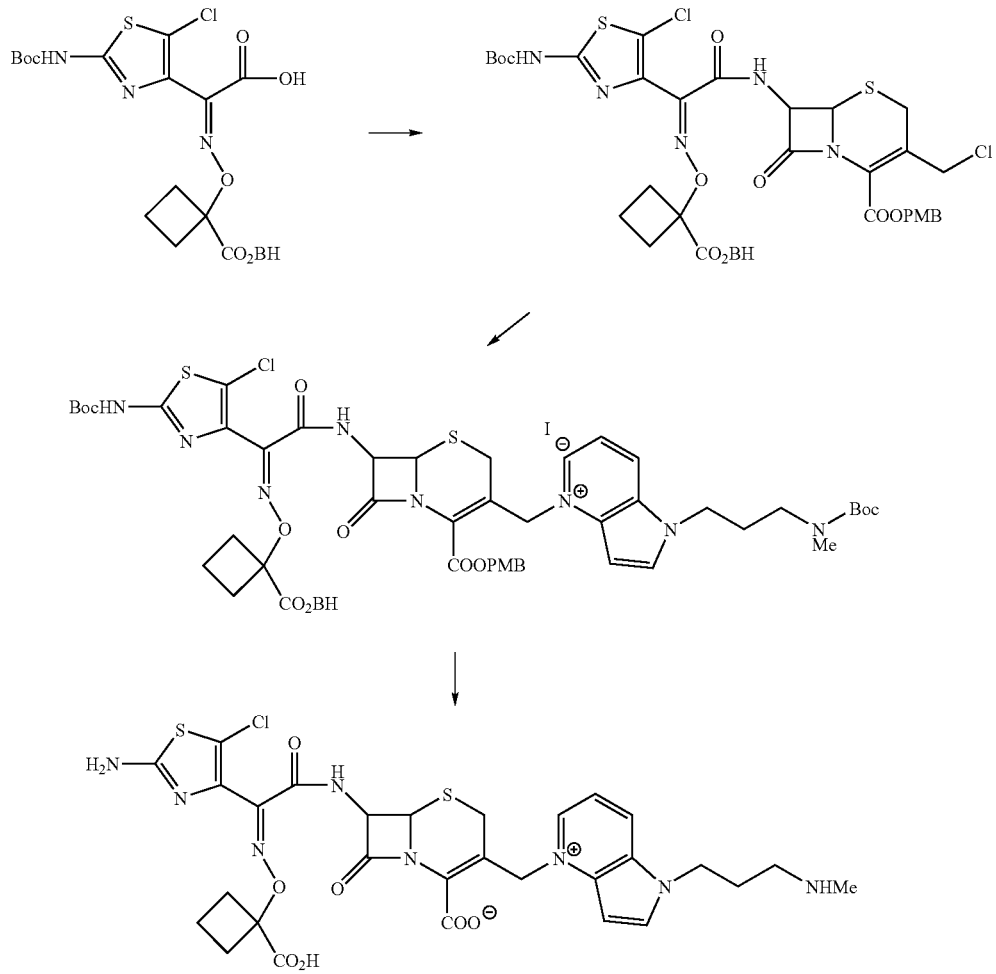

$^1$H-NMR (D$_2$O) δ: 1.90 (2H, m), 2.31 (4H, m), 2.44 (2H, m), 2.68 (3H, s), 3.05 (2H, t, J=8.1 Hz), 3.17 and 3.39 (2H, ABq, J=18.0 Hz), 4.54 (2H, t, J=6-9 Hz), 5.20 (1H, d, J=4.8 Hz), 5.56 and 5.69 (2H, A3q, J=15.0 Hz), 5.83 (1H, d, J=4.8 Hz), 7.04 (1H, d, J=3.3 Hz), 7.69 (1H, dd, J=6.3 and 8.4 Hz), 8-12 (1H, d, J=3.3 Hz), 8.60 (1H, d, J=8.4 Hz), 8.64 (1H, d, J=6.3 Hz). IR (KBr) cm$^{-1}$: 3398, 2948, 1774, 1610, 1538, 1498, 1458, 1392, 1287, 1236, 1158, 1120, 1064, 1032. MS(ESI): 703$^+$(M+H$^+$). Elemental analysis as $C_{29}H_{31}ClN_8SO_7S_2 \cdot 6.5H_2O$. Calc.: C, 42.46; H, 5.41; N, 13.66; Cl, 4.32 S, 7.82(%). Found: C, 42.34; H, 4.87; N, 13.71; Cl, 4.39; S, 7.79(%).

7-side Chain $^1$H-NMR (d$_6$-DMSO) δ: 1.47 (9H, s), 1.75-2.00 (2H, m), 2.20-2.38 (2H, m), 2.44-2.54 (2H, m), 6.82 (1H, s), 7.1-7.5 (10H, m), 12.0 (1H, brs). IR (KBr) cm$^{-1}$: 3209, 3064, 3031, 2980, 2955, 1719, 1619, 1554, 1495, 1454, 1394, 1370, 1295, 1249, 1204, 1155, 1067, 1037. MS(ESI): 586$^+$(M+H$^+$). Elemental analysis as $C_{28}H_{30}ClN_8O_7S_1 \cdot 1.3H_2O$. Calc.: C, 55.18; H, 5.06; N, 6.89; Cl, 5.82; S, 5.26(%). Found: C, 55-17; H, 4.92; N, 7.289; Cl, 5.65; S, 5.24(%).

3-chloromethyl Compound:

$^1$H-NMR (CDCl$_3$) δ: 1.53 (9H, s), 2.05-2.18 (2H, m), 2.47-2.78 (4H, m), 3.26 and 3.51 (2H, ABq, J=18.3 Hz), 3.82 (3H, s), 4.40 and 4.56 (2H, ABq, J=12.0 Hz), 4.96 (1H, d, J=4.8 Hz), 5.24 (1H, d, J=5.1 Hz), 5.21 and 5.27 (2H, ABq, J=12.0 Hz), 5.97 (1H, dd, J=5.1 and 9.6 Hz), 6.90 (2H, d, J=8.7 Hz), 6.92 (1H, s), 7.25-7.31 (10H, m), 7.35 (2H, d, J=8.7 Hz), 7.44 (1H, d, J=9.6 Hz), 8.00 (1H, s). IR (r) cm$^{-1}$: 3378, 3285, 3063, 3031, 2978, 2836, 1790, 1722, 1613, 1585, 1549, 1515, 1454, 1385, 1368, 1300, 1247, 1203, 1156, 1112, 1098, 1063, 1034. MS(ESI): 936$^+$(+H$^-$).

Quarternary Ammonium Salt Ester:

$^1$H-NMR (d$_6$-DMSO) δ: 1.36 (9H, brs), 1.46 (9H, s), 1.79-2.09 (2H, m), 2.03 (2H, quintet-like), 2.30-2.61 (4H, m), 2.77 (3H, brs), 3.17 (2H, t-like), 3.30 and 3.42 (2H, ABq, J=13.2 Hz), 3.76 (3H, s), 4.43 (2H, t-like), 5.21 (1H, d, J=4.8 Hz), 5.22 and 5.31 (2H, ABq, J=11.7 Hz), 5.71 (2H, brs), 6.01 (1H, dd, J=4.8 and 8.7 Hz), 6.82 (1H, s), 6.90 (2H, d, J=8.4 Hz), 6.96 (1H, d, J=3.3 Hz), 7.21-7.44 (12H, m), 7.78 (1H, dd, J=6.3 and 8.1 Hz), 8.42 (1H, d, J=3.3 Hz), 8.63 (1H, d, J=6.3 Hz), 8.88 (1H, d, J=8.1 Hz), 9.77 (1H, d, J=8.7 Hz), 12.1 (1H, brs). IR (KBr) cm$^{-1}$: 3424, 3061, 2975, 1791, 1718, 1685, 1630, 1613, 1584, 1550, 1515, 1495, 1455, 1392, 1367, 1298, 1248, 1155, 1123, 1065, 1030, 1018.

EXAMPLE 24

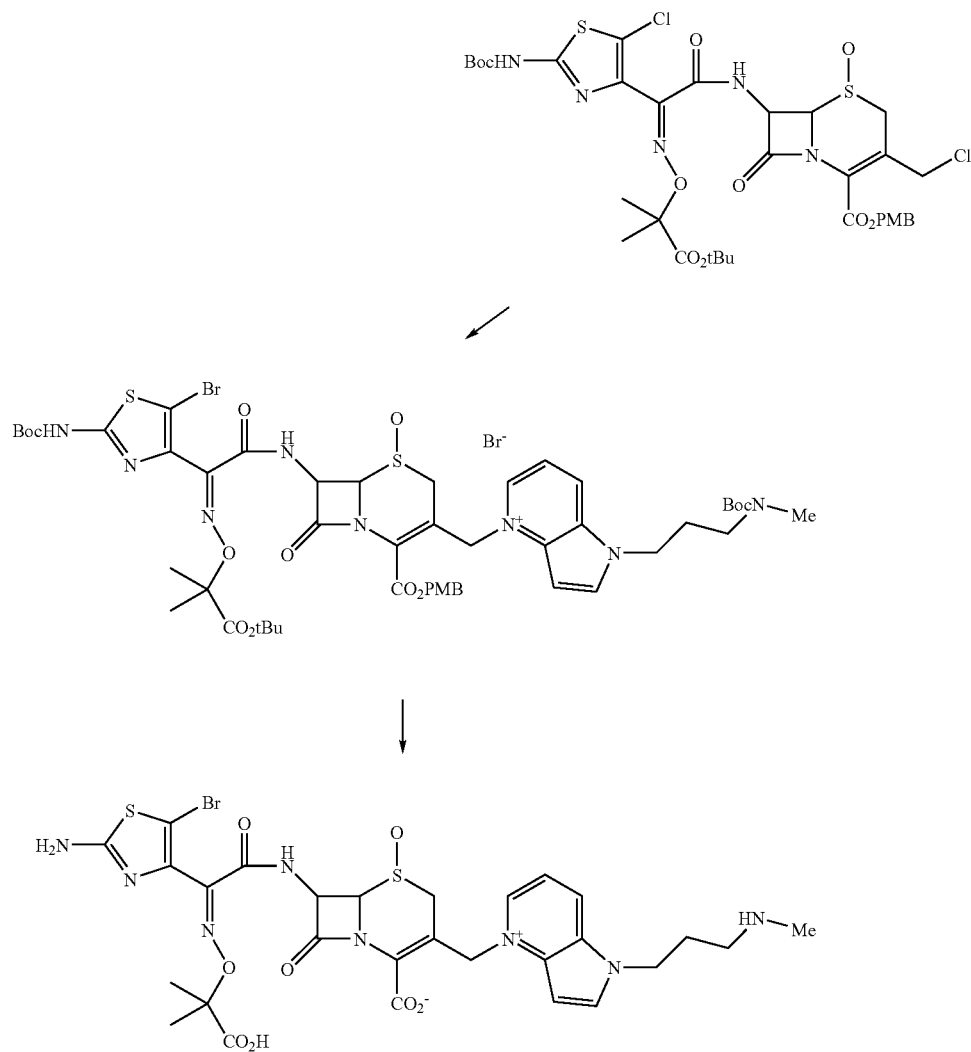

$^1$H-NMR (D2O) δ: 1.50 (6H, br s), 2.30 (2H, q like), 2.69 (3H, s), 3.06 (2H, t, J=7.8 Hz), 3.38 and 3.63 (2H, ABq, J=18.3 Hz), 4.52 (2H, m), 4.98 (1H, d, J=4.8 Hz), 5.63 and 5.75 (2H, ABq, J=153 Hz), 6.05 (1H, d, J=4.8 Hz), 7.06 (1H, d, J=3.3 Hz), 7-69 (1H, dd, J=6.0, 8.1 Hz), 8.13 (1H, d, J=3.3 Hz), 8.59 (1H, d, J=8.1 Hz), 8.67 (1H, d, J=6.0 Hz). IR (KBr) cm$^{-1}$: 3412, 1784, 1618, 1535, 1396, 1361, 1159, 858, 760. Elemental analysis as $C_{28}H_{31}N_8O_8S_2Br \cdot 6.4H_2O$ Calc.: C, 38.79; H, 5.09; N, 12.93; S, 7.40; Br, 9.22(%). Found: C, 38.82; H, 4.85; N, 12.90; S, 7.43; Br, 9.02(%).

Quarternary Ammonium Salt Ester (S-Oxide):

IR (KBr) cm$^{-1}$: 3427, 2978, 2935, 1802, 1722, 1687, 1549, 1516, 1458, 1390, 1367, 1250, 1153, 1030, 766.

3-chloromethyl Compound (S-Oxide):

$^1$H-NMR (CDCl$_3$) δ: 1.42 (9H, s), 1.52 (9H, s), 1.61 (6H, br s), 3.43 and 3.82 (2H, ABq, J=18.6 Hz), 3.82 (3H, s), 4.24 and 5.03 (2H, ABq, J=12.6 Hz), 4.59 (1H, dd, J=1.2, 5.1 Hz), 5.24 and 5.30 (2H, ABq, J=12 Hz), 6.19 (1H, dd, J=5.1, 9.6 Hz), 6.92 and 7.37 (4H, A2B2q, J=6.6 Hz), 7.94 (1H, d, J=10.2 Hz), 8.37 (1H, br s).

EXAMPLE 25

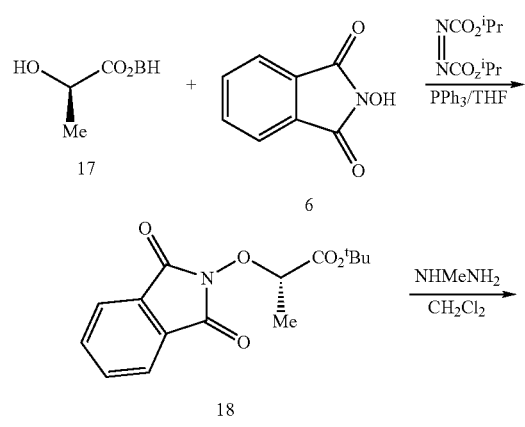

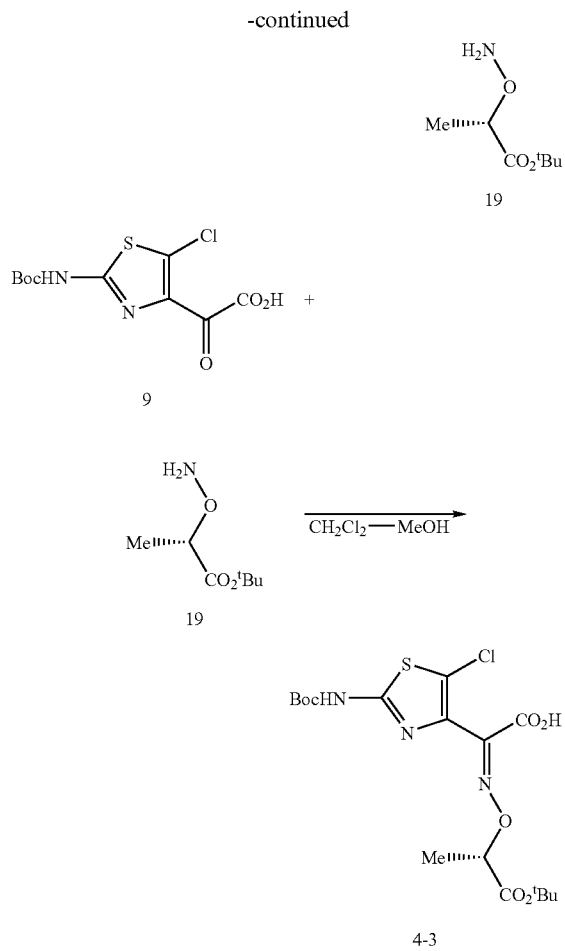

(1) To a solution of compound 17 (4.85 g) in THF 38 ml, were added triphenylphosphine (5.71 g) and hydroxyphtalimide (3.55 g) and the mixture was stirred under ice-cooling. Diisopropyl azodicarbonate (4.3 ml) was added dropwise and the mixture was allowed to stand at 4° C. overnight. The mixture was concentrated in vacuum, purified with silica gel chromato, and crystallized from eter/hexane to give compound 18 (7.6 g).

$^1$H-NMR (CDCl$_3$) δ: 1.67 (3H, d, J=7.2 Hz), 5.05 (1H, q, J=7.2 Hz), 6.93 (1H, s), 7.22-7.32 (10H, m), 7.70-7.79 (4H, m). IR (KBr) cm$^{-1}$: 1791, 1736, 1284, 700. FABMS: m/z 402 [M+H]+, 803 [2M+H]+.

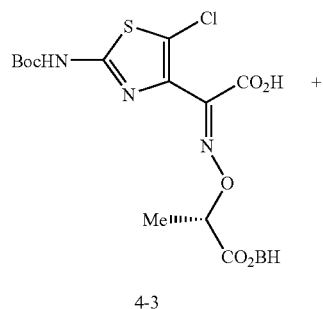

4-3

(2) To a solution of compound 18 (4.82 g) in CH$_2$Cl$_2$ 12 ml, was added at −25° C. methyl hydrazine 0.63 ml and the mixture was stirred for 1.5 hr. The obtained crystal was collected by filtration and the filtrate was diluted with MeOH 25 ml. Carboxylic acid 9 (3.7 g) was added under ice-cooling and the mixture was stirred for 2 hr and allowed to stand at 4° C. overnight. The reaction solution was concentrated in vacuum and dissolved to AcOEt, which was washed with NaHCO$_3$ water, hydrochloric acid water, and saline, then dried over MgSO$_4$ and evaporated to give compound 4-3 (4.74 g)

$^1$H-NMR (d$_6$-DMSO) δ: 1.46 (3H, d, J=6.9H), 1.47 (9H, s), 5.00 (1H, q, J=6.9 Hz), 6.85 (1H, s), 7.26-7.42 (10H, m), 12.06 (1H, s). IR (KBr) cm$^{-1}$: 3422, 3193, 3062, 3032, 2983, 1740, 1719, 1602, 1554, 1453, 1370, 1250, 1155, 1096, 1038, 967, 744, 699. FABMS: m/z 560 [M+H]+, 1119 [2M+H]+.

(3) To a solution of carboxylic acid 4-3 (3.50 g, 6.25 mmol) and ACLE.HCl 10 (2.53 g 6.25 mmol) in CH$_2$Cl$_2$ 21 ml, were added WSCD.HCl (1.20 g 1 eq) and Pyridine (0.51 ml, 1.0 eq) under ice-cooling, and the mixture was stirred at the same temperature for 1 hr. The reaction solution was washed with brine, dried with anhydrous MgSO$_4$, concentrated in vacuum, and purified with silica gel chromato to give a foam-like residue 11-3 (4.60 g).

H-NMR (CDCl$_3$) δ: 1.53 (9H, s), 1.64 (3H, d, J=7.2 Hz), 3.39 and 3.58 (2H, ABq, J=18.3 Hz), 3.81 (3H, s), 4.42 and 4.59 (2H, ABq, J=12 Hz), 4.97 (1H, d, J=5.1 Hz), 5.08 (1H, q, J=7.2 Hz), 5.20 and 5.27 (2H, ABq, J=11.7 Hz), 6.01 (1H, dd, J=5.1, 9.3 Hz), 6.88-6.91 (3H, m), 7.06-7.35 (12H, m), 7.85 (1H, d, J=9.3 Hz), 8.15 (1H, br s). IR (KBr) cm$^{-1}$: 3281, 2980, 2935, 2836, 1790, 1719, 1612, 1552, 1515, 1454, 1369, 1247, 1155, 1035, 700. FABMS: m/z 910 [M+H]+.

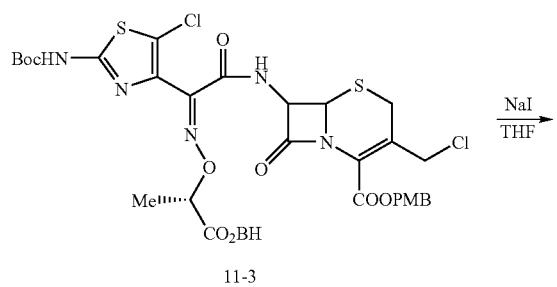

11-3

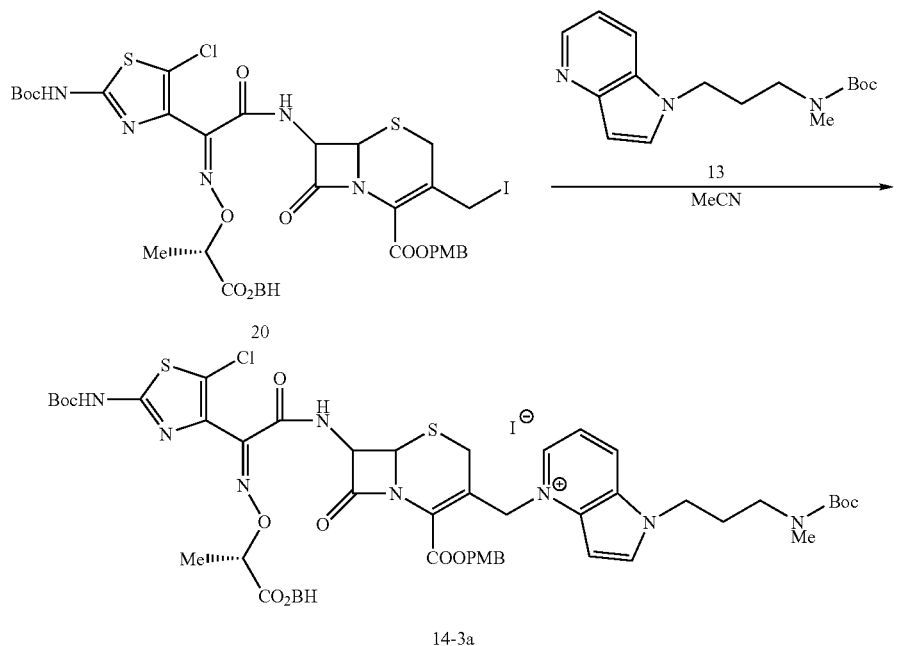

14-3a (4) To a solution of Cl-compound 11-3 (4.60 g, 5.05 mmol) in THF cooled to 13° C., was added NaI (2.65 g 3.5 eq) and the mixture was stirred for 30 min. The reaction solution was poured to $Na_2S_2O_3$ aq.—EtOAc and the organic layer was separated, washed with brine, dried with anhydrous $MgSO_4$, concentrated in vacuum to give a foam-like residue 20 (5.07 g).

H-NMR(CDCl3) δ: 1.53 (9H, s), 1.65 (3H, d, J=7.2 Hz), 3.39 and 3.67 (2H, ABq, J=17.7 Hz), 3.81 (3H, s), 4.33 and 4.45 (2H, ABq, J=9.3 Hz), 4.96 (1H, d, J=5.1 Hz), 5.08 (1H, q, J=7.2 Hz), 5.20 and 5.28 (2H, ABq, J=11.7 Hz), 5.95 (1H, dd, J=5.1, 9.0 Hz), 6.88-6.92 (3H, m), 7.23-7.39 (12H, m), 7.78 (1H, d, J=9.0 Hz), 8.01 (1H, br s). IR (KBr) cm$^{-1}$: 3383, 3284, 2980, 2836, 1790, 1719, 1613, 1551, 1516, 1369, 1246, 1153, 1037, 700.

ABMS: m/z 1002 [M+H]+.

(5) To a solution of a material for 3-side chain, 13 (174 mg, 0.60 mmol) in MeCN 1 ml, was added iode compound 20 (570 mg, 0.60 mmol) under ice-cooling, and the mixture was stirred at the same temperature for 3 hr and at room temperature for 2 hr. A mixture of Toluene/$Et_2O$/n-Hexane (1:30:30) was added dropwise thereto and the precipitated powder was collected by filtration to give quaternary salt 14-3a (675 mg).

$^1$H-NMR (CDCl$_3$) δ: 1.46 (9H, s), 1.51 (9H, s), 1.61 (3H, d, J=7.2 Hz), 2.21 (2H, m), 2.88 (3H, s), 3.19 and 3.89 (2H, ABq, J=18.9 Hz), 3.33 (2H, m), 3.80 (3H, s), 4.42 (2H, t like), 5.04-5.15 (4H, m), 5.22 and 5.30 (2H, ABq, J=12 Hz), 5.84 and 5.75 (2H, ABq, J=14.7 Hz), 5.98 (1H, dd, J=5.1, 8.7 Hz), 6.89 (3H, m), 7.25-7.36 (12H, m), 7.54 (1H, t like), 7.75 (H, d, J=7.8 Hz), 8.25 (1H, m), 8.56 (1H, d, J=8.7 Hz), 8.95 (1H, d, J=5.7 Hz). IR (KBr) cm$^{-1}$: 3423, 2976, 2932, 1792, 1718, 1687, 1613, 1550, 1515, 1496, 1454, 1367, 1248, 1154, 759, 701.

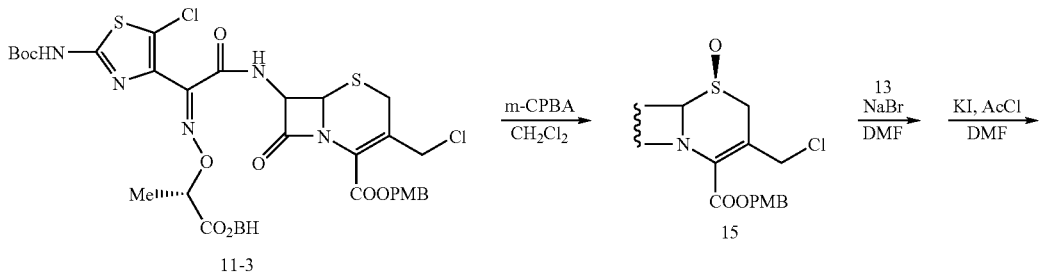

-continued

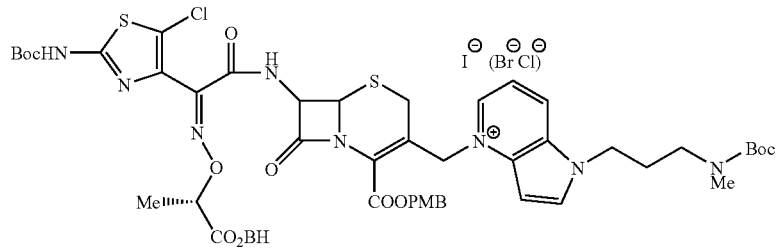

14-3

(6) To a solution of Cl-compound 11-3 (2.13 g, 2-33 mmol) in CH$_2$Cl$_2$ 10 ml, was added dropwise a solution of m-CPBA (purity:>65%, 495 mg 0.81eq) in CH$_2$Cl$_2$ 8 ml at −50° C. and the mixture was stirred at the same temperature for 30 min. 5% Na$_2$S$_2$O$_3$ aq. was added thereto and the organic layer was washed with NaHCO$_3$ aq. and brine, dried over anhydrous MgSO$_4$, then concentrated in vacuum. To the obtained foam-like residue was added Et$_2$O/n-Hexane to give oxide 15 (about 2 g) as powder.

H-NMR (CDCl$_3$) δ: 1.53 (9H, s), 1.64 (3H, d, J=7.2 Hz), 3.29 and 3.70 (2H, ABq, J=18.6 Hz), 3.81 (3H, s), 4.23 and 4.99 (2H, ABq, J=12.6 Hz), 4.44 (1H, d, J=5.1 Hz), 5.10 (1H, q, J=7.2 Hz), 5.26 (2H, m), 6.16 (1H, dd, J=5.1, 9.6 Hz), 6.88-6.94 (3H, m), 7.25-7.375 (12H, m), 7.90 (1H, d, J=9.6 Hz), 8.32 (1H, br s). IR (KBr) cm$^{-1}$: 3425, 2979, 2937, 1804, 1720, 1613, 1553, 1516, 1454, 1369, 1249 1155, 1037, 701.

(7-1) To a solution of a material for 3-side chain, 13 (324 mg 1.1 eq), in DMF 1.8 ml, were added oxide 15 (1.22 g, 1.31 mmol) and NaBr (271 mg 2 eq) and the mixture was stirred in nitrogen atomosphere at room temperature for 1.5 hr. DMF 2 ml and KI 1.28 g were added thereto and the mixture was cooled to −40° C., to which was added dropwise AcCl 0.40 ml and the mixture was stirred at −10° C. for 3 hr. The reaction solution was poured to a phosphate buffer of pH 6 containing NaCl and Na$_2$S$_2$O$_3$, then the precipitates were collected by filtration, dissolved to acetone, and concentrated in vacuum. To the residue was added Et$_2$O/n-Hexane to give quaternary salt 14-3(1.77 g).

$^1$H-NMR (CDCl$_3$) δ: 1.48 (9H, s), 1.51 (9H, s), 1.62 (3H, d, J=7.2 Hz), 2.21 (2H, m), 2.91 (3H, s), 3.24 and 3.82 (2H, ABq, J=18.9 Hz), 3.36 (2H, m), 3.81 (3H, s), 4.43 (2H, t like), 5.09 (1H, q, J=7.2 Hz), 5-16 (1H, d, J=5.1 Hz), 5-24 and 5.31 (2H, ABq, J=11.7 Hz), 5.58 and 5.75 (2H, ABq, J=14.7 Hz), 5.99 (1H, dd, J=5.1, 8.7 Hz), 6.86 (1H, s), 6.87 (2H, d, J=8.7 Hz), 7.00 (1H, br s), 7.24-7.38 (12H, m), 7.55 (1H, t like), 7.78 (H, d, J=8.7 Hz), 8.25 (1H, br s), 8.47 (1H, d, J=10.2 Hz), 8.50 (1H, d, J=6 Hz). IR (KBr) cm$^{-1}$: 3423, 2976, 2932, 1792, 1718, 1687, 1613, 1248 1154, 759, 701. (7-2) To a solution of a material for 3-side chain, 13 (174 mg, 0.600 mmol) in MeCN 1 ml, was added iode compound 20 (570 mg, 0.60 mmol as reduced purity) under ice-cooling and the mixture was stirred at the same temperature for 3 hr and at room temperature for 2 hr. A mixture of Toluene/Et$_2$O/n-Hexane (1:30:30) was added dropwise thereto and the precipitated powder was collected by filtration to give quaternary salt 14-3a 675 mg.

(8) To a solution of quaternary salt 14-3 (about 1.3 mmol) in CHCl$_2$-MeNO$_2$ 30 ml and anisole 1.7 ml, was added an AlCl$_3$-MeNO$_2$ solution (1.5M, 7 ml) in nitrogen atomosphere under ice-cooling and the mixture was stirred for 1 hr. Ice, 1N HCl—CH$_3$CN and Et$_2$O were added thereto and the water layer was separated, concentrated in vacuum, and subjected to HP-20 chromato. The collected eluate was lyophilized to give compound 16-3 (450 mg) as powder.

$^1$H-NMR (D$_2$O) δ: 1.43 (3H, d, J=7.2 Hz), 2.31 (2H, q like), 2.68 (3H, s), 3.05 (2H, t, J=8 Hz), 3.18 and 3.37 (2H, ABq, J=18 Hz), 4.53 (2H, t like), 4.65 (1H, q, J=7.2 Hz), 5.17 (1H, d, J=4.8 Hz), 5.54 and 5.70 (2H, ABq, J=15 Hz), 5.86 (1H, d, J=4.5 Hz), 7.03 (1H, d, J=3.6 Hz), 7.69 (1H, dd, J=6, 8.4 Hz), 8.13 (1H, d, J=36 Hz), 8.60 (1H, d, J=8.4 Hz), 8.64 (1H, d, J=6 Hz). IR (KBr) cm$^{-1}$: 3398, 1775, 1603, 1541, 1392, 1363, 1320, 1286, 1033, 762. Positive ESIMS: m/z 677 [M+H]+. Negative ESIMS: m/z 675 [M−H]−. Elemental analysis as C$_{27}$H$_{29}$N$_8$O$_7$S$_2$Cl, 6.2H$_2$O Calc.: C, 41.11; H, 5.29; N, 14.20; S, 8.13; Cl, 4.49(%). Found: C, 40.88; H, 4.88; N, 14.23; S, 8.05; Cl, 4.57(%).

EXAMPLE 26

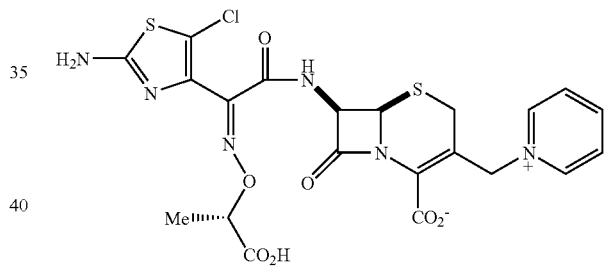

$^1$H-NMR (D$_2$O) δ: 1.51 (3H, d, J=7.25 Hz), 3.22 and 3.64 (Abq, J=17.9 Hz), 4.83 (1H, q, J=7-2 Hz), 5.28 (1H, d, J=4.8 Hz), 5.35 and 5.58 (2H, ABq, J=14.6 Hz), 5.90 (1H, d, J=4.8 Hz), 8.09 (2H, t-like), 8.57 (2H; t, J=7.8 Hz), 8.95 (2H, d, J=5.7 Hz). IR (KBr) cm$^{-1}$: 3410, 3060, 1780, 1674, 1627, 1538, 1481, 1445, 1389, 1341, 1219, 1186, 1153, 1100, 1035. MS(ESI): 567$^+$ (M+H)$^+$. Elementary Analysis as C$_{21}$H$_{19}$ClN$_6$O$_7$S$_2$.2.9H$_2$O. Calculated: C, 40.73; H, 4.04; N, 13.57; Cl, 5.73; S, 10.36(%). Found: C, 40.67; H, 3.87; N, 13.45; C, 5.50; S, 10.36(%).

EXAMPLE 27

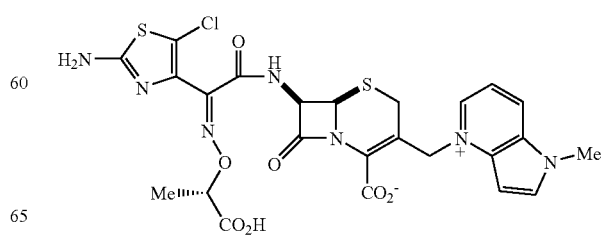

$^1$H-NMR (d$_6$-DMSO) δ: 1.36 (3H, d, J=7.1 Hz), 2.97 and 3.25 (2H, Abq, J=17.3 Hz), 4.03 (3H, s), 4.55 (1H, q, J=7.1 Hz), 4.97 (1H, d, J=5.1 Hz), 5.61-5.72 (3H, m), 5.60 and 5.73 (2H, ABq, J=15.2 Hz), 7.37 (1H, d, J=3.3 Hz), 7.41 (1H, s), 7.78 (1H, dd, J=6.3, 8.2 Hz), 8.28 (TH, d, J=3.3 Hz), 8.74 (1H, d, J=8.2), 9.16 (1H, d, J=6.3 Hz), 9.61 (1H, brs). IR (KBr) cm$^{-1}$: 3423, 2986, 1778, 1674, 1618, 1538, 1500, 1469, 1416, 1368, 1324, 1281, 1222, 1187, 1154, 1094, 1062, 1032. MS(ESI): 620$^+$ (M+H)$^+$. Elementary Analysis as C$_{24}$H$_2$ClN$_7$O$_7$S$_2$.2.6 H$_2$O. Calculated: C, 43.22; H, 4.11; N, 14.70; Cl, 5.32; S, 9.62(%). Found: C, 43.16; H, 3.99; N, 14.88; Cl, 5.12; S, 9.61(%).

EXAMPLE 28

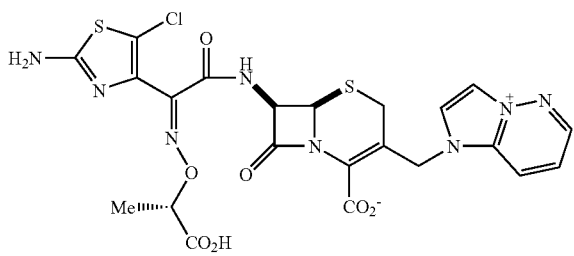

$^1$H-NMR (D$_2$O) δ: 1.50 (3H, d, J=6.9 Hz), 3.20 and 3.58 (2H, ABq, J=17.7 Hz), 4.80 and 4.84 (2H, ABq, J=6.9 Hz), 5.24 (1H, d, J=4.8 Hz), 5.37 and 5.42 (2H, ABq, J=16.2 Hz), 5.87 (1H, d, J=4.8 Hz), 7.90 (1H, dd, J=4.5, 94 Hz), 8.25 (1H, d, J=2.3 Hz), 8.44 (1H, d, J=2.3 Hz), 8.66 (1H, d, J=9.4 Hz), 8.94 (1H, dd, J=1.5, 4.5 Hz). IR (KBr) cm$^{-1}$: 3416, 3136, 2939, 1776, 1674, 1625, 1535, 1447, 1383, 1346, 1317, 1232, 1185, 1155, 1100, 1066, 1035. MS(FAB): 607$^+$ (M+H)$^+$. Elementary Analysis as C$_{22}$H$_{19}$ClN$_8$O$_7$S$_2$.2.8 H$_2$O. Calculated: C, 40.19; H, 3.77; N, 17.04; C, 5.39; S, 9.75(%). Found: C, 40.10; H, 3.56; N, 17.01; Cl, 5.20; S, 9.73(%).

EXAMPLE 29

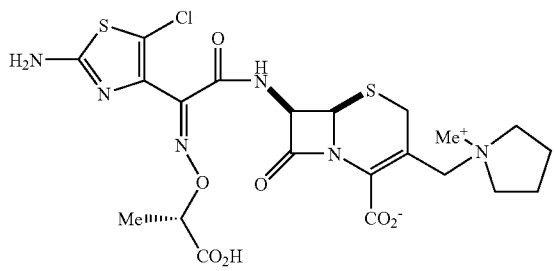

$^1$H-NMR (D$_2$O) δ: 1.55 (3H, d, J=7.2 Hz), 2.22 (4H, brs), 2.99 (3H, s), 3.46 and 3.92 (2H, ABq, J=17.0 Hz), 3.53 (4H, m), 3.99 and 4.74 (2H, ABq, J=13.79 Hz), 4.85 (1H, q, J=7.2 Hz), 5.36 (1H, d, J=5.1 Hz), 5.90 (1H, d, J=5.1 Hz). IR (KBr) cm$^{-1}$: 3416, 1780, 1676, 1616, 1538, 1459, 1345, 1285, 1236, 1180, 1097, 1068, 1036. MS(FAB): 573$^+$ (M+H)$^+$. Elementary Analysis as C$_{21}$H$_{25}$ClN$_6$O$_7$S$_2$.4.0 H$_2$O Calculated: C, 39.10; H, 5.16; N, 13.03; C, 5.50; S, 9.94(%). Found: C, 38.86; H, 4.64; N, 13.00; Cl, 5.30; S, 9.90(%).

EXAMPLE 30

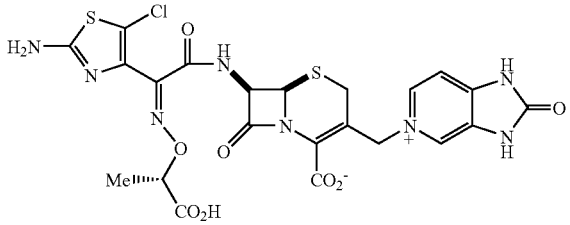

$^1$H-NMR (d$_6$-DMSO) δ: 1.37 (3H, d, J=7.1 Hz), 3.15 and 3.50 (ABq, J=17.6 Hz), 4.54 (1H, q, J=7.1 Hz), 4.96 and 5.58 (21, ABq, J=13.4 Hz), 5.11 (1H d, J=4-9 Hz), 5.73 (1K, dd, J=4.9, 8.9 Hz), 7.41 (2H, s), 7.52 (1H, d, J=6.6 Hz), 8.70 (2H, d, J=6.6 Hz), 9.14 (1H, s), 9.75 (1H, brs). IR (KBr) cm$^{-1}$: 3414, 3086, 1738, 1661, 1620, 1527, 1446, 1390, 1351, 1307, 1210, 1118, 1066, 1036. MS(ESI): 623$^+$ (M+H)$^+$. Elementary Analysis as C$_{22}$H$_{19}$ClN$_8$O$_8$S$_2$.3.7 H$_2$O. Calculated: C, 38.31; H, 3.86; N, 16.25; Cl, 5.14; S, 9.30(%). Found: C, 38.18; H, 3.51; N, 16.22; Cl, 4.85; S, 9.24(%).

EXAMPLE 31

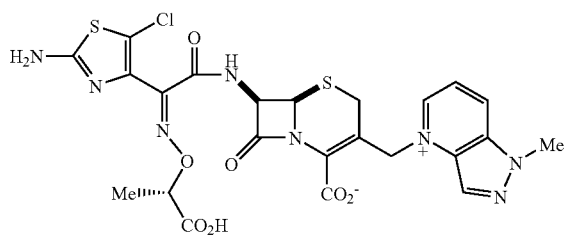

$^1$H-NMR (d$_6$-DMSO) δ: 1.36 (3H, d, J=7.1 Hz), 3.03 and 3.32 (ABq, J=17.6 Hz), 4.29 (3H, s), 4.55 (1H, q, J=7.1 Hz), 5.00 (1H, d, J=5.0 Hz), 5.69 (1H, dd, J=5.0, 8.6 Hz), 5.75 and 5.818 (2H, ABq, J=14.1 Hz), 7.42 (2H, s), 8.12 (1H, dd, J=5.6, 8.8 Hz), 9.08 (1H, d, J=8.8 Hz), 9.15 (1H, s), 9.46 (1H, d, J=5.6 Hz), 9.56 (1H, d, J=8.6 Hz). IR (KBr) cm$^{-1}$: 3415, 1779, 1675, 1617, 1538, 1483, 1442, 1392, 1372, 1348, 1291, 1236, 1188, 1155, 1100, 1063, 1034. MS(ESI): 621$^+$ (M+H)$^+$. Elementary Analysis as C$_{23}$H$_{21}$ClN$_8$O$_7$S$_2$.3.1H$_2$O. Calculated: C, 40.81; H, 4.05; N, 16.55; Cl, 5.24; S, 9.47(%). Found: C, 40.85; H, 3.85; N, 16.73; Cl, 5.01; S, 9.46(%).

EXAMPLE 32

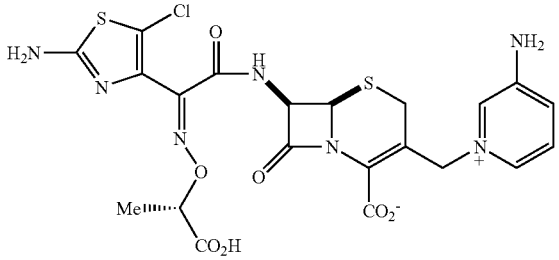

¹H NMR (d₆-DMSO) δ: 1.39 (3H, d, J=7.1 Hz), 3.01 and 3.46 (2H, ABq, J=17.6 Hz), 4.56 (1H, q, J=7.1 Hz), 5.00 and 5.55 (2H, ABq, J=13.4 Hz), 5.06 (1H, d, J=5.1 Hz), 5.70 (1H, dd, S=5.1 Hz), 6.74 (2H, brs), 7.42 (2H, brs), 7.55 (1H, d, J=8.5 Hz), 7.68 (1H, dd, J=8.5, 5.7 Hz), 8.38 (1H, d, J=5.7 Hz), 8.51 (1H, brs), 9.67 (1H, brs). IR (KBr) cm⁻¹: 3351, 3208, 1777, 1629, 1538, 1512, 1445, 1391, 1346, 1232, 1190, 1155, 1098, 1065, 1034. MS(ESI): 582⁺ (M+N)⁺. Elementary Analysis as $C_{21}H_{20}ClN_7O_7S_2 \cdot 3.6H_2O$. Calculated; C, 38.99; H, 4.24; N, 15.16; Cl, 5.48; S, 9.91(%). Found: C, 38.84; H, 3.84; N, 15.23; Cl, 5.34; S, 9.67(%).

EXAMPLE 33

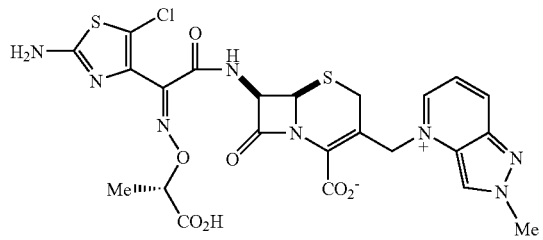

¹H (d₆-DMSO) δ: 1.37 (3H, d, J=6.9 Hz), 3.10 and 3.34 (2H, ABq, J=17.3 Hz), 4.39 (3H, s), 4.55 (1H, q, J=6.9 Hz), 5.01 (1H, d, J=4.9 Hz), 5.60 and 5.73 (2H, ABq, J=14.3 Hz), 5.68 (1H, dd, J=4.9, 9.0 Hz), 7.42 (2H, s), 7.97 (1H, dd, J=5.5, 8.6 Hz), 9.04 (1N, d, J=8.6 Hz), 9.42 (1H, d, J=5.5 Hz), 9.59 (2H, brs). IR (KBr) cm⁻¹: 3419, 1778, 1634, 1615, 1538, 1454, 1408, 1356, 1329, 1295, 1235, 1176, 1156, 1100, 1073, 1035, 1011. MS (EST): 621⁺ (M+H)⁺. Elementary Analysis as $C_{23}H_{21}ClN_8O_7S_2 \cdot 3.2H_2O$. Calculated: C, 40.70; H, 4.07; N, 16.51; Cl, 5.22; S, 9.45(%). Found: C, 40.48; H, 3.61; N, 16.42; Cl, 5.16; S, 9.46(%).

EXAMPLE 34

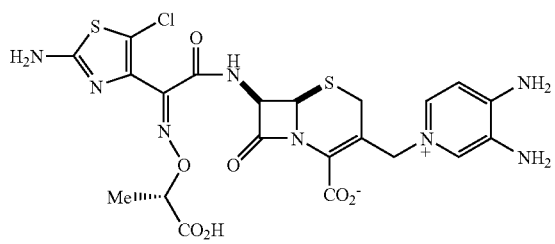

¹H-NMR (d₆-DMSO) δ: 1.39 (3H, d, J=7.1 Hz), 2.95 and 3.41 (2H, ABq, J=17.7 Hz), 4.57 (1H, q, J=7.1 Hz), 4.70 and 5.22 (2H, ABq, J=13-8 Hz), 5.05 (1H, d, J=4.89 Hz), 5.66 (2H, brs), 5.71 (1H, dd, J=4.8, 8.7 Hz), 6.73 (1H, d, J=6.9 Hz), 7.42 (4H, brs), 7.98 (2H, m). IR (KBr) cm⁻¹: 3379, 3213, 1775, 1645, 1577, 1542, 1446, 1360, 1308, 1235, 1184, 1156, 1065, 1035. MS(ESI): 597+W+H)⁺. Elementary Analysis as $C_{21}H_{21}ClN_8O_7S_2 \cdot 3.1H_2O$. Calculated: C, 38-63; H, 4.20; N, 17.16; Cl, 5.43; S, 9.82(%). Found: C, 38.51; H, 3.83; N, 17.22; Cl, 541; S, 9.75(%).

EXAMPLE 35

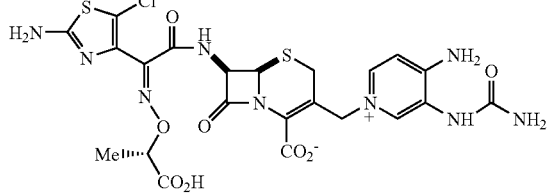

¹H-NMR (d₆-DMSO) a: 1.40 (3H, d, J=7.1 Hz), 3.09 and 3.48 (2H, ABq, J=17.7 Hz), 457 (1H, q, J=7.1 Hz), 4.85 and 5.22 (2H, ABq, J=13.8 Hz), 5.09 (1H, d, J=4.9 Hz), 5.76 (1H, dd, J=4.9 Hz), 6.58 (2H, brs), 6.95 (1H, d, J=6.5 Hz), 7.40 (2H, s), 7.96 (2H, brs), 8.28 (1H, d, J=6.5 Hz), 8.82 (1H, brs), 9.25 (1H, brs), 9.77 (1H, brs). IR (KBr) cm⁻¹: 3364, 3205, 1775, 1657, 1540, 1493, 1447, 1355, 1270, 1182, 1146, 1109, 1066, 1034. MS(ESI): 640M⁺ (M+H)⁺. Elementary Analysis as $C_{22}H_{22}ClN_9O_8S_2 \cdot 3.0 H_2O$. Calculated: C, 38.07; H, 4.07; N, 18.16; Cl, 5.11; S, 9.24(%). Found: C, 37.72; H, 3.67; N, 17.97; Cl, 5.03; S, 9.02(%).

EXAMPLE 36

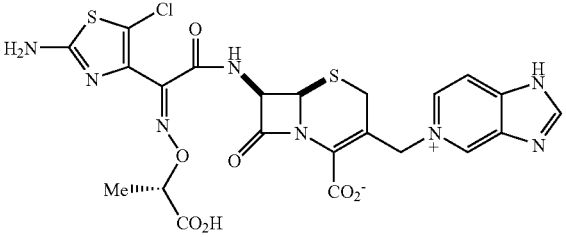

1H-NMR (d₆-DMSO) δ: 1.36 (3H, d, J=7.0 Hz), 3.10 and 3.54 (2H, ABq, J=17.6 Hz), 4.55 (1H, q, J=7.0 Hz), 5.14 (1H, d, J=5.0 Hz), 5.20 and 5.68 (2H, ABq, J=13.8 Hz), 5.77 (1H, dd, J=5.0, 9.1 Hz), 7.40 (2H, brs), 8.18 (1H, d, J=6.6 Hz), 8.83 (1H, brs), 8.87 (1H, d, J=6.6 Hz), 9.68 (1H, d, J=9.1 Hz), 9.80 (1H, brs). IR (KBr) cm⁻¹: 3412, 1777, 1614, 1539, 1444, 1377, 1305, 1187, 1108, 1066, 1036. MS(ESI): 607⁺ (M+H)⁺. Elementary Analysis as $C_{22}H_{19}ClN_8O_7S_2 \cdot 2.7H_2O$. Calculated: C, 40.30; H, 3.75; N, 17.09; Cl, 5.41; S, 9.78(%). Found: C, 40.22; H, 3.55; N, 17.05; Cl, 5.35; S, 9.57(%).

EXAMPLE 37

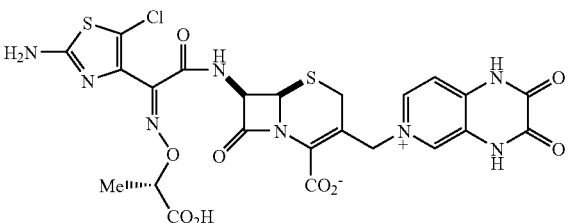

¹H-NMR (d₆-DMSO) δ: 1.38 (3H, d, J=7.1 Hz), 3.07 and 3.49 (2H, ABq, J=17.4 Hz), 4.57 (1H, q, J=7.1 Hz), 5.09 (1H, d, J=4.8 Hz), 5.12 and 5.55 (2H, ABq, J=13.5 Hz), 5.75 (1H, dd, J=4.8, 8.2 Hz), 7.41 (2H, s), 7.48 (1H, d, J=6.2 Hz), 8.70 (1H, d, J=6.2 Hz), 8.90 (1H, brs), 9.62 (1H, d, J=8.2 z). IR (KBr) cm⁻¹: 3421, 3195, 3088, 2988, 1776, 1720, 1639, 1532, 1375, 1237, 1175, 1137, 1066, 1035. MS(ESI): 651⁺ (M+H)⁺. Elementary Analysis as $C_{23}H_{19}ClN_8O_9S_2 \cdot 3.1H_2O$. Calculated: C, 39.08; H, 3.59; N, 15.85; Cl, 5.02; S, 9.07(%). Found: C, 39.05; H, 3.44; N, 15.81; Cl, 4.84; S, 8.83(%).

EXAMPLE 38

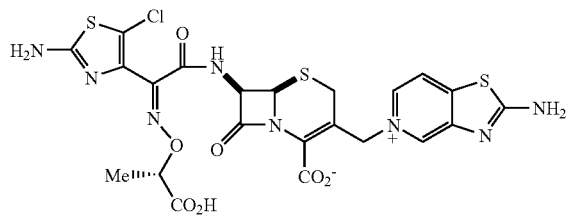

¹H-NMR (d₆-DMSO) δ: 137 (3H, d, J=6.9 Hz), 3.06 and 3.49 (2H, ABq, J=17.6 Hz), 4.51 (1H, q, J=6.9 Hz), 5.06 (1H, d, J=4.7 Hz), 5.04 and 5.61 (2H, ABq, J=12.9 Hz), 5.71 (1H, dd, J=4.7, 8.9 Hz), 7.42 (2H, s), 8.40 (1H, d, J=6.2 Hz), 8.64 (2H, s), 8.91 (1H, d, J=6.2 Hz), 9.39 (1H, s), 9.60 (1H, brs). IR (KBr) cm⁻¹: 3399, 3191, 1775, 1638, 1537, 1478, 1391, 1317, 1273, 1236, 1187, 1089, 1035. MS(ESI): 639⁺ (M+H)⁺. Elementary Analysis as $C_{22}H_{19}ClN_8O_7S_3 \cdot 3.4H_2O$ Calculated: C, 37.73; H, 3.71; N, 16.00; Cl, 5.06; S, 13.74 (%). Found: C, 37.61; H, 3.35; N, 16.12; Cl, 4.92; S, 13.56 (%).

EXAMPLE 39

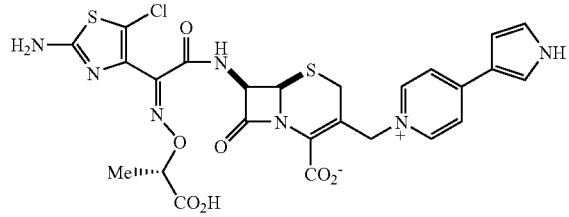

¹H-NMR (d₆-DMSO) δ: 1.37 (3H, d, J=6.9 Hz), 3.06 and 3.50 (2H, ABq, J=17.7 Hz), 4.53 (1H, q, J=6.9 Hz), 5.06 (1H, d, J=4.7 Hz), 4.91 and 5.45 (2H, ABq, J=12.5 Hz), 5.70 (1H, dd, J=4.7, 8.79 Hz), 6.85 (1H, s), 7.01 (1H, s), 7.41 (2H, s), 7.96 (1H, s), 8.15 (2H, d, J=5.7 Hz), 9.08 (2H, d, J=5.7 Hz), 9.73 (1H, brs), 11.85 (1H, brs). IR (KBr) cm⁻¹: 3410, 1774, 1636, 1560, 1474, 1354, 1218, 1152, 1107, 1037. MS(ESI): 632⁺ (M+H)⁺. Elementary Analysis as $C_{25}H_{22}ClN_7O_7S_2 \cdot 8.4H_2O$. Calculated: C, 38.33; H, 3.99; N, 12.52; Cl, 4.53; S, 8.19(%). Found: C, 37.89; H, 3.62; N, 12.41; Cl, 4.41; S, 7.93(%).

EXAMPLE 40

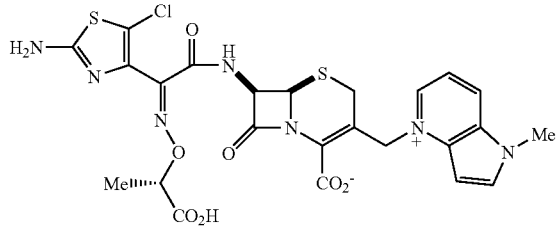

¹H-NMR (d₆-DMSO) δ: 1.37 (3H, d, J=7.1 Hz), 2.96 and 3.26 (2H, ABq, J=17.6 Hz), 4.02 (3H, s), 4.50 (2H, brs), 4.98 (1H, d, J=4.8 Hz), 5.67 (1H, brs), 7.34 (1H, d, J=3.0 Hz), 7.41 (2H, brs), 7.78 (1H d, J=6.0 Hz), 8.29 (1H, d, J=3.0 Hz), 8.75 (1H, d, J=7.9 Hz), 9.13 (1H, d, J=6.0, 7.9 Hz), 9.75 (1H, brs). IR (KBr) cm⁻¹: 3412, 1775, 1673, 1613, 1538, 1501, 1470, 1392, 1368, 1324, 1281, 1221, 1152, 1063, 1035. MS(ESI): 620⁺ (M+H)⁺. Elementary Analysis as $C_{23}H_{20}ClN_7O_7S_2 \cdot 2.1H_2O$. Calculated: C, 42.90; H, 3.79; N, 15-23; Cl, 5.51; S, 9.96(%). Found: C, 42.91; H, 3.76; N, 15.34; C, 5.47; S, 9.90(%).

EXAMPLE 41

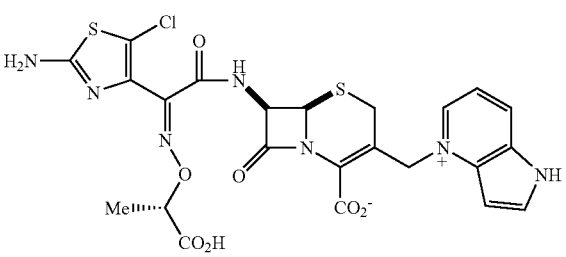

¹H-NMR (d₆-DMSO) δ: 1.37 (3H, d, J=7.1 Hz), 3.03 and 3-28 (2H, ABq, J=17.4 Hz), 4-56 (1H, q, J=7.1 Hz), 5.01 (1H, d, J=4.8 Hz), 5.69 (3H, m), 7.32 (1H, d, J=2.9 Hz), 7.41 (2H, s), 7.67 (1H t-like), 8.27 (1H, d, J=2.9 Hz), 8.60 (1H, d, 18.4 Hz), 9.06 (1H, d, J=5.7 Hz), 9.68 (1H, brs), 13.45 (1H, brs). IR (KBr) cm⁻¹: 3410, 2938, 1777, 1673, 1613, 1537, 1457, 1385, 1361, 1225, 1185, 1156, 1114, 1033. MS(ESI): 606⁺ (M+H)⁺. Elementary Analysis as $C_3H_{20}ClN_7O_7S_2 \cdot 2.5H_2O$. Calculated: C, 42.43; H, 3.87; N, 15.06; Cl, 5.45; S, 9.85(%). Found: C, 42.44; H, 3.69; N, 14.90; Cl, 5.24; S, 9.94(%).

EXAMPLE 42

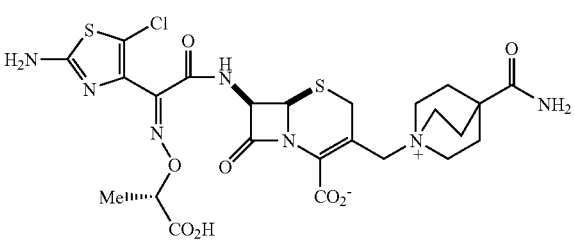

$^1$H-NMR (D2O) δ: 1.55 (3H, d, J=7.1 Hz), 2.19 (6H, t-like), 3.39-3.56 (7H, m), 3-89 (1H, d, J=16.8 Hz), 3.93 (1H, d, J=13.9 Hz), 4.62 (1H, d, J=13.9 Hz), 4.86 (1H, m), 5.36 (1H, d, J=5.0 Hz), 5.90 (1H, d, f 5.6 Hz). IR (KBr) cm$^{-1}$: 3371, 1779, 1671, 1614, 1538, 1466, 1389, 1343, 1236, 1183, 1099, 1070, 1035. MS(ESI): 642$^+$ (M+H)$^+$. Elementary Analysis as $C_{24}H_{28}ClN_7O_8S_2$.5.6$H_2O$. Calculated: C, 38.80; H, 5.32; N, 13.20; Cl, 4.77; S, 8.63(%). Found: C, 38.57; H, 4.76; N, 13.24; Cl, 4.56; S, 8.32(%).

EXAMPLE 43

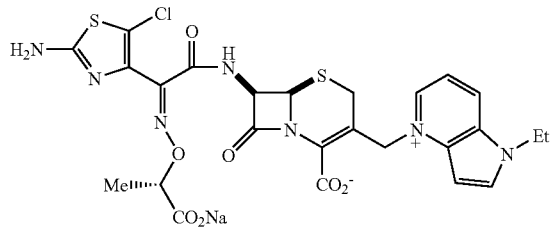

$^1$H-NMR (d$_6$-DMSO) δ: 1.31 (3H, d, J=7.1 Hz), 1.44 (3H, t, J=7.2 Hz), 2.96 and 3.25 (2H, ABq, J=17.1 Hz), 4.32 (1H, q, J=7.1 Hz), 4.45 (2H, q, 17.2 Hz), 4.93 (1H, d, J=5.1 Hz), 5.68 (2H, t-like), 5.75 (1H, dd, J=5.1, 9.0 Hz), 7.31 (2H, s), 7.39 (1H, d, J=3.5 Hz), 7.78 (1H, dd, J=6.1, 8.1 Hz), 8.37 (1H, d, J=3.5 Hz), 8.81 (1H, d, J=8.1 Hz), 9.21 (1H, d, J=6.1 Hz), 12.10 (1H, d, J=9.0 Hz). IR (KBr) cm$^{-1}$: 3409, 2982, 1772, 1604, 1539, 1496, 1460, 1394, 1362, 1317, 1289, 1230, 1185, 1153, 1106, 1033. MS(ESI): 634$^+$ (+H)$^+$. Elementary Analysis as $C_{25}H_{23}ClN_7N_8O_7S_2$.3.7$H_2O$. Calculated: C, 41.55; H, 4.24; N, 13.57; Cl, 4.91; S, 8.87; Na, 3.18(%). Found: C, 41.48; H, 3.96; N, 13.60; Cl, 4.84; S, 8.87; Na, 3.26(%).

EXAMPLE 44

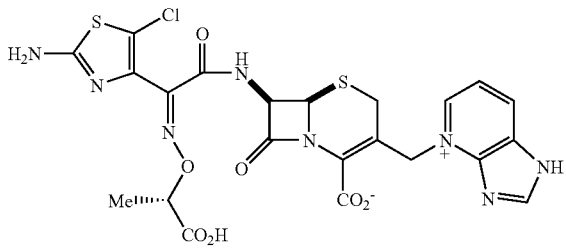

$^1$H-NMR (d$_6$-DMSO) δ: 1.35 (3H, d, J=6.9 Hz), 3.12 and 3.49 (2H, ABq, J=17.9 Hz), 4.54 (1H, q, J=6.9 Hz), 5.12 (1H, d, J=4.8 Hz), 5.57 and 5.68 (2H, ABq, J=14.1 Hz), 5.81 (1H, dd, J=4.8, 8-9 Hz), 7.42 (2H, s), 7.52 (1H, t-like), 8.55 (2H, brs), 8.71 (1H, d; J=6.6 Hz), 9.54 (1H, d, J=8.9 Hz). IR (KBr) cm$^{-1}$: 3416, 1777, 1674, 1608, 1538, 1449, 1387, 1311, 1230, 1187, 1158, 1102, 1072, 1032. MS(ESI): 607$^+$ (M+H)$^+$. Elementary Analysis as $C_{22}H_{19}ClN_3O_7S_2$.2.3$H_2O$. Calculated: C, 40.75; H, 3.67; N, 17.28; Cl, 5.47; S, 9.89(%). Found: C, 40.72; H, 3.55; N, 17.35; Cl, 5.51; S, 9.90(%).

EXAMPLE 45

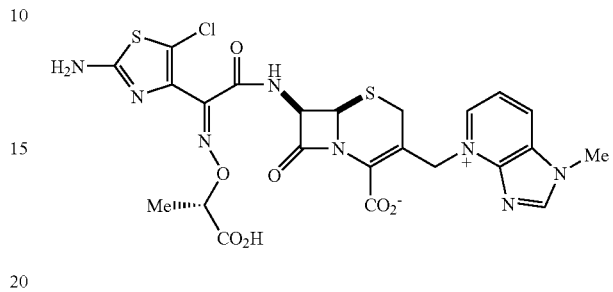

$^1$H-NMR (d$_6$-DMSO) δ: 1.34 (3H, d, J=6.9 Hz), 3.00 and 3.51 (2H, ABq, J=17.6 Hz), 4.07 (3H, s), 4.53 (1H, q, J=6.9 Hz), 5.02 (1H, d, J=5.4 Hz), 5.68-5.74 (3H, n), 7.41 (2H, s), 7.97 (1H, t-like), 8.89 (1H, d, J=7.8 Hz), 9.04 (1H, s), 9.66 (2H, m). IR (KBr) cm$^{-1}$: 3416, 1778, 1674, 1615, 1538, 1497, 1464, 1362, 1316, 1266, 1235, 1188, 1155, 1100, 1063, 1033. MS(ESI): 621$^+$ (M+H)$^+$. Elementary Analysis as $C_{23}H_{21}ClN_8O_7S_2$.2.3$H_2O$. Calculated: C, 41.70; H, 3.89; N, 16.91; Cl, 5.35; S, 9.68(%). Found: C, 41.67; H, 3-85; N, 16.90; Cl, 5.27; S, 9.60(%).

EXAMPLE 46

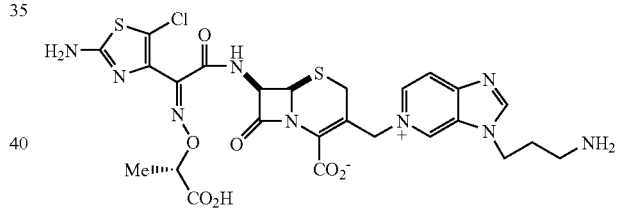

$^1$H-NMR (D$_2$O) δ: 1.43 (3H, d, J=7.2 Hz), 2.35 (2H, m), 3.12 (2H, t-like), 3.19 and 3.68 (2H, ABq, J=17.7 Hz), 4.61 (3H, q-like), 5.28 (1H, d, J=5.1 Hz), 5.33 and 5.67 (2H, ABq, J=14.7 Hz), 5.86 (1H, d, J=5.1 Hz), 8.21 (1H, d, J=6.3 Hz), 8.70 (1H, d, J=6.3 Hz), 8.90 (1H, brs), 9.71 (1H, s). IR (KBr) cm$^{-1}$: 3410, 1773, 1606, 1538, 1478, 1450, 1384, 1315, 1284, 1214, 1170, 1117, 1083, 1033. MS(ESI): 664$^+$ (M+H)$^+$. Elementary Analysis as $C_{25}H_{26}ClN_9O_7S_2$.3.6$H_2O$. Calculated: C, 41.19; H, 4.59; N, 17.29; Cl, 4.86; S, 8.80(%). Found: C, 41.25; H, 4.49; N, 17.07; Cl, 4.87; S, 8.50(%).

EXAMPLE 47

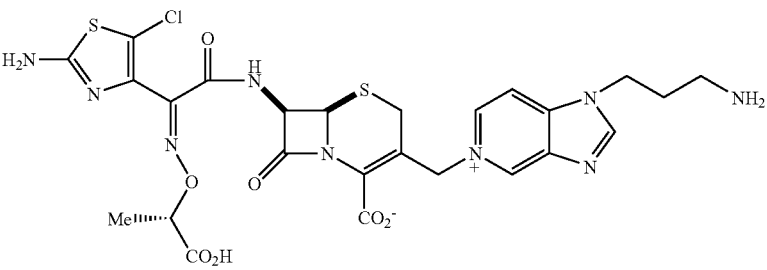

¹H-NMR (D₂O) δ: 1.42 (3H, d, J=6.9 Hz), 2.34 (2H, m), 3.10 (2H, t-like), 3.18 and 3.63 (2H, ABq, J=17.9 Hz), 4.55-4.67 (3H, m), 5.27 (1H, d, J=5.0 Hr), 5.35 and 5.66 (2H, ABq, J=143 Hz), 5.87 (1H, d, J=5.0 Hz), 8.22 (1H, d, J=6.9 Hz), 8.79 (2H, d-like), 9.49 (1H, s). IR (KBr) cm⁻¹: 3410, 1773, 1606, 1539, 1515, 1458, 1395, 1363, 1310, 1216, 1185, 1137, 1107, 1066, 1033. MS(ESI): 664⁺ (M+H)⁺. Elementary Analysis as $C_{25}H_{26}ClN_9O_7S_2 \cdot 3.2H_2O$. Calculated: C, 4.060; H, 4.52; N, 17.47; Cl, 4.91; S, 8.89(%). Found: C, 41.63; H, 4.48; N, 17.40, Cl, 4.82; S, 8.3(%).

EXAMPLE 48

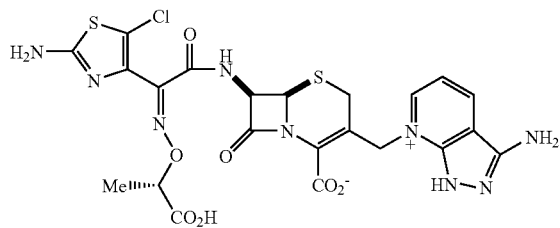

¹H-NMR (d₆-DMSO) δ: 1.34 (3H, d, J=6.9 Hz), 2.84 and 3.51 (2H, ABq, J=17.4 Hz), 4.51 (1H, q, J=6.9 Hz), 5.11 (1H, d, J=4.6 Hz), 5.14 and 5.54 (2H, ABq, J=14.4 Hz), 5.72 (1H, dd, J=4.6, 9.0 Hz), 6.59 (1H, brs), 7.34-7.40 (3H, m), 8.77 (2H, d-like), 9.58 (1H, brs). IR (KBr) cm⁻¹: 3414, 1774, 1638, 1574, 1538, 1446, 1391, 1367, 1334, 1227, 1182, 1078, 1036. MS(ESI): 662⁺ (M+H)⁺. Elementary Analysis as $C_{22}H_{20}ClN_9O_7S_2 \cdot 2.4H_2O$. Calculated: C, 39.72; H, 3.76; N, 18.95; Cl, 5.33; S, 9.649(%). Found: C, 39.77; H, 3.69; N, 19.04; Cl, 5.27; S, 9.49(%).

EXAMPLE 49

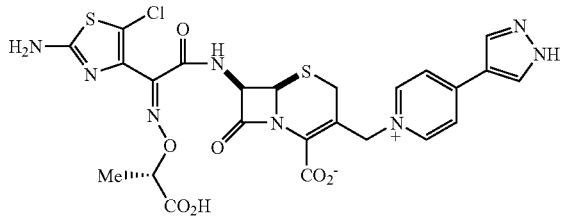

¹H-NMR (d₆-DMSO): 1.37 (3H, d, J=7.0 Hz), 3.09 and 3.51 (2H, ABq, J=17.6 Hz), 4.54 (1H, q, J=7.0 Hz), 4.99 and 5.51 (2H, ABq, J=12.8 Hz), 5.70 (1H, dd, J=4.7, 8.7 Hz), 7.42 (2H, s), 8.30 (2H, d, J=6.5 Hz), 8.59 (2H, brs), 9.58 (1H, d, J=8.7 Hz), 13.7 (1H, brs). IR (KBr) cm⁻¹: 3314, 3194, 1777, 1671, 1637, 1570, 1538, 1470, 1391, 1344, 1285, 1221, 1156, 1100, 1065, 1034. MS(ESI): 633⁺ (M+H)⁺. Elementary Analysis as $C_{24}H_{21}ClN_8O_7S_2 \cdot 2.5H_2O$. Calculated: C, 42.51; H, 3.86; N, 16.52; Cl, 5.23; S, 9.46(%). Found: C, 42.44; H, 3.67; N, 16.68; Cl, 5.36; S, 9.36(%).

EXAMPLE 50

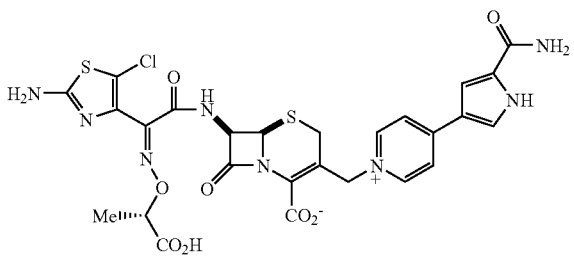

¹H-NMR (d₆-DMSO) δ: 1.37 (3H, d, J=7.1 Hz), 3.09 and 3.51 (2H, ABq, J=17.4 Hz), 4.76 (1H, q, J=7.1 Hz), 4.94 and 5.49 (2H, ABq, J=12.5 Hz), 5.07 (1H, d, J=4.7 Hz), 5.72 (1H, dd, J=4.7, 8.6 Hz), 7.27 (1H, brs), 7.41 (2H, s), 7.62 (1H, brs), 7.94 (1H, brs), 8.06 (1H, brs), 8.18 (2H, d, J=5.9 Hz), 9.16 (2H, d, J=5.9 Hz), 9.81 (1H, brs), 12.5 (1H, brs). IR (KBr) cm⁻¹: 3402, 1775, 1718, 1636, 1608, 1570, 1550, 1441, 1393, 1343, 1288, 1220, 1150, 1035. MS(ESI): 675⁺ (M+H)⁺. Elementary Analysis as $C_{26}H_{23}ClN_8O_8S_2 \cdot 5.1H_2O$. Calculated: C, 40.72; H, 4.36; N, 14.61; Cl, 4.62; S, 8.36(%). Found: C40 56; H, 3.97; N, 14.44; Cl, 5.09; S, 8.05(%).

EXAMPLE 51

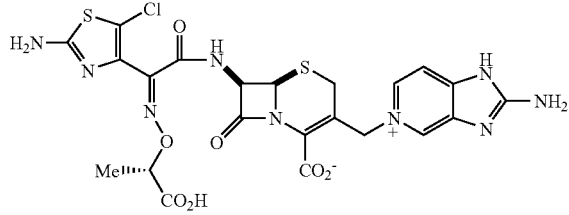

¹H-NMR (d₆-DMSO) δ: 1.34 (3H, d, S=7.0 Hz), 3.05 and 3.61 (2H, ABq, J=17.9 Hz), 4.52 (1H, q, J=7.0 Hz), 4.82 and 5.37 (2H, ABq, J=14.4 Hz), 5.14 (1H, d, J=5.0 Hz), 5.76 (1H, dd, J=5.0, 8.9 Hz), 7.37 (2H, brs), 7.43 (1H, d, J=6.9 Hz), 8.40 (2H, brs), 8.42 (1H, d, J=6.9 Hz), 9.63 (2H, brs). IR (KBr) cm⁻¹: 3336, 3192, 1774, 1662, 1617, 1573, 1539, 1489, 1393, 1332, 1246, 1188, 1153, 1119, 1066, 1034. MS(ESI): 622⁺ (M+H)⁺. Elementary Analysis as $C_{22}H_{20}ClN_9O_7S_2 \cdot 1.9H_2O$. Calculated: C, 40.26; H, 3.66; N, 19.21; Cl, 5.40; S, 9.77(%). Found: C, 40-48; H, 3.69; N, 19.26; Cl, 5.10; S, 9.48(%).

EXAMPLE 52

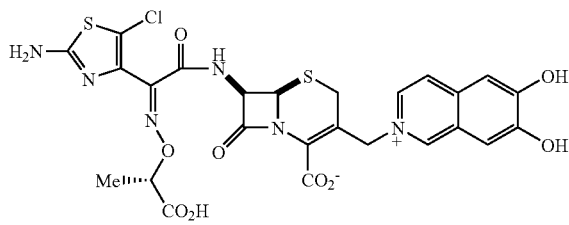

$^1$H-NMR (d$_6$-DMSO) δ: 1.37 (3H, d, J=7.0 Hz), 3.18 and 3.52 (2H, ABq, J=18.0 Hz), 4.56 (1H, q, J=7.0 Hz), 5.11 (2H, m), 5.48 (1H, q, J=13.8 Hz), 5.81 (H1H, q, J=4.7, 8.8 Hz), 7.12 (1H, rs), 7.41 (2H, s), 7.53 (1H, s), 7.83 (1H, d, J=6.0 Hz), 8.38 (1H, d, J=6.0 Hz), 9.24 (1H, brs), 9.63 (1H, d, J=8.8 Hz). IR (KBr) cm$^{-1}$: 3420, 1778, 1672, 1623, 1535, 1480, 1445, 1395, 1308, 1184, 1154, 1131, 1065, 1035. MS(ESI): 649$^+$ (M+H)$^-$. Elementary Analysis as C$_{25}$H$_{21}$ClN$_6$O$_9$S$_2$.2.1H$_2$O. Calculated: C, 43.71; H, 3.70; N, 12.23; Cl, 5.16; S, 9.34(%). Found: C, 44.06; H, 3.69; N, 12.31; Cl, 5.00; S, 9.94(%).

EXAMPLE 53

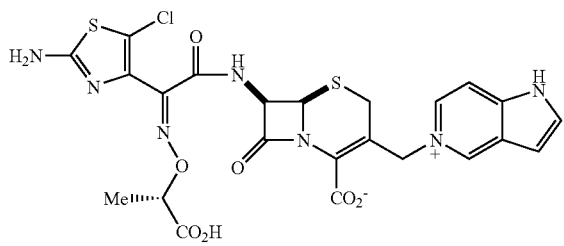

$^1$H-NMR (d$_6$-DMSO) δ: 1.35 (3H, d, J=7.0 Hz), 3.04 and 3.50 (2H, ABq, J=17.7 Hz), 4.54 (1H, q, J=7.0 Hz), 5.08 (OH, d, J=5.1 Hz), 5.15 and 5.65 (2H, ABq, J=13.7 Hz), 5.73 (OH, dd, J=5.1, 8.6 Hz), 7.01 (1H, d, J=3.3 Hz), 7.42 (2H, s), 7.94 (1H, d, J=3.3 Hz), 8.03 (1H, d, J=6.6 Hz), 8.88 (1H, d, J=6.6 Hz), 9.71 (1H, brs), 13.4 (1H, brs). IR (KBr) cm$^{-1}$: 3395, 3009, 2937, 1777, 1673, 1632, 1537, 1484, 1445, 1378, 1359, 1227, 1187, 1153, 1117, 1065, 1034. MS(ESI): 606$^+$ (M+H)$^+$. Elementary Analysis as C$_{23}$H$_{20}$ClN$_7$O$_7$S$_2$.2.2H$_2$O. Calculated: C, 42.78; H, 3.81; N, 15.19; Cl, 5.49; S, 9.93(%). Found: C, 42.87; H, 3.81; N, 15.20; C, 5.30; S, 9.86(%).

EXAMPLE 54

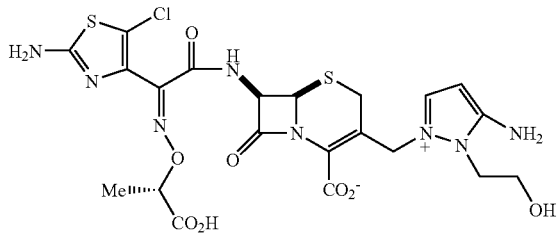

$^1$H-NMR (d$_6$-DMSO) δ: 1.41 (3H, d, J=7.0 Hz), 2.97 and 3.21 (2H, ABq, J=17.6 Hz), 3.58 (2H, brs), 4.58 (1H, q, J=7.0 Hz), 5.06 (TH, d, J=4.9 Hz), 5.10 and 5.23 (2H, ABq, J=15.9 Hz), 5.70 (1H, dd, J=4.9, 8.6 Hz), 5.83 (1H, d, 13.0 Hz), 7.26 (2H, s), 7.43 (2H, s), 8.08 (1H, d, J=3.0 Hz), 9.75 (1H, brs). IR (KBr) cm$^{-1}$: 3411, 2939, 1775, 1635, 1537, 1456, 1325, 1221, 1151, 1097, 1036. MS(ESI) 615$^+$ (M+H)$^+$. Elementary Analysis as C$_{21}$H$_{23}$ClN$_8$O$_8$S$_2$, 2.6H$_2$O. Calculated: C, 38.11; H, 4.29, N, 16.93; Cl, 5.36; S, 9.69(%). Found: C, 38.04; H, 3.93; N, 16.67; Cl, 5.49; S, 9.68(%).

EXAMPLE 55

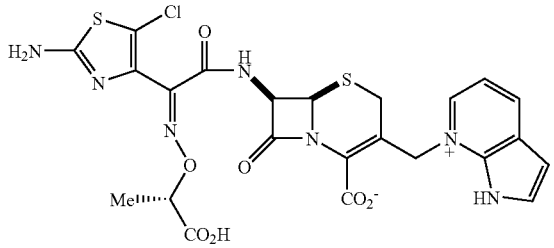

$^1$H-NMR (d$_6$-DMSO) δ: 1.30 (3H, d, J=7.0 Hz), 2.76 and 3.57 (2H, ABq, J=18.0 Hz), 4.48 (1H, q, J=7.0 Hz), 5.13 (1H, d, J=4.9 Hz), 5.24 and 5.90 (2H, ABq, J=14.3 Hz), 5.72 (1H, dd, J=4.9, 8.4 Hz), 6.89 (1H, d, J=3.3 Hz), 7.40 (1H, s), 7.58 (1H, dd, J=6.0, 7.8 Hz), 7.92 (1H, d, J=3.3 Hz), 8.71 (2H, m), 9.54 (1H, d, J=8.4 Hz). IR (KBr) cm$^{-1}$: 3413, 2934, 2718, 1777, 1675, 1616, 1537, 1480, 1461, 1362, 1230, 1189, 1112, 1034. MS(ESI): 606$^+$ (M+H)$^+$. Elementary Analysis as C$_{23}$H$_{20}$ClN$_7$O$_7$S$_2$.2.3H$_2$O. Calculated: C, 42.67; H, 3.83; N, 15.14; Cl, 5.48; S, 9.90(%). Found: C, 42.65; H, 3.82; N, 15.18; Cl, 5.40; S, 9.74(%).

EXAMPLE 56

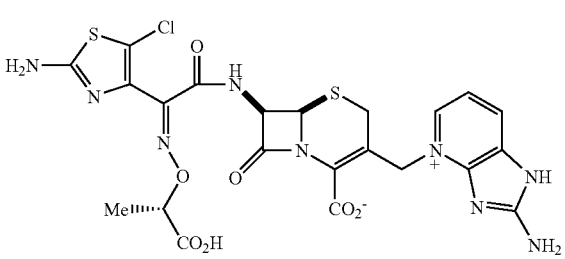

$^1$H-NMR (d$_6$-DMSO) δ: 1.39 (3H, d, J=7.1 Hz), 3.15 and 3.52 (2H, ABq, J=17.7 Hz), 4.56 (1H, q, J=7.1 Hz), 5.10 (1H, d, J=4.9 Hz), 5.36 (2H, brs), 5.80 (1H, dd, J=4.9, 8.6 Hz), 7.11 (1H, t, J=7.2 Hz), 7.69 (1H, d, J=7.2 Hz), 8.42 (3H, m), 9.84 (1H, brs). IR (KBr) cm$^{-1}$: 3352, 3151, 2712, 1772, 1665, 1607, 1583, 1543, 1490, 1443, 1408, 1390, 1368, 1341, 1300, 1211, 1160, 1106, 1083, 1060, 1031. MS(ESI): 622$^+$ (M+H)$^+$. Elementary Analysis as C$_{22}$H$_{20}$ClN$_9$O$_7$S$_2$.3.0H$_2$O. Calculated: C, 39.08; H, 3.88; N, 18.65; Cl, 5.24; S, 9.49(%). Found: C, 39.26; H, 3.83; N, 18.75; Cl, 5.33; S, 9.19(%).

EXAMPLE 57

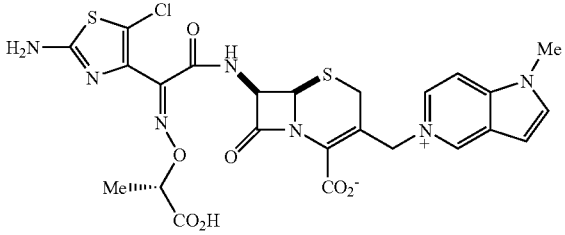

¹H-NMR (d₆-DMSO) δ: 1.34 (3H, d, J=6.9 Hz), 2.97 and 3.48 (2H, ABq, J=17.6 Hz), 3.98 (3H, s), 4.52 (1H, q, J=6.9 Hz), 5.05-5.12 (2H, m), 5.63-5.72 (2H, m), 7.09 (1H, d, J=3.1 Hz), 7.42 (2H, s), 7.94 (1H, d, J=3.1 Hz), 8.17 (1H, d, J=7.1 Hz), 9.49 (1H, d, J=7.1 Hz), 9.64 (1H, brs), 9.7 (1H, brs). IR (KBr) cm⁻¹: 3406, 3073, 2945, 1778, 1675, 1631, 1538, 1447, 1361, 1324, 1254, 1227, 1184, 1132, 1106, 1065, 1033. MS(FAB): 620 (M+H)⁺. Elementary Analysis as $C_{24}H_{22}ClN_7O_7S_2 \cdot 2.4H_2O$. Calculated: C, 43.46; H, 4.07; N, 1478; Cl, 5.34; S, 9.67(%). Found: C, 43.45; H, 4.03; N, 14.88; Cl, 5.25; S, 9.55(%).

EXAMPLE 58

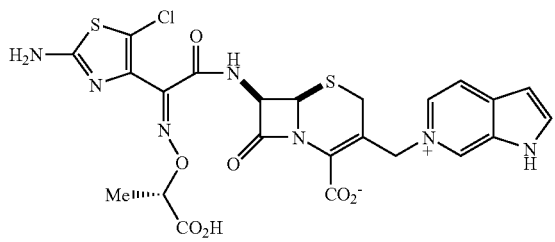

¹H-NMR (d₆-DMSO) δ: 1.35 (3H, d, J=6.9 Hz), 3.04 and 3.56 (2H, ABq, J=17.6 Hz) 4.53 (1H, q, J=7.0 Hz), 5.09-5.15 (2H, m), 5.68-5.76 (2H, m), 6.92 (1H, d, J=2.7 Hz), 7.40 (2H, s), 8.11 (1H, d, J=6.9 Hz), 8.30 (1H, d, J=2.7 Hz), 8.55 (1H, d, J=6.9 Hz), 9.84 (2H, brs), 14.7 (1H, brs). IR (KBr) cm⁻¹: 3326, 3195, 2938, 1777, 1674, 1612, 1537, 1461, 1375, 1312, 1234, 1187, 1145, 1065, 1034. MS(ESI): 606 (M+H)⁺. Elementary Analysis as $C_3H_{20}ClN_7O_7S_2 \cdot 2.5H_2O$. Calculated: C, 42.43; H, 3.87; N, 15.06; Cl, 5.45; S, 9.85(%). Found: C, 42.46; H, 3.74; N, 15.01; Cl, 5.33; S, 9.93(%).

EXAMPLE 59

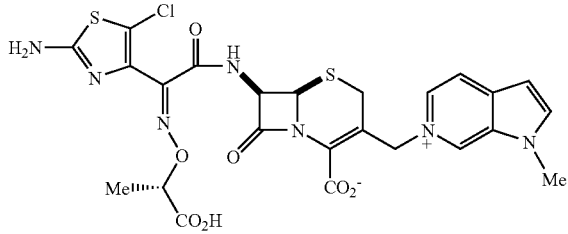

¹H-NMR (d₆-DMSO) δ: 1.34 (3H, d, J=7.0 Hz), 3.08 and 3.49 (2H, ABq, J=17.61 Hz), 4.04 (3H, s), 4.52 (1H, q, J=7.0 Hz), 5.05-5.12 (2H, m), 5.66-5.72 (2H, m), 6.92 (1H, d, J=2.9 Hz), 7.42 (2H, brs), 8.14 (1H, d, J=6.8 Hz), 8.28 (1H, d, J=2.9 Hz), 8.97 (1H, d, J=6.8 Hz), 9.64 (1H, brs), 9.80 (1H, brs). IR (KBr) cm⁻¹: 3410, 1777, 1676, 1614, 1537, 1486, 1447, 1423, 1378, 1326, 1260, 1230, 1161, 1096, 1065, 1033. MS(ESI): 620 (M+H)⁺. Elementary Analysis as $C_{24}H_{22}ClN_7O_7S_2 \cdot 2.4H_2O$. Calculated: C, 43.46, H, 4.07; N, 14.78; Cl, 5-34; S, 9.67(%). Found: C, 43.47; H, 3.97; N, 14.79; Cl, 5.21; S, 9.59(%).

EXAMPLE 60

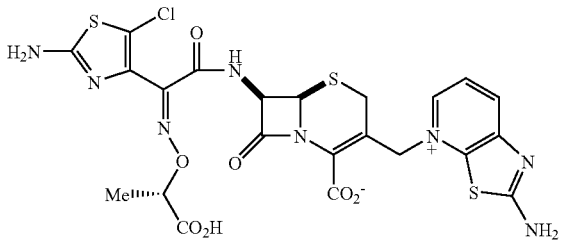

¹H-NMR (d₆-DMSO) δ: 1.39 (3H, d, J=7.1 Hz), 3.15 and 3.34 (2H, ABq, J=17.6 Hz), 4.56 (1H, q, J=7.1 Hz), 5.05 (1H, d, J=4.8 Hz), 5.47 (1H, d, J=14.1 Hz), 5.72-5.78 (2H, m), 7.41 (2H, brs), 7.84 (1H, dd, J=5.9, 8.1 Hz), 8.21 (1H, d, J=8.1 Hz), 8.83 (1H, d, J=5.9 Hz), 8.89 (2H, brs), 9.87 (1H, brs). IR Br) cm⁻¹: 3312, 3189, 1778, 1630, 1537, 1426, 1386, 1341, 1308, 1214, 1186, 1129, 1064, 1034. MS(FAB): 639⁺ (M+H)⁺. Elementary Analysis as $C22H_{19}ClN_8O_7S_3 \cdot 3.2H_2O$. Calculated: C, 37.92; H, 3.67; N, 16.08; Cl, 5.09; S, 13-81(%). Found: C, 37.95; H, 3.60; N, 16.04; Cl, 5.07; S, 13.60(%).

EXAMPLE 61

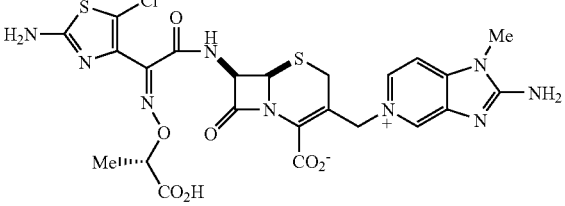

¹H-NMR (d₆-DMSO) δ: 1.35 (3H, d, J=7.0 Hz), 2.90 and 3.46 (2H, ABq, J=17.6 Hz), 3.66 (3H, s), 4.53 (1H, q, J=7.0 Hz), 4.96 and 5.56 (2H, ABq, J=13.7 Hz), 5.06 (1H, d, J=4.9 Hz), 5.69 (1H, dd, J=4.9, 8.9 Hz), 7.42 (2H, brs), 7.73 (2H, brs), 7.81 (1H, d, J=6.6 Hz), 8.81 (1H, d, J=6.6 Hz), 9.63 (1H, brs). IR (KBr) cm⁻¹: 3346, 3180, 1775, 1664, 1613, 1567, 1538, 1508, 1448, 1389, 1352, 1311, 1271, 1179, 1100, 1065, 1034. MS(FAB): 636⁺ (M+H)⁺. Elementary Analysis as $C_{23}H_{22}ClN_9O_7S_2 \cdot 2.7H_2O$. Calculated: C, 40.35; H, 4.03; N, 18.41; Cl, 5.18; S, 9.37(%). Found: C, 40.32; H, 3.90; N, 18.39; Cl, 5.14; S, 9.35(%).

EXAMPLE 62

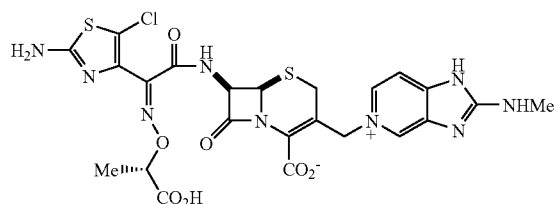

¹H-NMR (d₆-DMSO) δ: 1.35 (3H, d, J=7.0 Hz), 3.03-3.09 (4H, m), 3.61 (1H, d, J=18.0 Hz), 4.52 (1H, q, J=7.0 Hz), 4.83 and 5.40 (2H, ABq, J=14.0 Hz), 5.14 (1H, d, J=5.0 Hz), 5.77 (1H, dd, J=5.0, 8.7 Hz), 7.36 (21, brs), 7.48 (1H, d, J=6.8 Hz), 8.43 (1H, d, J=6.8 Hz), 9.33 (1H, brs), 9.59 (1H, brs), 9.70 (1H, brs). IR (KBr) cm$^{-1}$: 3370, 1775, 1644, 1579, 1538, 1479, 1394, 1329, 1239, 1188, 1121, 1066, 1034. MS(FAB): 636$^+$ (M+H)$^+$. Elementary Analysis as $C_{23}H_{22}ClN_9O_7S_2 \cdot 2.2H_2O$. Calculated: C, 40.88; H, 3.94; N, 18.66; Cl, 5.25; S, 9.49(%). Found: C, 41.07; H, 4.21; N, 18.30; Cl, 4.86; S, 8.86(%).

EXAMPLE 63

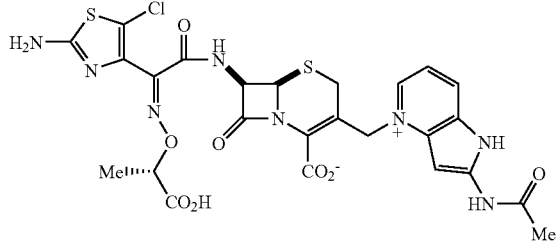

$^1$H-NMR (d$_6$-DMSO) δ: 1.41 (3H, d, J=7.0 Hz), 2.16 (3H, s), 3.10 (1H, d, J=17.1 Hz), 4.59 (1H, q, J=7.0 Hz), 5.08 (1H, d, J=5.1 Hz), 5.51 (2H, brs), 5.76 (1H, dd, J=5.1, 8.4 Hz), 6.87 (1H, s), 7.33 (1H, t-like), 7.39 (2H, brs), 8.01 (1H, brs), 8.59 (1H, d, J=6.0 Hz), 9.70 (1H, brs), 12.7 (1H, brs). IR (KBr) cm$^{-1}$: 3325, 1776, 1653, 1609, 1561, 1470, 1416, 1369, 1352, 1236, 1183, 1158, 1100, 1065, 1032. MS(FAB): 663$^+$ (M+H)$^+$. Elementary Analysis as $C_{25}H_{23}ClN_8O_8S_2 \cdot 3.2H_2O$. Calculated: C, 41.66; H, 4.11. N, 15.55, Cl, 4.92; S, 8.90(%). Found: C, 41.79; H, 4.14; N, 15.37; Cl, 4.82; S, 8.75(%).

EXAMPLE 64

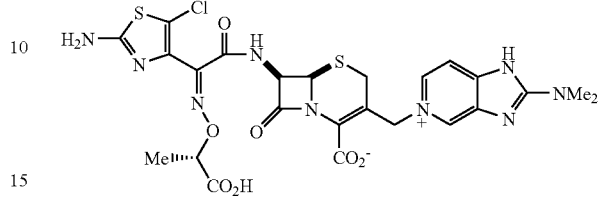

$^1$H-NMR (d$_6$-DMSO) δ: 1.36 (3H, d, J=7.1 Hz), 2.98 and 3.50 (2H, ABq, J=17.3 Hz), 3.21 (6H, s), 4.54 (1H, q, J=7.1 Hz), 5.00 and 5.48 (2H, ABq, J=13.5 Hz), 5.16 (1H, d, J=4.8 Hz), 5.72 (1H, dd, J=4.8, 9.0 Hz), 7.39 (2H, brs), 7.49 (1H, d, J=6.9 Hz), 8.44 (1H, d, J=6.9 Hz), 9.09 (1H, brs), 9.85 (1H, brs). IR (KBr) cm$^{-1}$: 3413, 2938, 1777, 1639, 1557, 1538, 1440, 1391, 1335, 1247, 1190, 1150, 1121, 1065, 1034. MS(FAB): 650++H)$^+$. Elementary Analysis as $C_{24}H_{24}ClN_9O_7S_2 \cdot 3.2H_2O$. Calculated: C, 40.73; H, 4.33; N, 17.81; Cl, 5.01; S, 9.06(%). Found: C, 40.73; H, 4.24; N, 17.75; Cl, 5.08; S, 9.10(%).

EXAMPLE 65

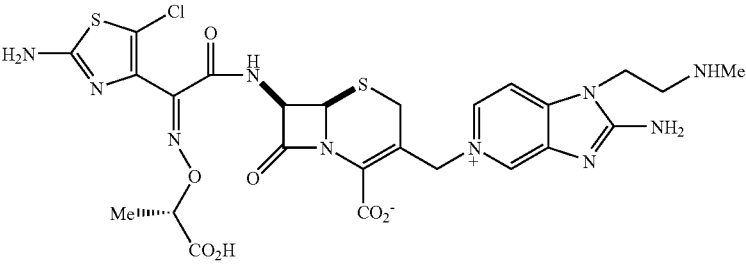

$^1$H-NMR (D$_2$O+DCl) δ: 1.55 (3H, d, J=7.1 Hz), 2.82 (3H, s), 3.36 and 3.75 (2H, ABq, J=18.5 Hz), 4.72 (2H, t, J=6.5 Hz), 4.99 (1H, q, J=7.1 Hz), 5.36 (1H, d, J=4.8 Hz), 5.40 and 5.86 (2H, ABq, J=14.9 Hz), 5.94 (1H, d, J=4.8 Hz), 8.09 (1H, d, J=6.8 Hz), 8.83 (1H, d, J=6.8 Hz), 9.06 (1H, s). IR (KBr) cm$^{-1}$: 3370, 3174, 1771, 1667, 1606, 1541, 1504, 1449, 1399, 1360, 1312, 1281, 1184, 1113, 1067, 1035. MS(FAB): 679$^+$ (M+H)$^+$. Elementary Analysis as $C_{25}H_{27}ClN_{10}O_7S_2 \cdot 4.0H_2O$. Calculated: C, 39.97; H, 4.70; N, 18.65; Cl, 4.72; S, 8.54(%). Found: C, 40.02, H, 4.64; N, 18.79; Cl, 4.60; S, 8.31(%).

EXAMPLE 66

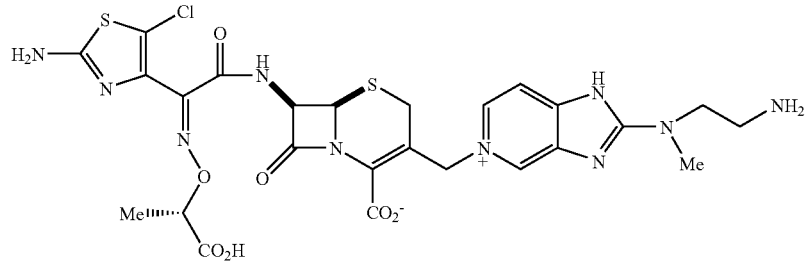

¹H-NMR (D₂O+DCl) δ: 1.55 (3H, d, J=7.1 Hz), 3.29-3.45 (6H, m), 3.69 (1H, d, J=18.3 Hz), 4.04 (2H, t, J=6.2 Hz), 4.98 (1H, q, J=7.1 Hz), 5.28-5.35 (2H, m), 5.70 (1H, s), 5.93 (1H, d, J=4.8 Hz), 7.68 (1H, d, J=4.6 Hz), 8.45 (1H, dd, J=1.2, 4.6 Hz), 8.73 (1H, d, J=1.2 Hz). IR (KBr) cm⁻¹: 3397, 1772, 1623, 1578, 1540, 1508, 1446, 1397, 1330, 1247, 1190, 1151, 1121, 1066, 1034. MS(FAB): 679⁺ (M+H)⁺. Elementary Analysis as $C_{25}H_{27}ClN_{10}O_7S_2 \cdot 4.3H_2O$. Calculated: C, 39.69; H, 4.74; N, 18.51; Cl, 4.69; S, 8.48(%). Found: C, 39.77; H, 4.70; N, 18.43; Cl, 4.59; S, 8.48(%).

EXAMPLE 67

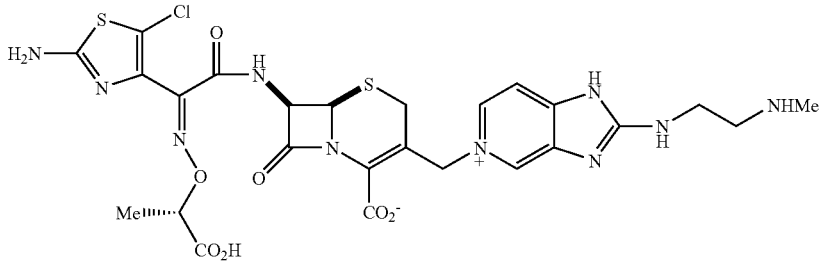

¹H-NMR (D₂O+DCl) δ: 1.54 (3H, d, J=7.1 Hz), 2.80 (3H, s), 3.29 and 3.66 (2H, ABq, J=18.3 Hz), 3.41 (21, t, J=5.8 Hz), 3.89 (2H, t, J=5.8 Hz), 4.96 (1H, q, J=7.1 Hz), 5.27-5.33 (2H, m), 5.61 (1H, d, J=14.8 Hz), 5.93 (1H, d, J=4.8 Hz), 7.67 (1H, d, J=6.8 Hz), 8.43 (1H, d, J=6.8 Hz), 8.71 (1H, s). IR (KBr) cm⁻¹: 3388, 1773, 1626, 1540, 1477, 1395, 1361, 1238, 1186, 1152, 1120, 1065, 1035. MS(FAB): 679⁺(M+H)⁺. Elementary Analysis as $C_{25}H_{27}ClN_{10}O_7S_2 \cdot 3.7 H_2O$. Calculated: C, 40.26; H, 4.65; N, 18.78; Cl, 4.75; S, 8.60(%). Found: C, 40.23; H, 4.60; N, 18.76; Cl, 4.79; S, 8.51(%).

EXAMPLE 68

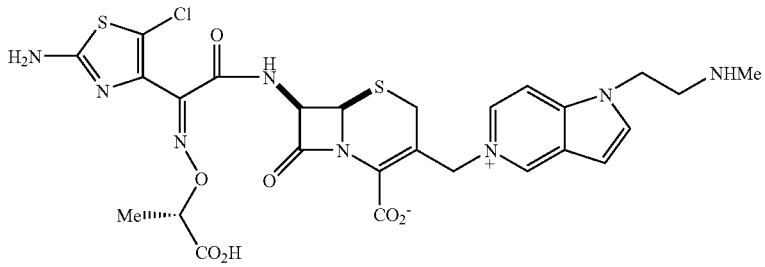

¹H-NMR (D₂O) δ: 1.42 (3H, d, J=6.9 Hz), 2.74 (3H, s), 3.17 (1H, d, J=18.0 Hz), 3.56-3.61 (3H, m), 4.61-4.76 (3H, m), 5.23-5.31 (2H, m), 5.54 (1H, d, J=14.7 Hz), 5.56 (1H, d, J=4.5 Hz), 7.12 (1H, d, J=3.4 Hz), 7.80 (1H, d, J=3.4 Hz), 7.99 (1H, d, J=7.0 Hz), 852 (1H, d, J=7.0 Hz), 9.086 (1H, s). IR (KBr) cm⁻¹: 3398, 2452, 1773, 1604, 1540, 1514, 1494, 1448, 1395, 1363, 1286, 1223, 1187, 1119, 1065, 1034. MS(FAB): 663⁺ (M+H)⁺. Elementary Analysis as $C_{26}H_{27}ClN_8O_7S_2 \cdot 4.0H_2O$. Calculated: C, 42.48; H, 4.80; N, 15.24; Cl, 4.82; S, 8.72(%). Found: C, 42.45; H, 4.57; N, 15.20; C, 14.86; S, 8.70(%).

EXAMPLE 69

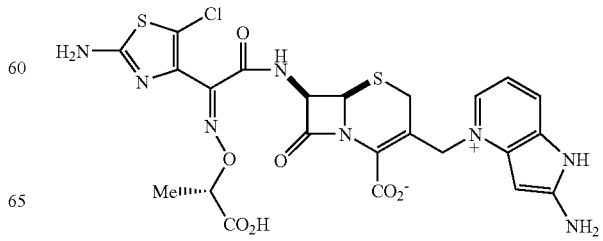

¹H-NMR (d₆-DMSO) δ: 1.39 (3H, d, J=7.0 Hz), 3.02 and 3.31 (2H ABq, J=17.7 Hz), 4.57 (1H, q, J=7.0 Hz), 5.05 (1H, d, J=4.9 Hz), 5.22 and 5.35 (2H, ABq, J=14.4 Hz), 5.75 (TH, dd, J=4.9, 9.0 Hz), 5.87 (1H, s), 6.84 (1H, t-like), 7.39 (2H, brs), 7.49 (1H, d, J=7.5 Hz), 7.82 (1H, brs), 8.09 (1H, d, J=6.6 Hz), 9.86 (1H, brs), 12.9 (1H, brs). IR (KBr) cm⁻¹: 3338, 3198, 1773, 1640, 1581, 1540, 1497, 1427, 1364, 1329, 1285, 1239, 1192, 1159, 1099, 1034. MS(FAB): 621⁺ (M+H)⁺. Elementary Analysis as $C_{23}H_{21}ClN_8O_7S_2 \cdot 2.9H_2O$. Calculated: C, 41.03; H, 4.01; N, 16.64; Cl, 5.27; S, 9.52(%). Found: C, 41.01; H, 3.90; N, 16.64; Cl, 5.37; S, 9.49(%).

EXAMPLE 70

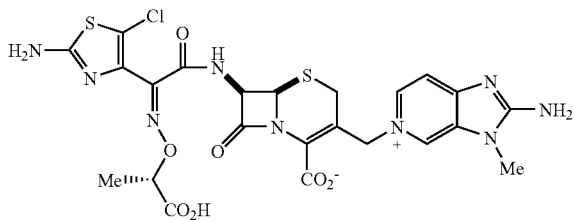

¹H-NMR (d₆-DMSO) δ: 1.36 (3H, d, J=7.1 Hz), 3.01 and 3.47 (2H, ABq, J=17.7 Hz), 3.60 (3H, s), 4-53 (1H, q, J=7.1 Hz), 4.90 and 5.50 (21, ABq, J=13.7H), 5.04 (1H, d, J=4.9 Hz), 5.69 (1H, dd, J=4.9, 9.0 Hz), 7.40 (2H, brs), 7.51 (1H, d, J=6.8 Hz), 8.14 (2H, brs), 8.82 (1H, d, J=6.8 Hz), 9.13 (1H, brs), 4.68 (1H, brs). IR (KBr) cm⁻¹: 3354, 3190, 1774, 1658, 1557, 1485, 1467, 1389, 1347, 1231, 1162, 1094, 1066, 1035. MS(FAB): 636' (M+H)⁺. Elementary Analysis as $C_{11}H_{22}ClN_9O_7S_2 \cdot 3.2H_2O$. Calculated: C, 39.82; H, 4.13; N, 18.17; Cl, 5.11; S, 9.24(%). Found: C, 39.85; H, 4.07; N, 18.08; Cl, 5.02, S, 9.12(%).

EXAMPLE 71

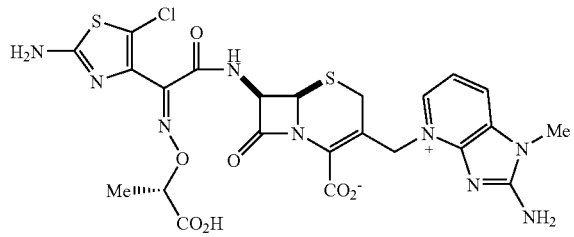

¹H-NMR (D₂O+DCl) δ: 1.54 (3H, d, J=7.2 Hz), 3.33 and 3.59 (2H ABq, J=18.5 Hz), 3.67 (3H, s), 4.99 (1H, q, 17.2 Hz), 5.29 (1H, d, J=4.8 Hz), 5.22 and 5.65 (21, ABq, J=15.2 Hz), 5.91 (m, d, J=4.8 Hz), 7.33 (1H, dd, J=6.5, 7.8 Hz), 7.91 (1H, d, J=7.8 Hz), 8.10 (1H, d, J=6.5 Hz). IR (KBr) cm⁻¹: 3455, 3351, 3288, 3041, 2949, 2899, 1746, 1699, 1671, 1651, 1625, 1606, 1579, 1533, 1494, 1462, 1447, 1422, 1404, 1364, 1354, 1303, 1275, 1254, 1227, 1209, 1189, 1173, 1155, 1140, 1091, 1076, 1064, 1026. MS(FAB): 636⁺ (M+H)⁺. Elementary Analysis as $C_{23}H_{22}ClN_9O_7S_2 \cdot 2.5H_2O$. Calculated: C, 42.82; H, 3.59; N, 19.54; Cl, 5.50; S, 9.94(%). Found: C, 42.84; H, 3.55; N, 19.51; Cl, 5.43; S, 10.00(%).

EXAMPLE 72

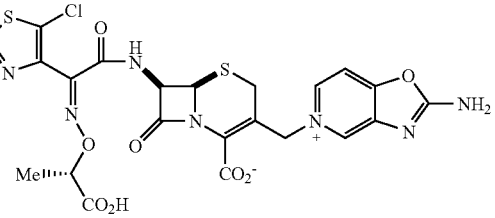

¹H-NMR (d₆-DMSO) δ: 1.37 (3H, d, J=7.1 Hz), 3.00 and 3.49 (2H, ABq, 117.7 Hz), 4.54 (1H, q, J=7.1 Hz), 5.02 and 5.63 (2H, ABq, J=13.7 Hz), 5.07 (1H, d, J=5.0 Hz), 5.72 (1H, dd, J=5.0, 8.7 Hz), 7.41 (2H, brs), 8.12 (1H, d, J=7.1 Hz), 8.72 (2H, brs), 9.10 (1H, d, J=7.1 Hz), 9.45 (1H, brs), 9.55 (1H, d, J=8.7 Hz). IR(KBr) cm⁻¹: 3385, 1776, 1692, 1617, 1538, 1492, 1363, 1287, 1223, 1188, 1150, 1103, 1066, 1036. MS(FAB): 623⁺ (M+H)⁺. Elementary Analysis as $C_{22}H_{19}ClN_8O_8S_2 \cdot 2.9H_2O$. Calculated: C, 39.13; H, 3.70; N, 16.59; Cl, 5.25; S, 9.50(%). Found: C, 39.04; H, 3.55; N, 16.69; Cl, 5.12; S, 9.52(%).

EXAMPLE 73

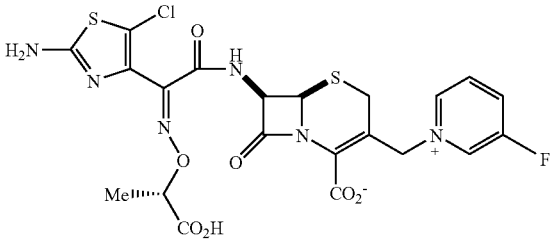

¹H-NMR (d₆-DMSO) δ: 1.38 (3H, d, J=7.0 Hz), 3.15 and 3.50 (2H, ABq, J=17.6 Hz), 4.55 (1H, q, J=7.0 Hz), 5.07 (1H, d, J=5.1 Hz), 5.11 (1H, d, J=13.2 Hz), 5.65-5.74 (2H, m), 7.41 (2H, brs), 8.24-8.31 (1H, m), 8.62-8.68 (1H, m), 9.46 (1H, d, J=6.0 Hz), 9.52 (1H, d, J=8.7 Hz), 9.89 (1H, brs). IR (KBr) cm⁻¹: 3411, 3068, 2943, 1778, 1673, 1616, 1538, 1503, 1446, 1390, 1345, 1275, 1189, 1137, 1097, 1065, 1035. MS(FAB): 585⁺ (M+H)⁺. Elementary Analysis as $C_{21}H_{18}ClFN_6O_7S_2 \cdot 2.9H_2O$. Calculated: C, 39.58; H, 3.76; N, 13.19; Cl, 5.56; S, 10.06(%). Found: C, 39.52; H, 3.59; N, 13.24; Cl, 5.65; S, 10.25(%).

EXAMPLE 74

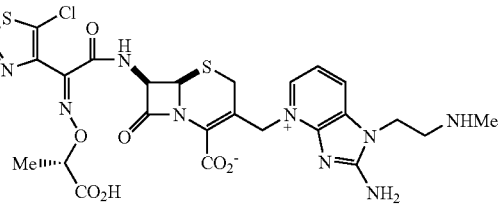

¹H-NMR (d₆-DMSO) δ: 1.54 (3H, d, J=7.1 Hz), 2.78 (3H, s), 3.37 (1H, d, J=18.3 Hz), 3.54-3.62 (3H, m), 4.57 (2H, t, J=6.5 Hz), 4.98 (1H, q, J=7.1 Hz), 5.27 (1H, d, J=4-8 Hz), 5.49 and 5.71 (2H, ABq, J=15.2 Hz), 5.91 (1H, d, J=4.8 Hz), 7.34 (1H, t-like), 8.00 (1H, d, J=7.8 Hz), 8.17 (1H, d, J=6.6 Hz). IR (KBr) cm⁻¹: 3398, 2451, 1771, 1666, 1603, 1562, 1493, 1396, 1362, 1315, 1387, 1224, 1165, 1090, 1034. MS(FAB): 679⁺ (M+H)⁺. Elementary Analysis as $C_{25}H_{27}ClN_{10}O_7S_2 \cdot 3.6H_2O$. Calculated: C, 40.36; H, 4.63; N, 18.83; Cl, 4.77; S, 8.62(%). Found: C, 40.32; H, 4.68; N, 18.84; Cl, 4.87; S, 8.77(%).

EXAMPLE 75

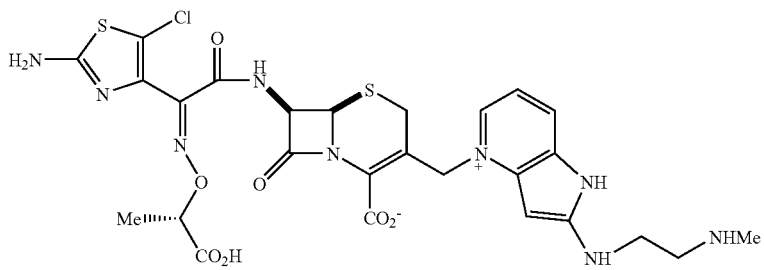

$^1$H-NMR (D$_2$O+DCl) δ: 1.54 (3H, d, J=7.1 Hz), 2.64 (3H, s), 3.25 and 3.45 (2H ABq, J=18.3 Hz), 3.38 (2H, t, J=5.9 Hz), 3.76 (2H, t, J=5.9 Hz), 4.98 (1H, q, J=7.1 Hz), 5.26 (1H, d, J=4.8 Hz), 5.39 and 5.48 (2H, ABq, J=15.5 Hz), 5.89 (1H, d, J=4.8 Hz), 7.10 (1H, t-like), 7.73 (1H, d, J=7.8 Hz), 7.94 (1H, d, J=6.6 Hz). IR (KBr) cm$^{-1}$: 3389, 1771, 1590, 1540, 1428, 1395, 1360, 1317, 1284, 1192, 1158, 1113, 1058, 1033. MS(FAB): 678$^+$ (M+H)$^+$. Elementary Analysis as C$_{26}$H$_{28}$ClN$_9$O$_7$S$_2$.3.3H$_2$O. Calculated: C, 42.34; H, 4.73; N, 17.09; Cl, 4.81; S, 8.69(%). Found: C, 42.11; H, 4.67; N, 17.00, Cl, 4.94; S, 9.09(%).

EXAMPLE 76

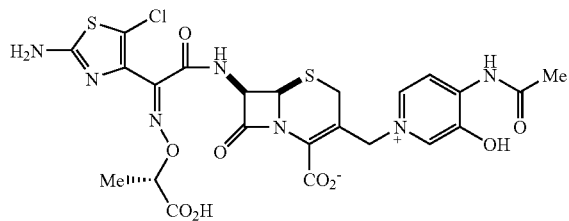

$^1$H-NMR (d$_6$-DMSO) δ: 1.40 (3H, d, J=7.1 Hz), 2.26 (3H, s), 3.12 and 3.45 (2H, ABq, J=17.7 Hz), 4.59 (1H, q, J=7.1 Hz), 5.20 (1H, d, J=4.9 Hz), 5.78 (1H, dd, J=4.9, 9.2 Hz), 7.41 (2H, brs), 8.12 (1H, d, J=6.3 Hz), 8.39 (1H, brs), 8.47 (1H, d, J=6.3 Hz), 9.60 (1H, d, J=9.2 Hz), 10.05 (1H, brs). IR (KBr) cm$^{-1}$: 3330, 1777, 1674, 1623, 1529, 1475, 1379, 1314, 1230, 1141, 1102, 1066, 1036. MS(ESI): 640$^+$ (M+H)$^+$. Elementary Analysis as C$_{23}$H$_{22}$ClN$_7$O$_9$S 2.8H$_2$O. Calculated C, 40.01; H4903; N, 14.20; Cl, 5.13; S, 9.29(%). Found: C, 39.92; H, 3.90; N, 14.32; Cl, 5.27; S, 9.31(%).

EXAMPLE 77

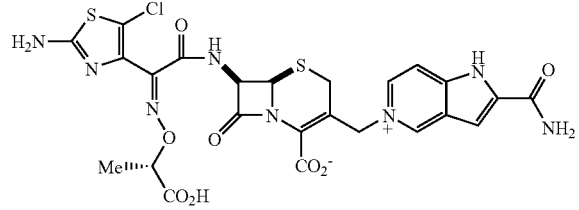

$^1$H-NMR (d$_6$-DMSO) δ: 1.35 (3H, d, J=6.9 Hz), 3.05 and 3.48 (2H, ABq, J=17.6 Hz), 4.53 (1H, q, J=6.9 Hz), 5.06 (1H, d, J=4.8 Hz), 5.13 (1H, d, J=13.8 Hz), 5.64-5.73 (2H, m), 7.40 (21, brs), 7.66 (1H, s), 7.87 (1H, brs), 7.94 (1H, d, J=6.9 Hz), 8.51 (1H, brs), 8-97 (1H, d, J=6.9 Hz), 9.62 (1H, brs),9.81 (1H, brs). IR (KBr) cm$^{-1}$: 3327, 3195, 1775, 1677, 1613, 1540, 1375, 1335, 1240, 1182, 1152, 1116, 1066, 1036. MS(ESI): 649$^+$ (M+H)$^+$. Elementary Analysis as C$_{24}$H$_{21}$ClN$_8$O$_8$S$_2$.2.4H$_2$O. Calculated: C, 41.64; H, 3.76; N, 16.19; Cl, 5.12; S, 9.26(%). Found: C, 41.70; H, 3.71; N, 16.24; Cl, 5.00; S, 9.063(%).

EXAMPLE 78

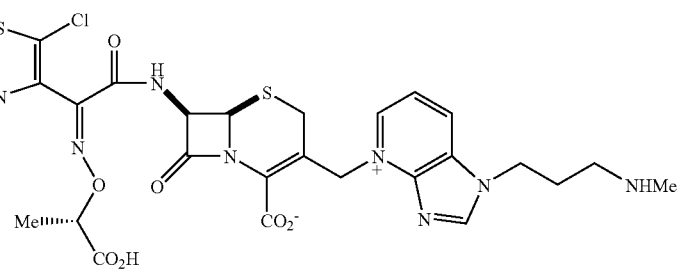

¹H-NMR (D₂O) δ: 1.43 (3H, d, J=7.1 Hz), 2.39 (2H, quint. J=7.8 Hz), 2.72 (3H, s), 3.15 (2H, t, J=7.8 Hz), 3.26 and 3.62 (2H, ABq, J=18.0 Hz), 4.59-4.69 (3H, m), 5.23 (1H, d, J=4.8 Hz), 5.62 (1H, d, J=14.7 Hz), 5.70-5.75 (2H, m), 7.89 (1H, dd, J=6.3, 8.3 Hz), 8.78 (1H, d, J=8.3 Hz), 8.86 (1H, brs), 8.88 (1H, d, J=6.3 Hz).

IR (KBr) cm⁻¹: 3397, 2464, 1773, 1602, 1541, 1490, 1463, 1389, 1313, 1287, 1237, 1187, 1159, 1115, 1064, 1034.

MS(ESI): 678⁺ (M+H)⁺. Elementary Analysis as $C_{26}H_{28}ClN_9O_7S_2 \cdot 3.7H_2O$. Calculated: C, 41.93; H, 4.79; N, 16.93; Cl, 4.76; S, 8.61(%). Found: C, 41.93; H, 4.74, N, 16.89; Cl, 4.53; S, 8.58(%).

EXAMPLE 79

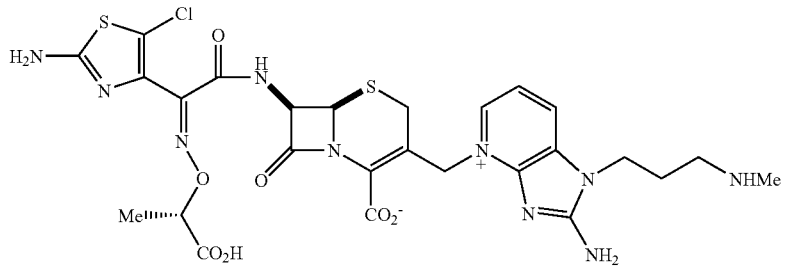

¹H-NMR (D₂O) δ: 1.44 (3H, d, J=7.0 Hz), 2.20 (2H, m), 2.70 (3H, s), 3.12 (2H, m), 3.24 and 3.50 (2H, ABq, J=17.9 Hz), 4.22 (2H, t, J=7.1 Hz), 4.55 (1H, q, J=7.0 Hz), 5.18 (1H, d, J=4.8 Hz), 5.25 and 5.56 (2H, ABq, J=14.7 Hz), 5.84 (1H, d, J=4.8 Hz), 7.30 (1H, tike), 7.89 (1H, d, S—7.8 Hz), 8.12 (1H, d, J=6.6 Hz). IR (KBr) cm⁻¹: 3363, 3181, 1772, 1651, 1600, 1565, 1494, 1394, 1364, 1315, 1288, 1223, 1163, 1091, 1034. MS(ESI): 693⁺ (M+H)⁺. Elementary Analysis as $C_{26}H_{29}ClN_{10}O_7S_2 + 2.9H_2O$. Calculated: C, 41.89; H, 4.71; N, 18.79; Cl, 476; S, 8.60(%). Found: C, 41.93; H, 4.73; N, 18.81; Cl, 4.51; S, 8.51(%).

EXAMPLE 80

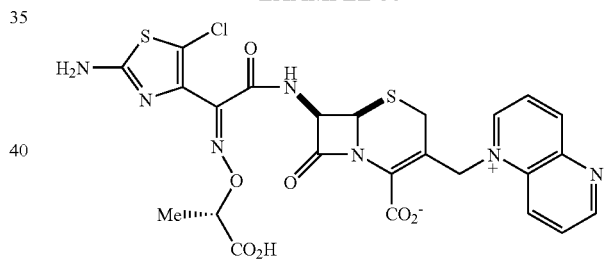

¹H-NMR (D₂O+DCl) δ: 1.55 (3H, d, J=7.1 Hz), 3.35 and 3.63 (2H ABq, J=18.9 Hz), 5.39 (1H, d, J=5.1 Hz), 5.98 (1H, d, J=5.1 Hz), 6.03 and 6.24 (Zn, ABq, J=15.6 Hz), 8.40 (1H, dd, J=5.7, 8.7 Hz), 9.04 (1H, d, J=9.3 Hz), 9.29 (1H, d, J=8.7 Hz), 9.17-49.20 (2H, m). IR (KBr) cm⁻¹: 3411, 3197, 1778, 1675, 1617, 1538, 1521, 1456, 1376, 1339, 1285, 1230, 1189, 1152, 1098, 1066, 1035. MS(ESI): 618⁺ (M+H)⁺. Elementary Analysis as $C_{24}H_{20}ClN_7O_7S_2 \cdot 3.0H_2O$. Calculated: C, 42.89; H, 390; N, 14.59; Cl, 5.28; S, 9.54(%). Found: C, 42.91; H, 397; N, 12.66; Cl, 5.18; S, 9.51(%).

EXAMPLE 81

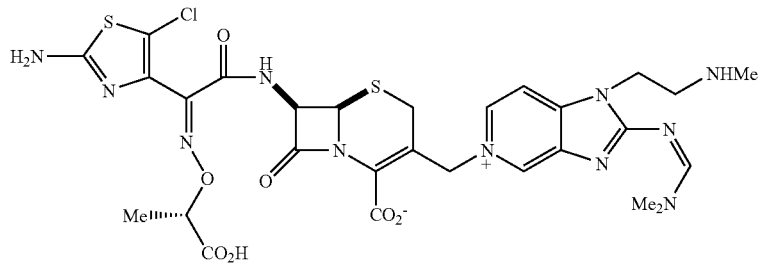

¹H-NMR (D₂O+DCl) δ 1.55 (3H, d, 37.2 Hz), 2.80 (3H, s), 3.38 and 3.77 (2H, ABq, J=18.9 Hz), 3.38 (3H, s), 3.45 (3H, s), 3.64 (2H, t, J=5.7 Hz), 4.76 (2H, t, J=5.7 Hz), 4.99 (1H, q. J=7.2 Hz), 5.37 (1H, d, J=4.8 Hz), 5.42 and 5.88 (2H, Aq, J=14.5 Hz), 5.95 (1H, d, J=4.8 Hz), 8.13 (1H, d, J=7.0 Hz), 8.68 (1H, brs), 8.84 (1H, dd, J=1.2, 7.0 Hz), 9.14 (1H, d, J=1.2 Hz). IR (KBr) cm⁻¹; 3406, 1773, 1632, 1535, 1497, 1421, 1389, 1352, 1309, 1237, 1183, 1114, 1065, 1034. MS(FAB): 734⁺ (M+H)⁺. Elementary Analysis as $C_{28}H_{32}ClN_{11}O_7S_2 \cdot 5.5H_2O$. Calculated C, 40.36; H, 520, N, 18.49, Cl, 4.25; S, 7.70(%). Found: C, 40.38; H, 5.03; N, 18.36; Cl, 4.52; S, 7.89(%).

EXAMPLE 82

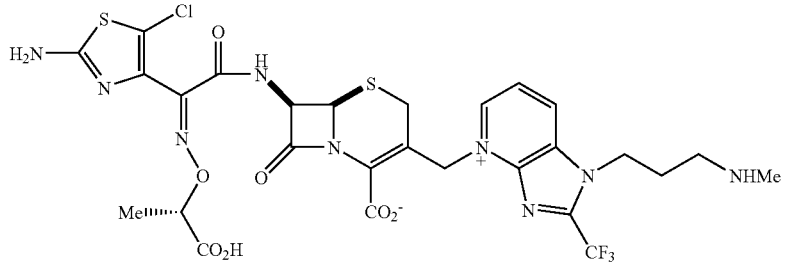

¹H-NMR (D₂O+DCl) δ: 1.44 (3H, d, J=6.9 Hz), 2.39 (2H, n), 2.73 (3H, s), 3.23 (2H, m), 3.30 and 3.68 (2H, ABq, J=18.0 Hz), 4.59-4.69 (3H, m), 5.24 (1H, d, J=5.0 Hz), 5.67 and 5.93 (2H, ABq, J=14.7 Hz), 5.88 (1H, d, J=5.0 Hz), 8.09 (1H, dd, J=8.2, 6.1 Hz), 8.99 (1H, d, J=8.2 Hz), 9.12 (1H, d, J=6.1 Hz). IR (KBr) cm⁻¹: 3403, 2467, 1776, 1604, 1540, 1482, 1458, 1437, 1394, 1352, 1317, 1269, 1195, 1155, 1121, 1096, 1065, 1034. MS(FAB): 7462⁺ (M+1H)⁺. Elementary Analysis as $C_{27}H_{27}ClF_3N_9O_7S_2 \cdot 3.7H_2O$. Calculated: C, 39.90; H, 4.27; N, 15.51; Cl, 4.36; S, 7.89(%). Found: C, 39.98; H, 4.33; N, 15.51; Cl, 4.12; S, 7.73(%).

EXAMPLE 83

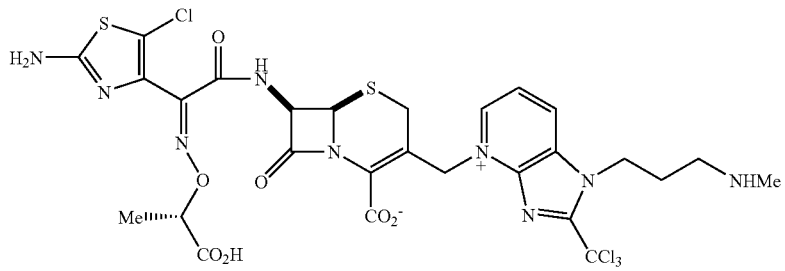

¹H-NMR (D₂O+DCl) δ: 1.56 (3H, d, J=6.9 Hz), 2.50 (2H, m), 2.77 (3H, s), 3.33 (2H, m), 3.59 and 3.72 (2H, ABq, J=18.3 Hz), 4.93-5.04 (3H, m), 5.27 (1H, d, J=5.1 Hz), 5.77 and 6.28 (2H, ABq, J=14.9 Hz), 5.92 (1H, d, J=5.1 Hz), 8.05 (1H, dd, J=8.4, 6.3 Hz), 8.99 (1H, d, J=8.4 Hz), 9.03 (1H, d, J=6.3 Hz). IR (KBr) cm⁻¹: 3400, 1776, 1604, 1539, 1450, 1392, 1350, 1321, 1287, 1224, 1159, 1063, 1033. MS(FAB): 794⁺ (M+H)⁺. Elementary Analysis as $C_{27}H_{27}Cl_4N_9O_7S_2 \cdot 3.3H_2O$. Calculated: C, 37.93; H, 3.96; N, 14.74; Cl, 16.59; S, 7.50(%). Found: C, 38-26; H, 4.00; N, 14.96; Cl, 15.25; S, 7.46(%).

EXAMPLE 84

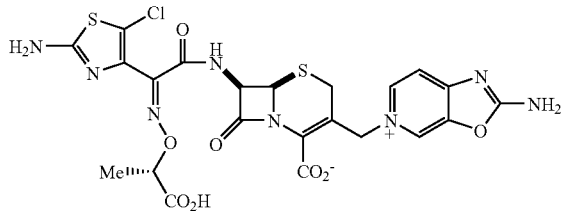

$^1$H-NMR (d$_6$-DMSO) δ: 1.37 (3H, d, J=7.1 Hz), 3.02 and 3.48 (2H, ABq, J=17.9 Hz), 4.54 (1H, q, J=7.1 Hz), 4.90 and 5.50 (2H, ABq, J=13.5 Hz), 5.05 (1H, d, J=4.8 Hz), 5.70 (1H, dd, J=4.8, 8.7 Hz), 7.41 (2H, brs), 7.69 (1H, d, J=6.8 Hz), 9.01 (1H, d, J=6.8 Hz), 9.33 (2H, brs), 9.58 (2H, brs). IR (KBr) cm$^{-1}$: 3393, 1776, 1687, 1615, 1559, 1513, 1484, 1377, 1326, 1284, 1213, 1188, 1154, 1106, 1066, 1034. MS(FAB): 623$^+$ (M+H)$^+$. Elementary Analysis as C$_{22}$H$_{19}$ClN$_8$O$_8$S$_2$.2.7H$_2$O. Calculated: C, 39.34; H, 3.66; N, 16.68; Cl, 5.28; S, 9.55(%). Found: C, 39.35; H, 3.67; N, 16.61; Cl, 5.26; S, 9.48(%).

EXAMPLE 85

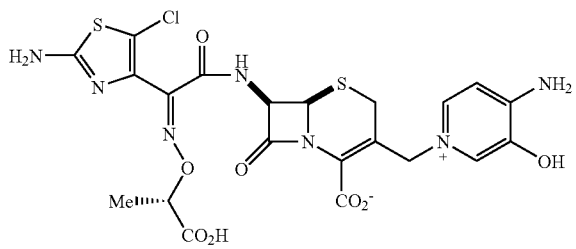

$^1$H-NMR (d$_6$-DMSO) δ: 1.39 (3H, d, J=6.9 Hz), 2.95 and 3.42 (2H ABq, J=17.4 Hz), 4.55 (1H, q, J=6.9 Hz), 4.73 and 5.21 (2H, ABq, J=13.8 Hz), 5.13 (1H, d, J=4.8 Hz), 5.71 (1H, dd, J=4.8, 8.7 Hz), 6.73 (1H, d, J=6.9 Hz), 7.40 (2H, brs), 7.99 (1H, d, J=639 Hz), 8.27 (1H, brs), 9.79 (1H, brs). IR (KBr) cm$^{-1}$: 3343, 3202, 1776, 1644, 1546, 1446, 1370, 1309, 1258, 1179, 1147, 1065, 1036. MS(FAB): 598$^+$ (M+H)$^+$. Elementary Analysis as C$_{21}$H$_{20}$ClN$_7$O$_7$S$_2$.2.6H$_2$O. Calculated: C, 39.11; H, 3.949; N, 15.20; Cl, 5.50; S, 9.94(%). Found: C, 39.18; H, 3.74; N, 15.14; Cl, 5.38; S, 9.82(%).

EXAMPLE 86

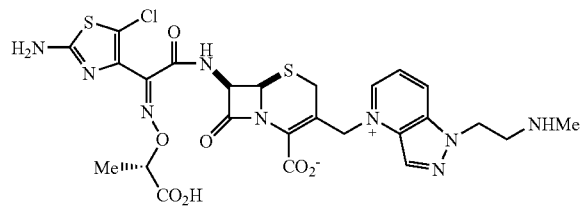

$^1$H-NMR (D$_2$O+DCl) δ: 1-44 (3H, d, J=7.1 Hz), 2.80 (3H, s), 3.20 and 3.53 (2H, ABq, J=17.9 Hz), 3.75 (2H, t, J=5.5 Hz), 4.66 (1H, q, J=7.1 Hz), 5.03 (2H, t, J=5.5 Hz), 5.23 (1H, d, J=5.0 Hz), 5.79 (2H, s), 5.88 (1H, d, J=5.0 Hz), 8.07 (1H, dd, J=8.7, 5.8 Hz), 8.82 (1H, s), 8-96 (1H, d, J=8.7 Hz), 9.05 (1H, d, J=5.8 Hz). IR (KBr) cm$^{-1}$: 3408, 1773, 1604, 1540, 1476, 1447, 1394, 1352, 1316, 1289, 1222, 1187, 1159, 1080, 1034. MS(FAB): 664$^+$ (M+H)$^+$, Elementary Analysis as C$_{25}$26$_9$ClN$_9$O$_7$S$_2$.3.0H$_2$O. Calculated: C, 41.81; H, 4.49; N, 17.55; Cl, 4.94; S, 8.93(%). Found: C, 41.86; H, 4.45; N, 17.66; Cl, 4.81; S, 871(%).

EXAMPLE 87

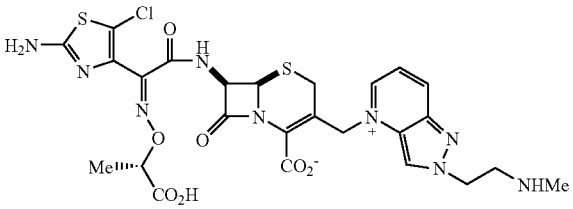

$^1$H-NMR (D$_2$O+DCl) δ: 1.44 (3H, d, J=7.1 Hz), 2.78 (3H, s), 3.11 and 3.52 (2H, ABq, J=17.9 Hz), 3.78 (2H, t, J=5.6 Hz), 4.66 (1H, q, J=7.1 Hz), 5.09 (2H, t, J=5.6 Hz), 5.23 (1H, d, J=4.8 Hz), 5.63 and 5.81 (2H, ABq, J=15.2 Hz), 5.85 (1H, d, J=4.8 Hz), 7.95 (1H, dd, J=9.0, 5.4 Hz), 8.97 (1H, d, J=9.0 Hz), 9.07 (1H, d, J=5.4 Hz), 9.21 (1H, brs). IR (KBr) cm$^{-1}$: 3408, 1773, 1603, 1540, 1476, 1447, 1394, 1352, 1316, 1289, 1223, 1187, 1159, 1080, 1034. MS(FAB): 664$^+$ (M+H)$^+$. Elementary Analysis as C$_{25}$H$_{26}$ClN$_9$O$_7$S$_2$.3.1H$_2$O. Calculated: C, 41.71; H, 4.51; N, 17.51; Cl, 4.92; S, 8.91(%). Found C, 41.75; H, 4.39; N, 17.57; Cl, 4.64; S, 8.71(%).

EXAMPLE 88

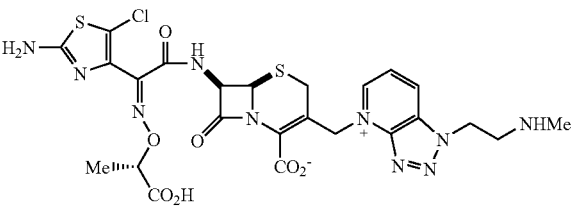

$^1$H-NMR (D$_2$O+DCl) δ: 1.55 (3H, d, J=7.2 Hz), 2.85 (3H, s), 3.53 and 3.80 (2H, ABq, J=18.0 Hz), 3.91 (2H, t, J=56.0 Hz), 5.34 (1H, d, J=4.8 Hz), 5.40 (2H, t, J=6.0 Hz), 5.96 (1H, d, J=4.8 Hz), 6.07 and 6.29 (2H, ABq, J=15.0 Hz), 8.28 (1H, dd, J=5.4, 8.4 Hz), 9.25 (1H, d, J=8.4 Hz), 9.34 (1H, d, J=5.4 Hz). IR (KBr) cm$^{-1}$: 3408, 2448, 1774, 1606, 1539, 1465, 1393, 1348, 1283, 1188, 1155, 1093, 1065, 1034. MS(ESI): 655 (M+H)$^+$. Elementary Analysis as C$_{24}$H$_{25}$ClN$_{10}$O$_7$S$_2$.3.6H$_2$O. Calculated: C, 39.49; H, 4.45; N, 19.19; Cl, 4.86; S, 8.79(%). Found: C, 39.50; H, 4.42; N, 19.21; Cl, 4.80; S, 8.67(%).

EXAMPLE 89

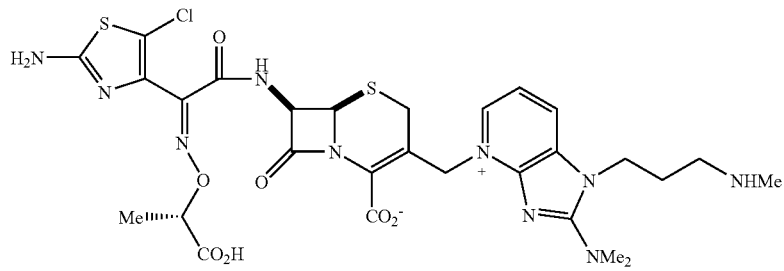

$^1$H-NMR (D$_2$O) δ: 1.44 (3H, d, J=7.0 Hz), 2.22 (2H, m), 2.70 (3H, a), 3.08 (2H, m), 3.27 and 3.51 (2H, ABq, J=18.0 Hz), 3.36 (6H, s), 4.36 (2H, t-like), 5.16 (1H, d, J=4.5 Hz), 5.22 and 5.67 (2H, ABq J=14.7 Hz), 5.83 (1H, d, J=4.5 Hz), 7.26 (1H, t-like), 7.35 (1H, d, J=7.8 Hz), 8.08 (1H, d, J=6.6 Hz). IR (KBr) cm$^{-1}$: 3399, 1773, 1629, 1584, 1541, 1501, 1419, 1350, 1320, 1226, 1167, 1137, 1064, 1033. MS(FAB): 721$^+$ (M+H)$^+$. Elementary Analysis as C$_{28}$H$_{33}$ClN$_{10}$O$_7$S$_2$.3.0H$_2$O. Calculated: C, 43.38; H, 5.07; N, 18.07; Cl, 4.57; S, 8.27(%). Found: C, 43.43; H, 5.05; N, 18.07, Cl,4.36; S, 8.10(%).

EXAMPLE 90

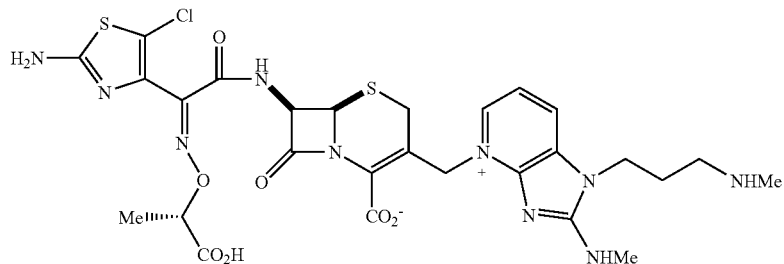

$^1$H-NMR (D$_2$O+DCl) δ: 1.56 (3H, d, J=7.5 Hz), 2.22 (2H, m), 2.72 (3H, s), 3.12-3.18 (5H, m), 3.46 and 3.60 (2H, ABq, J=18.5 Hz), 4.22 (2H, t, J=7.5 Hz), 5.01 (1H, q, J=7.5 Hz), 5.27 (1H, d, J=4.8 Hz), 5.27 (1H, d, J=4.8 Hz), 5.43 (1H, d, J=150 Hz), 5.85-5.91 (2H, m), 7.32 (1H, dd, J=6.7, 7.6 Hz), 7.92 (1H, d, J=7.6 Hz), 8.10 (1$H, d, J=6.7 Hz). IR (KBr) cm$^-$: 3398, 1773, 1642, 1596, 1541, 1496, 1412, 1392, 1366, 1316, 1222, 1165, 1139, 1099, 1064, 1034. MS(ESI): 707$^+$ (M+H)$^+$. Elementary Analysis as C$_{27}$H$_{31}$ClN$_{10}$O$_7$S$_2$.3.5H$_2$O. Calculated: C, 42.10; H, 4.97; N, 18.18; Cl, 4.60; S, 8.33(%). Found: C, 4209; H, 4.97; N, 18.19; Cl, 4.44, S,8.18(%).

EXAMPLE 91

[structure image]

$^1$H-NMR (D$_2$O+DCl) δ: 1.55 (3H, d, J=7.2 Hz), 2.33 (2H, d-like), 2.61 (2H, q-like), 3.25-3.39 (3H, m), 3.60 (1H, d, J=18.3 Hz), 3.72 (2H, d-like), 4.99 (I, q, J=7.2 Hz), 5.29 (1H, d, J=4.9 Hz), 5.50 and 5.69 (2H, ABq, J=15.0 Hz), 5.92 (l$, d, J=4.9 Hz), 7.33 (1H, t-like), 8.14 (2H, m). IR (KBr) cm$^{-1}$: 3380, 3182, 1772, 1601, 1555, 1491, 1440, 1395, 1362, 1317, 1287, 1225, 1169, 1092, 1033. MS(ESI): 705$^+$ (M+H)$^+$. Elementary Analysis as C$_{27}$H$_{29}$ClN$_{10}$O$_7$S$_2$.4.5H$_2$O. Calculated: C, 41.25; H, 4.87; N, 17.81; Cl, 4.51; S, 8.16(%). Found: C, 41.38, H, 4.79; N, 17.71; Cl, 4.19; S, 7.50(%).

EXAMPLE 92

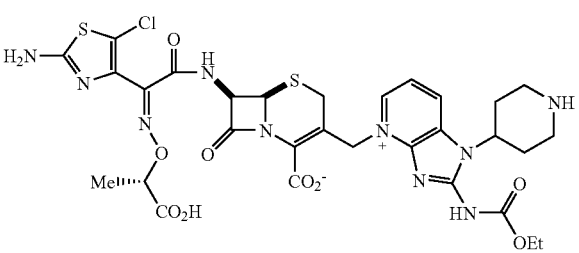

$^1$H-NMR (D$_2$O+DCl) δ: 1.36 (3H, d, J=7.1 Hz), 1.55 (3H, t, J=7.3 Hz), 2.38 (2H, d-like), 2.62-2.72 (2H, m), 3.27-3.35 (2Hm), 3.44 (1H, d, J=18.6 Hz), 3.68-3.74 (3H, m), 4.37 (2H, q, J=7.3 Hz), 4.99 (1H, q, J=7.1 Hz), 5.31 (1H, d, J=5.1 Hz), 5.73 (1H, d, J=15.1 Hz), 5.90-5.95 (2H, m), 7.74 (1H, dd, J=6.6, 7.9 Hz), 8.63 (1H, d, J=6.6 Hz), 8.69 (1H, d, J=7.9 Hz). IR (KBr) cm$^{-1}$: 3409, 2982, 2527, 1775, 1607, 1538, 1468, 1385, 1283, 1223, 1174, 1094, 1033. MS(ESI): 777$^+$ (M+H)$^+$. Elementary Analysis as C$_{30}$H$_{33}$ClN$_{10}$O$_9$S$_2$.4.8H$_2$O. Calculated: C, 41.72; H, 4.97; N, 16.22; Cl, 4.10; S, 743(%). Found: C, 41.68; H, 4.86; N, 16.33; C, 4.08; S, 7.46(%).

EXAMPLE 93

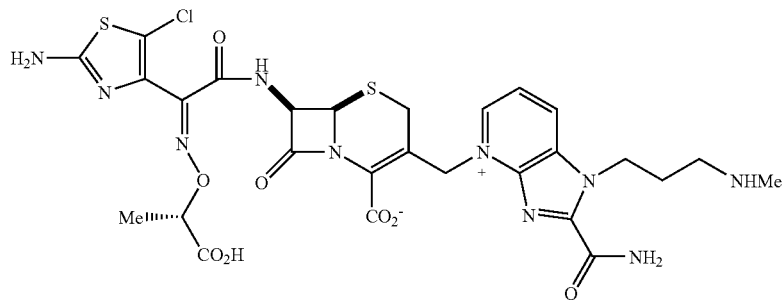

$^1$H-NMR (D$_2$O+DCl) δ: 1.56 (3H, d, J=5.4 Hz), 2.38 (2H, m), 2.74 (3H, s), 3.19 (2H, m), 3.54 (2H, m), 4.9 6 (3H, m), 5.19 (1H, brs), 5.62-6.32 (2H, m), 5.87 (1H, brs), 7.99 (1H, m), 8.93 (1H, d, J=7.5 Hz), 9.01 (1H, d, J=5.7 Hz). IR (KBr) cm$^{-1}$: 3399, 1771, 1698, 1667, 1602, 1540, 1460, 1394, 1358, 1327, 1287, 1221, 1187, 1152, 1082, 1061, 1034. MS(ESI): 721$^+$ (M+H$^+$). Elementary Analysis as C$_{27}$H$_{29}$ClN$_{10}$O$_8$S$_2$.5.0H$_2$O. Calculated: C, 39.97; H, 4.85; N, 17.27; Cl, 4.37; S, 7.91(%). Found: C, 39.88; H, 4.45; N, 17.07; C, 4.40; S, 7.99(%).

EXAMPLE 94

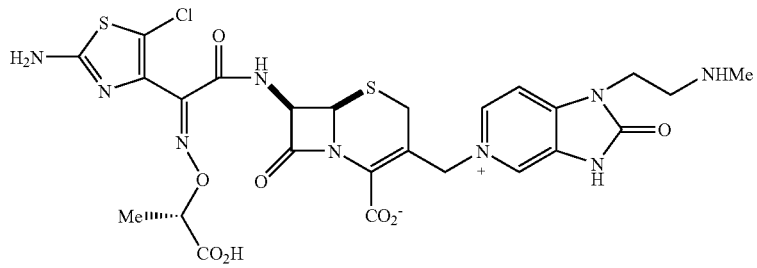

$^1$H-NMR (D$_2$O+DCl) δ: 1.55 (3H, d, J=7.1 Hz), 2.79 (3H, s), 3.35 and 3.54 (2H, ABq, J=18.5 Hz), 3.54 (2H, t, J=5.6 Hz), 4.44 (2H, t, J=5.6 Hz), 4.99 (1H, q, J=7.1 Hz), 5.36 (1H, d, J=5.0 Hz), 5.31 and 5.79 (2H, ABq, J=14.7 Hz), 5.94 (1H, d, J=5.0 Hz), 7.79 (1H, d, J=6.7 Hz), 8.65 (1H, dd, J=1.2, 6.7 Hz), 8.72 (1H, brs). IR (KBr) cm$^{-1}$: 3395, 3086, 1748, 1660, 1611, 1528, 1448, 1396, 1353, 1313, 1288, 1212, 1188, 1156, 1136, 1111, 1106, 1035. MS(ES): 680' (M+H)$^+$. Elementary Analysis as C$_{25}$H$_{26}$ClN$_9$O$_8$S$_2$.3.4H$_2$O. Calculated: C, 40.50; H, 4.46; N, 17.00; Cl, 4.78; S, 8.56(%). Found: C, 40.73; H, 4.45; N, 17.10; Cl, 4.65; S, 8.35(%).

EXAMPLE 95

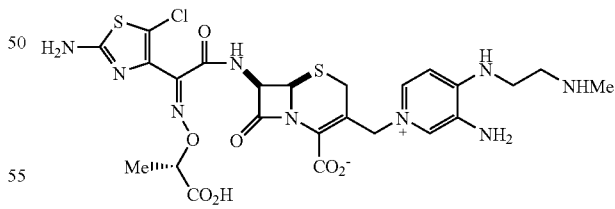

$^1$H-NMR (D$_2$O+DCl) δ: 1.56 (3H, d, J=7.1 Hz), 2.79 (3H, s), 3.31 and 3.66 (2H, ABq, J=18.3 Hz), 3.40 (2H, t, J=5.9 Hz), 3.85 (2H, t, J=5.9 Hz), 4.96-5.03 (2H, m), 5.33 (1H, d, J=5.1 Hz), 5.41 (1H, d, J=14.7 Hz), 5.93 (1H, d, J=5.1 Hz), 6.95 (1H, d, J=7.2 Hz), 7.71 (1H, d, J=1.8 Hz), 8.05 (1H, dd, J=1.8, 7.2 Hz). IR (KBr) cm$^{-1}$: 3368, 1773, 1627, 1556, 1455, 1395, 1349, 1321, 1287, 1190, 1158, 1093, 1065, 1034. MS(ESI): 654$^+$ (M+H)$^+$. Elementary Analysis as C$_{24}$H$_{28}$ClN$_9$O$_7$S$_2$.3.1H$_2$O. Calculated: C, 4060; H, 4.86; N, 17.76; Cl, 4.993; S, 9.03(%). Found: C, 40.63; H, 4.81; N, 17.74; Cl, 4.891; S, 8.88(%).

EXAMPLE 96

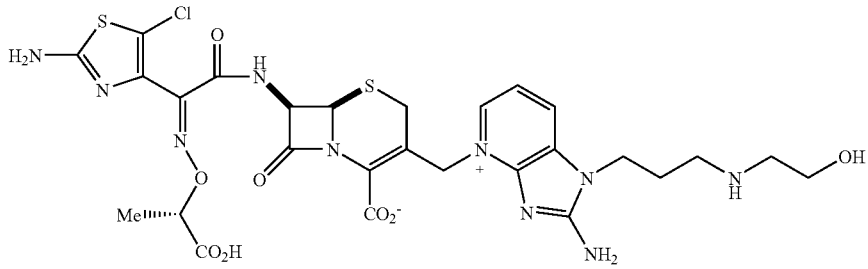

¹H-NMR (D$_2$O+DCl) δ: 1.55 (3H, d, J=7.0 Hz), 2.21-2.32 (2H, m), 3.20-3.25 (4H, m), 3.37 and 3.61 (2H, ABq, J=18.5 Hz), 3.83 (2H, t, J=5.0 Hz), 4.29 (2H, t, J=7.1 Hz), 4.99 (1H, q, J=7.0 Hz), 5.29 (1H, d, J=4.5 Hz), 5.50 and 5.68 (2H, ABq, J=15.2 Hz), 5.92 (1H, d, J=4.5 Hz), 7.34 (2H, t-like), 7.66 (1H, d, J=7.8 Hz), 8.13 (1H, d, i=6.6 Hz). IR (KBr) cm⁻¹: 3368, 1773, 1627, 1556, 1455, 1395, 1349, 1321, 1287, 1090, 1158, 1093, 1065, 1034. MS(ESI): 723⁺ (M+H)⁺. Elementary Analysis as C$_{27}$H$_{31}$ClN$_{10}$O$_8$S$_2$.2.8H$_2$O. Calculated: C, 41.92; H, 4.77; N, 18.11; Cl, 4.58; S, 8.29(%). Found: C, 41.93; H, 4.73; N, 18.06; Cl, 4.46; S, 8.17(%).

EXAMPLE 97

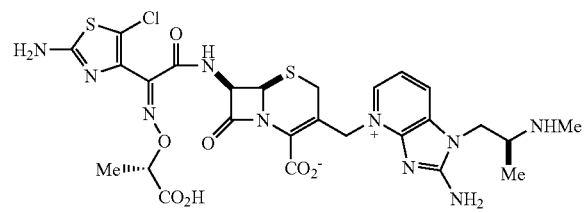

¹H-NMR (D$_2$O+DCl) δ: 1.43 (3H, d, J=6.9 Hz), 1.55 (3H, d, J=7.2 Hz), 2.78 (3H, s), 3.40 and 3.61 (2H, ABq, J=18.6 Hz), 3.83-3.95 (1H, m), 4.39-4.60 (2H, m), 5.00 (1H, q, J=6.9 Hz), 5.29 (1H, d, J=4.8 Hz), 5.51 and 5.72 (2H, ABq, J=15.2 Hz), 5.92 (1H, d, J=4.8 Hz), 7.34 (1H, dd, J=6.9, 8.1 Hz), 8.02 (1H, d, J=8.1 Hz), 8.18 (1H, d, J=6.9 Hz). IR (KBr) cm⁻¹: 3372, 3185, 1772, 1667, 1600, 1563, 1493, 1394, 1353, 1317, 1287, 1225, 1166, 1090, 1033. MS(ESI): 693 (M+H)⁺. Elementary Analysis as C$_{26}$H$_{29}$ClN$_{10}$O$_7$S$_2$.2.7H$_2$O. Calculated: C, 42.10; H, 4.67; N, 18-88; C, 4.78; S, 8.65(%). Found: C, 42.15; H, 4.72; N, 18.88, Cl,4.61; S, 8.40(%).

EXAMPLE 98

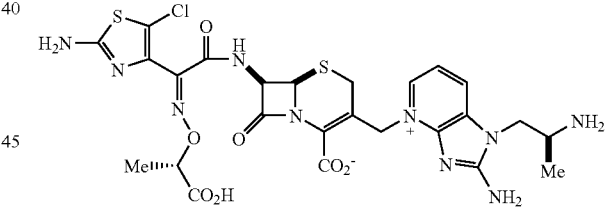

¹H-NMR (D$_2$O+DCl) δ: 1.44 (3H, d, J=6.3 Hz), 1.55 (3H, d, J=7.2 Hz), 3.38 and 3.59 (2H, ABq, J=18.6 Hz), 3.96 (1H, m), 4.41 (2H, d, J=5.7 Hz), 4.98 (1H, q, J=7.2), 5.27 (1H, d, J=4.7 Hz), 5.47 and 5.71 (2H, ABq, J=14.6 Hz), 5.91 (1H, d, J=4.7 Hz), 7.35 (1H, m), 8.00 (1H, d, J=8.1 Hz),8-17 (1H, d, J=6.9 Hz). IR (KBr) cm⁻¹: 3358, 3184, 1771, 1651, 1563, 1494, 1396, 1365, 1317, 1288, 1225, 1166, 1090, 1034. MS(ESI): 679⁺ (M+H⁺). Elementary Analysis as C$_{25}$H$_{27}$ClN$_{10}$O$_7$S$_2$.2.9H$_2$O. Calculated: C, 41.06; H, 4.52; N, 19.15; Cl, 4.85; S, 8.77(%). Found: C, 41.06; H, 4.46; N, 19.14; Cl, 4.75; S, 8.62(%).

EXAMPLE 99

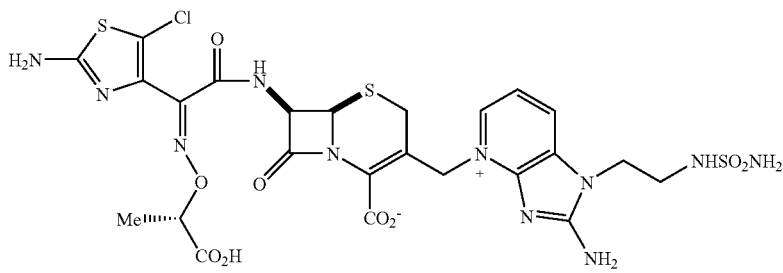

$^1$H-NMR (D$_6$-DMSO) δ: 1.36 (3H, d, J=7.0 Hz), 2.96 and 3.47 (2H, ABq, J=17.7 Hz), 3.26 (2H, brs), 4.21 (2H, brs), 4.53 (1H, q, J=7.0 Hz), 5.03 (1H, q, J=5.1 Hz), 5.26 and 5.38 (2H, ABq, J=13.5 Hz), 5.72 (1H, dd, J=5.1, 9.0 Hz), 6.67 (2H, brs), 6.83 (1H, brs), 7-30 (1H, t-like), 7.41 (2H, brs), 7.93 (1H d, J=7.5 Hz), 8.51 (1H, brs), 8.81 (1H, d, J=6.6 Hz), 9.80 (1H, brs). IR (KBr) cm$^{-1}$: 3382, 3194, 1766, 1667, 1651, 1609, 1568, 1496, 1444, 1389, 1345, 1304, 1214, 1156, 1076, 1036. MS(ESI): 744$^+$ (M+H)$^+$. Elementary Analysis as C$_{24}$H$_{26}$ClN$_{11}$O$_9$S$_3$.3.0H$_2$O. Calculated: C, 36.11; H, 4.04; N, 19.30; Cl, 4.44; S, 12.05(%). Found: C, 35.88; H, 3.93; N, 19.18; Cl, 4.54; S, 12.17(%).

EXAMPLE 100

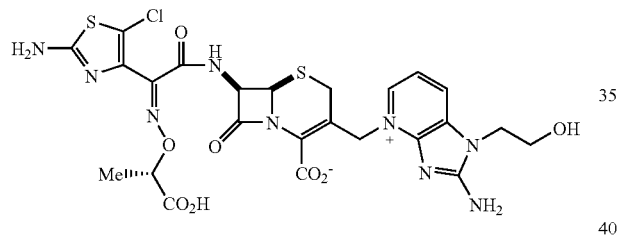

$^1$H-NMR (D$_2$O+DCl) δ: 1.54 (3H, d, J=6.9 Hz), 3.36 and 3.61 (2H, ABq, J=18.6 Hz), 3.97 (2H, t, J=4.8 Hz), 4.30 (2H, t, J=4.8 Hz), 5.29 (1H, d, J=4.8 Hz), 5.54 and 5.68 (2H, ABq, 1-15.3 Hz), 5.92 (1H, d, J=4.8 Hz), 7.34 (1H, t-like), 7.97 (1H d, J=7.8 Hz), 8.14 (1H, d, J=6.9 Hz). IR (KBr) cm$^{-1}$: 3357, 3190, 1758, 1669, 1648, 1618, 1574, 1540, 1492, 1460, 1443, 1412, 1395, 1362, 1342, 1297, 1265, 1236, 1210, 1168, 1074, 1028. MS (ES): 666$^+$ (M+H)$^+$. Elementary Analysis as C$_{24}$H$_{24}$ClN$_9$O$_3$S$_2$.1.7H$_2$O. Calculated: C, 41.37; H, 3.96; N, 18.09; Cl, 5.09; S, 9.20(%). Found: C, 41.53; H, 3.80; N, 18.19; Cl, 4.64; S, 8.79(%).

EXAMPLE 101

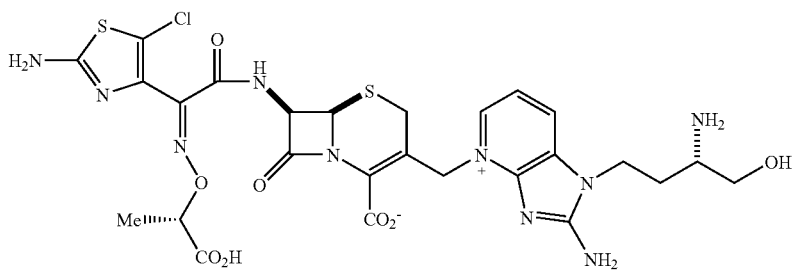

$^1$H-NMR (D$_2$O+DCl) δ: 1·55 (3H, d, J=7.1 Hz), 2.20 (2H, m), 3.37 (1H, d, J=18.3 Hz), 3.50-3.64 (2H, m), 3.77 (1H, dd, J=6.0, 12.3 Hz), 3.94 (1H, dd, J=4.2, 12.3 Hz), 4.30 (2H, t, 17.8 Hz), 5.30 (1H, d, J=4.8 Hz), 5.51 and 5.68 (2H, ABq, J=15.2 Hz), 5.92 (1H, d, J=4.81 Hz), 7.35 (1H, t-like), 8.00 (1H d, J=7.8 Hz), 8.14 (1H, d, J=6.6 Hz). IR (KBr) cm$^r$: 3613, 3415, 3339, 3191, 1763, 1703, 1670, 1620, 1570, 1532, 1497, 1443, 1392, 1357, 1345, 1309, 1289, 1265, 1214, 1168, 1154, 1084, 1061, 1029. MS(ESI): 709$^+$ (M+H)$^+$. Elementary Analysis as C$_{26}$H$_{29}$ClN$_{10}$O$_8$S$_2$·2.3H$_2$O. Calculated: C, 41.60; H, 4.51; N, 18.66; Cl, 4.72; S, 8.54(%). Found: C, 41.66; H, 4.19; N, 18.68; Cl, 4.65; S, 7.87(%).

EXAMPLE 102

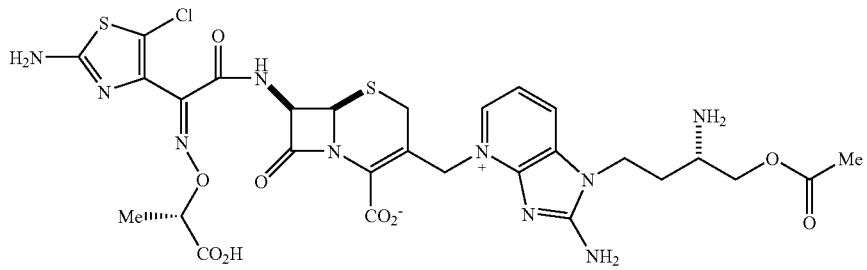

$^1$H-NMR (D$_2$O+DCl) δ: 1.55 (3H, d, J=7.2 Hz), 2.13 (3H, s), 2.17-2.35 (2H, m), 3.38 and 3.61 (2H, ABq, J=18.6 Hz), 3.74-3.81 (1H, m), 4.24-4.44 (4H, m), 4.99 (1H, q, J=7-2 Hz), 5.29 (1H, d, J=4.8 Hz), 5.51 and 5.69 (2H, ABq, J=15.0 Hz), 5.92 (1H, d, J=4.8 Hz), 7.36 (1H, dd, J=6.6, 8.1 Hz), 8.00 (1H d, J=8.1 Hz), 8.15 (1H, d, J=6.6 Hz), fit (KBr) cm$^{-1}$: 3371, 3182, 1773, 1651, 1604, 1562, 1495, 1393, 1367, 1317, 1285, 1229, 1166, 1035. MS(ESI): 751$^+$ (M+H)$^+$. Elementary Analysis as C$_{28}$H$_{31}$ClN$_{10}$O$_9$S$_2$·3.4H$_2$O. Calculated: C, 41.39; H, 4.69; N, 17.24; Cl, 4.36; S, 7.89(%). Found: C, 41.23; H, 4.31; N, 17.10; Cl, 4.01, S, 7.97(%).

EXAMPLE 103

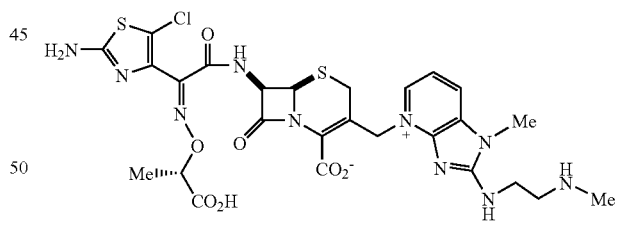

$^1$H-NMR (D$_2$O+DCl) δ: 1.55 (3H, d, J=7.5 Hz), 3.37-3.57 (4H, m), 3.67 (3H, s), 3.93-4.02 (2H, m), 5.00 (1H, sept, J=7.5 Hz), 5.25 (1H, d, J=5.1 Hz), 5.46 and 5.93 (2H, ABq, J=15.0 Hz), 5.91 (1H, d, J=5.1), 7.53 (1H, t, J=6.6 Hz), 7.94 (1H, d, J=6.6 Hz), 8.15 (1H, d, J=6.6 Hz). IR (KBr) cm$^{-1}$: 3309, 1773, 1636, 1598, 1539, 1501, 1452, 1390, 1357, 1317, 1285, 1142, 1093, 1072, 1034, 988. MS(ESI): 693$^+$ (M+H)$^+$. Elementary Analysis as C$_{26}$H$_{29}$ClN$_{10}$O$_7$S$_2$·3.9H$_2$O Calculated: C, 41.89; H, 4.71; N, 18.79; Cl, 4.76; S, 8.60(%). Found: C, 42.03; H, 4.98; N, 18.70; Cl, 4.60; S, 8.57(%).

EXAMPLE 104

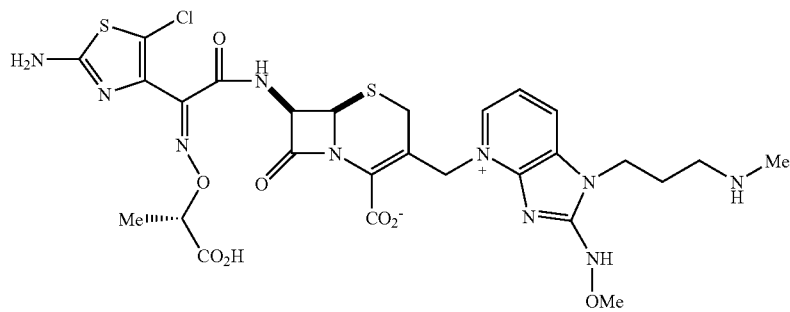

¹H-NMR (D₂O+DCl) δ: 1.54 (3H, d, J=7.2 Hz), 2.17-2.30 (2H, m), 2.72 (3H, s), 3.11-3.20 (2H, m), 3.36 and 3.66 (2H, ABq, J=18.3 Hz), 3.94 (3H, s), 4.18-4.27 (2H, m), 4.97 (1H, sept, J=7.2 Hz), 5.30 (1H, d, J=5.1 Hz), 5.60 and 5.73 (2H, ABq, J=15.2 Hz), 5.92 (1H, d, J=5.1 Hz), 7.44-7.50 (1H, m), 8.14 (1H, d, J=8.1 Hz), 8.28 (1H, d, J=6.3 Hz). IR (KBr) cm⁻¹: 3398, 1775, 1599, 1490, 1393, 1315, 1223, 1162, 1095, 1063, 1035, 968. MS(ESI): 723⁺ (M+H)⁺. Elementary Analysis as $C_{17}H_{31}ClN_{10}O_8S_2 \cdot 3.7H_2O$. Calculated ° C., 41.06; H, 4.90; N, 17.73; Cl, 4.49; S, 8.12(%). Found: C, 41.11; H, 4.67; N, 17.59; Cl, 4.59; S, 8.01(%).

EXAMPLE 105

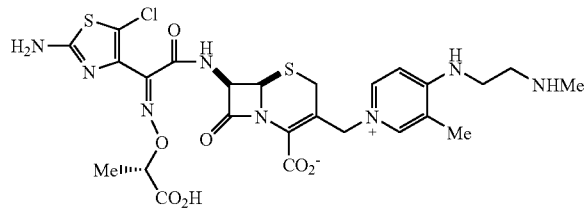

¹H-NMR (D₂O+DCl): δ1.45 (3H, d, J=6.9 Hz), 2.18 (3H, s), 2.76 (3H, s), 3.15 and 3.55 (2H, ABq, J=18.0 Hz), 3.34 (2H, t, J=6.0 Hz), 3.80 (2H, t, J=6.0 Hz), 4.68 (1H, q, J=6.9 Hz), 4.89 and 5.09 (2H, ABq, J=14.7 Hz), 5.23 (1H, d, J=4.8 Hz), 5.85 (1H, d, 14.8 Hz), 6.93 (1H, d, J=7.2 Hz), 8.08 (1H, brs), 8.22 (1H, d, J=7.2 Hz). IR (KBr) cm⁻¹: 3383, 1773, 1649, 1554, 1449, 1395, 1288, 1213, 1190, 1154, 1094, 1065, 1035. MS(ESI): 653⁺ (M+H)⁺. Elementary Analysis as $C_{25}H_{29}ClN_8O_7S_2 \cdot 3.0H_2O$. Calculated: C, 42.46; 1H, 4.99; N, 1585; Cl, 5.01, S,9.07(%). Found: C, 42.47; H, 4.77; N, 15.81; Cl, 5.86; S, 8.84(%).

EXAMPLE 106

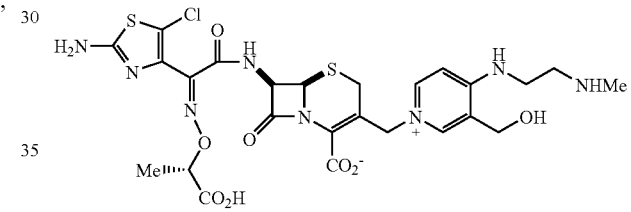

¹H-NMR (D₂O+DCl) δ: 1.45 (3H, d, J=7.2 Hz), 2.76 (3H, s), 3.16 and 3.58 (2H, ABq, J=17.4 Hz), 3.36 (2H, t, J=6.3 Hz), 3.82 (2H, t, J=6.3 Hz), 4.64-4.72 (3H, m), 4.91 and 5.13 (2H, ABq, J=14.17 Hz), 5.24 (1H, d, J=4.8 Hz), 5.86 (1H, d, J=4.8 Hz), 7.02 (1H, d, J=7.5 Hz), 8.24 (1H, brs), 8.29 (1H, d, J=7.5 Hz). IR (KBr) cm⁻¹: 3366, 1772, 1651, 1588, 1551, 1457, 1395, 1288, 1205, 1150, 1094, 1035. MS(ESI): 669⁺ (+H)⁺. Elementary Analysis as $C_{25}H_{29}ClN_8O_8S_2 \cdot 3.3H_2O$. Calculated: C, 41.21; H, 4.93; N, 15.38; Cl, 4.87; S, 8.50(%). Found: C, 41.38; H, 4.73; N, 15.53; Cl, 4.77; S, 8.51(%).

EXAMPLE 107

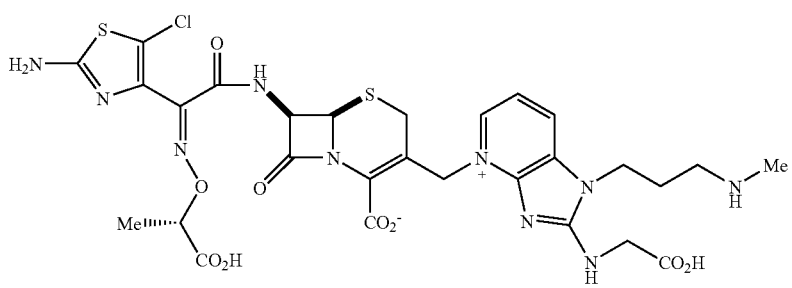

¹H-NMR (D₂O+DCl) δ: 1.56 (3H, d, J=6.9 Hz), 2.18-2.31 (2H, m), 2.71 (3H, s), 3.11-3.19 (2H, m), 3.43 and 3.51 (2H, A-Bq, J=17.9 Hz), 4.25-4.35 (2H, m), 4.43 (2H, s), 4-18 (1H, sept, J=6.9 Hz), 5.20 (1K, d, J=4.8 Hz), 5.35 and 5.91 (2H, ABq, J=15.2 Hz), 5.90 (1H, d, J=4.8 Hz), 7.34-7.40 (1H, m), 8.02 (1H, d, J=7.5 Hz), 8.18 (1H, d, J=6.6 Hz). IR (KBr) cm⁻¹: 3409, 1774, 1635, 1593, 1540, 1496, 1390, 1314, 1228, 1188, 1165, 1112, 1073, 1034, 984, 759. MS(FAB): 751⁺ (M+H)⁺. Elementary Analysis as $C_{28}H_{31}ClN_{10}O_9S_2 \cdot 2.3H_2O$. Calculated: C, 42.43; H, 4.53; N, 17.67; Cl, 4.47; S, 8.09(%). Found: C, 42.50; H, 4.16; N, 17.66; Cl, 4.40; S, 7.88(%).

EXAMPLE 108

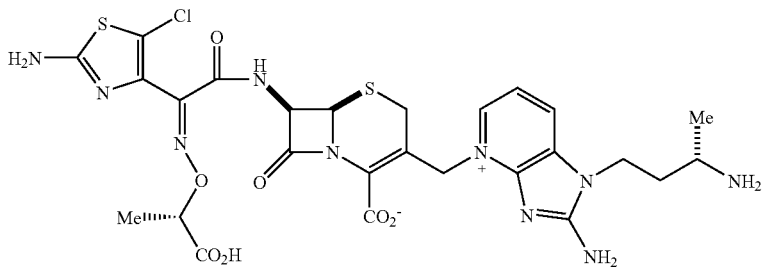

¹H-NMR (D₂O+DCl) δ: 1.43 (3H, d, J=6.9 Hz), 1.55 (3H, d, 7.1 Hz), 2.17 (2H, m), 3.35 and 3.59 (2H, ABq, J=18.6 Hz), 3.51 (1H, m), 4.28 (2H, t-like), 4.97 (1H, q, J=7.1) 5.27 (1H, d, J=4.8 Hz), 5.45 and 5.67 (2H, ABq, J=15.0 Hz), 5.91 (1H, d, 34.8 Hz), 7.3 (1H, t-like), 7.97 (1H, d, J=7.8 Hz), 8.13 (1H, d, J=6.9 Hz). IR (KBr) cm⁻¹: 3408, 1773, 1650, 1601, 1565, 1495, 1395, 1363, 1317, 1287, 1224, 1165, 1090, 1034. MS(ESI): 693⁺ (M+H⁺). Elementary Analysis as $C_{26}H_{29}ClN_{10}O_7S_2 \cdot 3.7H_2O$. Calculated: C, 41.10; H, 4.83; N, 18.43; Cl, 4.67; S, 8.44(%). Found: C, 41.15; H, 4.69; N, 18.33; Cl, 4.65; S, 8.17(%).

EXAMPLE 109

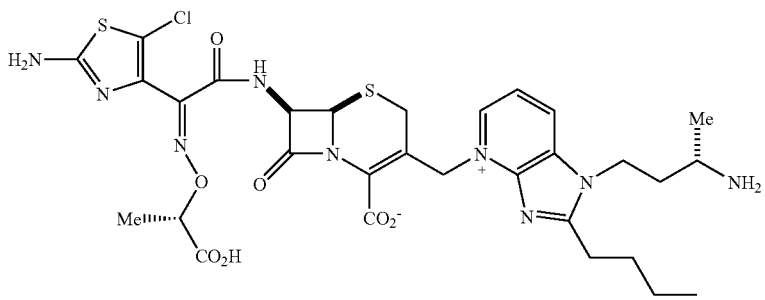

¹H-NMR (D₂O+DCl) δ: 0.97 (3H, t, J=7.4 Hz), 1.48 (2H, m), 1.55 (3H, d, J=7.2 Hz), 1.91 (2H, q. J=7.5 Hz), 2.23 (2H, m), 3.15 (21, t, J=7.5 Hz), 3.42 and 3.64 (2H, ABq, J=18.3 Hz), 3.61 (1H, m), 4.58 (2H, t like), 4.99 (1H, q, J=7.2), 5.28 (II, d, J=4.8 Hz), 5.73 and 6.02 (2H, ABq, J=15.0 Hz), 5.73 (1H, d, J=4.8 Hz), 7.79 (1H, t like), 8.67 (l, d, J=8.1 Hz), 8.72 (1H, d, J=6.3 Hz). IR (r) cm⁻¹: 3399, 2959, 2872, 1776, 1601, 1540, 1465, 1396, 1349, 1318, 1224, 1161, 1093, 1064, 1033. MS(ESI): 734⁺ (M+H⁺). Elementary Analysis as $C_{30}H_{36}ClN_9O_7S_2 \cdot 3.8H_2O$. Calculated: C, 44.89; H, 5.47 N, 15.70; Cl, 4.42; S, 7.99 (O). Found: C, 44.79; H, 5.22; N, 15-82; Cl, 4.32; S, 7.89(%).

EXAMPLE 110

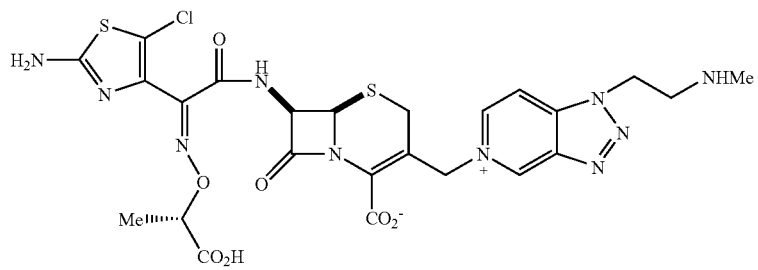

¹H-NMR (D₂O+DCl) δ: 1.53 (3H, d, J=7.2 Hz), 2-85 (3H, s), 3.39 and 3.80 (2H, ABq, J=18.6 Hz), 3.88 (2H, t, J=5-7 Hz), 4.97 (1H, q, J=7.2 Hz), 5.31 (2H, t, J=5.7 Hz), 5.37 (1H, d, J=4.7 Hz), 5.54-6.00 (2H, m), 5.95 (1H, d, J=4-7 Hz), 8.50 (1H, d, J=7.2 Hz), 8.96 (1H, d, J=7.2 Hz), 10.16 (1H, s). IR (KBr) cm⁻¹: 3407, 1774, 1609, 1539, 1483, 1447, 1394, 1359, 1287, 1190, 1155, 1104, 1066, 1034. MS(ESI)-665⁺ (M+H⁺). Elementary Analysis as $C_{24}H_{25}ClN_{10}O_7S_2 \cdot 3.2H_2O$. Calculated: C, 39.88; H, 4.38; N, 19.38; C, 4.91; S, 8.87(%). Found: C, 39.93; H, 4.02 N, 19.34; C, 4.76; S, 8.64(%).

EXAMPLE 111

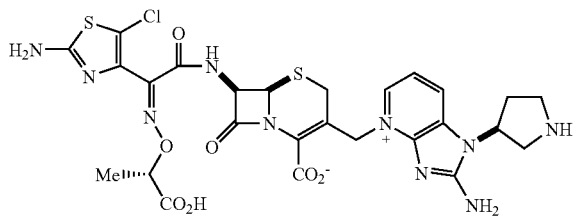

¹H-NMR (D₂O+DCl) δ: 1.55 (3H, d, J=7.2 Hz), 2.68 (2H, m), 3.36 and 3.60 (2H, ABq, J=18.6 Hz), 3.57 and 3.97 (4H, m), 4.99 (1H, m), 5.29 (1H, d, J=5.0 Hz), 5.50 and 5.69 (2H, ABq, J=15.2 Hz), 5.92 (1H, d, J=5.0 Hz), 7.34 (1H, t like), 8.06 (1H, d, J=7.5 Hz), 8.16 (1H, d, J=6.6 Hz). IR (KBr) cm⁻¹: 3410, 1771, 1606, 1556, 1491, 1440, 1396, 1363, 1319, 1224, 1167, 1092, 1034. MS(FAB): 691⁺ (M+H⁺). Elementary Analysis as $C_{26}H_{27}ClN_{10}O_7S_2 \cdot 4.6H_2O$. Calculated: C, 40.35; H, 4.71; N, 18.10; Cl, 4.58; S, 8.29(%). Found: C, 40.39; H, 4.17; N, 17.79; C, 4.49; S, 8.47(%).

EXAMPLE 112

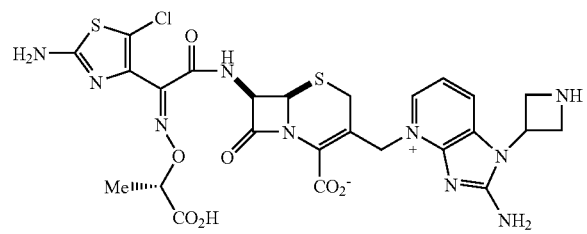

¹H-NMR (D₂O+DCl) δ: 1.55 (3H, d, J=7.5 Hz), 3.38 and 3.61 (2H, Aq, J=18-6 Hz), 4.59-4.68 (2H, m), 4.92-5.03 (2H, m), 5.29 (1H, d, J=4.8 Hz), 5-51 (1H, d, J=15.0 Hz), 5.67-5.78 (2H, m), 5.92 (1H, d, J=4.8 Hz), 7.40 (1H, dd, J=6.6, 8.1 Hz), 8.21 (1H, d, J=6.6 Hz), 8.29 (1H, d, J=8.1 Hz). IR (KBr) cm⁻¹: 3379, 1770, 1667, 1603, 1559, 1491, 1442, 1398, 1364, 1317, 1287, 1226, 1170, 1092, 1034. MS(ESI): 677⁺ (M+H⁺). Elementary Analysis as $C_{25_2}H_{25}ClN_{10}O_7S_2 \cdot 3.9H_2O$. Calculated: C, 40.18; H, 4-42; N, 18.74; Cl, 4.74; S, 8.58(%). Found: C, 40.36; H, 4.32; N, 18.37; Cl, 4.76; S, 8.39(%).

EXAMPLE 113

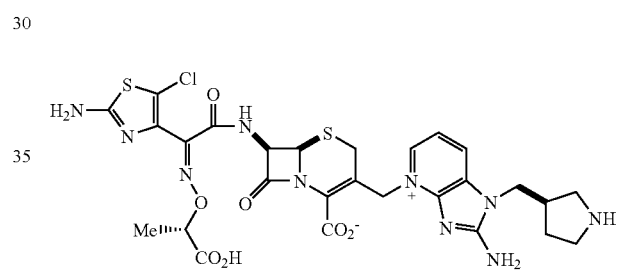

¹H-NMR (D₂O+DCl) δ: 1.55 (3H, d, J=7.2 Hz), 1.83-2.37 (4H, m), 3.29-3.62 (4H, m), 4.07 (1H, m), 4.58 (2H, d, J=7.2 Hz), 4.97 (1H, q, J=7.2 Hz), 5.27 (1H, d, J=5.0 Hz), 5.46 and 5.71 (2K, ABq, J=15.3 Hz), 5.91 (1H, d, J=5.0 Hz), 7.35 (1H, t-like), 8.02 (1H, d, J=7.8 Hz), 8.17 (1H, d, J=6.6 Hz). IR (KRr) cm⁻¹: 3417, 1772, 1650, 1605, 1563, 1494, 1394, 1362, 1317, 1222, 1167, 1093, 1033. MS(ESI): 705⁺ (M+H⁺). Elementary Analysis as $C_{27}H_{29}ClN_{10}O_7S_2 \cdot 4.1H_2O$. Calculated: C, 41.63; H, 4.81; N, 17.98; Cl, 4.55; S, 8.23(%). Found: C, 41.73; H, 4.66; N, 17.70; Cl, 4.74; S, 8.37(%).

EXAMPLE 114

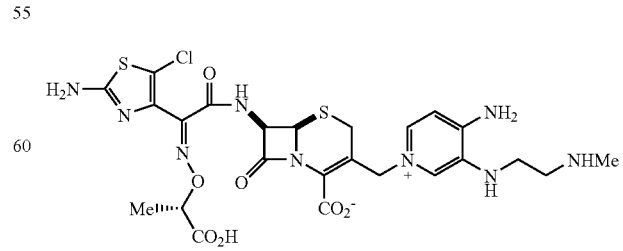

¹H-NMR (D₂O) δ: 1.44 (3H, d, J=6.9 Hz), 2.75 (3H, s), 3.11 and 3.57 (2H, ABq, J=17.7 Hz), 3.32 (2H, t, J=5.9 Hz), 3.51 (2H, t, J=5.9 Hz), 4.66 (1H, q, J=6.9 Hz), 4-77 and 5.12 (2H, ABq, J=14.4 Hz), 5.24 (1H, d, J=4.8 Hz), 5.69 (1H, d, J=4.8 Hz), 6.83 (1H, d, J=6.3 Hz), 7.86-7.89 (2H, m). IR (KBr) cm$^{-1}$: 3371, 1773, 1600, 1546, 1492, 1457, 1394, 1358, 1284, 1185, 1157, 1093, 1066, 1034. MS(FAB): 654$^+$ (M+H)$^+$. Elementary Analysis as $C_{24}H_{28}ClN_9O_7S_2 \cdot 2.7H_2O$. Calculated C, 41.02; H, 4.73; N, 17.94; Cl, 5.04; S, 9.13(%). Found: C, 41.14; H, 4.53; N, 17.91; Cl, 4173; S, 8.55(%).

EXAMPLE 115

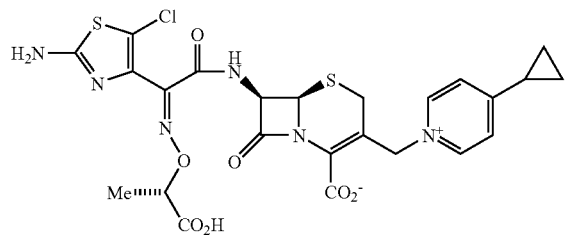

$^1$H-NMR (d$_6$-DMSO) δ: 1.07-1.18 (2H, m), 1.38 (3H, d, J=7.2 Hz), 1.38-1.47 (2H, m), 2.20-2.38 (1H, m), 3.02 (1H, d, J=17.7 Hz), 3.48 (1H, d, J=17.7 Hz), 4.55 (1H, q, J=7.2 Hz), 4.99 (1H, d, J=13.2 Hz), 5.05 (1H, d, J=4.2 Hz), 5.52 (1H, d, J=13.2 Hz), 5.70 (1H, dd, J=4.2, 8.4 Hz), 7.37-7.57 (2H, m), 7.82 (2H, d, J=6.0 Hz), 9.19 (2H, d, J=6.0 Hz), 9.58-9.73 (1H, m). IR (KBr) cm$^{-1}$: 3409, 3053, 1778, 1674, 1637, 1538, 1518, 1475, 1453, 1389, 1353, 1215, 1185, 1158, 1100, 1034. MS(FAB): 607$^+$(M+H$^+$). Elementary Analysis as $C_{24}H_{23}ClN_6O_7S_2$ 1.9H$_2$O. Calculated: C, 44.95; H, 4.21; N, 13.10; Cl, 5.53; S, 10.00(%). Found: C, 44.93; H, 14.35; N, 13.09; C, 5.44; S, 10.08(%).

EXAMPLE 116

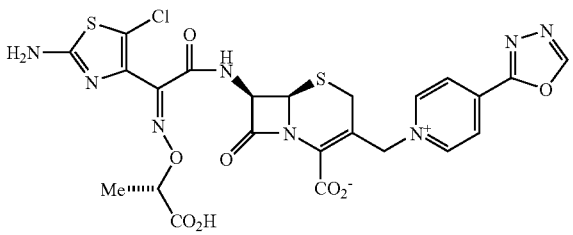

$^1$H-NMR (d$_6$-DMSO) δ: 1-37 (3H, d, J=6.9 Hz), 3.11 (1H, d, J=17.7 Hz), 3.53 (1H d, J=17.7 Hz), 4-54 (1H, q, J=6.9 Hz), 5.07 (1H, d, J=4.8 Hz), 5.21 (1H, d, J=13.8 Hz), 5.72 (1H, dd, J=4.8, 8.4 Hz), 5.77 (1H, d, J=13.8 Hz), 7.41 (2H, s), S-73 (2H, d, J=6.9 Hz), 9.51-9.82 (3H, m). IR (KBr) cm$^{-1}$: 3413, 1777, 1671, 1615, 1538, 1510, 1457, 1391, 1346, 1237, 1189, 1152, 1103, 1083, 1035. MS(FAB): 635$^+$ (M+H$^+$). Elementary Analysis as $C_{23}H_{19}ClN_8O_8S_2 \cdot 3.1H_2O$. Calculated: C, 39.98; H, 3.68; N, 16.22; Cl, 5.13; S, 9.28(%). Found: C, 39.83; H, 3.62; N, 16.25;Cl,5.25; S, 978(%).

EXAMPLE 117

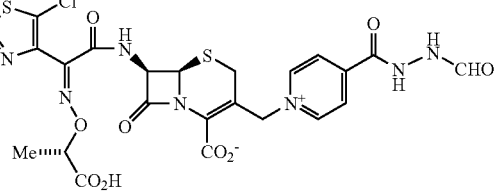

$^1$H-NMR (d$_6$-DMSO) δ: 1.37 (3H, d, J=6.9 Hz), 3.12 (1H, d, J=18.0 Hz), 3.50 (1H, d, J=18.0 Hz), 4.55 (1H, q, J=6.9 Hz), 5.06 (1H, d, J=5.1 Hz), 5.19 (1H, d, J=13.2 Hz), 5.68-5.79 (2H, m), 7.41 (2H, s), 8.16 (1H, s), 8.46 (2H, d, J=6.6 Hz), 9.49-9.75 (3H, m). IR (KBr) cm$^{-1}$: 3287, 3196, 3055, 2988, 1779, 1673, 1618, 1538, 1457, 1345, 1242, 1188, 1119, 1065, 1035. MS(FAB): 653$^+$ (M+H$^+$). Elementary Analysis as $C_{23}H_{21}ClN_8O_9S_2 \cdot 2.1H_2O$. Calculated: C, 39.98; H, 3.68; N, 16.22; Cl, 5.13; S, 9.28(%). Found: C, 39.97; H, 3.75; N, 16.57; Cl, 4.72; S, 8.79(%).

EXAMPLE 118

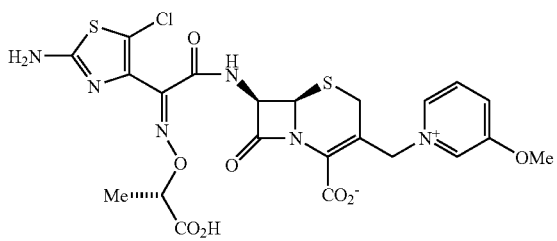

$^1$H-NMR (d$_6$-DMSO) δ: 1-38 (3H, d, J=6.9 Hz), 3.08 (1H, d, J=17.7 Hz), 3.50 (1H, d, J=17.7 Hz), 3.99 (3H, s), 4.55 (1H, q, J=6.9 Hz), 5.06 (1H, d, J=4.5 Hz), 5.08 (1H, d, J=12.9 Hz), 5.62 (1H, d, J=12.9 Hz), 5.71 (1H, dd, J=4.5, 8.1 Hz), 7.41 (2H, s), 8.08 (1H, dd, J=5.7, 8.7 Hz), 8.22 (1H, d, J=8.7 Hz), 9.11 (1H, d, J=5.7 Hz), 9.41 (1H, s), 9.54-9.66 (1H, m). IR (KBr) cm$^{-1}$: 3410, 2942, 1778, 1674, 1618, 1539, 1509, 1444, 1389, 1340, 1290, 1235, 1188, 1148, 1099, 1041, 1009. MS(FAB): 597$^+$ (M+H$^+$). Elementary Analysis as $C_{22}H_{21}ClN_6O_8S_2 \cdot 2.7H_2O$. Calculated: C, 40.92; H, 4.12; N, 13.02; Cl, 5.49; S, 9.93(%). Found: C, 40.94; H, 4.01; N, 13.12; Cl, 5.36; S, 9.91(%).

EXAMPLE 119

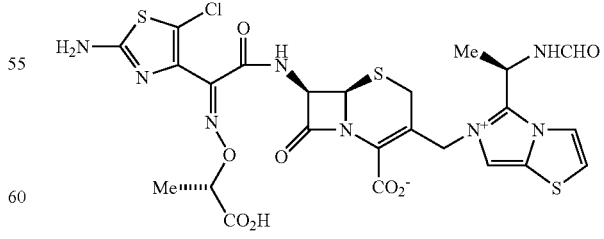

$^1$H-NMR (d$_6$-DMSO) δ: 1.39 (3H, d, J=7.2 Hz), 1.59 (3H, d, J=7.2 Hz), 3.09 (1H, d, J=17.4 Hz), 4.54 (1H, q, J=7.2 Hz), 5.00 (1H, d, J=5.4 Hz), 5.30 (1H, d, J=13.8 Hz), 5.42 (1H, d, J=13.8 Hz), 5.55-5.67 (1H, m), 5.72 (1H, dd, J=5.4, 8.4 Hz), 7.41 (2H, s), 7.79 (1H, d, J=4.2 Hz), 8.02-8.09 (2H, m), 8.30-8.39 (1H, m) 9.75 (1H, s). IR (KBr) cm$^{-1}$: 3410, 2353, 1775, 1669, 1612, 1537, 1447, 1382, 1319, 1289, 1237, 1185, 1152, 1098, 1068, 1034. MS(FAB): 683$^+$ (M+H$^+$). Elementary Analysis as $C_{24}H_{23}ClN_8O_8S_3 \cdot 4.0H_2O$. Calculated: C, 38.17; H, 4.14; N, 14.84; Cl, 4.69; S, 12.74(%). Found: C, 38.05; H, 4.10; N, 14.78; Cl, 4.97; S, 12.98(%).

EXAMPLE 120

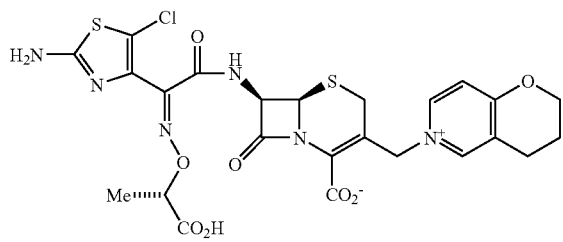

$^1$H-NMR (d$_6$-DMSO) δ: 1.38 (3H, d, J=6.6 Hz), 1.96-2.10 (2H, m), 2.79-2.90 (2H, m), 3.03 (1H, d, J=17.7 Hz), 3.47 (1H, d, J=17.7 Hz), 4.45-4.54 (2H, m), 4.54 (1H, q, J=6.6 Hz), 4.86 (1H, d, J=13.5 Hz), 5.04 (1H, d, J=4.8 Hz), 5.43 (1H, d, J=13.5 Hz), 5.70 (1H, dd, J=4.8, 8.4 Hz), 7.38-7.48 (3H, m), 9.04 (1H, s), 9.08 (1H, d, J=6.9 Hz), 9.64-9.82 (1H, m). IR (KBr) cm$^{-1}$: 3412, 3057, 1779, 1674, 1641, 1538, 1516, 1489, 1468, 1444, 1351, 1287, 1220, 1168, 1135, 1034, 1008. MS(FAB): 623$^+$ (+H$^+$). Elementary Analysis as $C_{24}H_{23}ClN_6O_8S_2 \cdot 2.0H_2O$. Calculated: C, 43.74; H, 4.13; N, 12.75; Cl, 5.38; S, 9.73(%). Found: C, 43.71; H, 3.94; N, 12.94; Cl, 5.13; S, 9.49(%).

EXAMPLE 121

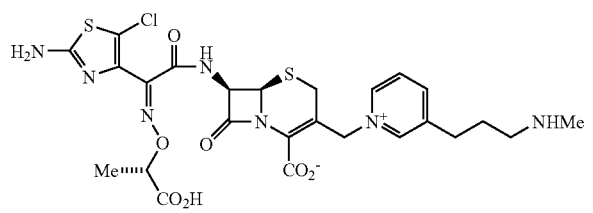

$^1$H-NMR (D$_2$O) δ: 1.45 (3H, d, J=7.2), 2.09 (2H, m), 2.71 (3H, s), 2.97 (2H, t, J=8.1 Hz), 3.10 (2H, t, J=8.1 Hz), 3.16 (1H, d, J=18.0 Hz), 3.65 (1H, d, J=18.0 Hz), 4.66 (1H, q, J=7.2 Hz), 5. 25 (1H, d, J=14.1 Hz), 5.28 (1H, d, J=5.1 Hz), 5.56 (1H, d, J=14.1 Hz), 5.88 (1H, d, J=5.1 Hz), 8.01 (1H, dd, J=6.6, 7.5 Hz), 8.45 (1H, d, J=7.5 Hz), 8.82 (1H, d, J=6.6 Hz), 8.93 (1H, brs). IR (KBr) cm$^{-1}$: 3398, 2822, 1776, 1674, 1605, 1539, 1507, 1469, 1393, 1351, 1286, 1238, 1191, 1149, 1094, 1066, 1033. MS(ESI) 638 (M+H)$^+$, 660 (M+Na)$^+$. Elementary Analysis as $C_{25}H_{28}ClN_7O_7S_2 \cdot 4.0H_2O$. Calculated: C, 42.28; H, 5.11; N, 13.81; Cl, 4.99; S, 9.03(%). Found: C, 42.27; H, 5.09; N, 13.80; Cl, 5.00; S, 9.08(%).

EXAMPLE 122

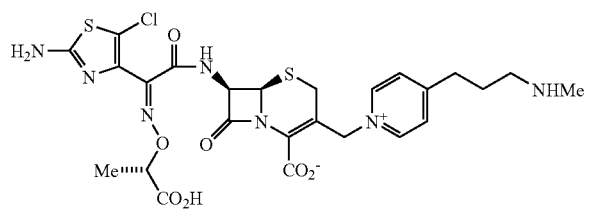

$^1$H-NMR (D$_2$O) δ: 1.36 (3H, d, J=6.9), 2.04 (2H, m), 2.64 (3H, s), 2.95 (2H, t, J=7.8 Hz), 3.03 (2H, t, J=7.8 Hz), 3.11 (1H, d, J=17.7 Hz), 3.55 (1H, d, J=17.7 Hz), 4.58 (1H, q, J=6.9 Hz), 5. 17 (1H, d, J=14.7 Hz), 5.19 (1H, d, J=4.8 Hz), 5.45 (1, d, J=14.7 Hz), 5.81 (1H, d, J=4.8 Hz), 7.86 (2H, d, J=6.9 Hz), 8.76 (2H, d, J=6.9 Hz). IR (KBr) cm$^{-1}$: 3397, 2821, 1776, 1606, 1538, 1467, 1394, 1350, 1287, 1231, 1187, 1152, 1094, 1066, 1033. MS(ESI): 638 (M+H)$^+$, 660 (M+Na)$^+$. Elementary Analysis as $C_{25}H_{28}ClN_7O_7S_2 \cdot 3.8H_2O$. Calculated: C, 42.50; H, 5.08; N, 13.88; Cl, 5.02; S, 9.08(%). Found: C, 42.34; H, 5.10; N, 13.97; Cl, 5.07, S, 9.29(%).

EXAMPLE 123

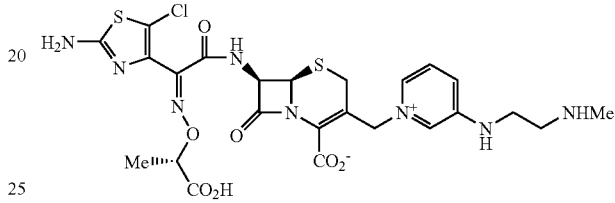

$^1$H-NMR (d$_6$-DMSO) δ: 1.41 (3H, d, J=6.9 Hz), 2.48 (3H, s), 2.81 (1H, d, J=17.4 Hz), 2.94-3.06 (2H, m), 3.30-3.40 (2H, m), 3.50 (1H, d, J=17.4 Hz), 4.47 (1H, q, J=6.9 Hz), 4.87 (1H, d, J=13.2 Hz), 5.12 (1H, d, J=5.4 Hz), 5.41 (1H, d, J=13.2 Hz), 5.82 (1H, dd, J=5.4, 9.0 Hz), 7.35 (2H, s), 7.58-7.74 (3H, m) 8.23-8.32 (1H, m), 9.11 (1H, s), 11.10-11.23 (1H, m). IR (KBr) cm$^{-1}$: 3362, 3086, 1774, 1593, 1539, 1511, 1458, 1394, 1353, 1288, 1184, 1154, 1095, 1065, 1033. MS(ESI): 639$^+$ (M+H$^+$). Elementary Analysis as $C_{24}H_{27}ClN_8O_7S_2 \cdot 3.0H_2O$. Calculated: C, 41.59; H, 4.80; N, 16.17; C, 5.11; S, 9.25(%). Found: C, 41.54; H, 4.67; N, 16.18; C, 5.17; S, 9.45(%).

EXAMPLE 124

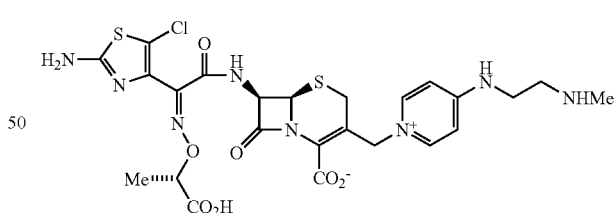

$^1$H-NMR (D$_2$O) δ: 1.45 (3H, d, J=6.9 Hz), 2.76 (3H, s), 3.17 (1H, d, J=18.0 Hz), 3.33 (2H, t, J=6.0 Hz), 3.58 (1H, d, J=18.0 Hz), 3.75 (2H, t, J=6.0 Hz), 4.66 (1H, q, J=6.9 Hz), 4.89 (1H, d, J=14.7 Hz), 5.09 (1H, d, J=14.7 Hz), 5.24 (1H, d, J=4.8 Hz), 5.86 (1H, d, J=4.8 Hz), 6.94 (2H, d, J=6.3 Hz), 8.04-8.35 (2H, m). IR (KBr) cm$^{-1}$: 3398, 3066, 1773, 1650, 1601, 1556, 1450, 1394, 1357, 1288, 1218, 1168, 1094, 1065, 1035. MS(FAB): 639$^+$ (M+H$^+$). Elementary Analysis as $C_{24}H_{27}ClN_8O_7S_2 \cdot 3.4 H_2O$. Calculated: C, 41.16; H, 4.86; N, 16.00; Cl, 5.06; S, 9.16(%). Found: C, 41.14; H, 4.69; N, 16.00; Cl, 4.97; S, 9.36(%).

Quaternary Salt Ester:

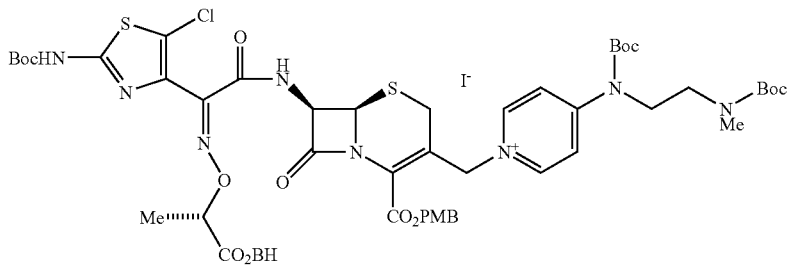

¹H-NMR (d₆-DMSO) δ: 1.15-1.40 (9H, m), 1.43-1.50 (12H, m), 1.54 (9H, s), 2.75-2.86 (3H, m), 3.20-3.38 (3H, m), 3.45 (1H, d, J=17.7 Hz), 3.76 (3H, s), 4.00-4.16 (2H, m), 4.90 (1H, q, J=69 Hz), 5.21 (1H, d, J=12.6 Hz), 5.21 (1H, d, J=5.1 Hz), 5.28 (1H, d, J=12.6 Hz), 5.41 (2H, s), 5.97 (1H, dd, J=5.1, 8.1 Hz), 6.83 (1H, s), 6.93 (2H, d, J=8.1 Hz), 7.20-7.44 (12H, m), 8.09 (2H, d, J=7.5 Hz), 8.73 (2H, d, J=7.5 Hz), 9.73 (1H, d, J=8.1 Hz), 12.08 (1H, am). IR (KBr) cm⁻¹: 3425, 2978, 2934, 1793, 1724, 1693, 1638, 1613, 1551, 1516, 1479, 1455, 1393, 1369, 1249, 1223, 1153, 1065, 1036. MS(FAB): 1225⁺(M⁺).

EXAMPLE 125

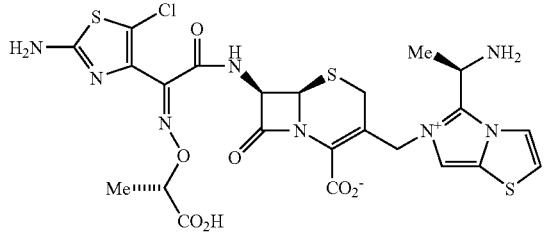

¹H-NMR (d₆-DMSO) δ: 1.39 (3H, d, J=6.9 Hz), 1.47 (3H, d, J=6.6 Hz), 3.15 (1H, d, J=17.4 Hz), 3.40 (3H, d, J=17.4 Hz), 4.55 (1H, q, J=6.9 Hz), 4.99-50.6 (2H, m), 5.27 (1H, d, J=13.8 Hz), 5.42 (1H, d, J=13.8 Hz), 5.71 (1H, dd, J=5.1, 9.0 Hz), 7.41 (2H, br s), 7.70 (1H, d, J=4.2 Hz), 8.06 (1H, m), 8.45 (1H, d, J=4.2 Hz), 9.78 (1H, br s). IR (KBr) cm⁻¹: 3394, 1773, 1670, 1613, 1537, 1446, 1354, 1183, 1152, 1094, 1066, 1035. MS(FAB): 655 (M+H)⁺, 1309 (2M+H)⁺. Elementary Analysis as C₂₃H₂₃ClN₈O₇S₃·3.6H₂O, Calculated: C, 38.37; H, 4.23; N, 15.56; Cl, 4.92; S, 13.36(%). Found: C, 38.61; H, 4.01; N, 15.58; Cl, 4.92; S, 13.08(%).

EXAMPLE 126

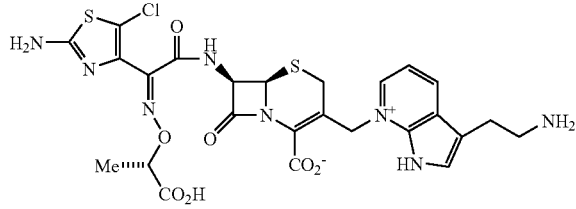

¹H-NMR (D₂O) δ: 1.38 (3H, d, J=7.2), 2.89 (1H, d, J=18.0 Hz), 3.17 (2H, t, J=7.2 Hz), 3.33 (2H, t, J=7.2 Hz), 3.70 (1H, d, J=18.0 Hz), 4.62 (1H, q, J=7.2 Hz), 5.20 (1H, d, J=15.0 Hz), 5.29 (1H, d, J=4.8 Hz), 5.83 (1H, d, J=4.8 Hz), 6.00 (1H, d, J=15.0 Hz), 7.58 (1H, br t. J=7.5 Hz), 7.64 (1H, s), 8.50 (1H, d, J=6.0 Hz), 8.65 (1H, d, J=75 Hz). IR (KBr) cm⁻¹: 3396, 3184, 2821, 1772, 1598, 1539, 1445, 1384, 1361, 1288, 1219, 1188, 1157, 1093, 1061, 1035. MS(FAB): 649 (M+H)⁺, 1297 (2M+H)⁺. Elementary Analysis as C₂₅H₂₅ClN₈O₇S₂·3.8H₂O. Calculated: C, 41.85; H, 4.58; N, 15.62; Cl, 4.94; S, 8.94(%). Found: C, 41.78; H, 4.34; N, 15.66; Cl, 4.98; S, 8.77(%).

EXAMPLE 127

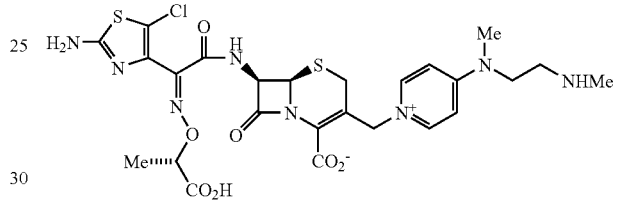

¹H-NMR (D₂O) δ: 1.46 (3H, d, J=6.9), 2.76 (3H, s), 3.18 (1H, d, J=18.0 Hz), 3.23 (3H, s), 3.36 (2H, t, J=6.9 Hz), 3.58 (1H, d, J=18.0 Hz), 3.95 (2H, t, J=6.9 Hz), 4.68 (1H, q, J=6.9 Hz), 4.91 (1H, d, J=15.0 Hz), 5.10 (1H, d, J=15.0 Hz), 5.24 (1H, d, J=4.8 Hz), 5.86 (1H, d, J=4.8 Hz), 7.01 (2H, d, J=7.5 Hz), 8.24 (2H, d, J=7.5 Hz). IR (KBr) cm⁻¹: 3408, 1775, 1650, 1606, 1556, 1450, 1404, 1359, 1286, 1235, 1164, 1106, 1064, 1034. MS(FAB): 653 (M+H)⁺, 1305 (2M+H)⁺. Elementary Analysis as C₂₅H₂₉ClN₈O₇S₂·3.7H₂O. Calculated: C, 41.72; H, 5.10; N, 15.77; Cl, 4.93; S, 8.91(%). Found: C, 41.79; H, 4.94; N, 15.48; Cl, 4.92; S, 8.78(%).

EXAMPLE 128

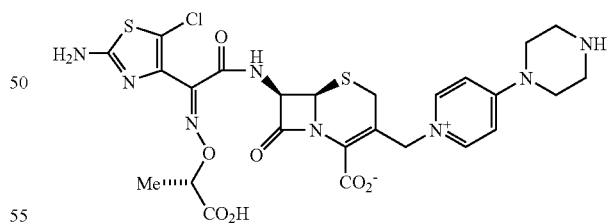

¹H-NMR (D₂O) δ: 1.45 (3H, d, J=69), 3.17 (1H, d, J=18.0 Hz), 3.45 (4H, m), 3.58 (1H, d, J=18.0 Hz), 3.97 (4H, m), 4.66 (1H, q, J=6.9 Hz), 4.92 (1H, d, J=15.0 Hz), 5.13 (1H, d, J=15.0 Hz), 5.24 (1H, d, J=4.8 Hz), 5.86 (1H, d, J=4.8 Hz), 7.15 (2H, d, J=7.8 Hz), 8.27 (2H, d, J=7.8 Hz). IR (KBr) cm⁻¹: 3398, 1771, 1649, 1603, 1544, 1450, 1385, 1362, 1283, 1239, 1175, 1151, 1093, 1065, 1035. MS(ESI): 651 (M+H)⁺, 673 (M+Na)⁺. Elementary Analysis as C₂₅H₂—ClN₈O₇S₂·3.7H₂O. Calculated: C, 41.83; H, 4.83; N, 15.61; Cl, 4.94; S, 8.93(%). Found: C, 41.79; H, 4.72; N, 15.71; Cl, 4.97; S, 8.96(%).

EXAMPLE 129

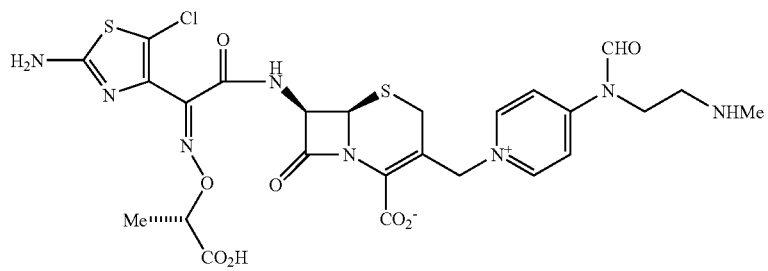

$^1$H-NMR (D$_2$O) δ: 1.52 (3H, d, J=7.2), 2.89 (3H/2, s), 3.04 (3H/2, s), 3.18 (1H, br d, J=18.0 Hz), 3.52-3.62 (5H, m), 4.84 (1H, q, J=7.2 Hz), 4.90 (1H, d, J=15.0 Hz), 5.05 (1H, d, J=15.0 Hz), 5.25 (1H, d, J=4.8 Hz), 5.86 (1H, d, J=4.8 Hz), 6.88 (2H, m), 7.88 (1H/2, s), 7.99 (1H/2, s), 8.02-8.19 (2H, m). IR (KBr) cm$^{-1}$: 3406, 1778, 1650, 1554, 1446, 1391, 1352, 1219, 1170, 1096, 1064, 1034. MS(ESI): 667 (M+H)$^+$. Elementary Analysis as C$_{25}$H$_{27}$ClN$_8$O$_8$S$_2$.2.7H$_2$O. Calculated: C, 41.95; H, 4.56; N, 15.66; Cl, 495; S, 8.96(%). Found C, 41.93; H, 4.40; N, 15.73; Cl, 5.12; S, 8.93(%).

EXAMPLE 130

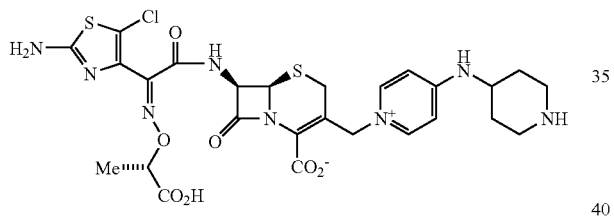

$^1$H-NMR (D$_2$O) δ: 1.44 (3H, d, J=6.6 Hz), 1.69-1.90 (2H, m), 2.20-2.34 (2H, m), 3.09-3.25 (3H, m), 3.44-3.62 (3H, m), 3.84-4.00 (1H, m), 4.65 (1H, q, J=6.6 Hz), 4.86 (1H, d, J=14.7 Hz), 5.06 (1H, d, J=14.7 Hz), 5.23 (1H, d, J=5.1 Hz), 5.86 (1H, d, J=5.1 Hz), 6.80-7.00 (2H, m), 7.96-8.28 (2H, m). IR (KBr) cm$^{-1}$: 3395, 2527, 1773, 1650, 1594, 1553, 1453, 1387, 1287, 1217, 1166, 1097, 1066, 1034. MS(FAB): 665$^+$ (M+H$^+$). Elementary Analysis as C$_{26}$H$_{29}$ClN$_8$O$_7$S$_2$.6.2 H$_2$O. Calculated: C, 40.20; H, 5.37; N, 14.42; Cl, 4.56; S, 8.26(%). Found: C, 40.13; H, 5.07; N, 14.45; Cl, 4.81; S, 8.37(%).

EXAMPLE 131

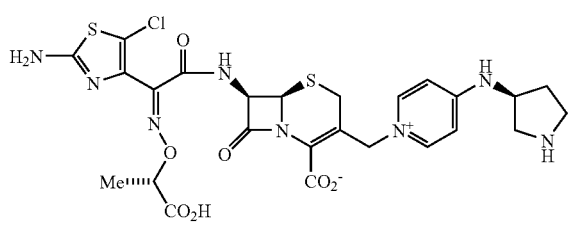

$^1$H-NMR (D$_2$O) δ: 1.56 (3H, d, J=7.2 Hz), 2.13-2.25 (1H, m), 2.45-2.58 (1H, m), 3.28 and 3.64 (2H, ABq, J=18.3 Hz), 3.36-3.77 (4H, m), 4.53-4.60 (1H, m), 4.96 (1H, q, J=6.9 Hz), 4.99 and 5.25 (2H, ABq, J=14.7 Hz), 5.30 (1H, d, J=4.8 Hz), 5.90 (1H, d, J=4.8 Hz), 6.82 (2H, d, J=7.2 Hz), 8.18 (1H, m).

IR (KBr) cm$^{-1}$: 1773, 1650, 1597, 1551, 1446, 1391, 1286, 1217, 1167.

MS(ESI): 651 (M+H)$^+$, 673 (M+Na)$^+$.

Elementary Analysis as C$_{25}$H$_{27}$ClN$_8$O$_7$S$_2$.2.7H$_2$O.

Calculated: C, 42.91; H, 4.67; N, 16.01; Cl, 5.07; S, 9.17 (%).

Found: C, 42.98; H, 4.64; N, 15.99; Cl, 4.97; S, 9.29(%).

EXAMPLE 132

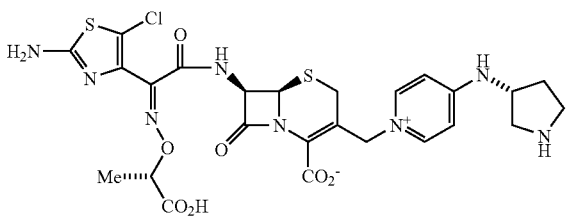

$^1$H-NMR (D$_2$O) δ: 1.56 (3H, d, J=7.2 Hz), 2.16-2.24 (1H, m), 2.46-2.58 (1H, m), 3.29 and 3.64 (2H, ABq, J=18.2 Hz), 3.37-3.78 (4H, m), 4.53-4.60 (1H, m,), 4.96 (1H, q, J=7.2 Hz), 5.00 and 5.26 (2H, ABq, J=14.7 Hz), 5.30 (1H, d, J=4.8 Hz), 5.90 (1H, d, J=4.8 Hz), 6.96 (2H, d, J=7.5 Hz), 8.20 (1H, m).

IR (KBr) cm$^{-1}$: 1774, 1650, 1595, 1551, 1446, 1391, 1286, 1218, 1167.

MS(ESI): 651 (M+H)$^{30}$, 673 (M+Na)$^+$.

Elementary Analysis as C$_{25}$H$_{27}$ClN$_8$O$_7$S$_2$.2.2H$_2$O.

Calculated: C, 43.47; H, 4.58; N, 16.22; Cl, 5.13; S, 9.28 (%).

Found: C, 43.40; H, 4.60; N, 16.25; Cl, 5.07; S, 9.28(%).

Quaternary Salt Ester:

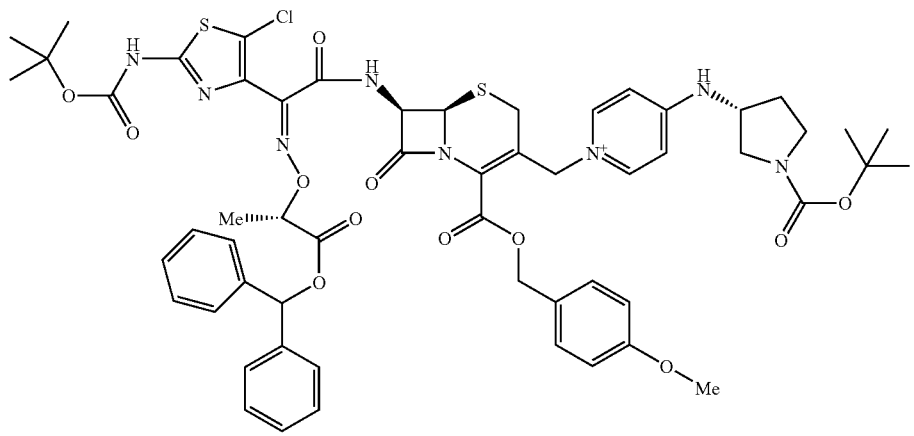

$^1$H-NMR (DMSO) δ: 1.41 (9H, s), 1.46-1.48 (12H, m), 1.78-1.96 (1H, m), 2.10-2.30 (1H, m), 3.11-3.25 (1H, m), 3.37, 3.49 (ABq, J=18.9 Hz), 3.54-3.76 (2H, m), 3.76 (3H, s), 4.19-4.36 (1H, m), 4.90 (1H, q, J=6.9 Hz), 5.04-5.15 (2H, m), 5.20 (1H, d, J=5.1 Hz), 5.21, 5.26 (2H,Abq, J=11.7 Hz), 5.96 (1H, dd, J=4-8 Hz, J=8.1 Hz), 6.84 (1H, s)6.866.97 (4H, m),7.07 (1H, d, J=7.8 Hz), 7.19, 7.48 (10H, m),8.07, 8.09 (1H, m),8.27 (1H, d, J=7.5 Hz), 8.92, 8.94 (1H, m),9.74 (1H, J=8.4 Hz), 12.11 (1H, s).

EXAMPLE 133

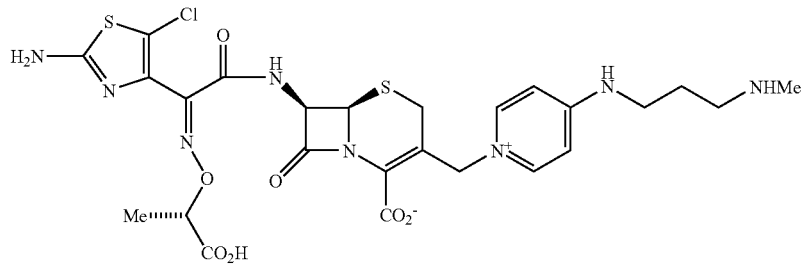

$^1$H-NMR (D$_2$O) δ: 1.45 (3H, d, J=6.9), 2.04 (3H, m), 2.72 (3H, s), 3.12 (2H, t, J=7.8 Hz), 3.16 (1H, d, J=18.0 Hz), 3.44 (2H, t, J=6.9 Hz), 3.56 (1H, d, J=18.0 Hz), 4.66 (1H, q, J=6.9 Hz), 4.86 (1H, d, J=14.4 Hz), 5.05 (1H d, J=14.4 Hz), 5.23 (1H, d, J=4.8 Hz), 5.86 (1H, d, J=4.8 Hz), 6.85 (21, d, J=7.5 Hz), 8.02-8.18 (2H, m). IR (KBr) cm$^{-1}$: 3397, 1773, 1651, 1598, 1556, 1462, 1395, 1360, 1288, 1216, 1168, 1093, 1065, 1034. MS (EST): 653 (M+H)$^+$, 675 (M+Na)$^+$. Elementary Analysis as C$_{25}$H$_{29}$ClN$_8$O$_7$S$_2$.3.8 H$_2$O. Calculated: C, 41.61; H, 5.11; N, 15.53; Cl, 4.91; S, 8.89(%). Found: C, 41.47; H, 5.08; N, 15.63; Cl, 5.15; S, 8.98(%).

EXAMPLE 134

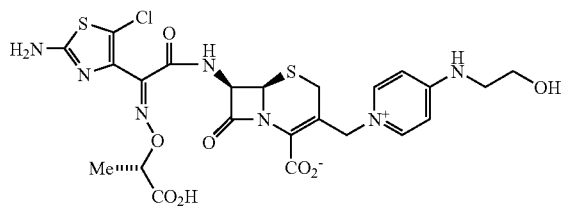

$^1$H-NMR (d$_6$-DMSO) δ: 1.39 (3H, d, J=6.9), 2.97 (1H, d, J=18.0 Hz), 3.34 (2H, m), 3.46 (1H, d, J=18.0 Hz), 3.59 (2H, t, J=5.1 Hz), 4.56 (1H, q, J=6.9 Hz), 4.65 (1H, d, J=13.5 Hz), 5.05 (1H, d, J=4.8 Hz), 5.16 (1H, d, J=13.5 Hz), 5.70 (1H, dd, J=4.8, 8.4 Hz), 6.94 (2H, m), 7.41 (2H, br s), 8.44 (1H, d, J=6.9 Hz), 8.59 (1H, d, J=7.5 Hz), 8.85 (1H, 5.4 Hz), 9.65 (1, br). IR (KBr) cm$^{-1}$: 3398, 1776, 1651, 1555, 1450, 1378, 1350, 1218, 1171, 1097, 1063, 1035. MS PSI): 626 (M+H)$^+$ 1251 (2M+H)$^+$. Elementary Analysis as C$_{23}$H$_{24}$ClN$_7$O$_8$S$_2$.2.3 H$_2$O. Calculated: C, 41.389; H, 4.32; N, 14.69; Cl, 5.31; S, 9.61(%). Found: C, 41.39; H, 4.34; N, 14.78; Cl, 5.11; S, 9.37(%).

EXAMPLE 135

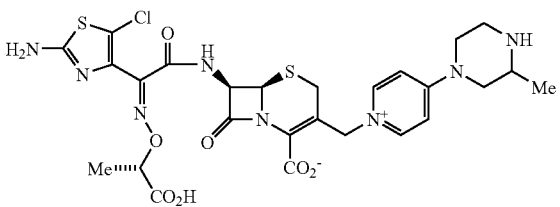

$^1$H-NMR (D$_2$O) δ: 140 (3H, d, J=6.3), 1.45 (3H, d, J=6.9 Hz), 3.17 (1H, d, J=18.0 Hz), 3.34 (1H, m), 3.55-3.61 (4H, m), 4.28-4.33 (2H, m), 4.66 (1H, q, J=6.9 Hz), 4.91 (1H, d, J=14.7 Hz), 5.12 (1H, d, J=14.7 Hz), 5.24 (1H, d, J=4.8 Hz), 5.86 (1H, d, J=4.8 Hz), 7.16 (2H, 4, J=7.2 Hz), 8.27 (2H, 4, J=7.2 Hz). IR(KBr) cm$^{-1}$: 3408, 1773, 1649, 1605, 1546, 1449, 1386, 1360, 1284, 1239, 1158, 1107, 1065, 1036. MS(ESI): 665 (M+H1), 687 (M+Na)$^+$. Elementary Analysis as $C_{26}H_{29}ClN_8O_7S_2 \cdot 4.5H_2O$. Calculated: C, 41.85; H, 5.13; N, 15.02; Cl, 4.75; S, 8.59(%). Found: C, 41.86; H, 4.84; N, 15.06; Cl, 4.74; S, 8.48(%).

EXAMPLE 136

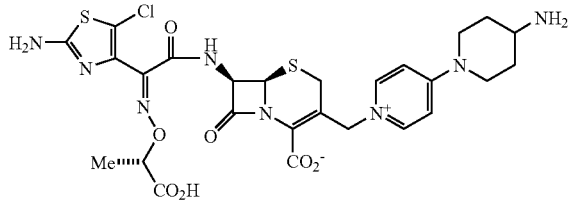

$^1$H-NMR (D$_2$O) δ: 1.32 (311, d, J=6.9), 1.57 (2H, m), 2.08 (2H, n), 3.04 (1H, d, J=17.4 Hz), 3.15 (2H, m), 3.48 (1H, m), 4.14 (2H, m), 4.53 (1H, q, J=6.9 Hz), 4.74 (1H, d, J=15.0 Hz), 4.94 (1H, d, J=15.0 Hz), 5.12 (1H, d, J=4.8 Hz), 5.73 (1H, d, J=4.8 Hz), 6.96 (2H, d, J=7.2 Hz), 8.02 (2H, d, J=7.2 Hz). IR (KBr) cm$^{-1}$: 3398, 1772, 1650, 1600, 1549, 1451, 1389, 1362, 1286, 1238, 1174, 1095, 1065, 1035. MS ESI): 665 M+H)$^+$, 687 (M+Na)$^+$. Elementary Analysis as $C_{26}H_{29}ClN_8O_7S_2 \cdot 4.3H_2O$. Calculated: C, 42.05; H, 5.10; N, 15.09; Cl, 4.77; S, 8.64(%). Found: C, 42.12; H, 5.16; N, 14.95; Cl, 4.68; S, 8.50(%).

EXAMPLE 137

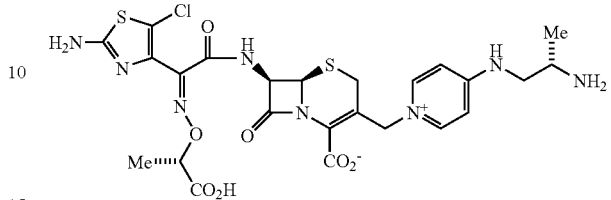

$^1$H-NMR (D$_2$O) δ: 1.36 (311, d, J=6.3 Hz), 1.45 (3H, d, J=6.6 Hz), 3.17 (1H d, J=18.0 Hz), 3.57 (1H, d, J=18.0 Hz), 3.58-3.72 (3H, m), 4.65 (1H, q, J=6.6 Hz), 4.87 (1H, d, J=14.4 Hz), 5.09 (1H, d, J=14.4 Hz), 5.23 (1H, d, J=5.1 Hz), 5.86 (1H, d, J=5.1 Hz), 6.93 (2H, d, J=6.9 Hz), 8.05-8.38 (2H, m). IR (KBr) cm$^{-1}$: 3294, 2983, 1774, 1650, 1592, 1555, 1456, 1395, 1360, 1287, 1218, 1167, 1092, 1065, 1034. MS(ESI): 639$^+$ (M+H$^+$). Elementary Analysis as $C_{24}H_{27}ClN_8O_7S_2 \cdot 2.8H_2O$. Calculated: C, 41.80; H, 4.77; N, 16.25; Cl, 5.14; S, 9.30(%). Found: C, 41.83; H, 4.64; N, 16.29; Cl, 4.96; S, 9.22(%).

EXAMPLE 138

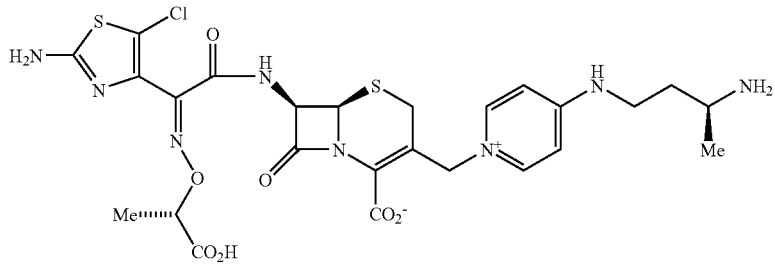

$^1$H-NMR (D$_2$O) δ: 1.35 (3H, d, J=6.3 Hz), 1.45 (3H, d, J=6.6 Hz), 1.82-2.13 (2H, m), 3.16 (1H, d, J=17.7 Hz), 3.35-3.50 (3H, m), 3.55 (1H, d, J=17.7 Hz), 4.65 (1H, q, J=6.6 Hz), 4.83 (1H, d, J=14.4 Hz), 5.05 (1H, d, J=14.4 Hz), 5.22 (1H, d, J=4.2 Hz), 5.85 (1H, d, J=4.2 Hz), 6.83 (2H, d, J=6.3 Hz), 7.95-8.25 (2H, m). IR (KBr) cm$^{-1}$: 3415, 3067, 2982, 1772, 1650, 1597, 1557, 1447, 1395, 1360, 1288, 1216, 1169, 1094, 1065, 1034. MS(FAB): 653$^+$ (M+H$^+$). Elementary Analysis as $C_{25}H_{29}ClN_8O_7S_2 \cdot 3.6H_2O$. Calculated: C, 41.82; H, 5.08; N, 15.61; Cl, 4.94; S, 8.93(%). Found: C, 41.89; H, 4.95; N, 15.54; Cl, 4.57; S, 8.60(%).

EXAMPLE 139

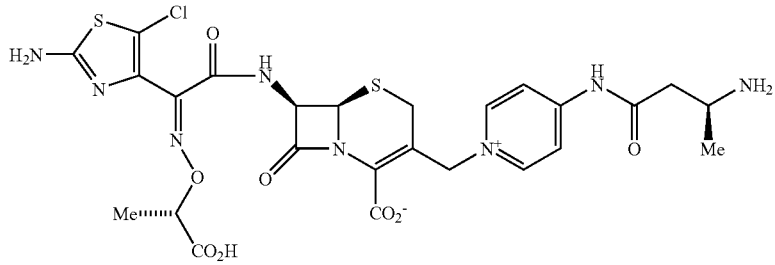

¹HNMR (D₂O) δ: 1.40 (3H, d, J=6.6 Hz), 1.44 (3H, d, J=6.9 Hz), 2.88-3.02 (2H, m), 3.17 (1H, d, J=17.7 Hz), 3.63 (1H, d, J=17.7 Hz), 3.88 (1H, m), 4.66 (1H, q, J=6.9 Hz), 5.13 (1H, d, J=14.7 Hz), 5.26 (1H, d, J=5.1 Hz), 5.40 (1H, d, J=14.4 Hz), 5.87 (1H, d, J=5.1 Hz), 8.07 (2H, d, J=7.2 Hz), 8.71 (2H, d, J=7.2 Hz). IR (KBr) cm⁻¹: 3388, 1775, 1716, 1607, 1537, 1517, 1464, 1394, 1328, 1287, 1182, 1159, 1101, 1066, 1035. MS(FAB): 667 (M+H)⁺, 1333 (2M+H)⁺. Elementary Analysis as $C_{25}H_{27}ClN_8O_8S_2 \cdot 3.7H_2O$. Calculated: C, 40.92; H, 4.73; N, 15.27; Cl, 4.83; S, 8.74(%). Found: C, 41.15; H, 4.46; N, 15.52; Cl, 4.57; S, 8.45(%).

EXAMPLE 140

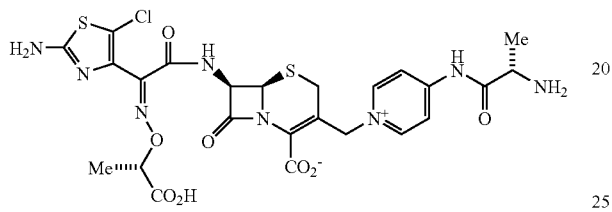

¹H-NMR (D₂O) δ: 1.31 (3H, d, J=7.2 Hz), 1.52 (3H, d, J=6.9 Hz), 3.06 (1H, d, J=18.1 Hz), 3.50 (1H, d, J=18.1 Hz), 4.20 (1H, q, J=6.9 Hz), 4.52 (1H, q, J=7.2 Hz), 5.03 (1H, d, J=14.4 Hz), 5.14 (1H, d, J=5.1 Hz), 5.29 (1H, d, J=14.4 Hz), 5.75 (1H, d, J=5.1 Hz), 8.00 (2H, d, J=7.2 Hz), 8.63 (2H, d, J=7.2 Hz). IR (KBr) cm⁻¹: 3398, 1775, 1730, 1612, 1538, 1516, 1466, 1397, 1356, 1327, 1288, 1197, 1158, 1110, 1066, 1035. MS(ESI): 653 (M+H)⁺. Elementary Analysis as $C_{24}H_{25}ClN_8O_8S_2 \cdot 2.7H_2O$. Calculated: C, 41.08; H, 4.37; N, 15.97; Cl, 5.05; S, 9.14(%). Found C, 41.13; H, 4.44; N, 15.94; Cl, 4.96; S, 8.94(%).

EXAMPLE 141

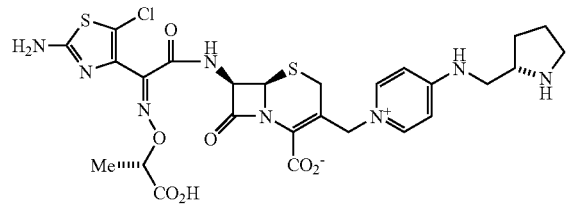

¹H-NMR (D₂O) δ: 1.44 (3H, d, J=7.5 Hz), 1.70-1.88 (1H, m), 1.98-2.20 (2H, m), 2.22-2.38 (1H, m), 3.17 (1H, d, J=17.7 Hz), 3.30-3.42 (2H, m), 3.57 (1H, dl, J=17.7 Hz), 3.70 (2H, d, J=6.3 Hz), 3.82-3.94 (1H, m), 4.66 (1H, q, J=7.5 Hz), 4.87 (1H, d, J=14.4 Hz), 5.10 (1H, d, J=14.4 Hz), 5.23 (1H, d, J=4.5 Hz), 5.85 (1H, d, J=4.5 Hz), 6.93 (2H, d, J=6.9 Hz), 8.05-8.30 (2H, m). IR (KBr) cm⁻¹: 3398, 3065, 2983, 1774, 1650, 1602, 1556, 1447, 1394, 1360, 1287, 1218, 1168, 1096, 1064, 1034. MS(FAB): 665⁺ (M+H⁺). Elementary Analysis as $C_{26}H_{29}ClN_8O_7S_2 \cdot 4.1H_2O$. Calculated: C, 42.26; H, 5.07; N, 15.16; Cl, 4.80; S, 8.68(%). Found: C, 42.29; H, 4.82; N, 15.26; Cl, 4-67; S, 8.53(%).

EXAMPLE 142

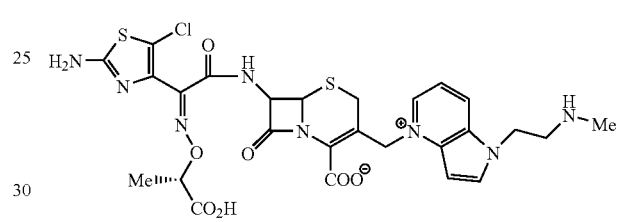

¹H-NMR (D₂O) δ: 1.44 (3H, d, J=7.2 Hz), 2.73 (3H, s), 3.17 and 3.38 (2H, ABq, J=18.0 Hz), 3.63 (2H, t, J=60 Hz), 4.65 (1H, q, J=7.2 Hz), 4.80 (2H, t, J=6.0 Hz), 5.17 (1H, d, J=4.8 Hz), 5.56 and 5.69 (2H, ABq, J=15.0 Hz), 5.85 (1H, d, J=4.8 Hz), 7.09 (1H, d, J=3.3 Hz), 7.73 (1H, dd, J=6.3 and 8.4 Hz), 8.15 (1H, d, J=3.3 Hz), 8.62 (1H, d, J=8.4 Hz), 8.68 (1H, d, J=6.3 Hz). IR (KBr) cm⁻¹: 3407, 2452, 1773, 1603, 1539, 1500, 1467, 1392, 1364, 1287, 1184, 1120, 1089, 1063, 1032. MS(FAB): 663⁺ (M+H⁺). Elementary Analysis as $C_{26}H_{27}ClN_8O_7S_2 \cdot 5.2H_2O$. Calculated: C, 41.26; H, 4.98; N, 14.81; Cl, 4-68; S, 8.47(%). Found: C, 41.41; H, 4.90; N, 14.55; C, 4.54; S, 8.46(%).

Quaternary Salt Ester:

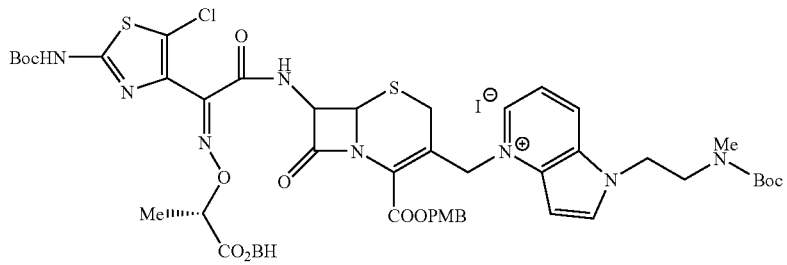

¹H-NMR (d₆-DMSO) δ: 1.04 (9H, brs), 1.43 (3H, d, 7.2 Hz), 1.46 (9H, s), 2.78 (3H, brs), 3.21 and 3.40 (2H, Abq, J=18.6 Hz), 3.60 (2H, m), 3.76 (3H, s), 4.60 (2H, t-like), 4.89 (1H, q, J=7.2 Hz), 5.20 (1H, d, J=5.1 Hz), 5.23 and 5.31 (2H, Abq, J=11.7 Hz), 5.71 (2H, brs), 5.97 (1H, dd, J=5.1 and 8.7 Hz), 6.82 (1H, a), 6.92 (2H, d, J=8.7 Hz), 7.01 (1H, d, J=3.3 Hz), 7.22-7.42 (12H, m), 7.83 (1H, brs), 8.30 (1H, d, J=3.3 Hz), 8.65 (1H, brs), 8.84 (1H, brs), 9.77 (1H, d, J=8.7 Hz), 12.1 (brs). IR (KBr) cm⁻¹: 3422, 3061, 3032, 2977, 2935, 1791, 1717, 1690, 1631, 1613, 1584, 1550, 1515, 1495, 1455, 1392, 1367, 1248, 1155, 1118, 1100, 1065, 1032, 1018. MS(FAB): 1149-($C_{17}H_{62}ClN_8O_{12}S_2^+$)

¹H-NMR (d₆-DMSO) δ: 1.42 (3H, d, J=7.2 Hz), 1.44 (9H, s) 1.46 (9H, s), 3.37 (2H, brs), 3.75 (3H, s), 4.89 (1H, q, J=7.2 Hz), 5.20 (1H, s, J=5.1 Hz), 5.21 and 5.29 (2H, Abq, J=12.0 Hz), 5.38 (2H, brs), 5.72 (2H, brs), 5.96 (1H, dd, J=5.1 and 8.7 Hz), 6.82 (1H, s), 6.89 (2H, d, J=8.7 Hz), 7.00 (1H, d, J=3.3 Hz), 7.22-7.42 (12H, m), 7.80 (1H, dd, J=6.3 and 8.4 Hz), 8.31 (1H, d, J=3.3 Hz), 8.62 (1H, d, J=6.3 Hz), 8.82 (1H, d, J=8.4 Hz), 9.76 (1H, d, J=8.7 Hz), 12.1 (brs).

IR (Kr) cm⁻¹: 3422, 3061, 3031, 2979, 2935, 1790, 1738, 1631, 1613, 1585, 1550, 1515, 1498, 1466, 1455, 1392, 1369, 1329, 1247, 1155, 1128, 1100, 1064, 1032.

MS(FAB): 1106⁺ ($C_{55}H_{57}ClN_7O_{12}S_2^+$).

EXAMPLE 143

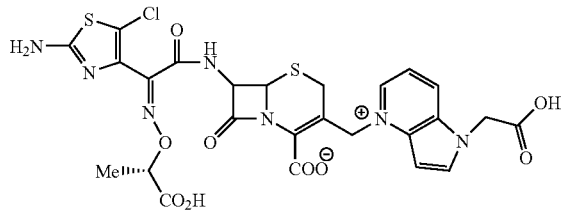

¹H-NMR (D₂O) δ: 1.43 (3H, d, J=7.2 Hz), 3.21 and 3.35 (2H, ABq, J=18.0 Hz), 4.64 (1H, q, J=7.2 Hz), 5.01 (2H, s), 5.17 (1H, d, J=4.8 Hz), 5.53 and 5.74 (2H, ABq, J=15.0 Hz), 5.89 (1H, d, J=4.8 Hz), 6.98 (1H, d, J=3.3 Hz), 7.67 (1H, dd, J=6.3 and 8.1 Hz), 8.04 (1H, d, J=3.3 Hz), 8.44 (1H, d, J=8.1 Hz), 8.62 (1H, d, J=6.3 Hz). IR (KBr) cm⁻¹: 3415, 2989, 2527, 1778, 1725, 1672, 1630, 1537, 1500, 1467, 1373, 1328, 1229, 1162, 1129, 1063, 1035. MS(ESI): 664⁺ (M+H⁺). Elementary Analysis as $C_{255}H_{22}ClN_7O_9S_2 \cdot 3.0H_2O$. Calculated: C, 41.81; H, 3.93; N, 13.65 Cl, 4.94; S, 8.93(%). Found: C, 41.75; H, 3.89; N, 13.71; Cl, 5.08; S, 8.84 (e).

Quaternary Salt Ester:

EXAMPLE 144

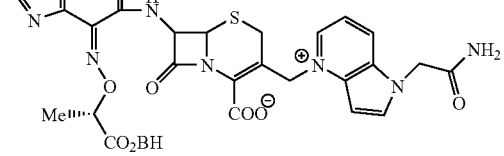

¹H-NMR (D₂O) δ: 1.43 (3H, d, J=6.9 Hz), 3.20 and 3.37 (2H, ABq, J=17.7 Hz), 4.64 (1H, q, J=6.9 Hz), 5.17 (1H, d, J=4.8 Hz), 5.27 (2H, s), 5.56 and 5.73 (2H, ABq, J=15.0 Hz), 5.88 (1H, d, J=4.8 Hz), 7.06 (1H, d, J=3.3 Hz), 7.70 (1H, dd, J=6.3 and 8.1 Hz), 8.07 (1H, d, J=3.3 Hz), 8.51 (1H, d, J=8.1 Hz), 8.67 (1H, d, J=6.3 Hz). IR (KBr) cm⁻¹: 3407, 3191, 2988, 1776, 1684, 1615, 1537, 1500, 1467, 1364, 1331, 1225, 1189, 1160, 1131, 1063, 1034. MS(ESI): 63⁺ (M+H⁺). Elementary Analysis as $C_{25}H_{23}ClN_8O_8S_2 \cdot 3.9H_2O$. Calculated: C, 40.95; H, 4.23; N, 15.28; Cl, 4.83; S, 8.74(%). Found: C, 40.93; H, 4.06; N, 15.26; Cl, 4.82; S, 8.64(%).

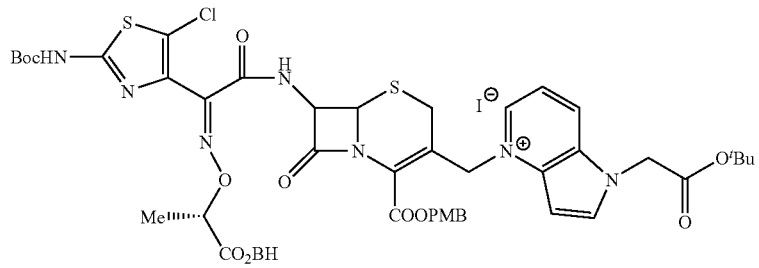

Quaternary Salt Ester:

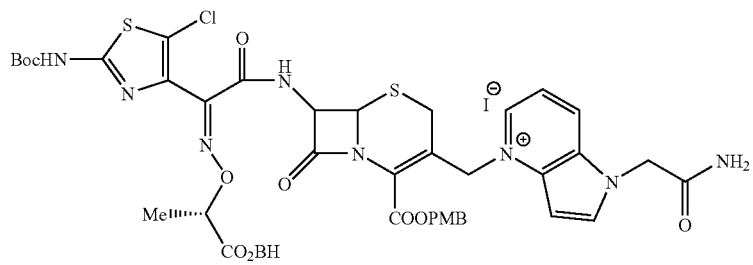

¹H-NMR (d₆-DMSO) δ: 1.45 (3H, d, J=6.9 Hz), 1.46 (9H, s), 3.39 (2H, brs), 3.75 (3H, s), 4.89 (1H, q, J=6.9 Hz), 5.17 (2H, brs), 5.20 (1H, d, J=4.8 Hz), 5.21 and 5.29 (2H, Abq, J=11.7 Hz), 5.70 (2H, brs), 5.96 (1H, dd, J=4.8 and 8.7 Hz), 6.82 (1H, s), 6.89 (2H, d, J=8.7 Hz), 6.96 (1H, d, J=3.3 Hz), 7.20-7.45 (12H, m), 7.76 (1H, dd, J=6.0 and 8.7 Hz), 7.79 (2H, brs), 8.29 (1H, d, J=3.3 Hz), 8.58 (1H, d, J=6.0 Hz), 8.73 (1H, d, J=8.7 Hz), 9.76 (1H, d, J=8.7 Hz), 12.1 (brs). IR (KBr) cm⁻¹: 3422, 3063, 2980, 2936, 1789, 1716, 1690, 1631, 1613, 1585, 1551, 1515, 1497, 1467, 1455, 1393, 1369, 1248, 1175, 1154, 1128, 1100, 1065, 1030, 1018. MS(FAB): 1049⁺ ($C_{51}H_{50}ClN_8O_{11}S_2^+$).

EXAMPLE 145

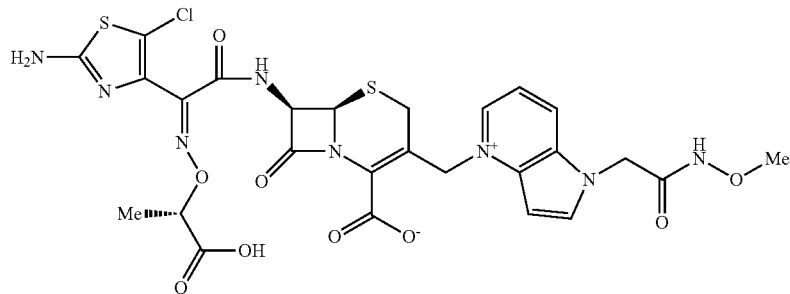

¹H-NMR (D₂O) δ: 1.44 (3H, d, J=7.2 Hz), 3.20 and 3.37 (2H, ABq, J=17.7 Hz), 3.73 (3H, s), 4.65 (1H, q, J=7.2 Hz), 5.17 (2H, s), 5.18 (1H, d, J=4.8 Hz), 5.56 and 5.73 (2H, ABq, J=15.0 Hz), 5.88 (1H, d, J=4.8 Hz), 7.06 (1H, d, J=3.3 Hz), 7.71 (1H, dd, J=6.3 and 8.1 Hz), 8.08 (1H, d, J=3.3 Hz), 8.53 (1H, d, J=8.1 Hz), 8.68 (1H, d, J=6.3 Hz). IR (KBr) cm⁻¹: 3422, 2985, 2938, 1778, 1678, 1615, 1537, 1501, 1466, 1442, 1365, 1330, 1225, 1188, 1159, 1129, 1065, 1034. MS(FAB): 693⁺ (M+H⁺). Elementary Analysis as $C_{26}H_{25}ClN_8O_9S_2 \cdot 3.9H_2O$, Calculated: C, 40.91; H, 4.33; N, 14.68; Cl, 4.64; S, 8.40(%).

Found: C, 40-78; H, 41.4 N, 14.77; Cl, 4.67; S, 8.54(%).

Quaternary salt Ester:

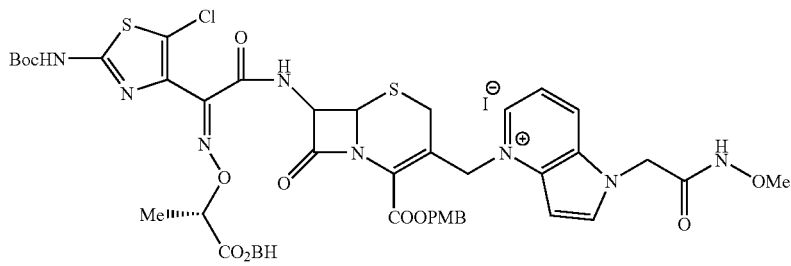

¹H-NMR (d₆-DMSO) δ: 1.44 (3H, d, J=7.2 Hz), 1.46 (9H, s), 3.39 (2H, brs), 3.68 (3H, s), 3.76 (3H, s), 4.89 (1H, q, J=7.2 Hz), 5.14 (2H, brs), 5.20 (1H, d, J=4.8 Hz), 5.21 and 5.28 (2H, Abq, J=11.4 Hz), 5.71 (2H, brs), 5.96 (1H, dd, J=4.8 and 8.7 Hz), 6.82 (1H, s), 6.88 (2H, d, J=8.7 Hz), 6.98 (1H, d, J=3.0 Hz), 7.20-7.41 (13H, m), 7.80 (1H, dd, J=6.0 and 8.1 Hz), 8.30 (1H, d, J=3.0 Hz), 8.59 (1H, d, J=6.0 Hz), 8.76 (1H, d, J=8.1 Hz), 9.76 (1H, d, J=8.7 Hz), 12.1 (brs). IR (KBr) cm⁻¹: 3428, 3101, 3063, 3031, 2980, 2937, 1789, 1717, 1632, 1613, 1585, 1550, 1515, 1497, 1466, 1391, 1369, 1326, 1247, 1175, 1155, 1127, 1100, 1064, 1032, 1018. MS(FAB): 1079⁺ ($C_{12}H_{52}ClN_8O_{12}S_2^+$).

¹H-NMR (d₆-DMSO) δ: 1.45 (3H, d, J=7.2 Hz), 1.46 (9H, s), 3.40 (2H, brs), 3.75 (6H, s), 4.74 (2H, brs), 4.89 (1H, q, J=7.2 Hz), 5.13 (2H, brs), 5.20 (1H, d, J=5.1 Hz), 5.21 and 5.28 (2H, Abq, J=12.0 Hz), 5.71 (2H, brs), 5.96 (1H, dd, J=5.1 and 8.7 Hz), 6.82 (1H, s), 6.89 (2H, d, J=8.7 Hz), 6.99 (1H, d, J=3.3 Hz), 7.19-7.49 (13H, m), 7.79 (1H, dd, J=6.3 and 8.7 Hz), 8.29 (1H, d, J=3.3 Hz), 8.61 (1H, d, J=6.3 Hz), 8.71 (1H, d, J=8.7 Hz), 9.76 (1H, d, J=8.7 Hz), 12.1 (brs). IR (KBr) cm⁻¹: 3421, 3063, 2978, 2936, 2836, 1790, 1716, 1631, 1612, 1585, 1549, 1514, 1497, 1465, 1369, 1325, 1248, 1176, 1154, 1125, 1100, 1064, 1030. MS(FAB): 1185⁺ ($C_{55}H_{58}ClN_8O_{13}S_2^+$).

EXAMPLE 146

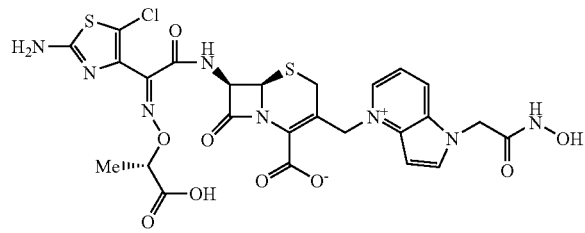

¹H-NMR (D₂O) δ: 1.43 (3H, d, J=7.2 Hz), 3.19 and 3.37 (2H, ABq, J=17.4 Hz), 4.65 (1H, q, J=7.2 Hz), 5.17 (1H, d, J=4.8 Hz), 5.19 (2H, s), 5.56 and 5.72 (2H, ABq, J=15.0 Hz), 5.87 (1H, d, J=4.8 Hz), 7.06 (1H, d, J=3.3 Hz), 7.71 (1H, dd, J=6.0 and 8.1 Hz), 8.08 (1H, d, J=3.3 Hz), 8.52 (1H, d, J=8.1 Hz), 8.68 (1H, d, J=6.0 Hz). IR (KBr) cm⁻¹: 3415, 2988, 1777, 1675, 1615, 1537, 1500, 1466, 1365, 1330, 1225, 1188, 1161, 1129, 1064, 1036. MS(FAB): 679⁺ (M+H⁺). Elementary Analysis as $C_{25}H_{23}ClN_8O_9S_2 \cdot 3.5\,H_2O$. Calculated: C, 40.46; H, 4.07; N, 15.10; Cl, 4.78; S, 8.64(%). Found: C, 40.45; H, 4.00; N, 15.08; Cl, 4.72; S, 8.57(%).

Quaternary Salt Ester:

EXAMPLE 147

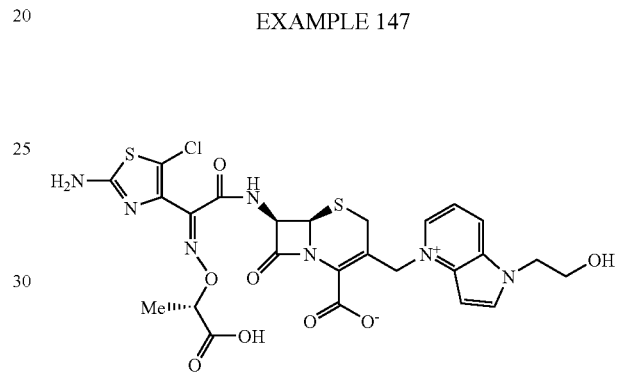

¹H-NMR (D₂O) δ: 1.43 (3H, d, J=7.2 Hz), 3.18 and 3.34 (2H, ABq, J=18.0 Hz), 3.97 (2H, t, J=4.8 Hz), 4.54 (2H, t, J=4.8 Hz), 4.64 (1H, q, J=7.2 Hz), 5.16 (1H, d, J=4.8 Hz), 5.53 and 5.71 (2H, ABq, J=15.0 Hz), 5.87 (1H, d, J=4.8 Hz), 7.00 (1H, d, J=3.0 Hz), 7.67 (1H, dd, J=6.3 and 8.1 Hz), 8.12 (1H, d, J=3.0 Hz), 8.59 (1H, d, J=1 Hz), 8.62 (1H, d, J=6.3 Hz). IR(KBr) cm⁻¹: 3408, 2938, 1776, 1670, 1615, 1539, 1496, 1466, 1447, 1362, 1322, 1240, 1187, 1159, 1130, 1072, 1034. MS(FAB): 650⁺ (M+H⁺). Elementary Analysis as $C_{11}H_{24}ClN_7O_8S_2 \cdot 4.1\,H_2O$. Calculated: C, 41.48; H, 4.48; N, 13.54; C, 4.90; S, 8.86(%). Found: C, 41.48; H, 14.40; N, 13.59; C, 5.07; S, 8.88(%).

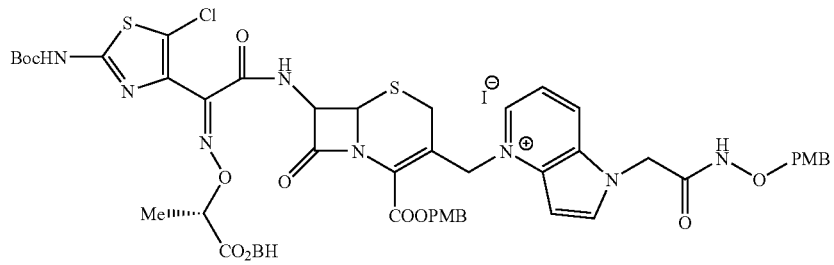

EXAMPLE 148

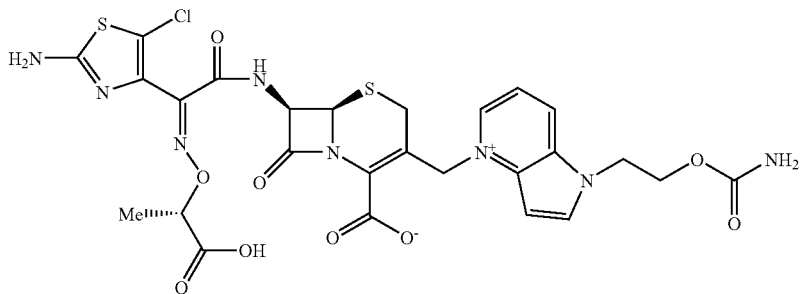

$^1$H-NMR (D$_2$O) δ: 1.44 (3H, d, J=6.9 Hz), 3.16 and 3.31 (2H, ABq, J=18.0 Hz), 4.43 (2H, t, J=4.5 Hz), 4.65 (1H, q, J=6.9 Hz), 4.68 (2H, t, J=4.5 Hz), 5.17 (1H, d, J=5.1 Hz), 5.54 and 5.71 (2H, ABq, J=15.0 Hz), 5.87 (1H, d, J=5.1 Hz), 7.01 (1H, d, J=3.0 Hz), 7.69 (1H, dd, J=6.3 and 8.1 Hz), 8.12 (1H, d, J=3.0 Hz), 8.6 (1H, d, J=8.1 Hz), 8.63 (1H, d, J=6.3 Hz). IR (KBr) cm$^{-1}$: 3415, 3193, 2987, 1777, 1718, 1673, 1614, 1537, 1497, 1466, 1447, 1364, 1328, 1225, 1188, 1135, 1080, 1034. MS(FAB): 693$^+$ (M+H$^+$). Elementary Analysis as C$_{26}$H$_{25}$ClN$_8$O$_9$S$_2$.3.0H$_2$O. Calculated: C, 41.80; H, 4.18; N, 15.00; Cl, 4.75°; S, 8.58(%). Found: C, 41.68; H, 4.19; N, 14.79; Cl, 4.78; S, 8.91(%).

EXAMPLE 149

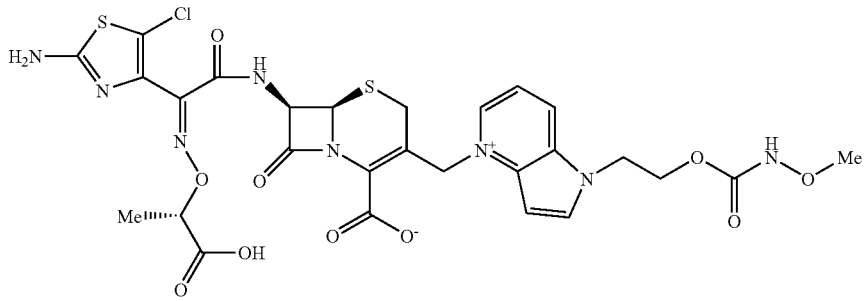

$^1$H-NMR D$_2$O) δ: 1.43 (3H, d, J=7.2 Hz), 3.15 and 3.31 (2H, ABq, J=17.7 Hz), 3.47 (3H, s), 4.54 (2H, t, J=4.8 Hz), 4.64 (1H, q, J=7.2 Hz), 4.72 (2H, t, J=48 Hz), 5.17 (1H, d, J=4.8 Hz), 5.54 and 5.71 (2H, ABq, J=15.0 Hz), 5.87 (1H, d, J=4.8 Hz), 7.02 (1H, d, J=3.3 Hz), 7.71 (1H, dd, J=6.3 and 8.4 Hz), 8.13 (1H, d, J=3.3 Hz), 8.62 (1H, d, J=8.4 Hz), 8.64 (1H, d, J=6.3 Hz). IR (KBr) cm$^{-1}$: 3416, 2984, 2939, 1778, 1731, 1674, 1615, 1538, 1498, 1466, 1445, 1364, 1326, 1286, 1264, 1189, 1123, 1035. MS(FAB): 723$^+$ (M+H$^+$). Elementary Analysis as C$_{27}$H$_{27}$ClN$_8$O$_{10}$S$_2$.3.7H$_2$O. Calculated: C, 41.06; H, 4.39; N, 14.19; Cl, 4.49; S, 8.12(%). Found: C, 40.93; H, 4.29; N, 14.32; Cl, 4.63; S, 8.14(%).

EXAMPLE 150

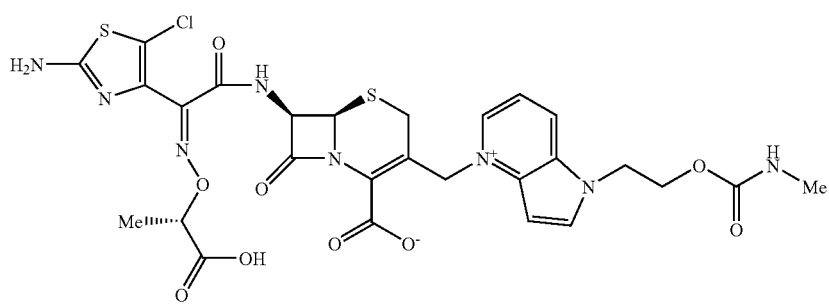

¹H-NMR (D₂O) δ: 1.43 (3H, d, J=7.2 Hz), 2.45 (3H, s), 3.15 and 3.31 (2H, ABq, J=17.7 Hz), 4.44 (2H, brs), 4.64 (1H, q, J=7.2 Hz), 4.69 (2H, brs), 5.17 (1H, d, J=4.8 Hz), 5.54 and 5.71 (2H, ABq, J=15.3 Hz), 5.87 (1H, d, J=4.8 Hz), 7.01 (1H, d, J=3.0 Hz), 7.69 (1H, dd, J=6.0 and 8.4 Hz), 8.11 (1H, d, J=3.0 Hz), 8.60 (1H, d, J=8.4 Hz), 8.64 (1H, d, J=6.0 Hz). IR (KBr) cm⁻¹: 3401, 2984, 1779, 1710, 1676, 1617, 1538, 1498, 1466, 1364, 1326, 1265, 1187, 1135, 1097, 1033. MS(FAB): 707⁺ (M+H⁺). Elementary Analysis as C₂₇H₂₇ClN₈O₉S₂.3.5H₂O. Calculated: C, 42-11; H, 4.45; N, 14.55; C, 4.60; S, 8.33(%). Found: C, 42.18; H, 4.37; N, 14.52; Cl, 4.63; S, 8.12(%).

EXAMPLE 151

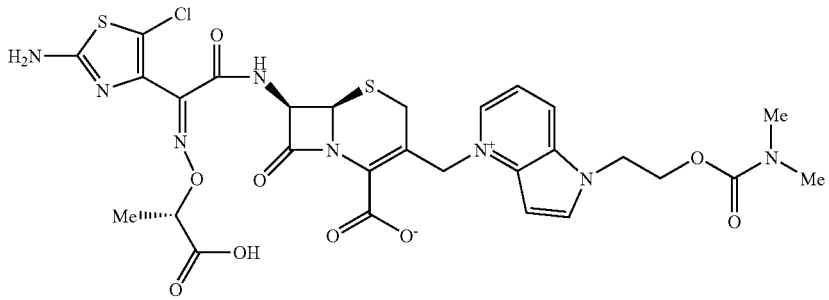

¹H-NMR (D₂O) δ: 1.43 (3H, d, J=7.2 Hz), 2.66 (3H, s), 2.70 (3H, s), 3.14 and 3.30 (2H, ABq, J=17.7 Hz), 4.46 (2H, t, J=4.8 Hz), 4.64 (1H, q, J=7.2 Hz), 4.72 (2H, t, J=4.8 Hz), 5.17 (1H, d, J=5.1 Hz), 5.55 and 5.71 (2H, ABq, J=15.3 Hz), 5.87 (1H, d, J=5.1 Hz), 7.02 (1H, d, J=3.3 Hz), 7.70 (1H, dd, J=6.6 and 8.1 Hz), 8.15 (1H, d, J=3.3 Hz), 8.64 (1H, d, J=8.1 Hz), 8.65 (1H, d, J=6.6 Hz). IR (KBr) cm⁻¹: 3422, 2938, 1779, 1690, 1617, 1538, 1497, 1466, 1363, 1325, 1287, 1190, 1135, 1098, 1066, 1034. MS(FAB): 721⁺ (M+H⁺) Elementary Analysis as C₂₈H₂₉ClN₈O₉S₂.3.8H₂O. Calculated: C, 42.88; H, 4.63; N, 14.29; Cl, 4.52; S, 8.18(%). Found: C, 42.81; H, 4.62; N, 14.23; Cl, 4.50; S, 8.38(%).

EXAMPLE 152

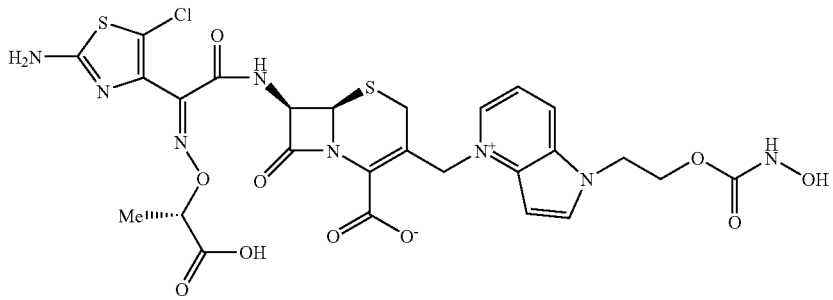

¹H-NMR (D₂O) δ: 1.43 (3H, d, J=7.2 Hz), 3.17 and 3.32 (2H, ABq, J=17.7 Hz), 4.52 (2H, t, J=4.8 Hz), 4.65 (1H, q, J=7.2 Hz), 4.71 (2H, t, J=4.8 Hz), 5.17 (1H, d, J=4.8 Hz), 5.53 and 5.71 (2H, ABq, J=15.0 Hz), 5.87 (1H, d, J=4.8 Hz), 7.00 (1H, d, J=3.3 Hz), 7.70 (1H, dd, J=6.0 and 8.4 Hz), 8.11 (1H, d, J=3.3 Hz), 8.61 (1H, d, J=8.4 Hz), 8.63 (1H, d, J=6.0 Hz). IR (KBr) cm⁻¹: 3307, 2938, 1777, 1728, 1673, 1613, 1537, 1498, 1466, 1364, 1326, 1285, 1188, 1122, 1034. MS (FAB): 709⁺ (M+H⁺). Elementary Analysis as C₂₆H₂₅Cl N₈O₁₀S₂.3.5H₂O. Calculated: C, 40.44; H, 4.18; N, 14.51; Cl, 4-59; S, 8.31(%). Found: C, 40.45; H, 4.15; N, 14.48; Cl, 4.70; S, 8.41(%).

EXAMPLE 153

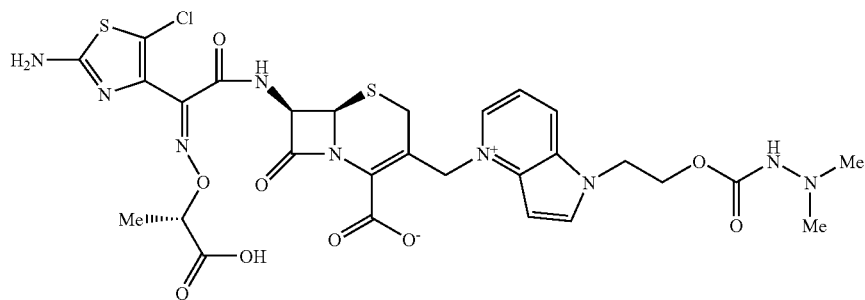

$^1$H-NMR (D$_2$O) δ: 1.44 (3H, d, J=7.2 Hz), 2.33 (6H, s), 3.17 and 3.33 (2H, ABq, J=17.7 Hz), 4.48 (2H, brs), 4.65 (1H, q, J=7.2 Hz), 4.69 (2H, brs), 5-18 (1H, d, J=4.8 Hz), 5.54 and 5.71 (2H, ABq, J=14.7 Hz), 5.87 (1H, d, J=4.8 Hz), 7.03 (1H, d, J=3.3 Hz), 7.72 (1H, dd, J=6.0 and 8.7 Hz), 8.13 (1H, d, J=3.3 Hz), 8.60 (1H, d, J=8.7 Hz), 8.64 (1H, d, J=6.0 Hz). IR (KBr) cm$^{-1}$: 3412, 2900, 2960, 1779, 1723, 1671, 1626, 1541, 1498, 1466, 1449, 1427, 1364, 1326, 1286, 1244, 1187, 1163, 1135, 1114, 1035. MS(FAB): 636$^+$ (M+H$^+$). Elementary Analysis as C$_{23}$H$_{30}$ClN$_9$O$_9$S$_2$.4.2H$_2$O. Calculated: C, 41.42; H, 4.77; N, 15.53; Cl, 4.37; S, 7.90(%). Found: C, 41.36; H, 4.55; N, 15.46; Cl, 4.36 S,8.17(%).

EXAMPLE 154

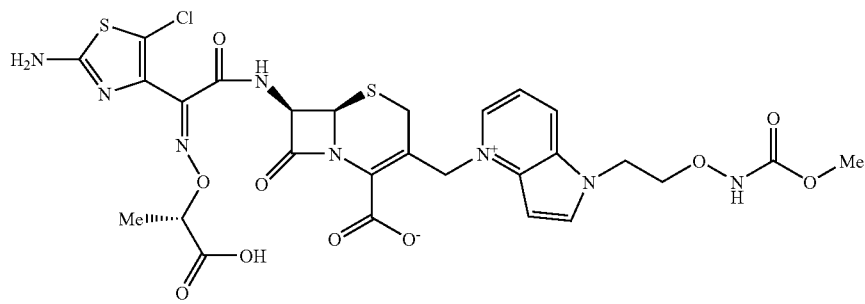

$^1$H-NMR (D$_2$O) δ: 1.43 (3H, d, J=6.9 Hz), 3.17 and 3.33 (2H, ABq, J=17.7 Hz), 3.62 (3H, s), 4.29 (2H, t, J=4.8 Hz), 4.64 (1H, q, J=6.9 Hz), 4.69 (2H, t, J=4.8 Hz), 5.17 (1H, d, J=4.5 Hz), 5.54 and 5.72 (2H, ABq, J=15.0 Hz), 5.87 (1H, d, J=4.5 Hz), 7.02 (1H, d, J=3.3 Hz), 7.68 (1H, dd, J=6.3 and 8.4 Hz), 8.18 (1H, d, J=3.3 Hz), 8.61 (1H, d, J=8.4 Hz), 8.63 (1H, d, J=6.3 Hz). IR (KBr) cm$^{-1}$: 3415, 2988, 2953, 1778, 1674, 1616, 1538, 1498, 1466, 1363, 1321, 1285, 1190, 1132, 1062, 1035. MS(FAB): 723$^+$ (M+H$^+$). Elementary Analysis as C$_{27}$H$_{27}$ClN$_8$O$_{10}$S$_2$.4.1H$_2$O. Calculated: C, 40.69; H, 4.45; N, 14.06; C, 4.45; S, 8.05(%). Found: C, 40.47; H, 4.28; N, 14.18; Cl, 4.88; S, 8.56(%).

EXAMPLE 155

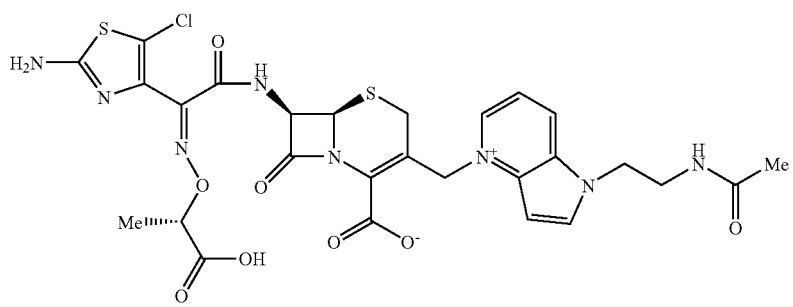

$^1$H-NMR (D$_2$O) a: 1.43 (3H, d, J=6.9 Hz), 1.74 (3H, s), 3.18 and 3.33 (2H, ABq, J=17.7 Hz), 3.62 (2H, t, J=5.4 Hz), 4.53 (2H, t, J=5.4 Hz), 4.65 (1H, q, J=6.9 Hz), 5.18 (1H, d, J=4.8 Hz), 5.53 and 5.71 (2H, ABq, J=14.7 Hz), 5.87 (1H, d, J=4.8 Hz), 6.99 (1H, d, J=3.0 Hz), 7.69 (1H, dd, J=6.3 and 8.4 Hz), 8.07 (1H, d, J=3.0 Hz), 8.57 (1H, d, J=8.4 Hz), 8.62 (1H, d, J=6.3 Hz). IR (KBr) cm$^{-1}$: 3400, 2938, 1777, 1629, 1540, 1497, 1467, 1450, 1368, 1323, 1288, 1240, 1189, 1159, 1134, 1095, 1035. MS(FAB): 691$^+$ (M+H$^+$). Elementary Analysis as C$_{27}$H$_{27}$ClN$_8$O$_8$S$_2$·4.1H$_2$O. Calculated: C, 41.51; H, 4.77; N, 14.34; Cl, 4.54; S, 8.21(%). Found: C, 41.33; H, 4.56; N, 14.36: C, 4.88; S, 8.39(%).

EXAMPLE 156

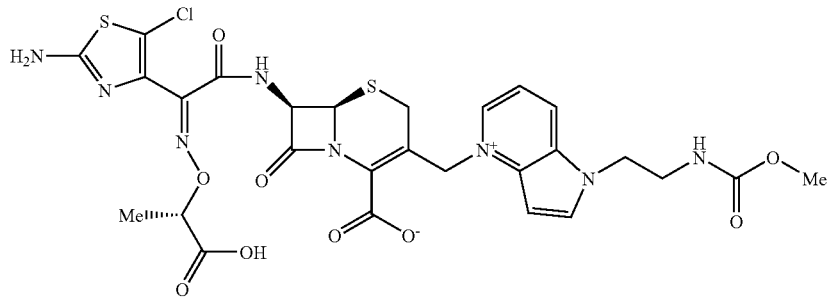

$^1$H-NMR (D$_2$O) δ: 1.43 (3H, d, J=7.5 Hz), 3.15 and 3.32 (2H, ABq, J=17.7 Hz), 3.91 (3H, s), 3.57 (2H, brs), 4.51 (2H, m), 4.65 (1H, q, J=7.5 Hz), 5.17 (1H, d, J=4.8 Hz), 5.55 and 5.70 (2H, ABq, J=14.7 Hz), 5.87 (1H, d, J=4.8 Hz), 7.00 (1H, d, J=3-3 Hz), 7.69 (1H, dd, J=6.0 and 8.1 Hz), 8.09 (1H, d, J=3.3 Hz), 8.59 (1H, d, J=8.1 Hz), 8.64 (1H, d, J=6.0 Hz). IR (KBr) cm$^{-1}$: 3410, 2987, 2940, 1777, 1677, 1626, 1537, 1499, 1466, 1365, 1322, 1271, 1191, 1157, 1132, 1096, 1035. MS(FAB): 07$^+$ (M+H$^+$). HR-MS(FAB): calcd for C$_{21}$H$_{28}$ClN$_8$O$_9$S$_2$ 707.1109 found 707.1106.

EXAMPLE 157

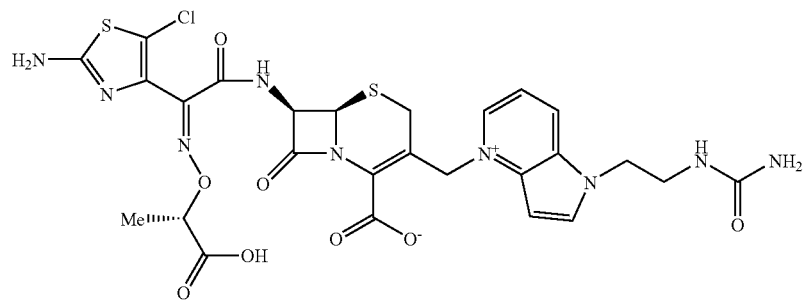

$^1$H-NMR (D$_2$O) δ: 1.44 (3H, d, J=6.9 Hz), 3.18 and 3.33 (2H, ABq, J=17.7 Hz), 3.54 (2H, t, J=4.5 Hz), 4.49 (2H, t, J=4.5 Hz), 4.65 (1H, q, J=6.9 Hz), 5.17 (1H, d, J=5.1 Hz), 5.52 and 5.70 (2H, ABq, J=15.0 Hz), 5.87 (1H, d, J=5.1 Hz), 6.98 (1H, d, J=3.3 Hz), 7.67 (1H, dd, J=6.3 and 8.1 Hz), 8.07 (1H, d, J=3.3 Hz), 8.55 (1H, d, J=8.1 Hz), 8.60 (1H, d, J=6.3 Hz). IR (KBr) cm$^{-1}$: 3375, 1773, 1660, 1609, 1543, 1497, 1466, 1451, 1362, 1288, 1240, 1188, 1159, 1133, 1098, 1035. MS(FAB): 692$^+$ (M+H$^+$). HR-MS(FAB): calcd for C$_{26}$H$_{27}$ClN$_9$O$_8$S$_2$ 692.1113 found 692.1100. Elementary Analysis as C$_{26}$H$_{26}$ClN$_9$O$_8$S$_2$·4.3H$_2$O. Calculated: C, 40.58; H, 4.53; N, 16.38; Cl, 4.61; S, 8.33(%). Found C, 40.46; H, 4.38; N, 16.84; Cl, 5.26; S, 7.73(%).

EXAMPLE 158

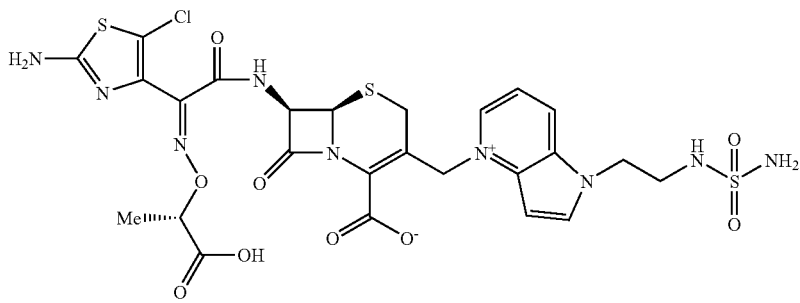

$^1$H-NMR (D$_2$O) δ: 1.43 (3H, d, J=7.2 Hz), 3.14 and 3.31 (2H, ABq, J=17.7 Hz), 3.53 (2H, t-like), 4.57 (2H, t-like), 4.64 (1H, q, J=7.2 Hz), 5.17 (1H, d, J=4-8 Hz), 5.54 and 5.70 (2H, ABq, J=15.0 Hz), 5.87 (1H, d, J=4.8 Hz), 7.00 (1H, d, J=3.3 Hz), 7.68 (1H, dd, J=6.3 and 8.4 Hz), 8.13 (1H, d, J=3.3 Hz), 8.62 (1H, d, J=8.4 Hz), 8.62 (1H, d, J=6.3 Hz). IR (KBr) cm$^{-1}$: 3316, 1775, 1671, 1611, 1538, 1497, 1467, 1448, 1363, 1326, 1241, 1157, 1134, 1097, 1035. MS(FAB): 728$^+$ (M+H$^+$). Elementary Analysis as C$_{25}$H$_{26}$ClN$_9$O$_9$S$_3$.3.6H$_2$O. Calculated: C, 37.86; H, 4.22; N, 15.90; Cl, 4.47; S, 12.13(%). Found: C, 37.88; H, 4.10; N, 15.92; Cl, 4.37; S, 12.00(%). IR (KBr) cm$^{-1}$: 3316, 1775, 1671, 1611, 1538, 1497, 1467, 1448, 1363, 1326, 1241, 1157, 1134, 1097, 1035. MS(FAB): 728$^+$ (M+H$^+$). Elementary Analysis as C25H$_{26}$Cl N$_9$O$_3$S$_3$.3.6H$_2$O. Calculated: C, 37.86; H, 4.22; N, 15.90; Cl, 4.47; S, 12.13(%). Found: C, 37.88; H, 4.10; N, 15.92; Cl, 4.37; S, 12.00(%).

EXAMPLE 159

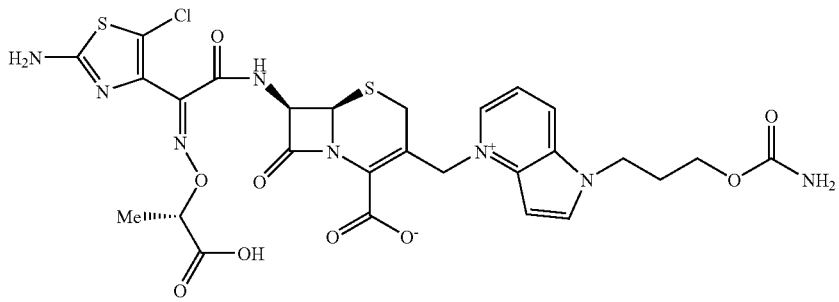

$^1$H-NMR (D$_2$O) δ: 1.44 (3H, d, J=6.9 Hz), 2.25 (2H, m), 3.17 and 3.33 (2H, ABq, J=17.7 Hz), 3.95 (2H, t, J=5.7 Hz), 4.54 (2H, t, J=6.3 Hz), 4.65 (1H, q, J=6.9 Hz), 5.17 (1H, d, J=5.1 Hz), 5.53 and 5.70 (2H, ABq, J=15.0 Hz), 5.87 (1H, d, J=5.1 Hz), 7.00 (1H, d, J=3.3 Hz), 7.67 (1H, dd, J=6.3 and 8.4 Hz), 8.12 (1H, d, J=3.3 Hz), 8.59 (1H, d, J=8.4 Hz), 8.61 (1H, d, J=6.3 Hz). IR (KBr) cm$^{-1}$: 3402, 3193, 2985, 1777, 1710, 1673, 1612, 1539, 1497, 1457, 1362, 1331, 1239, 1189, 1132, 1103, 1078, 1036. MS(FAB): 707$^+$ (M+H$^+$). Elementary Analysis as C$_{27}$H$_{27}$ClN$_8$O$_9$S$_2$.3.4H$_2$O. Calculated: C, 42.20; H, 4.43; N, 14.58; Cl, 4.61; S, 8.35(%). Found: C, 42.19; H, 4.34; N, 14.60; Cl, 4.54; S, 8.23(%).

EXAMPLE 160

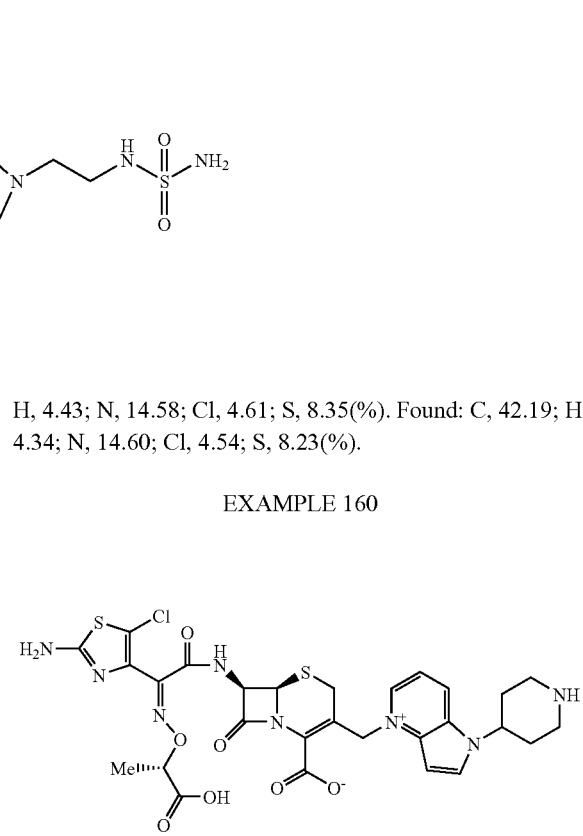

$^1$H-NMR (D$_2$O) δ: 1.43 (3H, d, J=7.2 Hz), 2.26-2.42 (4H, m), 3.15 and 3.34 (2H, ABq, J=17.7 Hz), 3.28 (2H, dt, J=3.0 and 12.6 Hz), 3.64 (2H, d, J=12.6 Hz), 4.65 (1H, q, J=7.2 Hz), 4.91-5.00 (1H, m), 5.16 (1H, d, J=4.8 Hz), 5.55 and 5.69 (2H, ABq, J=15.0 Hz), 5.85 (1H, d, J=4.8 Hz), 7.06 (1H, d, J=3.6 Hz), 7.69 (1H, d, J=6.3 and 8.4 Hz), 8.23 (1H, d, J=3.6 Hz), 8.64 (1H, d, J=8.4 Hz), 8-65 (1H, d, J=6.3 Hz). IR (KBr) cm$^{-1}$: 3397, 2528, 1773, 1599, 1539, 1494, 1461, 1396, 1360, 1315, 1285, 1185, 1128, 1068, 1032. MS(FAB): 689$^+$ (M+H$^+$). Elementary Analysis as C$_{28}$H$_{29}$ClN$_8$O$_7$S$_2$.6.5H$_2$O. Calculated: C, 41.71; H, 5.25; N, 13.90; Cl, 4.40; S, 7.95(%). Found: C, 41.69; H, 5.13; N, 13.96; Cl, 435; S, 7.78(%).

EXAMPLE 161

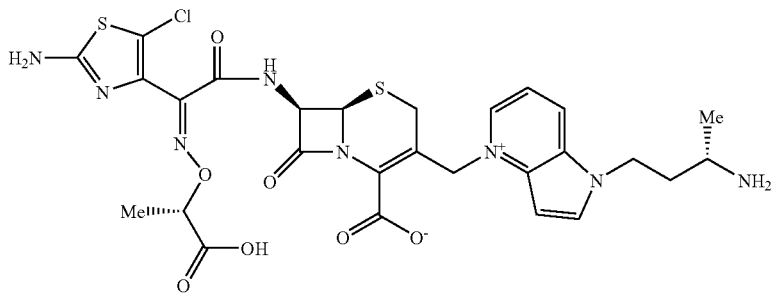

$^1$H-NMR (D$_2$O) δ: 1.36 (3H, d, J=6.9 Hz), 1.43 (3H, d, J=7.2 Hz), 2.10-2.37 (2H, m), 3.16 and 3.36 (2H, ABq, J=17.7 Hz), 3.31-3.42 (1H, m), 4.52 (2H, t-like), 4.65 (1H, q, J=7.2 Hz), 5.17 (1H, d, J=4.8 Hz), 5.54 and 5.69 (2H, ABq, J=15.0 Hz), 5.85 (1H, d, J=4.8 Hz), 7.02 (1H, d, J=3.3 Hz), 7.69 (1H, dd, J=6.0 and 8.7 Hz), 8.14 (1H, d, J=3.3 Hz), 8.59 (1H, d, J=8.7 Hz), 8.63 (1H, d, J=6.0 Hz). IR (KBr) cm$^{-1}$: 3388, 2981, 1775, 1591, 1539, 1499, 1458, 1393, 1363, 1286, 1221, 1186, 1160, 1114, 1062, 1033. MS(FAB): 677$^+$ (M+H$^+$). Elementary Analysis as C$_{27}$H$_{29}$ClN$_8$O$_7$S$_2$.5.4 H$_2$O. Calculated: C, 41.87; H, 5.18; N, 14.47; Cl, 4.58; S, 8.28(%). Found: C, 41.81; H, 4.96; N, 14.40; C, 4.69; S, 8.30(%).

EXAMPLE 162

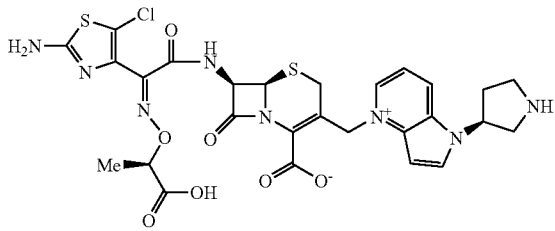

$^1$H-NMR (D$_2$O) δ: 1.42 (3H, d, J=6.9 Hz), 2.30 (1H, m), 2.54 (1H, m), 3.19 and 3.33 (2H, ABq, J=18.0 Hz), 3.42-3.59 (2H, m), 3.72-3.78 (1H, m), 3.88-3.94 (1H, m), 4.63 (1H, q, J=6.9 Hz), 5.18 (1H, d, J=4.8 Hz), 5.36 (1H, m), 5.53 and 5.72 (2H, ABq, J=15.3 Hz), 5.82 (1H, d, J=4.8 Hz), 7.00 (1H, d, J=3.6 Hz), 7.69 (1H, dd, J=6.0 and 8.4 Hz), 8.08 (1H, d, J=3.6 Hz), 8.62 (1H, d, J=6.0 Hz), 8.63 (1H, d, J=8.4 Hz). IR (KBr) cm$^{-1}$: 3387, 1770, 1667, 1605, 1543, 1495, 1461, 1399, 1359, 1321, 1285, 1202, 1149, 1131, 1081, 1058, 1029. MS(ESI): 675$^+$ (M+H$^+$). Elementary Analysis as C$_{27}$H$_{27}$ClN$_8$O$_7$S$_2$.6.0H$_2$O.0.2(C$_3$H$_7$OH). Calculated: C, 41.68; H, 5.15; N, 14.09; Cl, 4.46; S, 8.06(%). Found: C, 41.53; H, 5.05; N, 14.16; C, 4.35; S, 7.82(%).

EXAMPLE 163

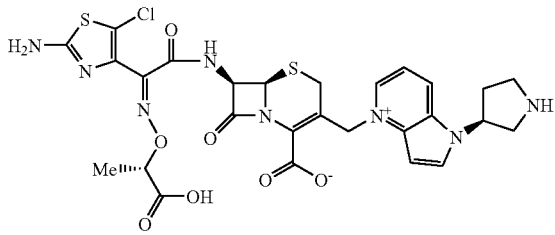

$^1$H-NMR (D$_2$O) δ: 1.44 (3H, d, J=7.2 Hz), 2.30 (1H, m), 2.53 (1H, m), 3.19 and 3.33 (2H, ABq, J=17.7 Hz), 3.42-3.59 (2H, m), 3.72-3.78 (1H, m), 3.88-3.94 (1H, m), 4.66 (1H, q, J=7.2 Hz), 5.18 (1H, d, J=5.1 Hz), 5.38 (1H, m), 5.52 and 5.71 (2H, ABq, J=15.0 Hz), 5.87 (1H, d, J=5.1 Hz), 7.00 (1H, d, J=3.6 Hz), 7.69 (1H, dd, J=6.3 and 8.4 Hz), 8.08 (1H, d, J=3.6 Hz), 8.62 (1H, d, J=6.3 Hz), 8.64 (1H, d, J=8.4 Hz). IR (KBr) cm$^{-1}$: 3406, 2978, 1772, 1601, 1541, 1497, 1461, 1395, 1364, 1313, 1287, 1222, 1186, 1161, 1132, 1094, 1065, 1034. MS(ESI): 675$^+$ (M+H$^+$). Elementary Analysis as C$_{27}$H$_{27}$ClN$_8$O$_7$S$_2$ 3.2H$_2$O.0.45(C$_3$H$_7$OH). Calculated: C, 44.81; H, 4.91; N, 14.75; Cl, 4.67; S, 8.44(%). Found: C, 44.79; H, 4.97; N, 14.64; Cl, 4.61; S, 8.28(%).

EXAMPLE 164

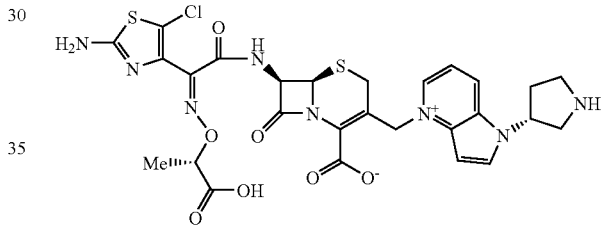

$^1$H-NMR (D$_2$O) δ: 1.44 (3H, d, J=7.2 Hz), 2.30 (1H, m), 2.54 (1H, m), 3.19 and 3.33 (2H, ABq, J=18.0 Hz), 3.42-3.59 (2H, m), 3.72-3.77 (1H, m), 3.88-3.94 (1H, m), 4.65 (1H, q, J=7.2 Hz), 5.18 (1H, d, J=4.8 Hz), 5.38 (1H, m), 5.52 and 5.72 (2H, ABq, J=14.7 Hz), 5.88 (1H, d, J=4.8 Hz), 7.00 (1H, d, J=3.3 Hz), 7.69 (1H, dd, J=6.0 and 8.4 Hz), 8.08 (1H, d, J=3.3 Hz), 8.62 (1H, d, J=6.0 Hz), 8.65 (1H, d, J=8.4 Hz). IR (KBr) cm$^{-1}$: 3397, 2982, 1773, 1602, 1540, 1497, 1462, 1395, 1364, 1316, 1287, 1186, 1132, 1092, 1064, 1034. MS(ESI): 675$^+$ (M+H$^+$). Elementary Analysis as C$_{27}$H$_{27}$ClN$_8$O$_7$S$_2$.5.0H$_2$O0.1(C$_3$H$_7$OH). Calculated: C, 42.52; H, 4.94; N, 14.53; Cl, 4.60; S, 8.32(%). Found: C, 42.54; H, 4.95; N, 14.29; Cl, 5.01; S, 8.09(%).

EXAMPLE 165

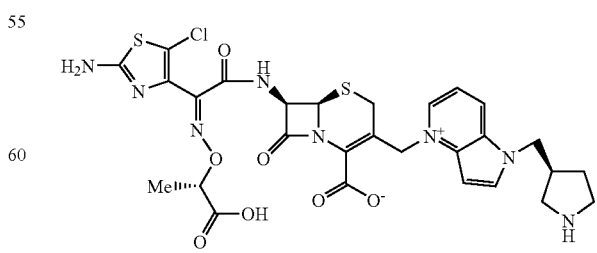

$^1$H-NMR (D$_2$O) δ: 1.43 (3H, d, J=6.9 Hz), 1.76-1.89 (1H, m), 2.08-2.18 (1H, m), 2.98-3.52 (5H, m), 3.18 and 3.37 (2H, ABq, J=18.3 Hz), 4.55 (2H, d, J=6.3 Hz), 4-65 (1H, q, J=6.9

Hz), 5.18 (1H, d, J=4.8 Hz), 5.55 and 5.70 (2H, ABq, J=15.0 Hz), 5.86 (1H, d, J=4.8 Hz), 7.04 (1H, d, J=3.3 Hz), 7.70 (1H, dd, J=6.3 and 8.1 Hz), 8.15 (1H, d, J=3.3 Hz), 8.63 (1H, d, J=8.1 Hz), 8.65 (1H, d, J=6.3 Hz). IR (KBr) cm$^{-1}$: 3397, 2982, 1774, 1602, 1539, 1499, 1454, 1391, 1363, 1319, 1286, 1185, 1158, 1129, 1092, 1064, 1033. MS(FAB): 689$^+$ (M+H$^+$). Elementary Analysis as $C_{28}H_{29}ClN_8O_7S_2 \cdot 4.9H_2O$. Calculated: C, 43.26; H, 5.03; N, 14.41; Cl, 4.56; S, 8.25(%). Found: C, 43.23; H, 5.01; N, 14.42; Cl, 4.47; S, 8.14(%).

EXAMPLE 166

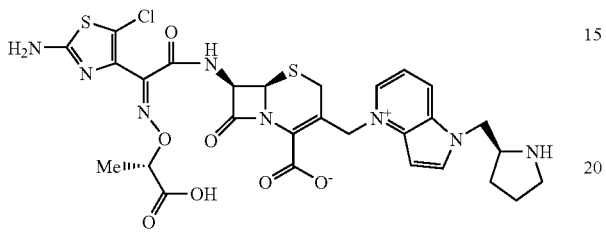

$^1$H-NMR (D$_2$O) δ: 1.43 (3H, d, J=6.9 Hz), 1.81-1.94 (1H, m), 2.02-2.34 (3H, m), 3.18 and 3.39 (2H, ABq, J=17.7 Hz), 3.26-3.49 (2H, m), 4.09-4.19 (1H, m), 4.65 (1H, q, d=6.9 Hz), 4.75 (2H, brs), 5.18 (1H, d, J=4.8 Hz), 5.57 and 5.71 (4H, ABq, J=15.3 Hz), 5.86 (1H, d, J=4.8 Hz), 7.10 (1H, d, J=3:0 Hz), 7-74 (1H, dd, J=6.3 and 8.4 Hz), 8.17 (1H, d, J=3.0 Hz), 8.66 (1H, d, J=8.4 Hz), 8.69 (1H, d, J=6.3 Hz). IR (KBr) cm$^{-1}$: 3396, 2982, 1775, 1602, 1540, 1501, 1465, 1391, 1364, 1287, 1186, 1158, 1131, 1092, 1064, 1033. MS(FAB): 689$^+$ (M+H$^+$). Elementary Analysis as $C_{28}H_{29}ClN_8O_7S_2 \cdot 4.9H_2O$. Calculated: C, 43.26; H, 5.03; N, 14.41; Cl, 4.56; S, 8.25(%). Found: C, 43.54; H, 5.01; N, 14.32 Cl,4.40; S, 7.96(%).

EXAMPLE 167

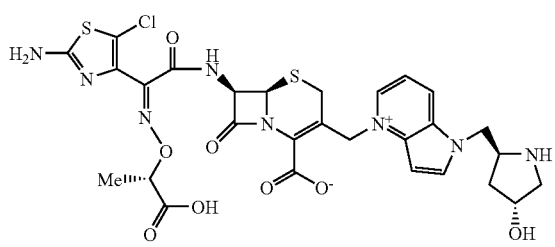

$^1$H-NMR (D$_2$O) δ: 1.44 (3H, d, J=7.2 Hz), 2.02-2.31 (2H, m), 3.18 and 3.40 (2H, ABq, J=17.7 Hz), 3.30 (1H, d, J=12.9 Hz), 3.65 (1H, dd, J=4-8 and 12.9 Hz), 4.37-4.50 (1H, m), 4.66 (1H, q, J=7.2 Hz), 4.63-4.74 (1H, m), 4.86 (2H, m), 5.19 (1H, d, J=5.1 Hz), 5.58 and 5.71 (2H, ABq, J=15.0 Hz), 5.86 (1H, d, J=5.1 Hz), 7.12 (1H, d, J=3. Hz), 7.75 (1H, dd, d=6.0 and 8.4 Hz), 8.19 (1H, s, J=3.3 Hz), 8.67 (1H, d, J=8.4 Hz), 8.69 (1H, d, J=6.0 Hz). IR (KBr) cm$^{-1}$: 3395, 2984, 1774, 1603, 1539, 1502, 1465, 1392, 1364, 1322, 1287, 1221, 1186, 1132, 1091, 1066, 1034. MS(FAB): 705$^+$ (M+H$^+$). Elementary Analysis as $C_{28}H_{29}ClN_8O_8S_2 \cdot 4.5H_2O$. Calculated: C, 42.77; H, 4.87 N, 14.25; Cl, 4.51; S, 8.16(%). Found: C, 42.69; H, 4.51; N, 14.46; Cl, 4.36; S, 8.04(%).

EXAMPLE 168

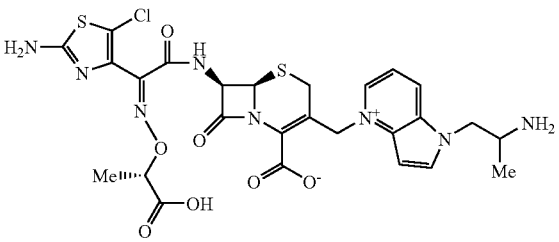

$^1$H-NMR (D$_2$O) δ: 1.39 (3H, d, J=6.6 Hz), 1.43 (3H, d, J=6.9 Hz), 3.18 and 3.38 (2H, ABq, J=17.7 Hz), 3.99 (1H, q-like), 4.65 (1H, q, J=6.9 Hz), 4.66 (2H, t-like), 5.18 (1H, d, J=4.8 Hz), 5.57 and 5.71 (2H, ABq, J=15.0 Hz), 5.86 (1H, d, J=4.8 Hz), 7.11 (1H, d, J=3.0 Hz), 7.74 (1H, dd, J=6.3 and 8.4 Hz), 8.14 (1H, d, J=3.0 Hz), 8.64 (1H, d, J=8.4 Hz), 8.69 (1H, d, J=6.3 Hz). IR (KBr) cm$^{-1}$: 3397, 2983, 1773, 1597, 1539, 1502, 1466, 1395, 1364, 1325, 1289, 1181, 1112, 1063, 1033. MS(FAB): 663$^+$ (M+H$^+$). Elementary Analysis as $C_{26}H_{27}ClN_8O_7S_2 \cdot 4.7H_2O$. Calculated: C, 41.76; H, 4.91; N, 14.98; Cl, 4.74; S, 8.58(%). Found: C, 41.81; H, 4.80; N, 14.92 Cl,4.70; S, 8.59(%).

EXAMPLE 169

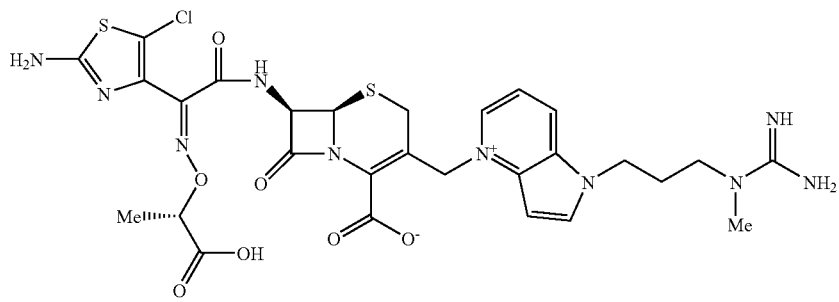

¹H-NMR (D₂O) δ: 1.43 (3H, d, J=7.2 Hz), 2.31 (2H, quintet, J=7.2 Hz), 2.91 (3H, s), 3.17 and 3.37 (2H, ABq, J=17.7 Hz), 3.38 (2H, t, J=7.2 Hz), 4.48 (2H, t, J=7.2 Hz), 4.65 (1H, q, J=7.2 Hz), 5.18 (1H, d, J=4.8 Hz), 5.56 and 5.69 (2H, ABq, J=15.0 Hz), 5.85 (1H, d, J=4.8 Hz), 7.05 (1H, d, J=3.3 Hz), 7.69 (1H, dd, J=6.0 and 8.7 Hz), 8.14 (1H, d, J=3.3 Hz), 8.59 (1H, d, J=8.7 Hz), 8.64 (1H, d, J=6.0 Hz). IR (KBr) cm⁻¹: 3373, 1774, 1600, 1540, 1498, 1457, 1392, 1363, 1321, 1286, 1184, 1127, 1082, 1033. MS(FAB): 719⁺ (M+H⁺). Elementary Analysis as $C_{28}H_{31}ClN_{10}O_7S_2 \cdot 4.3H_2O$. Calculated: C, 42.21; H, 5.01; N, 17.58; Cl, 4.45; S, 8.05(%). Found: C, 42.28; H, 4.87; N, 17.55; Cl, 4.19; S, 7.84(%).

EXAMPLE 170

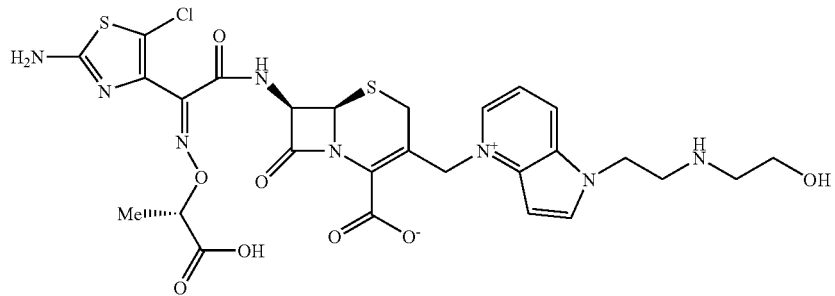

¹H-NMR (D₂O) δ: 1.43 (3H, d, J=7.2 Hz), 3.17 and 3.38 (2H, ABq, J=17.7 Hz), 3.22 (2H, m), 3.69 (2H, t, J=6.3 Hz), 3.81 (2H, m), 4.65 (1H, q, J=7.2 Hz), 4.83 (2H, t, J=6.3 Hz), 5.18 (1H, d, J=4.8 Hz), 5.57 and 5.71 (2H, ABq, J=15.0 Hz), 5.86 (1H, d, J=4.8 Hz), 7.10 (1H, d, J=33 Hz), 7.74 (1H, dd, J=6.0 and 8.4 Hz), 8.16 (1H, d, J=3.3 Hz), 8.64 (1H, d, J=8.4 Hz), 8.69 (1H, d, J=6.0 Hz). IR (KBr) cm⁻¹: 3385, 1773, 1601, 1539, 1500, 1466, 1393, 1364, 1287, 1186, 1139, 1112, 1064, 1033. MS(FAB) 693⁺ (M+H⁺). Elementary Analysis as $C_{27}H_{11}ClN_8O_5S_2 \cdot 2.9H_2O$. Calculated: C, 43.51; H, 4.71; N, 15.03; Cl, 4.76; S, 8.60(%). Found: C, 43.61; H, 4.80; N, 15.12; Cl, 4.48; S, 8.21(%).

EXAMPLE 171

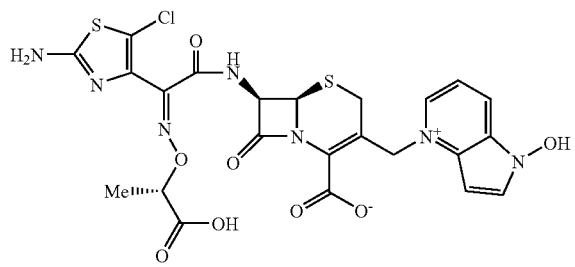

¹H-NMR (D₂O) δ: 1.43 (3H, d, J=7.2 Hz), 3.19 and 3.28 (2H, ABq, J=18.0 Hz), 4.64 (1H, q, J=7.2 Hz), 5.15 (1H, d, J=4.8 Hz), 5.41 and 5.65 (2H, ABq, J=15.0 Hz), 5.87 (1H, d, J=4.8 Hz), 6.58 (1H, d, J=3.3 Hz), 7.43 (1H, dd, J=6.3 and 8.1 Hz), 7.90 (1H, d, J=3.3 Hz), 8.37 (1H, d, J=8.1 Hz), 8.40 (1H, d, J=6.3 Hz). IR (KBr) cm⁻¹: 3468, 3144, 3116, 3099, 3080, 2980, 2951, 2924, 2870, 2341, 2276, 2256, 1934, 1891, 1754, 1618, 1580, 1499, 1449, 1429, 1365, 1345, 1309, 1237, 1227, 1208, 1187, 1159, 1114, 1054. MS(FAB): 622⁺ (M+H⁺). Elementary Analysis as $C_{23}H_{20}ClN_7O_8S_2 \cdot 3.5H_2O$. Calculated: C, 40.32; H, 3.97; N, 14.31; Cl, 5.17; S, 9.36(%). Found: C, 40.38; H, 3.90; N, 14-23; Cl, 5.36; S, 9.25(%).

EXAMPLE 172

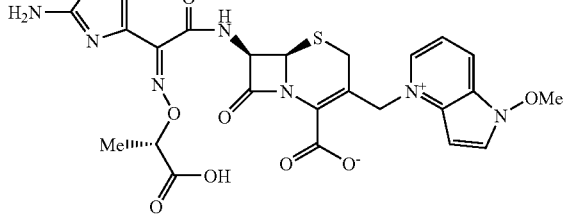

1H-NMR (D₂O) δ: 1.44 (3H, d, J=6.9 Hz), 3.18 and 3.37 (2H, ABq, J=17.4 Hz), 4.26 (s, 3H), 4.65 (1H, q, J=6.9 Hz), 5.18 (1H, d, J=4.8 Hz), 5.55 and 5.71 (2H, ABq, J=15.3 Hz), 5.88 (1H, d, J=4.8 Hz), 6.91 (1H, d, J=3.6 Hz), 7.74 (1H, dd, J=6.3 and 8.1 Hz), 8.31 (1H, d, J=3.6 Hz), 8-65 (1H, d, J=8.1 Hz), 8.68 (1H, d, J=6.3 Hz). IR (KBr) cm⁻¹: 3410, 3134, 2941, 1778, 1674, 1614, 1537, 1457, 1364, 1234, 1211, 1188, 1155, 1120, 1058, 1034. MS(ESI): 636⁺ (M+H⁺). Elementary Analysis as $C_{24}H_{22}ClN_7O_8S_2 \cdot 3.2H_2O$. Calculated: C, 41.55; H, 4.13; N, 14.13; Cl, 5.11; S, 9.24(%). Found: C, 41.62; H, 4.21; N, 14.26; C, 4.90; S, 9.08(%).

Quaternary Salt Ester:

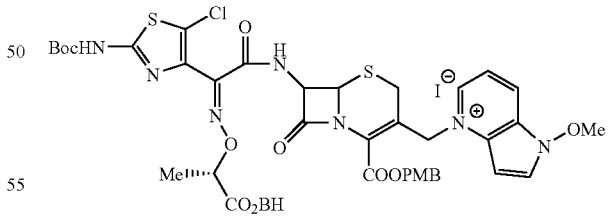

¹H-NMR (dc-DMSO) δ: 1.44 (3H, d, J=6.9 Hz), 1.46 (9H, s), 3.34 and 3.42 (2H, Abq, J=18.0 Hz), 3.76 (3H, s), 4.26 (3H, s), 4.89 (1H, q, J=6.9 Hz), 5.19 (1H, d, J=5.1 Hz), 5.22 and 5.29 (2H, Abq, J=11.7 Hz), 5.68 and 5.75 (2H, Abq, J=15.3 Hz), 5.97 (1H, dd, J=5.1 and 8.4 Hz), 6.82 (1H, s), 6.89 (2H, d, J=9.0 Hz), 6.95 (1H, d, J=3.6 Hz), 7.20-7.42 (12H, m), 7.84 (1H, dd, J=6.0 and 8.1 Hz), 8.67 (1H, d, J=6.0 Hz), 8.73 (1H, d, J=3.6 Hz), 8.86 (1H, d. J=8.1 Hz), 9.76 (1H, d, J=8.4 Hz), 12.1 (rs). IR (KBr) cm⁻¹: 3394, 3131, 3091, 3061, 3031, 2978, 2937, 1789, 1719, 1632, 1613, 1549, 1515, 1495, 1455, 1391, 1368, 1247, 1176, 1154, 1119, 1063, 1032. MS (FAB): 1222⁺ ($C_{50}H_{49}ClN_7O_{11}S_2^+$).

EXAMPLE 173

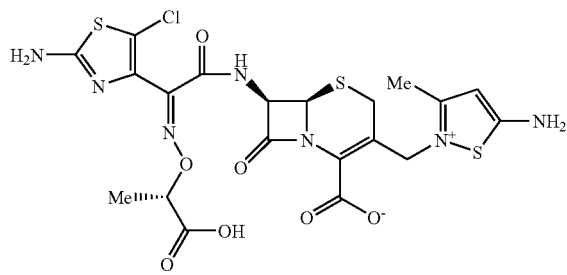

$^1$H-NMR (D₂O) δ: 1.47 (3H, d, J=6.9 Hz), 2.43 (3H, s), 3.26 and 3.62 (2H, ABq, J=17.7 Hz), 4.66 (1H, q, J=6.9 Hz), 4.79 and 4.95 (2H, ABq, J=14.7 Hz), 5.26 (1H, d, J=4.8 Hz), 5.88 (1H, d, J=48 Hz), 6.26 (1H, s). IR (KBr) cm⁻¹: 3312, 3190, 1776, 1671, 1617, 1535, 1460, 1392, 1337, 1187, 1134, 1100, 1064, 1034. MS(FAB): 602⁺ (M+H⁺). Elementary Analysis as $C_{20}H_{20}ClN_7O_7S_3$·2.5H₂O. Calculated: C, 37.12; H, 3.89; N, 15.15; Cl, 5.48; S, 14.87(%). Found: C, 36.94; H, 3.98; N, 14.93; Cl, 5.42; S, 15.09(%).

EXAMPLE 174

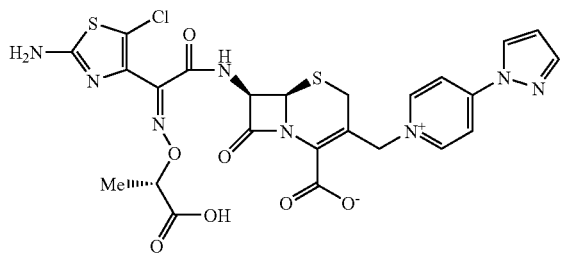

$^1$H-NMR (D₂O) δ: 1.44 (3H, d, J=7.2 Hz), 3.26 and 3.66 (2H, ABq, J=18.0 Hz), 4.64 (1H, q, J=7.2 Hz), 5.25 and 5.50 (2H, ABq, J=14.4 Hz), 5.28 (1H, d, J=4.8 Hz), 5.89 (1H, d, J=4.8 Hz), 6.78 (1H, dd, J=1.8 and 3.0 Hz), 8.04 (1H, d, J=1.8 Hz), 8.27 and 8.94 (2H, ABq, J=7.2 Hz), 8.53 (1H, d, J=3.0 Hz). IR (KBr) cm⁻¹: 3417, 3135, 1779, 1673, 1639, 1537, 1480, 1446, 1397, 1360, 1217, 1159, 1116, 1036. MS(FAB): 633⁺ (M+H⁺). Elementary Analysis as $C_{24}H_{21}ClN_8O_7S_2$·2.7H₂O. Calculated: C, 42.29; H, 3.90; N, 16.44; Cl, 5.20; S, 9.41(%). Found: C, 42.41; H, 3.97; N, 16.42; Cl, 4.93; S, 9.24(%).

EXAMPLE 175

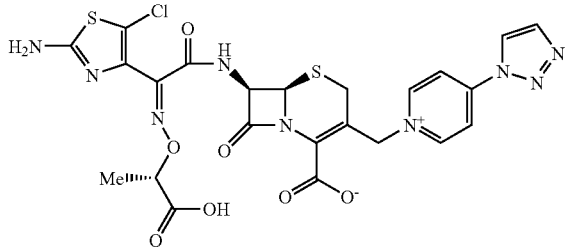

$^1$H-NMR (D₂O) δ: 1.44 (3H, d, J=6-9 Hz), 3.28 and 3.70 (2H, ABq, J=18.0 Hz), 4.65 (1H, q, J=6.9 Hz), 5.30 (1H, d, J=5.1 Hz), 5.36 and 5.63 (2H, ABq, J=14.7 Hz), 5.92 (1H, d, J=5.1 Hz), 8.07 (1H, S, J=1.8 Hz), 8.59 and 9.18 (2H, ABq, J=7.5 Hz), 8.85 (1H, d. J=1.8 Hz). IR (KBr) cm⁻¹: 3415, 3132, 1778, 1673, 1638, 1530, 1475, 1341, 1247, 1186, 1159, 1125, 1095, 1064, 1032. MS(FAB): 634⁺ (M+H⁺). Elementary Analysis as $C_{23}H_{20}ClN_9O_7S_2$·2.6H₂O. Calculated: C, 40.57; H, 3.73; N, 18.51; C, 5.21; S, 9.42(%). Found: C, 40.61; H, 3.67; N, 18.52; Cl, 4.96; S, 9.20(%).

EXAMPLE 176

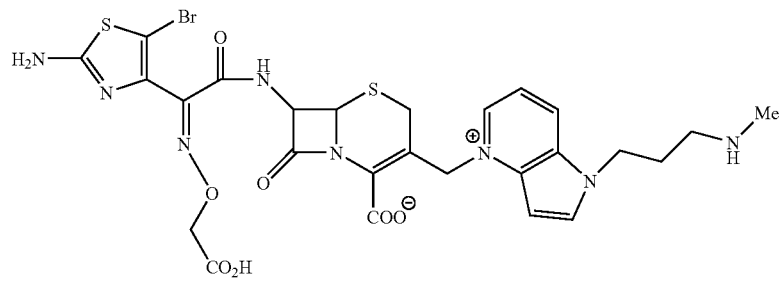

¹H-NMR (D₂O) δ: 2.30 (2H, m), 2.67 (3H, s), 3.05⁄2H, m), 3.15 and 3.38 (2H, ABq, J=17.7 Hz), 4.52 (2H, t, J=6.6 Hz), 4.55 (2H, s), 5.17 (1H, d, J=4.8 Hz), 5.56 and 5.67 (2H, ABq, J=15.0 Hz), 5.85 (1H, d, J=4.8 Hz), 7.04 (1H, d, J=3.3 Hz), 7.68 (1H, dd, J=6.3 and 8.1 Hz), 8.11 (1H, d, J=3.3 Hz), 8.59 (1H, d, J=8.1 Hz), 8.64 (1H, d, J=6.3 Hz). IR (KBr) cm⁻¹: 3418, 1771, 1607, 1534, 1497, 1466, 1391, 1360, 1317, 1152, 1119, 1052, 1020. MS(ESI): 707⁺ (M+H⁺). Elementary Analysis as $C_{25}H_{27}BrN_8O_7S_2$ 5.4H₂O. Calculated: C, 38.80; H, 4.73; N, 13.92; Br, 9.93; S, 7.97(%). Found: C, 38.80; H, 4.46; N, 14.04; Br, 9.66; S, 8.01(%).

$C_{26}H_{25}ClN_8O_7S_2 \cdot 4.5H_2O$. Calculated: C, 42.08; H, 4.62; N, 15.10; Cl, 4.78; S, 8.64(%). Found: C, 42.05; H, 4.60; N, 15.23; Cl, 4.50; S, 8.34(%).

EXAMPLE 178

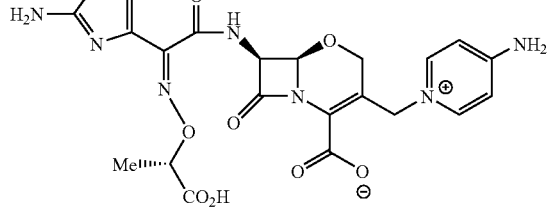

Quaternary Salt Ester:

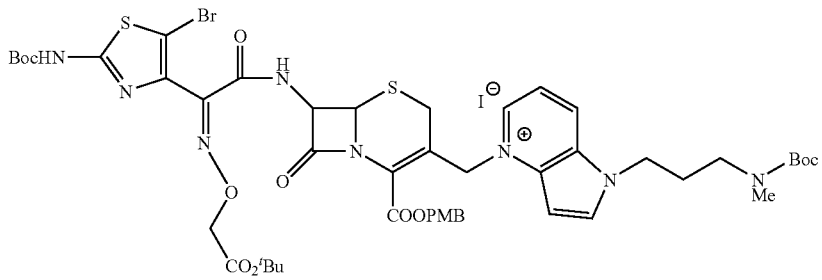

¹H-NMR (d₆-DMSO) δ: 1.40 (9H, s), 1.46 (18H, s), 2.03 (2H, m), 2.78 (3H, brs), 3.18 (2H, t, J=6.6 Hz), 3.26 and 3.43 (2H, Abq, J=18.3 Hz), 3.75 (3H, s), 4-43 (2H, t-like), 4.55 (2H, s), 5.17 (1H, d, J=4.8 Hz), 5.21 and 5.28 (2H, Abq, J=11.7 Hz), 5.65 and 5.73 (2H, ABq, J=15.0 Hz), 5.94 (1H, dd, J=4.8 and 8.7 Hz), 6.88 and 7.32 (4H, Abq, J=8.7 Hz), 7.00 (1H, d, J=3.3 Hz), 7.79 (1H, dd, J=6.0 and 8.1 Hz), 8.43 (1H, d, J=3.3 Hz), 8.60 (1H, d, J=6.0 Hz), 8.88 (1H, d, J=8.1 Hz), 9.61 (1H, d, J=8.7 Hz), 12.1 (brs) IR (KBr) cm⁻¹: 3428, 3060, 2976, 2933, 1790, 1720, 1686, 1630, 1613, 1584, 1548, 1515, 1496, 1455, 1393, 1368, 1300, 1247, 1156, 1078, 1062, 1024. MS(ESI): 1083⁺ ($C_{46}H_{60}BrN_8O_{12}S_2^+$).

¹H-NMR (D₂O) δ: 1.37 (3H, d, J=6.9 Hz), 4.34 and 4.41 (2H, ABq, J=17.4 Hz), 4.61 (1H, q, J=6.9 Hz), 4.87 and 5-21 (2H, ABq, J=14.7 Hz), 5.31 (1H, d, J=3.9 Hz), 5.65 (1H, d, J=3.9 Hz), 6.83 and 8.08 (2H, ABq, J=7.2 Hz). IR(KBr) cm⁻¹: 3344, 3197, 1781, 1655, 1538, 1444, 1402, 1372, 1349, 1279, 1240, 1210, 1171, 1109, 1064, 1034. MS(FAB); 566⁺ (M+H⁺) Elementary Analysis as $C_{21}H_{20}ClN_7O_8S \cdot 3.0H_2O$. Calculated: C, 40.68; H, 4.23; N, 15.81; Cl, 5.72; S, 5.17(%). Found C, 40.56; H, 3.90; N, 15.83; Cl, 5.84; S, 5.18(%).

EXAMPLE 177

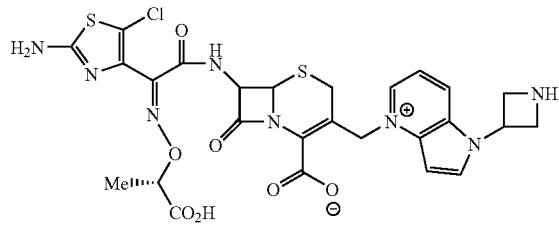

¹H-NMR (D₂O) δ: 1.43 (3H, d, J=6.9 Hz), 3.17 and 3.38 (2H, ABq, J=17.7 Hz), 4.65 (1H, q, J=6.9 Hz), 4.70-4.75 (4H, m), 5.18 (1H, d, J=4.8 Hz), 5.57 and 5.71 (2H, ABq, J=15.3 Hz), 5.86 (1H, d, J=4.8 Hz), 5.95 (1H, quintet-like), 7.20 (1H, d, J=3.6 Hz), 7.73 (1H, dd, J=6.3 and 8.4 Hz), 8.53 (1H, d, J=3.6 Hz), 8.60 (1H, d, J=8.4 Hz), 8.70 (1H, d, J=6.3 Hz). IR (KBr) cm⁻¹: 3407, 2985, 2670, 1773, 1604, 1539, 1502, 1463, 1394, 1364, 1286, 1185, 1136, 1090, 1064, 1032. MS(FAB): 661⁺ (M+H⁺). Elementary Analysis as

EXAMPLE 179

¹H-NMR (D₂O) δ: 1.38 (3H, d, J=7.2 Hz), 3.33 (2H, t, J=6.0 Hz), 3.73 (2H, t, J=6.0 Hz), 4.34 and 4.45 (2H, ABq, J=17.4 Hz), 4.63 (1H, q, J=7.2 Hz), 4.78 and 5.32 (2H, ABq, J=14.7 Hz), 5.33 (1H, d, J=3.9 Hz), 5.63 (1H, d, J=3.9 Hz), 6.83 (2H, d-like), 8.08(2H,m). IR(KBr) cm⁻¹: 3396, 3067, 1779, 1649, 1601, 1556, 1448, 1403, 1371, 1350, 1279, 1217, 1171, 1107, 1063, 1033. MS(FAB): 623⁺ (M+H⁺). Elementary Analysis as $C_{24}H_{27}ClN_8O_5S \cdot 4.9H_2O$. Calculated: C,

EXAMPLE 180

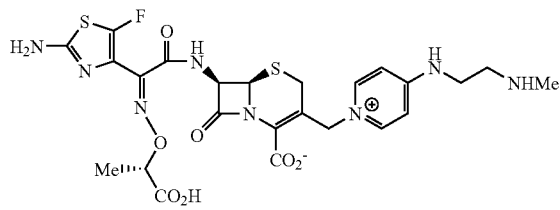

$^1$H-NMR (D$_2$O) δ: 1.31 (3H, d, J=7.2 Hz), 2.64 (3H, s), 3.03 (1H, d, J=17.1 Hz), 3.21 (2H, t, J=6.0 Hz), 3-45 (1H, d, J=17.1 Hz), 3.61 (2H, t, J=6.0 Hz), 4.51 (1H, q, J=7.2 Hz), 4.76 (1H, d, J=15.0 Hz), 4.97 (1H, d, J=15.0 Hz), 5.10 (1H, d, J=4.2 Hz), 5.70 (1H, d, J=4.2 Hz), 6.81 (2H, d, J=63 Hz), 8.01-8.13 (2H, m). IR (KBr) cm$^{-1}$: 3388, 3066, 1773, 1650, 1590, 1557, 1533, 1450, 1394, 1355, 1320, 1289, 1217, 1169, 1094, 1064, 1036. MS(FAB): 623$^+$ (M+H$^+$). Elementary Analysis as C$_{24}$H$_{27}$FN$_8$O$_7$S$_2$.3.8H$_2$O. Calculated: C, 41.71; H, 5.05; N, 16.21; F, 2.75; S, 9.28(%). Found: C, 41.69; H, 4.92; N, 16.23; F, 2.51; S, 9.05(%).

EXAMPLE 181

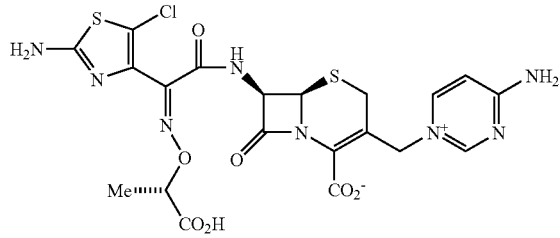

$^1$H-NMR (D$_2$O) δ: 1.52 (3H, d, J=6.9 Hz), 3.25 (1H, d, J=17.7 Hz), 3.63 (1H, d. J=17.7 Hz), 4.84 (1H, q, J=6.9 Hz), 4.88 (1H, d, J=14.7 Hz), 5.06 (1H, d, J=14.7 Hz), 5.26 (1H, d, J=5.1 Hz), 5.87 (1H, d, J=5.1 Hz), 6.85 (1H, d, J=7.5 Hz), 8.21 (1H, dd, J=1.5, 7.5 Hz), 8.68 (1H, d, J=1.5 Hz). IR (KBr) cm$^{-1}$: 3397, 3198, 1776, 1659, 1539, 1494, 1445, 1391, 1372, 1238, 1169, 1103, 1065, 1037. MS(FAB): 583 (M+H)$^+$, 1165 (2M+H)$^+$. Elementary Analysis as C$_{20}$H$_{19}$ClN$_8$O$_7$S$_2$.2.1H$_2$O. Calculated: C, 38.69; H, 3.77; N, 18.05; Cl, 5.71; S, 10.33(%). Found: C, 38.81; H, 3.70; N, 18.01; Cl, 5.54; S, 10.05(%Y).

EXAMPLE 182

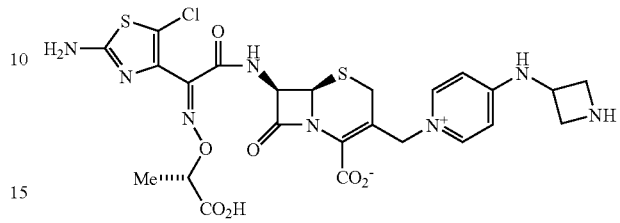

$^1$H-NMR D$_2$O) δ: 1.44 (3H, d, J=6.9 Hz), 3.16 (1H, d, J=17.7 Hz), 3.57 (1H, d, J=17.7 Hz), 4.21 (2H, m), 4.52 (2H, m), 5.11 (1H, d, J=14.4 Hz), 5.24 (1H, d, J=4.8 Hz), 5.86 (1H, d, J=4.8 Hz), 6.89 (2H, m), 8.23 (2H, m). IR (KBr) cm$^{-1}$: 3399, 3059, 1772, 1649, 1601, 1551, 1445, 1361, 1288, 1217, 1167, 1095, 1065, 1035. MS (FAB): 637 (M+H)$^+$, 1273 (2M+H)$^+$. Elementary Analysis as C$_{24}$H$_{21}$ClN$_8$O$_7$S$_2$.2.2H$_2$O. Calculated: C, 42.60; H, 4.38; N, 16.56; Cl, 5.24; S, 9.48(%). Found: C, 42.67; H, 4.31; N, 16.71; Cl, 5.16; S, 9.08(%).

EXAMPLE 183

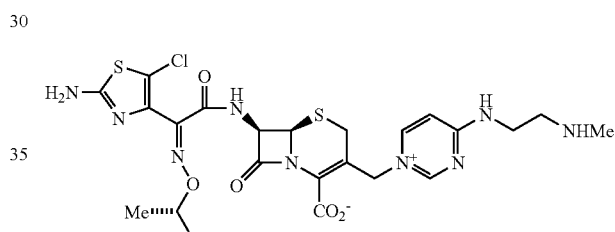

$^1$H-NMR (D$_2$O) δ: 1.33 (3H, d, J=6.9 Hz), 2.62 (3H, s), 3.12 (1H, d, J=18.0 Hz), 3.22 (2H, t, J=5.7 Hz), 3.53 (1H, d, J=18.0 Hz), 3.82 (2H, t, J=5.7 Hz), 4.54 (1H, q, J=6.9 Hz), 4.75 (1H, d, J=14.7 Hz), 4.96 (1H, d, J=14.7 Hz), 5.13 (1H, d, J=5.1 Hz), 5.74 (1H, d, J=5.1 Hz), 6.77 (1H, d, J=7.5 Hz), 8.12 (1H, br d, J=7.5 Hz), 8.70 (1H, br s). IR (KBr) cm$^{-1}$: 3409, 1775, 1652, 1605, 1538, 1509, 1447, 1394, 1370, 1287, 1170, 1095, 1065, 1035. MS(FAB): 640 M+H)$^+$, 1279 (2M+H)$^+$. Elementary Analysis as C$_{23}$H$_{26}$ClN$_9$O$_7$S$_2$.3.5H$_2$O. Calculated C, 39.29; H, 4.73; N, 17.93; Cl, 5.04; S, 9.12(%). Found: C, 39.43; H, 4.68; N, 17.74; Cl, 5.00; S, 8.95(%).

EXAMPLE 184

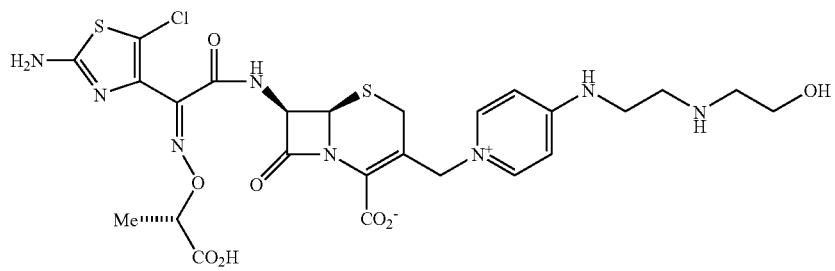

¹H-NMR (D₂O) δ: 1.45 (3H, d, J=6.9 Hz), 3.17 (1H, d, J=18.0 Hz), 3.24 (2H, t, J=5.1 Hz), 3.39 (2H, t, J=6.3 Hz), 3.57 (1H, d, J=18.0 Hz), 3.77 (2H, t, J=6.3 Hz), 3.85 (2H, t, J=5.1 Hz), 4.66 (1H, q, J=6.9 Hz), 488 (1H, d, J=15.0 Hz), 5.09 (1H, d, J=15.0 Hz), 5.24 (1H, d, J=4.8 Hz), 5-86 (1H, d, J=4.8 Hz), 6.94 (2l, d, J=6-9 Hz), 8.19 (2H, m). IR (KBr) cm⁻¹: 3378, 1774, 1650, 1598, 1556, 1448, 1394, 1358, 1286, 1218, 1168, 1093, 1066, 1034. MS(FAB): 669 (M+H)⁺. Elementary Analysis as $C_{21}H_{29}ClN_8O_8S_2 \cdot 2.7H_2O$. Calculated: C, 41.83; H, 4.83; N, 15.61; Cl, 4.94; S, 8.93(%). Found: C, 41.76; H, 4.61; N, 15.80; Cl, 4.78; S, 8.65(%).

EXAMPLE 185

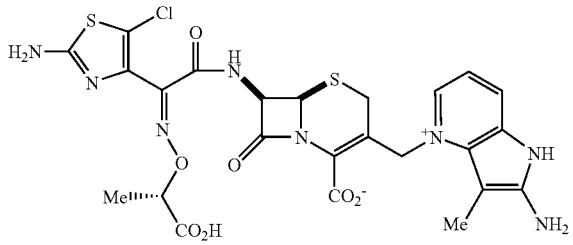

¹H-NMR (d₆-DMSO) δ: 1.39 (3H, d, J=6.9 Hz), 2.21 (3H, brs), 2.97 and 3.48 (2H, ABqt, J=17.7 Hz), 4.57 (1H, q, J=6.9 Hz), 5.09 (1H, d, J=4.8 Hz), 5.41 (2H, brs), 5.77 (1H, dd, J=4.8, 8.4 Hz), 6.75 (1H, t-like), 7.37-7.39 (3H, m), 7.70 (2H, brs), 8.05 (1H, d, J=5.4 Hz), 9.96 (1H, brs), 13.5 (1H, brs). IR (KBr) cm⁻¹: 3339, 3195, 1773, 1646, 1603, 1567, 1479, 1424, 1394, 1338, 1286, 1227, 1190, 1161, 1094, 1035. MS(FAB): 635⁺ (M+H)⁺. Elementary Analysis as $C_{24}H_{23}ClN_8O_7S_2 \cdot 2.3H_2O$. Calculated: C, 42.61; H, 4.11; N, 16.56; Cl, 5.24; S, 9.48(%). Found: C, 42.72; H, 4.27; N, 16.53; Cl, 5.02; S, 9.13(%).

EXAMPLE 186

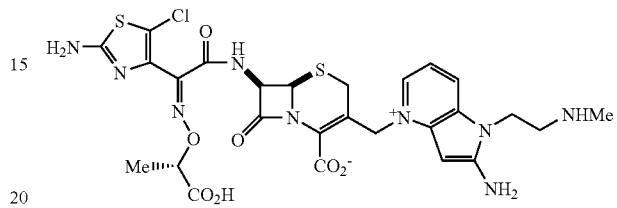

¹H-NMR (D₂O+DCl) δ: 1.54 (3H, d, J=7.5 Hz), 2.76 (3H, s), 3.24 and 3.46 (2H, ABqt, J=18.6 Hz), 3.51 (2H, t, J=6.3 Hz), 4.56 (2H, t, J=6.3 Hz), 4.98 (1H, q, J=7.5 Hz), 5.27 (1H, d, J=4.8 Hz), 5.36 and 5.49 (2H, ABq, J=15.9 Hz), 5.91 (1H, d, J=4.8 Hz), 7.11 (1H, dd, J=6.3, 7.8 Hz), 7.80 (1H, d, J=7.8 Hz), 7.95 (1H, d, J=6.3 Hz). IR (KBr) cm⁻¹: 3369, 2457, 1761, 1646, 1564, 1475, 1435, 1398, 1360, 1317, 1284, 1191, 1164, 102, 1036. MS(FAB): 678⁺ (M+H)⁺. Elementary Analysis as $C_{26}H_{28}ClN_9O_7S_2 \cdot 3.2H_2O$. Calculated: C, 42.44; H, 4.71; N, 17.13; Cl, 4.82; S, 8.72(%). Found: C, 42.15; H, 4.41; N, 17.15; Cl, 4.86; S, 8.68(%).

EXAMPLE 187

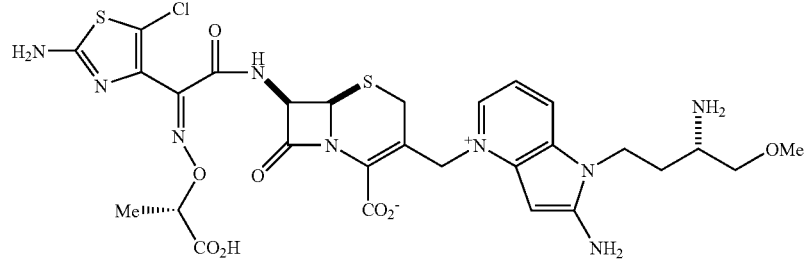

¹H-NMR (D₂O+DCl) δ: 1.55 (3H, d, J=6.9 Hz), 2.16-2.24 (3H, n), 3.37 (1H, d, J=18.3 Hz), 3.43 (3H, s), 3.57-3.76 (4H, m), 4.31 (2H, t, J=8.1 Hz), 4.79 (1H, d, J=5.1 Hz), 4.99 (1H, q, J=6.9 Hz), 5.49 and 5.69 (2H, ABq, J=15.0 Hz), 5.92 (1H, d, J=5.1 Hz), 7.35 (1H, dd, J=6.6, 7.8 Hz), 7.97 (1H, d, J=7.8 Hz), 8.14 (1H, d, J=6.6 Hz). IR (KBr) cm⁻¹: 3378, 3183, 1773, 1650, 1565, 1495, 1441, 1395, 1352, 1316, 1287, 1223, 1165, 1095, 1034. MS(FAB): 723⁺ (M+H)⁺. Elementary Analysis as $C_{27}H_{31}ClN_{10}O_8S_2 \cdot 2.6H_2O$. Calculated: C, 42.11; H, 4.74; N, 18.19; Cl, 4.60; S, 8.33(%). Found: C, 42.14; H, 4.54; N, 18.19; Cl, 4.50; S, 8.16(%).

EXAMPLE 188

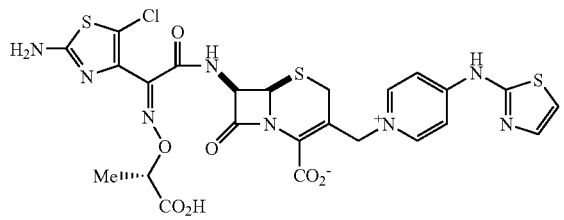

¹H-NMR (d₆-DMSO) δ: 1.39 (3H, d, J=6.9 Hz), 3.07 and 3.49 (2H, d, J=17.7 Hz), 4.56 (1H, q, J=6.9 Hz), 4.92 and 5.38 (2H, ABq, J=13.5 Hz), 5.07 (1H, d, J=5.4 Hz), 5.73 (1H, dd, J=5.4, 9.0 Hz), 7.35 (1H, d, J=3.3 Hz), 7.40 (2H, brs), 7.54 (1H, d, J=3.3 Hz), 8.05 (2H, brs), 8.90 (2H, brd, J=72 Hz), 9.70 (1H, brs). IR (KBr) cm⁻¹: 3416, 2984, 1777, 1643, 1547, 1515, 1476, 1461, 1348, 1204, 1161, 1102, 1063, 1036. MS(FAB): 665⁺ (M+H)⁺. Elementary Analysis as $C_{24}H_{11}ClN_8O_7S_3 \cdot 2.5H_2O$. Calculated: C, 40.59; H, 3.69; N, 15.78; Cl, 4.99; S, 13.55(%). Found: C, 40.41; H, 3.62; N, 16.01; Cl, 5.03; S, 13.25(%).

EXAMPLE 189

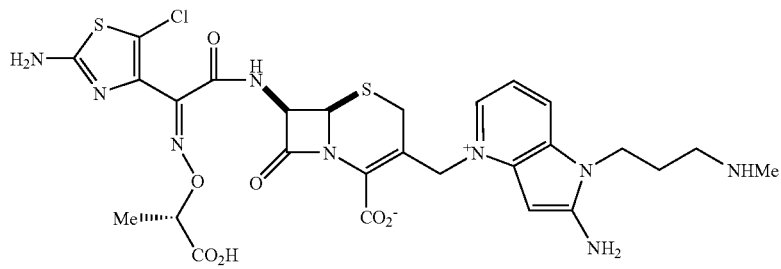

¹H-NMR (D₂O+DCl) δ: 1.54 (3H, d, J=6.9 Hz), 2.14-2.24 (2H, m), 2.71 (3H, s), 3.11 (2H, t, J=8.4 Hz), 3.25 and 3.48 (2H, ABqt, J=18.3 Hz), 4.28 (2H, t, i=7.5 Hz), 4.99 (1H, q, J=6.9 Hz), 5.29 (1H, d, J=4.8 Hz), 5.34 and 5.51 (2H, ABq, J=15.6 Hz), 5.91 (1H, d, J=4.8 Hz), 7.08 (1H, dd, 1-6.6, 7.5 Hz), 7.78 (1H, d, J=7.5 Hz), 7.91 (1H, d, J=6.6 Hz). IR (KBr) cm⁻¹: 3341, 3177, 1772, 1646, 1564, 1473, 1439, 1394, 1346, 1284, 1190, 1162, 1092, 1058, 1034. MS(FAB): 692⁺ (M+H)⁻. Elementary Analysis as $C_{27}H_{30}ClN_9O_7S_2 \cdot 3.8H_2O$. Calculated: C, 42.63; H, 4.98; N, 16.57; Cl, 4.66; S, 8.43(%). Found: C, 42.69; H, 4.81; N, 16.49; C, 4.67; S, 8.51(%).

EXAMPLE 190

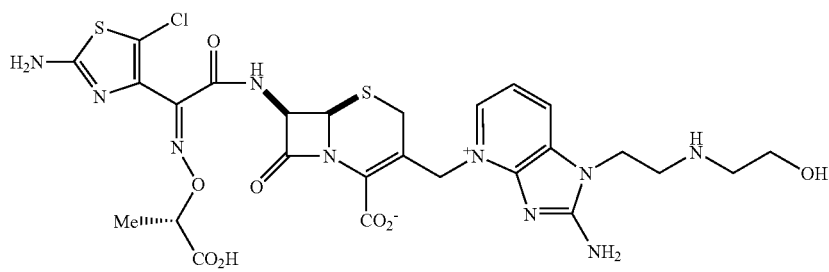

¹H-NMR (D₂O+DCl) δ: 1.55 (3H, d, J=6.9 Hz), 3.27 (2H, t, J=8.3 Hz), 3.36 and 3.59 (2H, ABq, J=18.3 Hz), 3.61 (2H, t, J=6.8 Hz), 3.86 (2l, t, J=8.3 Hz), 4.98 (1H, sept, J=6.9 Hz), 5.27 (1H, d, J=4.8 Hz), 5.47 and 5.70 (2H, ABq, J=15.2 Hz), 7.32-7.38 (1H, m), 8.01 (1H, d, J=7.5 Hz), 8.16 (1H, d, J=6.9 Hz). IR (KBr) cm⁻¹: 3371, 3184, 1772, 1667, 1603, 1563, 1395, 1351, 1316, 1222, 1170, 1072, 1034, 984, 867, 758. MS(FAB): 709⁺ (M+H)⁺. Elementary Analysis as C₂₆H₂₉ClN₁₀O₈S₂.2.6H₂O. Calculated: C, 41.31; H, 4.56; N, 18.53; Cl, 4.69; S, 8.48(%). Found: C, 41.22; H, 4.37; N, 18.51; Cl, 5.27; S, 8.25(%).

EXAMPLE 191

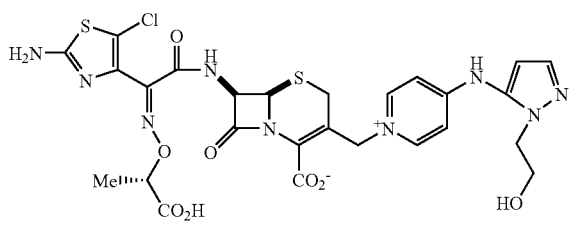

¹H-NMR (d₆-DMSO) δ: 1.39 (3H, d, J=6.9 Hz), 3.04 and 3.486 (2H, ABqt, J=17.4 Hz), 3.67 (2H, t, J=5.4 Hz), 4.07 (2H, t, J=5.4 Hz), 4.57 (1H, q, J=6.9 Hz), 4.84 and 5.30 (2l, ABq, J=13.8 Hz), 5.06 (1H, d, J=4.8 Hz), 5.72 (1H, dd, J=4.8, 8.7 Hz), 6.31 (1H, d, J=1.8 Hz), 7.14 (2H, brs), 7.41 (2H, brs), 7.57 (1H, d, J=1.8 Hz), 8.72 (1H, d, J=7.2 Hz), 9.65 (1H, brs), 10.8 (1H, brs). IR (KBr) cm⁻¹; 3308, 2948, 1777, 1648, 1608, 1541, 1456, 1357, 1212, 1165, 1109, 1065, 1036. MS(FAB): 692⁺ (M+H)⁺. Elementary Analysis as C₂₆H₂₆ClN₉O₈S₂.2.2H₂O. Calculated: C, 42.68; H, 4.19; N, 17.23; Cl, 4.84; S, 8.78(%). Found: C, 42.79H, 4.10; N, 17.32; Cl, 4.47; S, 8.45(%).

EXAMPLE 192

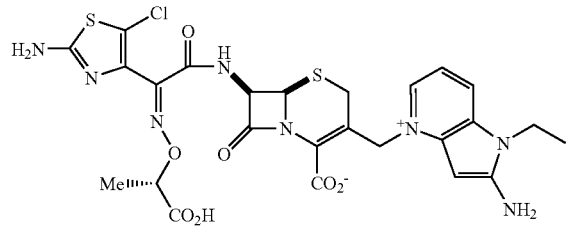

¹H-NMR (d₆-DMSO) δ: 1.20 (3H, t, J=6.9 Hz), 1.38 (3H, d, J=7.2 Hz), 2.94 and 3.27 (2H, ABqt, J=17.4 Hz), 4.16 (2H, q, J=6.9 Hz), 4.55 (2H, q, J=7-2 Hz), 5.00 (1H, d, J=4.8 Hz), 5.22 and 5.34 (2H, ABq, J=14.4 Hz), 5.68 (1H, dd, J=4.8, 9.0 Hz), 6.05 (1H, s), 6.99 (1H, dd, S=6.6, 7.5 Hz), 7.40 (2H, brs), 7.79 (1H, d, J=7.5 Hz), 7.88 (2H, brs), 8.27 (1H, d, J=6.6 Hz), 9.78 (1H, brs). IR (KBr) cm⁻¹: 3346, 3189, 2985, 2936, 1777, 1646, 1594, 1563, 1474, 1441, 1386, 1342, 1285, 1191, 1162, 1098, 1036. MS(FAB): 649⁺ (M+H)⁺. Elementary Analysis as C₂₅H₂₅ClN₈O₇S₂.2.3H₂O. Calculated: C, 43.48; H, 4.32; N, 16.23; Cl, 15.13; S, 9.29(%). Found: C, 43.48; H, 4.21; N, 16.28; Cl, 4.80; S, 8.98(%).

EXAMPLE 193

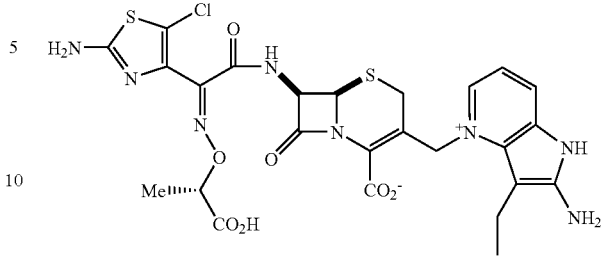

¹H-NMR (d₆-DMSO) δ: 1.04 (3H, t, J=752 Hz), 1.40 (3H, d, J=6.9 Hz), 2.60-2.70 (2H, m), 2.97 and 3.49 (2H, ABqt, J=17.4 Hz), 4.57 (1H, q, J=6.9 Hz), 5.10 (1H, d, J=4.8 Hz), 5-24 and 5.46 (2H, ABq, J=14.7 Hz), 5.78 (1H, dd, J=4.8, 8.1 Hz), 6.75 (1H, tike), 7.37-7.39 (3H, m), 7.72 (2H, brs), 8.00 (1H, brs), 9.92 (1H, brs), 13.1 (1H, brs). IR (KBr) cm⁻¹: 3341, 3196, 2972, 2934, 1176, 1633, 1567, 1475, 1423, 1344, 1225, 1187, 1159, 1101, 1058, 1033. MS(FAB): 649⁺ (M+H)⁺. Elementary Analysis as C₂₅H₂₅ClN₈O₇S₂.2.6H₂O. Calculated: C, 43.15; H, 4.37; N, 16.10; Cl, 5.09; S, 9.21(%). Found: C, 43.25; H, 4.18; N, 16.06; Cl, 4.81; S, 8.86(%).

EXAMPLE 194

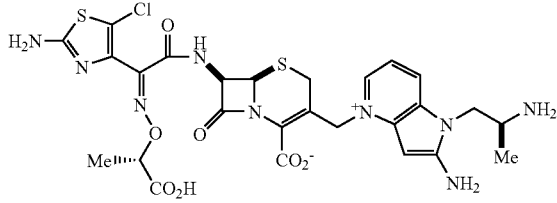

¹H-NMR (D₂O+DCl) δ: 1.41 (3H, d, J=6.3 Hz), 1.54 (3H, d, J=6.9 Hz), 3.26 and 3.49 (2H, ABqt, J=18.3 Hz), 3.87-3.99 (1H, m), 4.35-4.49 (2H, m), 5.29 (1H, d, J=4.8 Hz), 5.36 and 5.53 (2H, ABq, J=15.3 Hz), 5.91 (1H, d, J=4.8 Hz), 7.11 (1H, dd, J=6.3, 7.8 Hz), 7.83 (1H, d, J=7.8 Hz), 7.95 (1H, d, J=6.3 Hz). IR (KBr) cm⁻¹: 3353, 3176, 1756, 1647, 1561, 1436, 1398, 1355, 1318, 1284, 1236, 1165, 1092, 1036. MS(FAB): 678⁺ (M+H)⁺. Elementary Analysis as C₂₆H₂₉ClN₉O₇S₂.3.2H₂O. Calculated: C, 42-38; H, 4.84; N, 17.11; Cl, 4.81; S, 8.70(%). Found: C, 42.46; H, 4.69; N, 17.11; C, 4.58; S, 8.47(%).

EXAMPLE 195

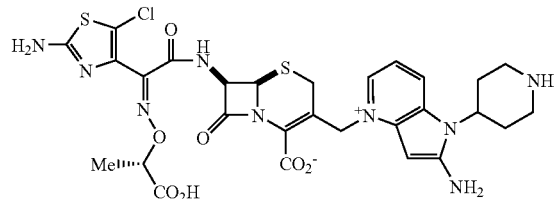

¹H-NMR (D₂O+DCl) δ: 1.54 (3H, d, J=6.9 Hz), 2.24 (3H, s), 2.26 (2H, d-like), 2.62-2.74 (2H, m), 3.19-3.34 (3H, m), 3.46 (1H, d, J=18.3 Hz), 3.72 (2H, d-like), 4.69-4.78 (1H, m), 4.99 (1H, q, J=6.9 Hz), 5.29 (1H, d, J=4.8 Hz), 535 and 5.53 (2H, ABq, J=15.6 Hz), 5.91 (1H, t-like), 7.08 (1H, t-like), 7.94 (2H, t-like). IR (KBr) cm$^{-1}$: 3355, 3184, 1771, 1594, 1559, 1476, 1434, 1395, 1349, 1317, 1283, 1188, 1166, 1066, 1033, 1001. MS(FAB): 704$^+$ (M+H)$^+$. Elementary Analysis as $C_{28}H_{30}ClN_9O_7S_2 \cdot 3.6H_2O$. Calculated: C, 43.73; H, 4.88; N, 16.39; Cl, 4.61; S, 8.34(%). Found: C, 43.74; H, 4.65; N, 16.50; Cl, 4.40; S, 8.13(%).
EXAMPLE A
According to the above Examples, the following compound (I) is synthesized.
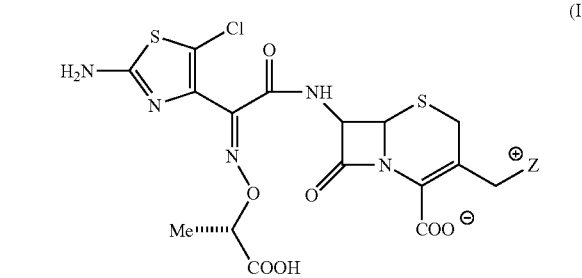
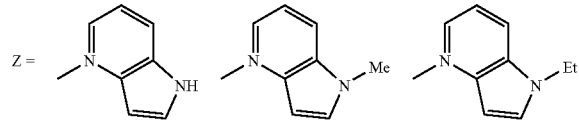
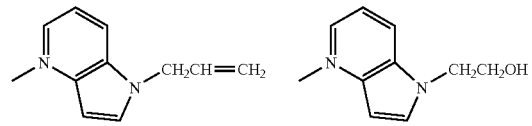
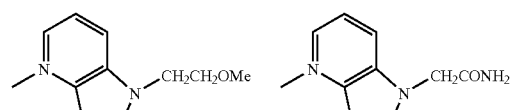
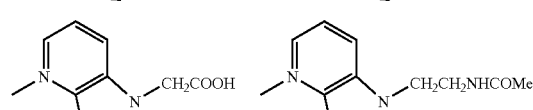
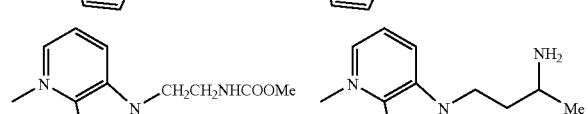
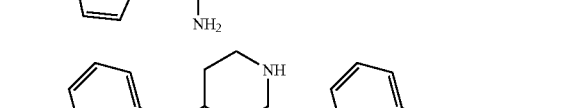
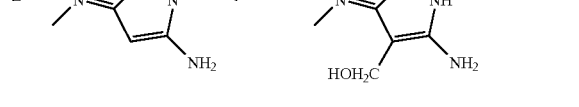
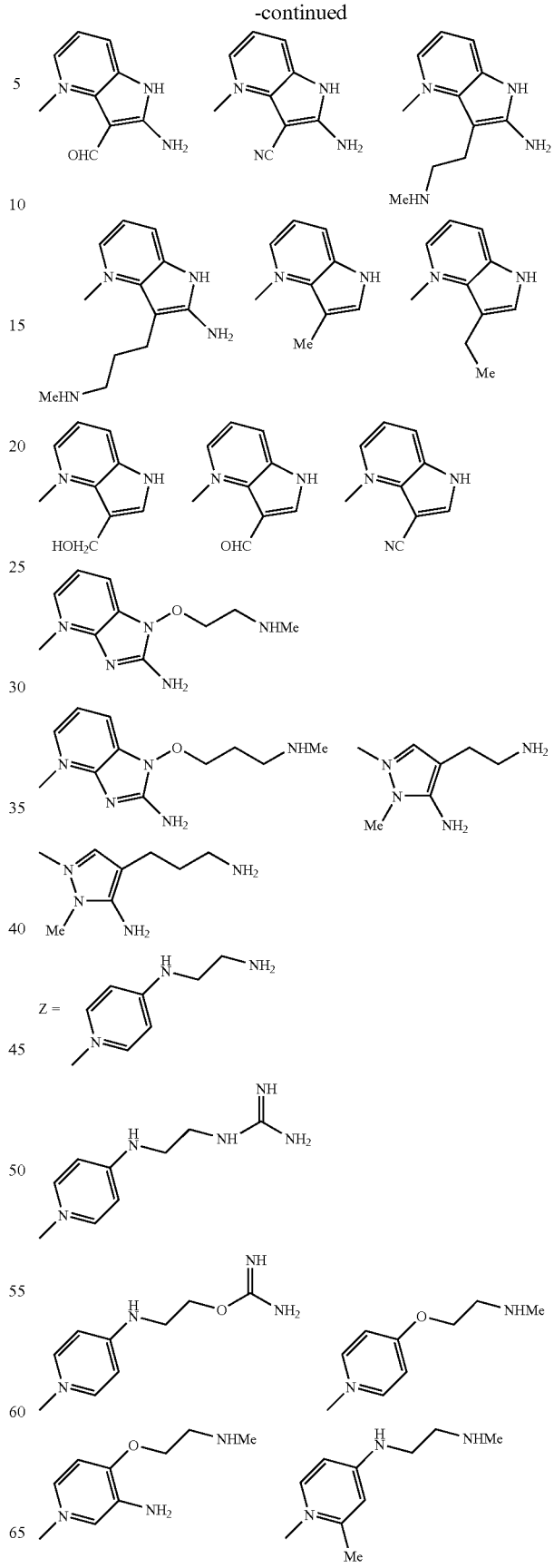

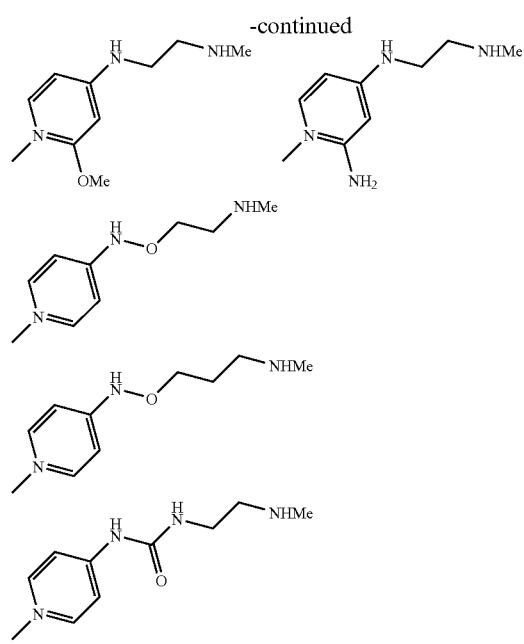

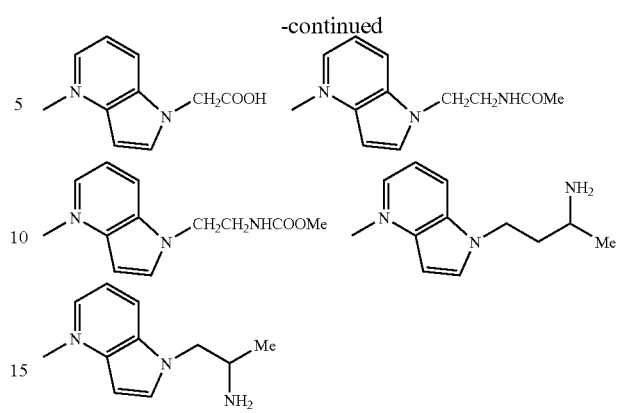

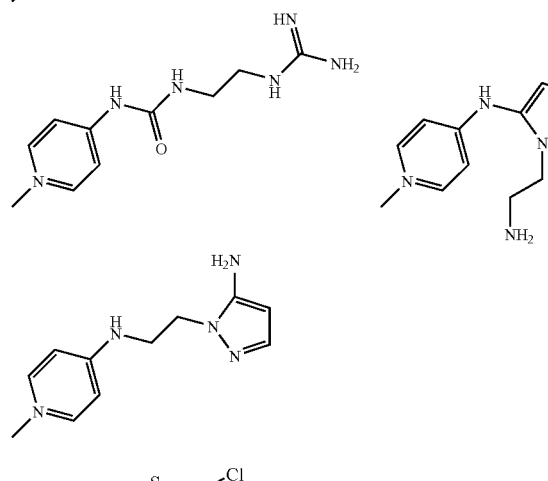

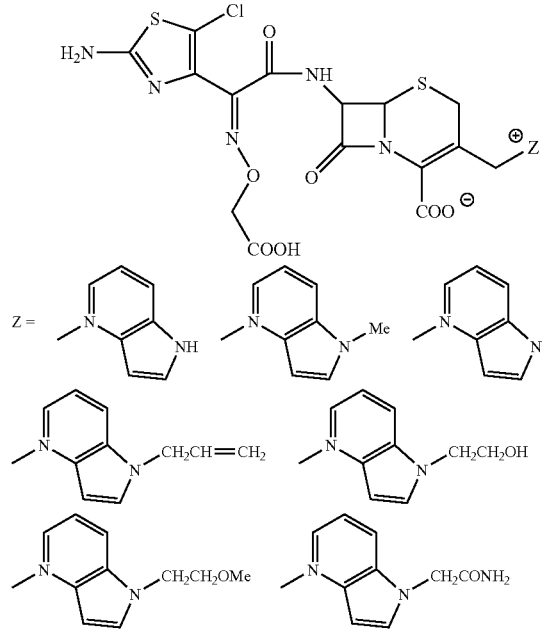

Experiment 1

The MIC (minimum inhibitory concentration) value of the invention compounds against various bacterial was determined by the usual agar dilution method. The result is shown in Table 1.

TABLE 1

(unit: µg/ml)

| Example No | S. aureus SR3637 (H-MRSA)*1 | S. epidermidis SR25009 (MRSE)*2 | E. cloacae SR4321 (Bla++)*3 | P. aeruginosa SR24-12 *3 |
|---|---|---|---|---|
| Ref. 1 | >128 | >128 | 64 | 64 |
| Ex. 1 | 64 | 32 | 16 | 8 |
| Ex. 3 | 32 | 32 | 16 | 8 |
| Ex. 4 | 16 | 8 | 4 | 8 |
| Ex. 5 | 16 | 8 | 8 | — |
| Ex. 8 | 32 | 32 | 4 | 4 |
| Ex. 9 | 16 | 8 | 2 | 4 |
| Ex. 18 | 8 | 4 | 2 | 4 |
| Ex. 19 | 16 | 8 | 1 | 8 |
| Ex. 20 | 16 | 16 | 8 | 4 |
| Ex. 79 | 8 | 8 | 2 | 4 |
| Ex. 98 | 8 | 8 | 2 | 2 |
| Ex. 124 | 16 | 8 | 4 | 4 |
| Ex. 132 | 16 | 8 | 4 | 4 |

*1 Methicillin High-Resistant *Staphylococcus Aureus*
*2 Methicillin High-Resistant *Staphylococcus Epidermidis*
*3 AmpC High-Production Cephem Resistant Strain
Ref 1

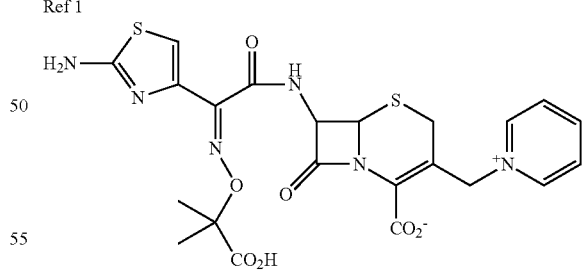

The above result shows that the invention compounds, having a substituent such as halogen on the aminothiazole ring, possesses a potent antibacterial activity against various bacteria including H-MRSA, H-MRSE and *P.aeruginosa* in comparison with Ref 1 compound, Ceftazidime.

FORMULATION EXAMPLE 1

The invention compound of Example 1 and a pH adjusting agent are filled as powder to prepare an injection agent.

INDUSTRIAL UTILITY

The invention compounds exhibit a potent antibacterial activity against various bacteria including Gram-positive bacteria and Gram-negative bacteria. In particular, the invention compounds are stable against β-lactamase and extremely efficatious against cephem-resistant bacteria including C-class β-lactamase-producing *P. aeruginosa*. Further, the invention compounds have an excellent pharmacokinetics and a high water-solubility, thus preferably being suitable for an injection agent.

The invention claimed is:

1. A compound or pharmaceutically acceptable salt thereof, of the formula:

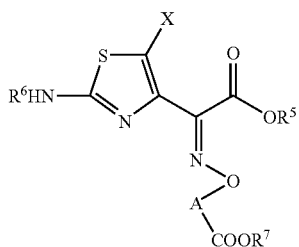 (IV)

wherein X is halogen, CN, carbamoyl optionally substituted with lower alkyl, lower alkyl, lower alkoxy, or lower alkylthio;

A-COOR$^7$ is of the formula:

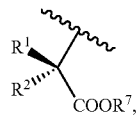

$R^1$ is hydrogen; $R^2$ is lower alkyl; $R^5$ is hydrogen or carboxy-protecting group; $R^6$ is hydrogen or amino-protecting group; and R7 is hydrogen or carboxy-protecting group.

2. A compound or pharmaceutically acceptable salt thereof according to claim 1, wherein X is halogen or lower alkyl.

3. A compound or pharmaceutically acceptable salt thereof according to claim 1, wherein X is halogen.

* * * * *